(12) United States Patent
Holmes-Davis et al.

(10) Patent No.: US 7,771,947 B2
(45) Date of Patent: Aug. 10, 2010

(54) METHODS AND COMPOSITIONS FOR RAPID LIGHT-ACTIVATED ISOLATION AND DETECTION OF ANALYTES

(75) Inventors: Rachel Anne Holmes-Davis, Lafayette, CA (US); Heather Koshinsky, El Cerrito, CA (US); Miaomiao Wang, El Cerrito, CA (US); Brian David Warner, Martinez, CA (US)

(73) Assignee: Investigen, Inc., Hercules, CA (US)

( * ) Notice: Subject to any disclaimer, the term of this patent is extended or adjusted under 35 U.S.C. 154(b) by 0 days.

(21) Appl. No.: 12/034,236

(22) Filed: Feb. 20, 2008

(65) Prior Publication Data

US 2008/0220436 A1 Sep. 11, 2008

Related U.S. Application Data

(60) Provisional application No. 60/903,116, filed on Feb. 23, 2007.

(51) Int. Cl.
*C12Q 1/68* (2006.01)
*C07H 21/02* (2006.01)
*C07H 21/04* (2006.01)

(52) U.S. Cl. ................... 435/6; 536/23.1; 536/24.3

(58) Field of Classification Search ............. 435/6; 536/231, 24.3
See application file for complete search history.

(56) References Cited

U.S. PATENT DOCUMENTS

| | | | |
|---|---|---|---|
| 4,355,023 A | 10/1982 | Ehrlich et al. | |
| 4,462,334 A | 7/1984 | Kim | |
| 4,704,692 A | 11/1987 | Ladner | |
| 4,946,778 A | 8/1990 | Ladner et al. | |
| 5,034,506 A | 7/1991 | Summerton et al. | |
| 5,326,692 A * | 7/1994 | Brinkley et al. | 435/6 |
| 5,491,063 A * | 2/1996 | Fisher et al. | 435/6 |
| 5,582,989 A | 12/1996 | Caskey et al. | |
| 5,635,352 A * | 6/1997 | Urdea et al. | 435/6 |
| 5,641,625 A | 6/1997 | Ecker et al. | |
| 5,677,124 A | 10/1997 | DuBois et al. | |
| 5,702,892 A | 12/1997 | Mulligan-Kehoe | |
| 5,705,333 A | 1/1998 | Shah et al. | |
| 5,714,331 A | 2/1998 | Buchardt et al. | |
| 5,719,262 A | 2/1998 | Buchardt et al. | |
| 5,723,290 A | 3/1998 | Eberwine et al. | |
| 5,736,336 A | 4/1998 | Buchardt et al. | |
| 5,750,373 A | 5/1998 | Garrard et al. | |
| 5,766,855 A | 6/1998 | Buchardt et al. | |
| 5,773,571 A | 6/1998 | Nielsen et al. | |
| 5,786,461 A | 7/1998 | Buchardt et al. | |
| 5,821,047 A | 10/1998 | Garrard et al. | |
| 5,919,625 A | 7/1999 | DuBois et al. | |
| 5,939,262 A | 8/1999 | Dasloske et al. | |
| 6,107,470 A | 8/2000 | Nielsen et al. | |
| 6,127,132 A | 10/2000 | Breitling et al. | |
| 6,131,580 A | 10/2000 | Ratner et al. | |
| 6,214,982 B1 | 4/2001 | Pasloske et al. | |
| 6,218,122 B1 | 4/2001 | Friend et al. | |
| 6,228,982 B1 | 5/2001 | Norden et al. | |
| 6,248,558 B1 | 6/2001 | Lin et al. | |
| 6,280,946 B2 | 8/2001 | Hyldig-Nielsen et al. | |
| 6,287,772 B1 | 9/2001 | Stefano et al. | |
| 6,355,421 B1 | 3/2002 | Coull et al. | |
| 6,357,163 B1 | 3/2002 | Buchardt et al. | |
| 6,391,558 B1 | 5/2002 | Henkens et al. | |
| 6,399,307 B1 | 6/2002 | Pasloske et al. | |
| 6,403,763 B1 | 6/2002 | Lowe | |
| 6,407,213 B1 | 6/2002 | Carter et al. | |
| 6,414,112 B1 | 7/2002 | Buchardt et al. | |
| 6,441,130 B1 | 8/2002 | Egholm et al. | |
| 6,451,968 B1 | 9/2002 | Egholm et al. | |
| 6,475,721 B2 | 11/2002 | Kleiber et al. | |
| 6,506,568 B2 * | 1/2003 | Shriver et al. | 435/6 |
| 6,838,243 B2 | 1/2005 | Lai et al. | |
| 7,273,704 B2 * | 9/2007 | Matsui et al. | 435/6 |
| 2003/0049673 A1 | 3/2003 | Atkinson | |
| 2003/0129627 A1 * | 7/2003 | Wolber | 435/6 |
| 2003/0157500 A1 | 8/2003 | Lowe | |
| 2003/0162699 A1 | 8/2003 | Lowe | |
| 2003/0211010 A1 * | 11/2003 | Nagaoka et al. | 422/64 |
| 2004/0224342 A1 * | 11/2004 | Oonaka et al. | 435/6 |

(Continued)

FOREIGN PATENT DOCUMENTS

CA 2 516 299 9/2004

(Continued)

OTHER PUBLICATIONS

Wilhelmsson et al. Genetic screening using the colour change of a PNA-DNA hybrid-binding cyanine dye. Nucleic Acids Research 30 (2) :e3, 4 pages (2002).*

(Continued)

*Primary Examiner*—Ethan Whisenant
(74) *Attorney, Agent, or Firm*—Brinks Hofer Gilson & Lione

(57) ABSTRACT

The present invention relates to novel methods for isolating a target molecule from a sample suspected of containing the target molecule. The methods of the present invention utilize solid substrates as a means for capturing, separating, and releasing target molecules, such as chemical or biological compounds. The present invention is specifically directed to novel approaches for capturing, separating and releasing such target molecules.

24 Claims, 25 Drawing Sheets

U.S. PATENT DOCUMENTS

| | | | |
|---|---|---|---|
| 2005/0214797 | A1 | 9/2005 | Lokhov et al. |
| 2005/0233360 | A1* | 10/2005 | Davies et al. ............... 435/6 |
| 2006/0004188 | A1 | 1/2006 | Leung et al. |
| 2006/0014191 | A1 | 1/2006 | Lao et al. |
| 2006/0147958 | A1* | 7/2006 | Koshinsky et al. .......... 435/6 |
| 2007/0231821 | A1* | 10/2007 | Bupp et al. ................. 435/6 |

FOREIGN PATENT DOCUMENTS

| | | | |
|---|---|---|---|
| EP | | 404097 | 6/1990 |
| EP | | 0368684 | 9/2004 |
| WO | WO 93/11161 | | 6/1993 |
| WO | WO 99/10536 | | 3/1999 |
| WO | WO 03/024314 | | 3/2003 |
| WO | WO 2004/025268 | | 3/2004 |
| WO | WO 2004/074447 | | 9/2004 |
| WO | WO 05/017181 | * | 2/2005 |
| WO | WO2005/017181 | * | 2/2005 |
| WO | WO2005017181 A2 | | 2/2005 |
| WO | WO 2005/021579 | | 3/2005 |
| WO | WO 2005/044923 | | 5/2005 |

OTHER PUBLICATIONS

Matthews et al. Review : Analytical Strategies for the use of DNA probes. Analytical Biochemistry 169: 1-25 (1988).*

"PNA Chemistry for the Expedite™ 8900 Nucleic Acid Synthesis System User's Guide," Applied Biosystems: Foster City, California. p. 1-114 (2001).

"Selective PCR amplification of functional immunoglobulin light chain from hybridoma containing the aberrant MOPC 21-derived V[symbol] by PNA-Mediated PCR Clamping" BioTechniques 26, p. 818-22 (1999).

Aartsma-Rus, A., et al., "Comparative analysis of antisense oligonucleotide analogs for targeted DMD exon 46 skipping in muscle cells," *Gene Ther*, 11(18): 1391-8 (2004).

Aberg, U. and V. Sundstrom, "Photochemical isomerization in the absence of a potential barrier: origin of wavelength-dependent ground-state recovery kinetics," *Chemical Physics Letters*, 185(6): 461-7 (1991).

Abes, S., et al., "Endosome trapping limits the efficiency of splicing correction by PNA-oligolysine conjugates," *J Control Release*, 110(3): 595-604 (2006).

Abibi, A., et al., "Specific versus nonspecific binding of cationic PNAs to duplex DNA," *Biophys J*, 2004. 86(5): 3070-89 (2004).

Adhikary, A., et al., "Ensemble and single-molecule fluorescence spectroscopic study of the binding modes of the bis-benzimidazole derivative Hoechst 33258 with DNA" *Nucleic Acids Research*, 31(8):2178-2186 (2003).

Adriaensen[a], L., et al., "A comparative study of carbocyanine dyes measured with TOF-SIMS and other mass spectrometric techniques," *Applied Surface Science*, 231-232: 348-352 (2004).

Albertshofer, K., et al., "Structure-activity relationship study on a simple cationic peptide motif for cellular delivery of antisense peptide nucleic acid," *J Med Chem*, 48(21): 6741-9 (2005).

Aldrian-Herrada, G., et al., "A peptide nucleic acid (PNA) is more rapidly internalized in cultured neurons when coupled to a retro-inverso delivery peptide. The antisense activity depresses the target mRNA and protein in magnocellular oxytocin neurons," *Nucleic Acids Res*, 26(21): 4910-6 (1998).

Almarsson, O, Bruice, T., "Peptide nucleic acid (PNA) conformation and polymorphism in PNA-DNA and PNA -RNA hybrids," *Proc. Natl. Acad. Sci. USA*, 90: 9542-6 (1993).

Almarsson, O., et al., "Molecular mechanics calculations of the structures of polyamide nucleic acid DNA duplexes and triple helical hybrids," *Proc Natl Acad Sci U S A*, 90(16): 7518-22 (1993).

Anikovsky, M., et al., "Photochemical investigation of the triplet state of 3,3'-diethylthiacarbocyanine iodide in the presence of DNA," *Russian Chemical Bulletin*, Int'l Ed., 50(7): 119-210 (2001).

Anikovsky, M.Y., A.S. Tatikolov, and V.A. Kuzmin, "Complex formation between 3,3'-diethylthiacarbocyanine iodide and DNA and its investigation in aqueous solution," *International Journal of Photoenergy*, 1: 1-5 (1999).

Anthoney, AD. and Twelves, CJ., "DNA: Still a Target Worth Aiming At? A Review of New DNA-Interactive Agents," *Am. J. Pharmacogenomics*, 1(1):67-81 (2001).

Arabzadeh, A., et al., "Studies on mechanism of 8-methoxypsoralen-DNA interaction in the dark," *International Journal of Pharmaceutics*, 237:47-55 (2002).

Armitage, B., et al., "Peptide nucleic acid (PNA)/DNA hybrid duplexes: intercalation by an internally linked anthraquinone," *Nucleic Acids Res*, 26(3): 715-20 (1998).

Armitage, B., et al., "Peptide nucleic acid-anthraquinone conjugates: strand invasion and photoinduced cleavage of duplex DNA," *Nucleic Acids Res*, 25(22): 4674-8 (1997).

Armitage, B.A., "The impact of nucleic acid secondary structure on PNA hybridization," *Drug Discov Today*, 8(5): 222-8 (2003).

Arya, DP., et al., "Neomycin Binding to Watson—Hoogsteen (W-H) DNA Triplex Groove: A Model," *J. Am. Chem. Soc.*, 125:3733-3744 (2003).

Atwell, G.J., et al., "DNA-Directed Alkylating Agents. 7. Synthesis, DNA Interaction, and Antitumor Activity of Bis(hydroxymethyl)- and Bis(carbamate)-Substituted Pyrrolizines and Imidazoles," *J. Med. Chem.*, 41:4744-4754 (1998).

Ausin, C., et al., "Synthesis of amino- and guanidino-G-clamp PNA monomers," *Org Lett*, 4(23): 4073-5 (2002).

Awad, M.M., et al., "Photoisomerization of Cyanines. A Comparative Study of Oxygen- and Sulfur-Containing Species," *J. Phys. Chem.*, 98(5): 1454-1458 (1994).

Bajor, Z., et al., "PNA-DNA chimeras containing 5-alkynyl-pyrimidine PNA units. Synthesis, binding properties, and enzymatic stability," *Nucleosides Nucleotides Nucleic Acids*, 22(10): 1963-83 (2003).

Bajor, Z., et al., "Synthesis, biophysical, and biochemical properties of PNA-DNA chimeras," *Nucleosides Nucleotides Nucleic Acids*, 22(5-8): 1215-7 (2003).

Baker, B.F., et al., "Discovery and analysis of antisense oligonucleotide activity in cell culture," *Methods*, 23(2): 191-8 (2001).

Baker, E.S., et al., "PNA/dsDNA complexes: site specific binding and dsDNA biosensor applications," *J Am Chem Soc*, 128(26): 8484-92 (2006).

Balss, K.M., et al., "DNA hybridization assays using temperature gradient focusing and peptide nucleic acids," *J Am Chem Soc*, 126(41): 13474-9 (2004).

Balss, K.M., et al., "Temperature Gradient Focusing of Matched and Partially Mismatched DNA/PNA Hybridizations," *National Institute of Standards and Technology*: Squaw Valley, CA. p. 1141-44 (2003).

Baptista, M. and G. Indig, "Mechanism of photobleaching of Ethyl Violet non-covalently bound to bovine serum albumin," *Chem. Commun.*, p. 1791-2 (1997).

Baraldi, I., et al., "Electronic spectra and trans-cis photoisomerism of carbocyanines. A theoretical (CS INDO CI) and experimental study," *Spectrochimica Acta*, 49A(4): 471-495 (1993).

Barawkar, D.A. and T.C. Bruice, "Deoxynucleic Guanidines/PNA (DNG/PNA) Chimeras: Oligonucleoside Analogue Containing Cationic Guanidinium and Neutral Amide Linkages," *J. Am. Chem. Soc.*, 121(44): 10418-10419 (1999).

Barawkar, D.A., et al., "Deoxynucleic Guanidine/Peptide Nucleic Acid Chimeras: Synthesis, Binding and Invasion Studies with DNA," *J. Am. Chem. Soc.*, 122(22): 5244-5250 (2000).

Barceló, F., et al., "Thermodynamic characterization of the multivalent binding of chartreusin to DNA," *Nucleic Acids Research*, 30(2):4567-4573 (2002).

Barone, G., et al., "Synthesis and DNA binding properties of DNA-PNA chimeras," *Nucleosides Nucleotides Nucleic Acids*, 22(5-8): 1089-91 (2003).

Barry, C.G., et al., "Thermally Inert Metal Ammines as Light-Inducible DNA-Targeted Agents. Synthesis, Photochemistry, and Photobiology of a Prototypical Rhodium (III)—Intercalator Conjugate," *Inorg. Chem.*, 41(26):7159-7169 (2002).

Baruah, H. and Bierbach, U., "Unusual Intercalation of acridin-9-ylthiourea into the 5'-GA/TC DNA base step from the minor groove: implications for the covalent DNA adduct profile of a novel platinum—intercalator conjugate," *Nucleic Acids Research*, 31(14):4138-4146 (2003).

Basile, A., et al., "Use of peptide nucleic acid probes for detecting DNA single-base mutations by capillary electrophoresis," *Electrophoresis*, 23(6): 926-929 (2002).

Bastide, L., et al., "Inhibition of a DNA-helicase by peptide nucleic acids," *Nucleic Acids Res*, 27(2): 551-4 (1999).

Basu, S. and E. Wickstrom, "Synthesis and characterization of a peptide nucleic acid conjugated to a D-peptide analog of insulin-like growth factor 1 for increased cellular uptake," *Bioconjug Chem*, 8(4): 481-8 (1997).

Bauer, O., et al., "Oligonucleotide fingerprinting by multiplex PNA hybridization and MALDI-TOF mass spectrometry detection," *Functional Genomics*: p. 92-93 (year not known).

Bazel, Y.R., Z.A. Kormosh, and A.A. Tolmachev, "State of Polymethine (Styryl and Carbocyanine) Indolium Derivatives in Aqueous Solution and Their Analytical Properties," *Journal of Analytical Chemistry*, 57(2): 118-124 (2002).

Beletskii, A., et al., "PNA interference mapping demonstrates functional domains in the noncoding RNA Xist/, *Proc Natl Acad Sci U S A*, 98(16): 9215-20 (2001).

Bengtsson, M., et al., "A new minor groove binding asymmetric cyanine reporter dye for real-time PCR," *Nucleic Acids Res*, 31(8): e45 (2003).

Benson, D.M., et al., "Digital imaging fluorescence microscopy: spatial heterogeneity of photobleaching rate constants in individual cells," *J Cell Biol*, 100(4): 1309-23 (1985).

Benson, S.C., et al., "Heterodimeric DNA-binding dyes designed for energy transfer: stability and applications of the DNA complexes," *Nucleic Acid Research*, 21(24):5720-5726 (1993).

Benson, S.C., Z. Zeng, and A.N. Glazer, "Fluorescence Energy-Transfer Cyanine Heterodimers with High Affinity for Double-Stranded DNA," *Analytical Biochemistry*, 231(1): 247-255 (1995).

Bentin, T. and P.E. Nielsen, "Enhanced peptide nucleic acid binding to supercoiled DNA: possible implications for DNA "breathing" dynamics," *Biochemistry*, 35(27): 8863-9 (1996).

Bentin, T. and P.E. Nielsen, "Superior duplex DNA strand invasion by acridine conjugated peptide nucleic acids," *J Am Chem Soc*, 125(21): 6378-9 (2003).

Bentin, T., et al., "Structural diversity of target-specific homopyrimidine peptide nucleic acid-dsDNA complexes," *Nucleic Acids Res*, 34(20): 5790-9 (2006).

Berezovin, D.N., et al., "Photoisomerization of Dicarbocyanine Dyes," *Plenum Publishing Corporation*, 51(6): 1265-70 (1989).

Berge, S.M., et al., "Pharmaceutical Salts," *J. Pharma. Sci.*, 66(1):1-19 (1977).

Berge, T., et al., "Structural perturbations in DNA caused by bis-intercalation of ditercalinium visualized by atomic force microscopy," *Nucleic Acids Research*, 30(13):2980-2986 (2002).

Beverina, L., et al., "New pi-extended water-soluble squaraines as singlet oxygen generators," *Org Lett*, 7(19): 4257-60 (2005).

Bhattacharya, B., et al., "Development of a new sensitive and efficient multiplex polymerase chain reaction (PCR) for identification and differentiation of different mycobacterial species," *Tropical Medicine and International Health*, 8(2)150-157 (2003).

Biessen, E.A., et al., "Design of a targeted peptide nucleic acid prodrug to inhibit hepatic human microsomal triglyceride transfer protein expression in hepatocytes," *Bioconjug Chem*,13(2): 295-302 (2002).

Bilmes, G.M., et al., "Laser-Induced Optoacoustic Studies of the Photoisomerization of the Laser Dye 3,3'-Diethyloxadicarrocyanine Iodide (DODCI)," *Chemical Physics Letters*, 134(4): 335-40 (1987).

Bilmes, G.M., et al., "Photophysical Processes of Polymethine Dyes. An Absorption, Emission, and Optoacoustic Study on 3,3'-Diethylthiadicarbocyanine Iodide," *J. Phys. Chem.*, 93(18): 6696-6699 (1989).

Bilmes, G.M., et al., "Spectrum, Energy Content, and Relaxation Mechanism of the Photoisomer of the Laser Dye 3,3'-Diethyloxadicarbocyanine Iodide. Laser- Induced Optoacoustic Studies," *J. Phys. Chem.*, 92(21): 5958-5962 (1988).

Biver, T., et al., "Kinetics and equilibria for the formation of a new DNA metal-intercalator: the cyclic polyamine Neotrien/copper(II) complex," *Journal of Inorganic Biochemistry*, 98:33-40 (2004).

Bockstahler, L.E., et al., "Peptide nucleic acid probe detection of mutations in *Mycobacterium tuberculosis* genes associated with drug resistance," *Biotechniques*, 32(3): 508-10, 512, 514 (2002).

Boe, S. and E. Hovig, "Photochemically induced gene silencing using PNA-peptide conjugates," *Oligonucleotides*, 16(2): 145-57 (2006).

Boffa, L.C., et al., "Invasion of the CAG triplet repeats by a complementary peptide nucleic acid inhibits transcription of the androgen receptor and TATA-binding protein genes and correlates with refolding of an active nucleosome containing a unique AR gene sequence," *J Biol Chem*, 271(22): 13228-33 (1996).

Boffa, L.C., et al., "Isolation of active genes containing CAG repeats by DNA strand invasion by a peptide nucleic acid," *Proc Natl Acad Sci U S A*, 92(6): 1901-5 (1995).

Boffa, L.C., et al., "Dihydrotestosterone as a selective cellular/nuclear localization vector for anti-gene peptide nucleic acid in prostatic carcinoma cells," *Cancer Res*, 60(8): 2258-62 (2000).

Boger, D.L., et al., "Thiazole Orange as the Fluorescent Intercalator in a High Resolution FID Assay for Determining DNA Binding Affinity and Sequence Selectivity of Small Molecules," *Biooroganic & Medicinal Chemistry*, 9:2511-2518 (2001).

Boll, I., R. Kramer, and A. Mokhir, "Hybridization dependent cleavage of internally modified disulfide-peptide nucleic acids," *Bioorg Med Chem Lett*, 15(3): 505-9 (2005).

Bonvicini, F., et al., "Peptide nucleic acid-based in situ hybridization assay for detection of parvovirus B19 nucleic acids," *Clin Chem*, 52(6): 973-8 (2006).

Boulme, F., et al., "Modified (PNA, 2'-O-methyl and phosphoramidate) anti-TAR antisense oligonucleotides as strong and specific inhibitors of in vitro HIV-1 reverse transcription", *Nucleic Acid Research*, 26(23): 5492-5500 (1998).

Boutorine, A.S., et al., "Stabilization of DNA Double and Triple Helices by Conjugation of Minor Groove Binders to Oligonucleotides," *Nucleosides, Nucleotides & Nucleic Acids*, 22(5-8):1267-1272 (2003).

Braasch et al., "Synthesis and Purification of Peptide Nucleic Acids," *Current Protocols in Nucleic Acid Chemistry*, 4.11.1-4.11.18 (2002).

Braasch, D.A. and D.R. Corey, "Novel antisense and peptide nucleic acid strategies for controlling gene expression," *Biochemistry*, 41(14): 4503-10 (2002).

Braasch, D.A. and D.R. Corey, "Synthesis, analysis, purification, and intracellular delivery of peptide nucleic acids," *Methods*, 23(2): 97-107 (2001).

Braña, M.F., et al., "Synthesis and antitumour activity of new dendritic polyamines—(imide-DNA-Intercalator) conjugates: potent Lck inhibitors," *Eur. J. Med. Chem.*, 37:541-551 (2002).

Brandt, O. and J.D. Hoheisel, "Peptide nucleic acids on microarrays and other biosensors," *Trends Biotechnol* 22(12): 617-22 (2004).

Brandt, O., et al., "PNA microarrays for hybridisation of unlabelled DNA samples," *Nucleic Acids Res*, 31(19): e119 (2003).

Brehm-Stecher, B.F., J.J. Hyldig-Nielsen, and E.A. Johnson, "Design and evaluation of 16S rRNA-targeted peptide nucleic acid probes for whole-cell detection of members of the genus *Listeria,*" *Appl Environ Microbiol*, 71(9): 5451-7 (2005).

Brichkin, S.B., et al., "Effects of Surfactants on the Spectral Properties of Carbocyanine Dyes in Solutions," *High Energy Chemistry*, 38(6): 373-380 (2004).

Brichkin, S.B., et al., "Spectral Properties of Carbocyanine Dyes in Solutions of Reverse AOT Micelles," *High Energy Chemistry*, 39(1): 15-19 (2005).

Briehn, C.A., et al., "Alternative Heterocycles for DNA Recognition: The Benzimidazole/Imidazole Pair," *Chem Eur. J.*, 9:2110-2122 (2003).

Brown, S.C., et al., "NMR solution structure of a peptide nucleic acid complexed with RNA," *Science*, 265(5173): 777-80 (1994).

Bruce, A.C., et al., "Complex formation between symmetrical thiacyanine dyes and aromatic heterocycles: evidence for molecular recognition," *Journal of Photochemistry and Photobiology A: Chemistry*, 119(3): 191-203 (1998).

Bukanov, N.O., et al., "PD-loop: a complex of duplex DNA with an oligonucleotide," *Proc Natl Acad Sci U S A*, 95(10): 5516-20 (1998).

Buston, J.E.H., F. Marken, and H.L. Anderson, "Enhanced chemical reversibility of redox processes in cyanine dye rotaxanes," *Chem. Commun.*, 11: 1046-1047 (2001).

Caimi, K., et al., "Sequence analysis of the direct repeat region in *Mycobacterium bovis*," *J Clin Microbiol*, 39(3): 1067-72 (2001).

Caldarelli, S., et al., "Synthesis and cellular uptake of a fluorescently labeled cyclic PNA-based compound," *Bioorg Med Chem Lett*, 14(17): 4435-8 (2004).

Caldarelli, S.A., et al., "A cyclic PNA-based compound targeting domain IV of HCV IRES RNA inhibits in vitro IRES-dependent translation," *Bioorg Med Chem*, 13(20): 5700-9 (2005).

Cao, R., et al., "A recoverable enzymatic microgel based on biomolecular recognition," *J Am Chem Soc*, 126(3): 726-7 (2004).

Cao, R., et al., "Synthesis and characterization of thermoreversible biopolymer microgels based on hydrogen bonded nucleobase pairing," *J Am Chem Soc*, 125(34): 10250-6 (2003).

Carpino, L.A. and A. El-Faham, "The Diisopropylcarbodiimide/1-Hydroxy-7-azabenzotriazole System: Segment Coupling and Stepwise Peptide Assembly," *Tetrahedron*, 55(22): 6813-6830 (1999).

Carrasco, C., et al., "Design of a Composite Ethidium—Netropsin—Anilinoacridine Molecule for DNA Recognition," *ChemBioChem*, 4:50-61 (2003).

Carreon, J.R., et al., "Thiazole Orange-Peptide Conjugates: Sensitivity of DNA Binding to Chemical Structure," *Organic Letters*, 6(4):517-519 (2004).

Castro, A., et al., "Single-Molecule Detection of Specific Nucleic Acid Sequences," *Los Alamos National Laboratory*: Springfield, VA., p. 64-74 (2000).

Chakrabarti, M.C. and F.P. Schwarz, "Thermal stability of PNA/DNA and DNA/DNA duplexes by differential scanning calorimetry," *Nucleic Acids Res*, 27(24): 4801-6 (1999).

Chakrabarti, R. and A.M. Klibanov, "Nanocrystals modified with peptide nucleic acids (PNAs) for selective self-assembly and DNA detection," *J Am Chem Soc*, 125(41): 12531-40 (2003).

Chandler, D.P. and A.E. Jarrell, "Enhanced nucleic acid capture and flow cytometry detection with peptide nucleic acid probes and tunable-surface microparticles," *Anal Biochem*, 312(2): 182-90 (2003).

Chandler, D.P., et al., "Affinity Capture and Recovery of DNA at Femtomolar Concentrations with Peptide Nucleic Acid Probes," *Analytical Biochemistry*, 283:241-249 (2000).

Chandler, D.P., et al., "Affinity purification of DNA and RNA from environmental samples with peptide nucleic acid clamps," *Appl Environ Microbiol*, 66(8): 3438-45 (2000).

Chapin, K. and M. Musgnug, "Evaluation of three rapid methods for the direct identification of *Staphylococcus aureus* from positive blood cultures," *J Clin Microbiol*, 41(9): 4324-7 (2003).

Chaput, J.C. and Szostak, J.W., "TNA Synthesis by DNA Polymerases," *J. Am. Chem. Soc.*, 125(31):9274-9275 (2003).

Chaput, J.C., et al., "DNA Polymerase-Mediated DNA Synthesis on a TNA Template," *J. Am. Chem. Soc.*, 125:856-857 (2003).

Chatteijee, S., et al. "Photochemistry of Carbocyanine Alkyltriphenylborate Salts: Intra-Ion-Pair Electron Transfer and the Chemistry of Boranyl Radicals," *J. Am. Soc.*, 112: 6229-38 (1990).

Cheah, I.K., et al., "Design and application of a peptide nucleic acid sequence targeting the p75 neurotrophin receptor," *Bioorg Med Chem Lett*, 13(14): 2377-80 (2003).

Chen, C., et al., "Single base discrimination of CENP-B repeats on mouse and human Chromosomes with PNA-FISH," *Mamm Genome*, 10(1): 13-8 (1999).

Chen, C., et al., "Electron transfer events in solutions of cyanine dyes," *Journal of Photochemistry and Photobiology A: Chemistry*, 89(1): 25-29 (1995).

Chen, C., et al., "Unique chromosome identification and sequence-specific structural analysis with short PNA oligomers," *Mamm Genome*, 11(5): 384-91 (2000).

Chen, J., et al., "A microsphere-based assay for multiplexed single nucleotide polymorphism analysis using single base chain extension," *Genome Res*, 10(4): 549-57 (2000).

Chen, Q., et al., "Interaction of a novel red-region fluorescent probe, Nile Blue, with DNA and its application to nucleic acids assay," *Analyst*, 124:901-906 (1999).

Cherny, D.Y., et al., "DNA unwinding upon strand-displacement binding of a thymine-substituted polyamide to double-stranded DNA," *Proc Natl Acad Sci U S A*, 90(5): 1667-70 (1993).

Chibisov, A.K., "Triplet States of Cyanine dyes and Reactions of Electron Transfer with their Participation," *Journal of Photochemistry*, 6(3): 199-214 (1976-77).

Chibisov, A.K., et al., "Dimerization kinetics of thiacarbocyanine dyes by photochemically induced concentration jump," *Chemical Physics Letters*, 386(4-6): 301-306 (2004).

Chibisov, A.K., et al., "Kinetics of salt-induced J-aggregation of an anionic thiacarbocyanine dye in aqueous solution," *Chemical Physics Letters*, 390(1-3): 240-245 (2004).

Chibisov, A.K., et al., "Photoprocesses in dimers of thiacarbocyanines," *Phys. Chem. Chem. Phys*, 1(7): 1455-1460 (1999).

Chibisov, A.K., et al., "Photosensitized processes in dicarbocyanine dyes induced by energy transfer: delayed fluorescence, trans → cis isomerization and electron transfer," *Journal of Photochemistry and Photobiology A: Chemistry*, 141(1): 39-45 (2001).

Christensen, U.B., and Pedersen, E.B., "Intercalating nucleic acids containing insertions of 1-O-(1-pyrenylmethyl)glycerol: stabilisation of dsDNA and discrimination of DNA over RNA," *Nucleic Acids Research*, 30(22):4918-4925 (2002).

Cichon, M.K., et al., "Efficient interstrand excess electron transfer in PNA: DNA hybrids," *J Am Chem Soc*, 124(47): 13984-5 (2002).

Clapp, P.J., et al., "Two-Dimensional Polymerization of Lipid Bilayers: Visible-Light-Sensitized Photoinitiation," *Macromolecules*, 30(1): 32-41 (1997).

Clivio, P., et al., "A Photochemical Approach to Highlight Backbone Effects in PNA," *J. Am. Chem. Soc.*, 119(22): 5255-5256 (1997).

Cochet, O., et al., "Selective PCR amplification of functional immunoglobulin light chain from hybridoma containing the aberrant MOPC 21-derived V kappa by PNA-mediated PCR clamping," *Biotechniques*, 26(5): 818-20, 822 (1999).

Coloma, M.J. and Morrison, S., "Design and production of novel tetravalent bispecific antibodies," *Nature Biotechnology*, 15:159-163 (Feb. 1997).

Cooper, M., et al., "Cy3B: improving the performance of cyanine dyes," *J Fluoresc*, 14(2): 145-50 (2004).

Corey, D.R., "Recognition of chromosomal DNA in human cells by peptide nucleic acids and small duplex RNAs," *Ann N Y Acad Sci*, 1058: 16-25 (2005).

Corradini, R., et al., "Direct enantiomeric separation of N-aminoethylamino acids: determination of the enantiomeric excess of chiral peptide nucleic acids (PNAs) by GC," *Tetrahedron: Asymmetry*, 10(11): 2063-2066 (1999).

Cox, A.J. and B.K. Matise, "Energy Transfer Between Coumarins in a Dye Laser," *Chemical Physics Letters*, 76(1): 125-128 (1980).

Cutrona, G., et al., "Effects in live cells of a c-myc anti-gene PNA linked to a nuclear localization signal," *Nat Biotechnol*, 18(3): 300-3 (2000).

D'Costa, M., et al., "Aminoethylprolyl Peptide Nucleic Acids (aep-PNA): Chiral PNA Analogues That Form Highly Stable DNA:aep-PNA$_2$ Triplexes," *Organic Letters*, 1(10):1513-1516 (1999).

Darmanyan, A.P. and V.A. Kuz'min, "Laser Photolysis of Dicarbocyanine Dyes," *Institute of Chemical Physics*, (3): 506-10 (1978).

Dassonneville, L., et al., "The Plant Alkaloid Usambarensine Intercalates into DNA and Induces Apoptosis in Human HL60 Leukemia Cells," *Anticancer Research*, 19:5245-5250 (1999).

Datta, B., C. Schmitt, and B.A. Armitage, "Formation of a PNA2-DNA2 hybrid quadruplex," *J Am Chem Soc*, 125(14): 4111-8 (2003).

D'Costa, M., V. Kumar, and K.N. Ganesh, "Aminoethylprolyl (aep) PNA: mixed purine/pyrimidine oligomers and binding orientation preferences for PNA: DNA duplex formation," *Org Lett*, 3(9): 1281-4 (2001).

D'Costa, M., V.A. Kumar, and K.N. Ganesh, "N7-guanine as a C+ mimic in hairpin aeg/aepPNA-DNA triplex: probing binding selectivity by UV-Tm and kinetics by fluorescence-based strand-invasion assay," *J Org Chem*, 68(11): 4439-45 (2003).

De Mesmaeker, A., et al., "Antisense Oligonucleotides," *Acc. Chem. Res.*, 28(9): 366-374 (1995).

Dees, E.C., et al., "A Phase I and Pharmacologic Evaluation of the DNA Intercalator CI-958 in Patients with Advanced Solid Tumors," *Clinical Cancer Research*, 6:3885-3894 (2000).

Demers, D.B., et al., "Enhanced PCR amplification of VNTR locus D1S80 using peptide nucleic acid (PNA)," *Nucleic Acids Res*, 23(15): 3050-5 (1995).

Demidov, V., et al., "Sequence selective double strand DNA cleavage by peptide nucleic acid (PNA) targeting using nuclease S1," *Nucleic Acids Res*, 21(9): 2103-7 (1993).

Demidov, V.V. and M.D. Frank-Kamenetskii, "Sequence-specific targeting of duplex DNA by peptide nucleic acids via triplex strand invasion," *Methods*, 23(2): 108-22 (2001).

Demidov, V.V. and M.D. Frank-Kamenetskii, "Two sides of the coin: affinity and specificity of nucleic acid interactions," *Trends Biochem Sci*, 29(2): 62-71 (2004).

Demidov, V.V., et al., "Fast complementation of split fluorescent protein triggered by DNA hybridization," *Proc Natl Acad Sci U S A*, 103(7): 2052-6 (2006).

Demidov, V.V., et al., "Stability of peptide nucleic acids in human serum and cellular extracts," *Biochemical Pharmacology*, 48(6):1310-1313 (1994).

Demidov, V.V., et al., "An artificial primosome: design, function, and applications," *Chembiochem*, 2(2): 133-9 (2001).

Demidov, V.V., et al., "Electron microscopy mapping of oligopurine tracts in duplex DNA by peptide nucleic acid targeting," *Nucleic Acids Res*, 22(24): 5218-22 (1994).

Demidov, V.V., et al., "Kinetics and mechanism of polyamide ("peptide") nucleic acid binding to duplex DNA," *Proc Natl Acad Sci U S A*, 92(7): 2637-41 (1995).

Demidov, V.V., et al., "Kinetics and mechanism of the DNA double helix invasion by pseudocomplementary peptide nucleic acids," *Proc Natl Acad Sci U S A*, 99(9): 5953-8 (2002).

Demidov, V.V., "PNA and LNA throw light on DNA," *Trends Biotechnol*, 21(1): 4-7 (2003).

Demidov, V.V., "PNA Openers for Duplex DNA: Basic Facts, Fine Tuning and Emerging Applications," CH 10, p. 1-19 (no date known).

Demidov, V.V., "Tough nuts to crack: encouraging progress in peptide nucleic acid hybridization to structured DNA/RNA targets," *Drug Discov Today*, 8(9): 390 (2003).

Dempcy, R.O., et al., "Linkers designed to intercalate the double helix greatly facilitate DNA alkylation by triplex-forming oligonucleotides carrying a cyclopropapyrroloindole reactive moiety," *Nucleic Acids Research*, 27(14):2931-2937 (1999).

Derossi, D., et al., "Cell Internalization of the Third Helix of the Antennapedia Homeodomain is Receptor-independent," *J. Biol. Chem.*, 271(30):18188-18193 (1996).

Derossi, D., et al., "The Third Helix of the Antennapedia Homeodomain Translocates through Biological Membranes," *J. Biol. Chem.*, 269(14):10444-10450 (1994).

Dervan, P.B., and Edelson, B.S., "Recognition of the DNA minor groove by pyrrole-imidazole polyamides," *Current Opinion in Structural Biology*, 13:284-299 (2003).

Devolve, A. et. al., "Charge dependent behavior of PNA/DNA/PNA triplexes in the gas phase," *J. of Mas Spectrom.*, 41: 1498-1508 (2006).

Dhar, S., et al., "Ternary Copper Complexes for Photocleavage of DNA by Red Light: Direct Evidence for Sulfur-to-Copper Charge Transfer and d-d Band Involvement," *J. Am. Chem. Soc.*, 125:12118-12124 (2003).

Di Giusto, D.A. and G.C. King, "Strong positional preference in the interaction of LNA oligonucleotides with DNA polymerase and proofreading exonuclease activities: implications for genotyping assays," *Nucleic Acids Res*, 32(3): e32 (2004).

Dias, N., et al., "Antisense PNA tridecamers targeted to the coding region of Ha-ras mRNA arrest polypeptide chain elongation," *J Mol Biol*, 294(2): 403-16 (1999).

Dieci, G., et al., "Inhibition of RNA polymerase III elongation by a T10 peptide nucleic acid," *J Biol Chem*, 276(8): 5720-5 (2001).

Diedrichsen, U., "Alanyl-PNA oligomers: A new system for intercalation," *Bioorganic & Medicinal Chemistry Letters*, 7(13): 1743-6 (1997).

Dienes, Z. and Vogel, P., "Asymmetric Synthesis and DNA Intercalation of (-)-6- [[(Aminoalkyl)oxy]methyl]-4-demethoxy-6,7-dideoxydaunomycinones,". *Org. Chem.*, 61:6958-6970 (1996).

DiPaolo, R.E., et al. "Photoisomerization Dynamics and Spectroscopy of the Polymethine Dye DTCI," *J. Phys. Chem.*, 99:13796-799 (1995).

Dittrich, P.S. and P. Schwille, "Photobleaching and stabilization of fluorophores used for single-molecule analysis with one- and two-photon excitation," *Appl. Phys. B- Lasers and Optics*, 73: 829-837 (2001).

Doyle, D.F., et al., "Inhibition of gene expression inside cells by peptide nucleic acids: effect of mRNA target sequence, mismatched bases, and PNA length," *Biochemistry*, 40(1): 53-64 (2001).

Dragulescu-Andrasi, A., et al., "A simple gamma-backbone modification preorganizes peptide nucleic acid into a helical structure," *J Am Chem Soc*, 128(31): 10258-67 (2006).

Dragulescu-Andrasi, A., et al., "Cell-permeable peptide nucleic acid designed to bind to the 5'-untranslated region of E-cadherin transcript induces potent and sequence-specific antisense effects" *With Supporting Information J Am Chem Soc*, 128(50): 16104-12 (2006).

Drewe, L.J., G. Brightwell, and E.A. Hall, "Detection of PCR products using PNA strand invasion," *Mol Cell Probes*, 14(5): 269-83 (2000).

Dryselius, R., et al., "Antibiotic-free bacterial strain selection using antisense peptide nucleic acid," *Biotechniques*, 35(5): 1060-4 (2003).

Dryselius, R., et al., "Variable coordination of cotranscribed genes in *Escherichia coli* following antisense repression," *BMC Microbiol*, 6:97 (2006).

Eachus, R.S., A.P. Marchetti, and A.A. Muenter, "The photophysics of silver halide imaging materials," *Annu Rev Phys Chem*, 50: 117-44 (1999).

Edman, C.F., et al., "Electric field directed nucleic acid hybridization on microchips," *Nucleic Acids Res*, 25(24): 4907-14 (1997).

Efimov, V., et al., "PNA-Related Oligonucleotide Mimics and Their Evaluation for Nucleic Acid Hybridization Studies and Analysis," *Nucleosides, Nucleotides & Nucleic Acids*, 20(4-7): 419-428 (2001).

Efimov, V.A., et al., "Hydroxyproline-based DNA mimics provide an efficient gene silencing in vitro and in vivo," *Nucleic Acids Res*, 34(8): 2247-57 (2006).

Efimov, V.A., O.G. Chakhmakhcheva, and E. Wickstrom, "Synthesis and application of negatively charged PNA analogues," *Nucleosides Nucleotides Nucleic Acids*, 24(10-12): 1853-74. (2005).

Efimov, V.A., V.N. Klykov, and O.G. Chakhmakhcheva, "Phosphono peptide nucleic acids with a constrained hydroxyproline-based backbone," *Nucleosides Nucleotides Nucleic Acids*, 22(5-8): 593-9 (2003).

Egholm, M., et al., "Efficient pH-independent sequence-specific DNA binding by pseudoisocytosine-containing bis-PNA," *Nucleic Acids Res*, 23(2): 217-22 (1995).

Egholm, M., et al., "Peptide Nucleic Acids (PNA) Oligonucleotide Analogues with an Acbiral Peptide Backbone," *J. Am. Chem. Soc.* 114(5): 1895-1897 (1992).

Egholm, M., et al., "PNA hybridizes to complementary oligonucleotides obeying the Watson-Crick hydrogen-bonding rules," *Nature*, 365(6446): 566-8 (1993).

Egholm, M., et al., "Recognition of Guanine and Adenine in DNA by Cytosine and Thymine Containing Peptide Nucleic Acids (PNA)," *J. Am. Chem. Soc.* 114(24): 9677-9678 (1992).

Elayadi, A.N., D.A. Braasch, and D.R. Corey, "Implications of high-affinity hybridization by locked nucleic acid oligomers for inhibition of human telomerase," *Biochemistry*, 41(31): 9973-81 (2002).

Eldrup, A.B., et al., "Substituted 1,8-naphthyridin-2(1H)-ones are superior to thymine in the recognition of adenine in duplex as well as triplex structures," *J Am Chem Soc.*, 124(13): 3254-62 (2002).

Eldrup, A.B., O. Dahl, and P.E. Nielsen, "A Novel Peptide Nucleic Acid Monomer for Recognition of Thymine in Triple-Helix Structures," *With Supporting Information J. Am. Chem. Soc.*, 119(45): 11116-11117 (1997).

Ellison, S.L., et al., "Routes to improving the reliability of low level DNA analysis using real-time PCR.," *BMC Biotechnol*, 6(33): 11 (2006).

Endo, T., et al., "Label-free detection of peptide nucleic acid-DNA hybridization using localized surface plasmon resonance based optical biosensor," *Anal Chem*, 77(21): 6976-84. (2005).

Eriksson, M. and P.E. Nielsen, "Solution structure of a peptide nucleic acid-DNA duplex," *Nat Struct Biol*, 3(5): 410-3 (1996).

Eriksson, M., et al., "Groove-binding unsymmetrical cyanine dyes for staining of DNA: dissociation rates in free solution and electrophoresis gels," *Nucleic Acids Research*, 31(21): 6235-6242 (2003).

Eriksson, M., P.E. Nielsen, and L. Good, "Cell permeabilization and uptake of antisense peptide-peptide nucleic acid (PNA) into *Escherichia coli*," *J Biol Chem*, 277(9): 7144-7 (2002).

Esiobu, N., et al., "The application of peptide nucleic acid probes for rapid detection and enumeration of eubacteria, *Staphylococcus aureus* and *Pseudomonas aeruginosa* in recreational beaches of S. Florida," *J Microbiol Methods*, 57(2): 157-62 (2004).

Esposito, V., et al., "PNA-DNA chimeras forming quadruplex structures," *Nucleosides Nucleotides Nucleic Acids*, 22(5-8): 1681-4 (2003).

Eurogentec, "Peptide Nucleic Acid (PNA)," p. 42-45 (2001).

Falkiewicz, B., et al., "Synthesis of new chiral peptide nucleic acid (PNA) monomers," *Nucleosides Nucleotides Nucleic Acids*, 20(4-7): 1393-7 (2001).

Fang, H., et al., "Identification and characterization of high affinity antisense PNAs for the human unr (upstream of N-ras) mRNA which is uniquely overexpressed in MCF-7 breast cancer cells," *Nucleic Acids Res*, 33(21): 6700-11 (2005).

Faruqi, A.F., M. Egholm, and P.M. Glazer, "Peptide nucleic acid-targeted mutagenesis of a chromosomal gene in mouse cells," *Proc Natl Acad Sci U S A*, 95(4): 1398-403 (1998).

Fassler, D. and M. Baezold, "Photoprocesses of adsorbed polymethine dyes," *Journal of Photochemistry and Photobiology A: Chemistry*, 64: 359-368 (1992).

Ferry, D.M., et al., "Sensitive liquid chromatographic assay for the basic DNA intercalator (N,N-dimethylaminoethyl)-9-amino-5-methylacridine-4-carboxamide and its nitrozrylmethyl quaternary prodrugs in biological samples," *Journal of Chromatography B*, 763:149-156 (2001).

Ficht, S., et al., "Single-nucleotide-specific PNA-peptide ligation on synthetic and PCR DNA templates", *J. Am. Chem. Soc.*, 126: 9970-81 (2004).

Fiebig, T., et al., "Femtosecond dynamics of the DNA intercalator ethidium and electron transfer with mononucleotides in water," *Proc. Natl. Acad. Sci. USA*, 96:1187-1192 (1999).

Finn, P.J., et al., "Synthesis and properties of DNA-PNA chimeric oligomers," *Nucleic Acids Res*, 24(17): 3357-63 (1996).

Footer, M., et al., "Biochemical evidence that a D-loop is part of a four-stranded PNA-DNA bundle. Nickel-mediated cleavage of duplex DNA by a Gly-Gly-His bis-PNA," *Biochemistry*, 35(33): 10673-9 (1996).

Franzini, R.M., et al., "Metal binding to bipyridine-modified PNA," *Inorg Chem*, 45(24): 9798-811 (2006).

Fraser, G.L., et al., "Antisense inhibition of delta-opioid receptor gene function in vivo by peptide nucleic acids," *Mol Pharmacol.*, 57(4): 725-31 (2000).

Gabig-Ciminska, M., "Developing nucleic acid-based electrical detection systems," *Microb Cell Fact*, 5:9 (2006).

Galbiati, S., et al., "Different approaches for noninvasive prenatal diagnosis of genetic diseases based on PNA-mediated enriched PCR," *Ann N Y Acad Sci*, 1075: 137-43 (2006).

Gamper, H.B., et al., "Strand Invasion of Supercoiled DNA by Oligonucleotides with a Triplex Guide Sequence," *J. Am. Chem. Soc.* 120(9): 2182-2183 (1998).

Ganesh, K.N. and P.E. Nielsen, "Peptide Nucleic Acids: Analogs and Derivatives," *Current Organic Chemistry*, 4(9): 931-943 (2000).

Gangamani, B.P., V.A. Kumar, and K.N. Ganesh, "Spermine conjugated peptide nucleic acids (spPNA): UV and fluorescence studies of PNA-DNA hybrids with improved stability," *Biochem Biophys Res Commun.*, 240(3): 778-82 (1997).

Gangamani, B.P., V.A. Kumar, and K.N. Ganesh, "Synthesis of NA(alpha)-(Purinyl/Pyrimidinyl acetyl)-4-Aminoproline Diastereomers with Potential Use in PNA Synthesis," *Tetrahedron*, 52(47): 15017-15030 (1996).

Garner, P., et al., "Modular nucleic acid surrogates. Solid phase synthesis of alpha-helical peptide nucleic acids (alpha PNAs)," *Org Lett*, 1(3): 403-5 (1999).

Gaylord, B.S., et al., "SNP detection using peptide nucleic acid probes and conjugated polymers: applications in neurodegenerative disease identification," *Proc Natl Acad Sci U S A*, 102(1): 34-9 (2005).

Geiger, A. et al., "PNA Array Technology in Molecular Diagnostics," *Nucleosides, Nucleotides and Nucleic Acids*, 17(9-11):1717-1724 (1998).

Germini, A., et al., "Detection of genetically modified soybean using peptide nucleic acids (PNAs) and microarray technology," *J Agric Food Chem.*, 52(14): 4535-40 (2004).

Germini, A., et al., "Development of a peptide nucleic acid array platform for the detection of genetically modified organisms in food," *J Agric Food Chem.*, 53(10): 3958-62 (2005).

Ghelli, S. and G. Ponterini, "Identification of the photoisomers of two carbocyanines by 1H NMR spectroscopy," *Journal of Molecular Structure*, 355(2): 193-200 (1995).

Gianolio, D.A. and McLaughlin, L.W., "Tethered Naphthalene Diimide Intercalators Enhance DNA Triplex Stability," *Bioorganic & Medicinal Chemistry*, 9:2329-2334 (2001).

Giesen, U., et al., "A formula for thermal stability (Tm) prediction of PNA/DNA duplexes," *Nucleic Acids Res*, 26(21): 5004-6 (1998).

Gildea, B. et. al., "PNA solubility enhancers," *Tetrahedron Letters*, 39: 7255-8 (1998).

Good, L. and P.E. Nielsen, "Inhibition of translation and bacterial growth by peptide nucleic acid targeted to ribosomal RNA," *Proc Natl Acad Sci U S A*, 95(5): 2073-6 (1998).

Good, L., et al., "Antisense PNA effects in *Escherichia coli* are limited by the outer-membrane LPS layer," *Microbiology*, 146(Pt 10): 2665-70 (2000).

Good, L., et al., "Bactericidal antisense effects of peptide-PNA conjugates," *Nat Biotechnol*, 19(4): 360-4 (2001).

Gorner, H., A.K. Chibisov, and T.D. Slavnova, "Kinetics of J-aggregation of cyanine dyes in the presence of gelatin," *J Phys Chem B Condens Matter Mater Surf Interfaces Biophys*, 110(9): 3917-23 (2006).

Govindaraju, T., et al., "(1S,2R/1R,2S)-aminocyclohexyl glycyl thymine PNA: synthesis, monomer crystal structures, and DNA/RNA hybridization studies," *Org Lett*, 5(17): 3013-6 (2003).

Govindaraju, T., et al., "Cyclohexanyl peptide nucleic acids (chPNAs) for preferential RNA binding: effective tuning of dihedral angle beta in PNAs for DNA/RNA discrimination," *J Org Chem.*, 71(1): 14-21 (2006).

Govindaraju, T., V.A. Kumar, and K.N. Ganesh, "(1S,2R/1R,2S)-cis-cyclopentyl PNAs (cpPNAs) as constrained PNA analogues: synthesis and evaluation of aeg-cpPNA chimera and stereopreferences in hybridization with DNA/RNA," *J Org Chem*, 69(17): 5725-34 (2004).

Govindaraju, T., V.A. Kumar, and K.N. Ganesh, "cis-Cyclopentyl PNA (cpPNA) as constrained chiral PNA analogues: stereochemical dependence of DNA/RNA hybridization," *Chem Commun (Camb)*, 7: 860-1 (2004).

Green, J.J., et al., "Kinetics of unfolding the human telomeric DNA quadruplex using a PNA trap," *J Am Chem Soc*, 125(13): 3763-7 (2003).

Green, M. and Loewenstein, P.M., "Autonomous Functional Domains of Chemically Synthesized Human Immunodeficiency Virus Tat Trans-Activator Protein," *Cell*, 55:1179-1188 (1988).

Greer, A., "Christopher Foote's discovery of the role of singlet oxygen [1O2 (1 Delta g)] in photosensitized oxidation reactions," *Acc Chem Res*, 39(11): 797-804 (2006).

Griffith, M.C., et al., "Single and Bis Peptide Nucleic Acids as Triplexing Agents: Binding and Stoichiometr" *With Supplementary Material J. Am. Chem. Soc.*, 117(2): 831-832 (1995).

Gruegelsiepe, H., O. Brandt, and R.K. Hartmann, "Antisense inhibition of RNase P: mechanistic aspects and application to live bacteria," *J Biol Chem*, 281(41): 30613-20 (2006).

Guelev, V., et al., "Changing DNA Grooves—A 1,4,5,8-Naphthalene Tetracarboxylic Diimide Bis-Intercalator with the Linker (β-Ala)$_3$-Lys in the Minor Groove," *J. Am. Chem. Soc.*, 124(12):2864-2865 (2002).

Guelev, V., et al., "Peptide bis-intercalator binds DNA via threading mode with sequence specific contacts in the major groove," *Chemistry & Biology*, 8:415-425 (2001).

Guerasimova, A., et al., "New tools for oligonucleotide fingerprinting," *Biotechniques*, 31(3): 490-5 (2001).

Guittat, L., et al., "Interactions of cryptolepine and neocryptolepine with unusual DNA structures," *Biochimie*, 85:535-547 (2003).

Haaima, G., et al., "Peptide Nucleic Acids (PNAs) Containing Thymine Monomers Derived from Chiral Amino Acids: Hybridization and Solubility Properties of D-Lysine PNA," *Angew. Chem. Int. Ed. Engl.*, 35(17): 1939-42 (1996).

Haaima, G., et al., "Increased DNA binding and sequence discrimination of PNA oligomers containing 2,6-diaminopurine," *Nucleic Acids Res*, 25(22): 4639-43 (1997).

Haaima, G., et al., "Peptide nucleic acids (PNA) derived from N-(N-methylaminoethyl)glycine. Synthesis, hybridization and structural properties," *New J. Chem.*, 23(8): 833-840 (1999).

Hakansson, A.E. and J. Wengel, "The adenine derivative of alpha-L-LNA (alpha-L-ribo configured locked nucleic acid): synthesis and high-affinity hybridization towards DNA, RNA, LNA and alpha-L-LNA complementary sequences," *Bioorg Med Chem Lett*, 11(7): 935-8 (2001).

Hamad-Schifferli, K., "DNA Hybridization: Electronic Control, in Dekker Encyclopedia of Nanoscience and Nanotechnology," *C.I.C. James A. Schwarz, Karol Putyera Editor.*: Cambridge, Massachusetts, p. 963-75 (2004).

Hamilton, S.E., et al., "Identification of determinants for inhibitor binding within the RNA active site of human telomerase using PNA scanning," *Biochemistry*, 36(39): 11873-80 (1997).

Hamilton, S.E., et al., "Specific and Nonspecific Inhibition of Transcription by DNA, PNA, and Phosphorothioate Promoter Analog Duplexes," *Bioorganic & Medicinal Chemistry Letters*, 6(23): 2897-2900 (1996).

Hansen, M.H., et al., "Detection of PNA/DNA hybrid molecules by antibody Fab fragments isolated from a phage display library," *Journal of Immunological Methods*, 203(2): 199-207 (1997).

Hanvey, J.C., et al., "Antisense and antigene properties of peptide nucleic acids," *Science*, 258(5087): 1481-5 (1992).

He, Y., et al., "Sequence-specific DNA strand cleavage by In-labeled peptide nucleic acids," *Eur J Nucl Med Mol Imaging*, 31(6): 837-45 (2004).

Heilemann, M., et al., "Carbocyanine dyes as efficient reversible single-molecule optical switch," *J Am Chem Soc*, 127(11): 3801-6 (2005).

Henderson, P.T., et al., "Long-distance charge transport in duplex DNA: the phonon-assisted polaron-like hopping mechanism," *Proc Natl Acad Sci U S A*, 96(15): 8353-8 (1999).

Herbert, H.E., et al., "Hydrogen-bonding interactions in peptide nucleic acid and deoxyribonucleic acid: a comparative study," *J Phys Chem B Condens Matter Mater Surf Interfaces Biophys*, 110(7): 3336-43 (2006).

Hicks, K.O., et al., "Extravascular Transport of the DNA Intercalator and Topoisomerase Poison N-[2-(Dimethylamino)ethyl]acridine-4-carboxamide (DACA): Diffusion and Metabolism in Multicellular Layers of Tumor Cells," *The Journal of Pharmacology and Experimental Therapeutics*, 297(3):1088-1098 (2001).

Hillery, E., et al., "Nondisruptive, sequence-specific coupling of fluorochromes to plasmid DNA," *Anal Biochem*, 352(2): 169-75 (2006).

Hiraku, Y., et al., "Distamycin A, a minor groove binder, changed enediyne-induced DNA cleavage sites and enhances apoptosis," *Nucleic Acids Research Supplement* (2): 95-96 (2002).

Hochman, J., et al., "An Active Antibody Fragment (Fv) Composed of the Variable Portions of Heavy and Light Chains," *Biochemistry*, 12(6):1130-1135 (1973).

Holden, M.A. and P.S. Cremer, "Light activated patterning of dye-labeled molecules on surfaces," *J Am Chem Soc*, 125(27): 8074-5 (2003).

Hollenstein, M., et al., "Fluorinated peptide nucleic acid," *Nucleosides Nucleotides Nucleic Acids*, 22(5-8): 1191-4 (2003).

Holt, L.J., et al., "The use of recombinant antibodies in proteomics," *Current Opinion in Biotechnology*, 11:445-449 (2000).

Homs, M.C.i., "DNA Sensors," *Analytical Letters*, 35(12): 1875-1894 (2002).

Huang, D., et al., "Development and validation of oxygen radical absorbance capacity assay for lipophilic antioxidants using randomly methylated beta-cyclodextrin as the solubility enhancer," *J Agric Food Chem*, 50(7): 1815-21 (2002).

Huang, X., et al., "Rational Design of Pyrrolo[1,2-a]benzimidazole-Based Antitumor Agents Targeting the DNA Major Groove," *Bioorganic Chemistry*, 28:324-337 (2000).

Huard, R.C., et al., "PCR-based method to differentiate the subspecies of the *Mycobacterium tuberculosis* complex on the basis of genomic deletions," *J Clin Microbiol*, 41(4): 1637-50 (2003).

Hyrup, B., et al., "A Flexible and Positively Charged PNA Analogue with an ethylene-Linker to the Nucleobase: Synthesis and Hybridization Properties," *Bioorganic & Medicinal Chemistry Letters*, 6(10): 1083-1088 (1996).

Ichiyama, S., et al., "Evaluation of Gen-Probe Amplified *Mycobacterium tuberculosis* Direct Test and Roche PCR-microwell plate hybridization method (Amplicor Mycobacterium) for direct detection of mycobacteria," *J Clin Microbiol*, 34(1): 130-3 (1996).

Igloi, G.L., "Automated detection of point mutations by electrophoresis in peptide-nucleic acid-containing gels," *Biotechniques*, 27(4): 798-800, 802, 804 passim (1999).

Igloi, G.L., "Variability in the stability of DNA-peptide nucleic acid (PNA) single-base mismatched duplexes: real-time hybridization during affinity electrophoresis in PNA-containing gels," *Proc Natl Acad Sci U S A*, 95(15): 8562-7 (1998).

Ikeda, H., et al., "Design of the photosensitized peptide nucleic acids for the analysis of geno-typing," *Nucleic Acids Res Suppl*, (1): 177-8 (2001).

Iliades, P., et al., "Triabodies: single chain Fv fragments without a linker form trivalent trimers," *FEBS Letters*, 409: 437-441 (1997).

Il'icheva, I.A., et al., "PNA Complexes of Polynucleotides and Polyamides: Structure of Two-and Three-Stranded Chimeric Helices Revealed by Conformational Analysis," *International Journal of Quantum Chemistry*, 21: 157-172 (1994).

Inoue, T., et al., "Fluorescence Property of Oxazole Yellow-linked Oligonucletoide. Triple Helix Formation and Photocleavage of Double-stranded DNA in the Presence of Spermine," *Bioorganic & Medicinal Chemistry*, 7:1207-1211 (1999).

Ishihara, T. and D.R. Corey, "Strand invasion by DNA-peptide conjugates and peptide nucleic acids," *Nucleic Acids Symp Ser*, (42): 141-2 (1999).

Ishihara, T. and D.R. Corey, "Rules for Strand Invasion by Chemically Modified Oligonucleotides," *J. Am. Chem. Soc.*, 121(10): 2012-2020 (1999).

Iyer, M., et al., "Accelerated hybridization of oligonucleotides to duplex DNA," *Journal of Biological Chemistry*, 270 (24): 14712-7 (1995).

Izvolsky, K.I., et al., "Sequence-specific protection of duplex DNA against restriction and methylation enzymes by pseudocomplementary PNAs," *Biochemistry*, 39(35): 10908-13 (2000).

Jackson, L., K., et al., "Altering the Reaction Specificity of Eukaryotic Ornithine Decarboxylase," *Biochemistry*, 39:11247-11257 (2000).

Jacquot, C., "Cycloadditions with Singlet Oxygen Mechanism and Substituent Directing Effects," p. 17-24 (2004).

Janowski, B.A., et al., "Inhibiting gene expression at transcription start sites in chromosomal DNA with antigene RNAs," *Nat Chem Biol*, 1(4): 216-22 (2005).

Janowski, B.A., et al., "Inhibiting transcription of chromosomal DNA with antigene peptide nucleic acids," *Nat Chem Biol*, 1(4): 210-5 (2005).

Jensen, K.K., et al., "Kinetics for hybridization of peptide nucleic acids (PNA) with DNA and RNA studied with the BIAcore technique," *Biochemistry*, 36(16): 5072-7 (1997).

Jisha, V.S., et al., "Site-selective binding and dual mode recognition of serum albumin by a squaraine dye," *J Am Chem Soc*, 128(18): 6024-5 (2006).

Johnson, I., et al., "De-intercalation of Ethidium Bromide and Acridine Orange by Xanthine Derivatives and Their Modulatory Effect on Anticancer Agents: A study of DNA-directed Toxicity Enlightened by Time Correlated Single Photon Counting," *J. Biomolecular Structure & Dynamics*, 20(5):677-685 (2003).

Jones, P.T., et al., "Replacing the complementarity-determining regions in a human antibody with those from a mouse," *Nature*, 321:522-525 (May 1986).

Jones, R.M., et al., "Building highly sensitive dye assemblies for biosensing from molecular building blocks," *Proc Natl Acad Sci U S A*, 98(26): 14769-72 (2001).

Jordan, S., et al., "New Hetero-Oligomeric Peptide Nucleic Acids with Improved Binding Properties to Complementary DNA," *Bioorganic & Medicinal Chemistry Letters*, 7(6): 687-690 (1997).

Jordan, S., et al., "Synthesis of New Building Blocks for Peptide Nucleic Acids Containing Monomers with Variations in the Backbone," *Bioorganic & Medicinal Chemistry Letters*, 7(6): 681-686 (1997).

Kabatc, J. and J. Paczkowski, "The photophysical and photochemical properties of the oxacarbocyanine and thiacarbocyanine dyes," *Dyes and Pigments*, 61: 1-16 (2004).

Kabatc, J., et al., "Cyanine borates revisited. Study of the kinetics of photoinitiated free radical polymerization via intermolecular electron transfer process," *The Royal Society of Chemistry*, 2: 287-295 (2002).

Kafwabulula, M., et al., "Evaluation of PCR-based methods for the diagnosis of tuberculosis by identification of mycobacterial DNA in urine samples," *Int. J. Tuberc. Lung Dis.*, 6(8):732-737 (2002).

Kaihatsu, K., et al., "Enhanced strand invasion by peptide nucleic acid-peptide conjugates," *Biochemistry*, 41(37): 11118-25 (2002).

Kaihatsu, K., et al., "Extending recognition by peptide nucleic acids (PNAs): binding to duplex DNA and inhibition of transcription by tail-clamp PNA-peptide conjugates," *Biochemistry*, 42(47): 13996-4003 (2003).

Kaihatsu, K., et al., "Recognition of chromosomal DNA by PNAs," *Chem Biol* 11(6): 749-58 (2004).

Kaihatsu, K., K.E. Huffman, and D.R. Corey, "Intracellular uptake and inhibition of gene expression by PNAs and PNA-peptide conjugates," *Biochemistry*, 43(45): 14340-7 (2004).

Kaminow, I.P., et al., "Photobleaching of Organic Laser Dyes in Solid Matrices," *Applied Optics*, 11(7): 1563-7 (1972).

Kapuscinski, J., "DAPI: A DNA-Specific Fluorescent Probe," *Biotechnic & Histochemistry*, 70(5):220-233 (1995).

Karadag, A., et al., "A novel technique based on a PNA hybridization probe and FRET principle for quantification of mutant genotype in fibrous dysplasia/McCune-Albright syndrome," *Nucleic Acids Res*, 32(7): e63 (2004).

Karkare, S. and D. Bhatnagar, "Promising nucleic acid analogs and mimics: characteristic features and applications of PNA, LNA, and morpholino," *Appl Microbiol Biotechnol*, 71(5): 575-86 (2006).

Karlsson, H. J., et al., "Groove-binding unsymmetrical cyanine dyes for staining of DNA: syntheses and characterization of DNA-binding," *Nucleic Acids Research*, 31(21):6227-6234 (2003).

Karlsson, J. J., et al., "Synthesis and DNA Binding Studies of a New Asymmetric Cyanine Dye Binding in the Minor Groove of [poly(dA-dT)]$_2$," *Bioorganic & Medicinal Chemistry*, 11:1035-1040 (2003).

Karras, J.G., et al., "Peptide nucleic acids are potent modulators of endogenous pre-mRNA splicing of the murine interleukin-5 receptor-alpha chain," *Biochemistry*, 40(26): 7853-9 (2001).

Karwowski, B., et al., "Stereocontrolled synthesis of LNA dinucleoside phosphorothioate by the oxathiaphospholane approach," *Bioorg Med Chem Lett*, 11(8): 1001-3 (2001).

Kassab, K., "Photophysical and photosensitizing properties of selected cyanines," *J Photochem Photobiol B:Biology*, 68(1): 15-22 (2002).

Keinicke, L., et al., "Alpha-L-RNA (alpha-L-ribo configured RNA): synthesis and RNA-selective hybridization of alpha-L-RNA/alpha-L-LNA chimera," *Bioorg Med Chem Lett*, 12(4): 593-6 (2002).

Keppler, M., et al., "DNA triple helix stabilization by a naphthylquinoline dimer," *FEBS Letters*, 447:223-226 (1999).

Kersebohm, T., et al., "Insertion of an internal dipeptide into PNA oligomers: thermal melting studies and further functionalization," *Bioorg Med Chem Lett*, 16(11): 2964-8 (2006).

Kim, J.H., et al., "Helical periodicity of (PNA)2.(DNA) triplexes in strand displacement complexes," *Nucleic Acids Res*, 27(14): 2842-7 (1999).

Kim, S.K., et al., "Right-Handed Triplex Formed between Peptide Nucleic Acid PNA-T8 and Poly(dA) Shown by Linear and Circular Dichroism Spectroscopy," *J Am Chem Soc*, 115(15): 6477-6481 (1993).

Kirschstein, O., et al., "Quantitative and sequence-specific analysis of DNA-ligand interaction by means of fluorescent intercalator probes," *J. Mol. Recognit.*, 13:157-163 (2000).

Kisko, J.L. and Barton, J.K., "Recognition of DNA Base Pair Mismatches by a Cyclometalated RH(III) Intercalator," *Inorg. Chem.*, 39:4942-4949 (2000).

Kitagawa, F., et al., "Design of a molecular beacon PNA," *Nucleic Acids Res Suppl.*, (2): 143-4 (2002).

Knudsen, H. and P.E. Nielsen, "Antisense properties of duplex- and triplex-forming PNAs," *Nucleic Acids Res*, 24(3): 494-500 (1996).

Koch, T., "Locked nucleic acids: a family of high affinity nucleic acid probes," *J. Phys. Condens. Matter*, 15: S1861-S1871 (2003).

Komiyama M, et al., "PNA for One-Base Differentiating Protection of DNA from Nuclease and Its Use for SNPs Detection," *Journal of the American Chemical Society*, 125(13):3758-3762 (2003).

Kondo, S., et al. "Synthesis of a novel intercalator based on 2,2'-binaphthalene bearing dimethylammonium groups," *Bioorganic & Medicinal Chemistry Letters*, 14:1641-1643 (2004).

Koppelhus, U., et al., "Efficient in vitro inhibition of HIV-1 gag reverse transcription by peptide nucleic acid (PNA) at minimal ratios of PNA/RNA," *Nucleic Acids Res*, 25(11): 2167-73 (1997).

Kornyushyna, O., et al., "Synthesis of a metallopeptide-PNA conjugate and its oxidative cross-linking to a DNA target," *Bioconjug Chem*, 16(1): 178-83 (2005).

Kosaganov, Y.N., et al., "Effect of temperature and ionic strength on the dissociation kinetics and lifetime of PNA-DNA triplexes," *Biochemistry*, 39(38): 11742-7 (2000).

Koshkin, A.A., "Syntheses and base-pairing properties of locked nucleic acid nucleotides containing hypoxanthine, 2,6-diaminopurine, and 2-aminopurine nucleobases," *J Org Chem*, 69(11): 3711-8 (2004).

Koshkin, A.A., et al., "A simplified and efficient route to 2'-O, 4'-C-methylene-linked bicyclic ribonucleosides (locked nucleic acid)," *J Org Chem*, 66(25): 8504-12 (2001).

Koshkin, A.A., et al., "LNA (Locked Nucleic Acid): An RNA Mimic Forming Exceedingly Stable LNA:LNA Duplexes," *J. Am. Chem. Soc.*, 120(50): 13252-13253 (1998).

Koshkin, A.A., et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron*, 54: 3607-3630 (1998).

Kosynkina, L., W. Wang, and T.C. Liang, "A Convenient Synthesis of Chiral Peptide Nucleic Acid (PNA) Monomers," *Tetrahedron Letters*, 35(29): 5173-5176 (1994).

Krieg, M. and J.M. Bilitz, "Structurally modified trimethine thiacarbocyanine dyes. Effect of N-alkyl substituents on antineoplastic behavior," *Biochem Pharmacol*, 51(11): 1461-7 (1996).

Krishnan-Ghosh, Y., et al., "A PNA4 quadruplex," *J Am Chem Soc*, 126(19): 5944-5 (2004).

Krupnik, O.V., et al., "Thermodynamics of the melting of PNA(2)/DNA triple helices," *J Biomol Struct Dyn*, 19(3): 535-42 (2001).

Krupnik, O.V., et al., "Stability and transformations of bis-PNA/DNA triplex structural isomers," *J Biomol Struct Dyn*, 21(4): 503-12 (2004).

Kuby, J., *Immunology*, Third Ed., W.H. Freeman and Company (1997).

Kuhn, H., Demidov, V., Frank-Kamenstskii, M.D., "An earring for the double helix: Assembly of topological links comprising duplex DNA and a circular oligodeoxynucleotide," *Journal of Biomolecular Structure & Dynamics, Conversation* 11, Issue #2 from the Proceedings of the Eleventh Conersation, University of Albany, SUNY, Jun. 15-19, 1999 (Adenine Press 2000).

Kuhn, H., et al., "Hybridization of DNA and PNA molecular beacons to single-stranded and double-stranded DNA targets," *J Am Chem Soc*, 124(6): 1097-103 (2002).

Kuhn, H., et al., "An experimental study of mechanism and specificity of peptide nucleic acid (PNA) binding to duplex DNA," *J Mol Biol*, 286(5): 1337-45 (1999).

Kuhn, H., et al., "Inducing and modulating anisotropic DNA bends by pseudocomplementary peptide nucleic acids," *Proc Natl Acad Sci U S A*, 101(20): 7548-53 (2004).

Kumar, V., et al., "Pyrrolidine Nucleic Acids: DNA/PNA Oligomers with 2-Hydroxyl/Aminomethyl-4-(thymin-1-yl)pyrrolidine-N-acetic acid," *Organic Letters*, 3(9):1269-1272 (2001).

Kumar, V.A. and K.N. Ganesh, "Conformationally constrained PNA analogues: structural evolution toward DNA/RNA binding selectivity," *Acc Chem Res*, 38(5): 404-12 (2005).

Kumar, V.A. and Meena, "Pyrrolidine PNA-DNA chimeric oligonucleotides with extended backbone," *Nucleosides, Nucleotides & Nucleic Acids*, 22(5-8): 1101-4 (2003).

Kumar, V.A., M. D'Costa, and K.N. Ganesh, "Engineering preferences of hairpin PNA binding to complementary DNA: effect of N7G in aeg/aep PNA backbone," *Nucleosides Nucleotides Nucleic Acids*, 20(4-7): 1187-91 (2001).

Kumar, V.A., "Structural pre-organization of peptide nucleic acids," *Nucleosides Nucleotides Nucleic Acids*, 22(5-8): 1045-8 (2003).

Kumar, V.A., "Structural Preorganization of Peptide Nucleic Acids: Chiral Cationic Analogues with Five- or Six-Membered Ring Structures," *Eur. J. Org. Chem*, 2002(13): 2021-2032 (2002).

Kurakin, A., H.J. Larsen, and P.E. Nielsen, "Cooperative strand displacement by peptide nucleic acid (PNA)," *Chem Biol*, 5(2): 81-9 (1998).

Kurreck, J., et al., "Design of antisense oligonucleotides stabilized by locked nucleic acids," *Nucleic Acids Res*, 30(9): 1911-8 (2002).

Kushon, S.A., et al., "Detection of Single Nucleotide Mismatches via Fluorescent Polymer Superquenching," *Langmuir*, 19(16): 6456-6464 (2003).

Kushon, S.A., et al., "Effect of secondary structure on the thermodynamics and kinetics of PNA hybridization to DNA hairpins," *J Am Chem Soc*, 123(44): 10805-13 (2001).

Kusumoto, Y. and H. Sato, "Energy Transfer between Rhodamine-6G and 3,3'-Diethylthiacarbocyanine Iodide Enhanced in the Premicellar Region," *Chemical Physics Letters*, 68(1): 13-16 (1979).

Kusumoto, Y., et al., "Energy Transfer Dye Laser: Confirmation of Energy Transfer by Reabsorption Effect," *Chemical Physics Letters*, 53(2): 388-90 (1978).

Kuwabara, T., et al., "Classification of DNA-binding mode of antitumor and antiviral agents by the electrochemiluminescence of ruthenium complex," *Analytical Biochemistry*, 314:30-37 (2003).

Kuzuya, A., J.-M. Zhou, and M. Komiyama, "DNA, PNA, and Their Derivatives for Precise Genotyping of SNPs," *Mini-Reviews in Organic Chemistry*, 1(1): 125-131 (2004).

Kvaerno, L., et al., "Synthesis of abasic locked nucleic acid and two seco-LNA derivatives and evaluation of their hybridization properties compared with their more flexible DNA counterparts," *J Org Chem*, 65(17): 5167-76 (2000).

Kyger EM, et al., "Detection of the Hereditary Hemochromatosis Gene Mutation by Real-Time Fluorescence Polymerase Chain and Peptide Nucleic Acid Clamping," *Analytical Biochemistry*, 260:142-148 (1998).

Lagerholm, B.C., et al., "Multicolor Coding of Cells with Cationic Peptide Coated Quantum Dots," *Nano Lett*, 4(10): 2019-2022 (2004).

Lansdorp, P.M., "Close encounters of the PNA kind," *Nat Biotechnol*, 14(13): 1653 (1996).

Larsen, H.J. and P.E. Nielsen, "Transcription-mediated binding of peptide nucleic acid (PNA) to double-stranded DNA: sequence-specific suicide transcription," *Nucleic Acids Res*, 24(3): 458-63 (1996).

Larsen, H.J., T. Bentin, and P.E. Nielsen, "Antisense properties of peptide nucleic acid," *Biochim Biophys Acta*, 1489(1): 159-66 (1999).

Latorra, D., et al., "Design considerations and effects of LNA in PCR primers," *Mol Cell Probes*, 17(5): 253-9 (2003).

Latorra, D., et al., "Enhanced allele-specific PCR discrimination in SNP genotyping using 3' locked nucleic acid (LNA) primers," *Hum Mutat*, 22(1): 79-85 (2003).

Lauretti, F., et al., "Use of acridine orange staining for the detection of rotavirus RNA in polyacrylamide gels," *Journal of Virological Methods*, 114:29-35 (2003).

Lawton, G.R. and D.H. Appella, "Nonionic side chains modulate the affinity and specificity of binding between functionalized polyamines and structured RNA," *J Am Chem Soc*, 126(40): 12762-3 (2004).

Lee, H.J., et al., "Imaging gene expression in the brain in vivo in a transgenic mouse model of Huntington's disease with an antisense radiopharmaceutical and drug-targeting technology," *J Nucl Med*, 43(7): 948-56 (2002).

Lehtola, M.J., et al., "Fluorescence in situ hybridization using peptide nucleic acid probes for rapid detection of *Mycobacterium avium* subsp. avium and *Mycobacterium avium* subsp. paratuberculosis in potable-water biofilms," *Appl Environ Microbiol*, 72(1): 848-53 (2006).

Leijon, M., M. Mousavi-Jazi, and M. Kubista, "LightUp probes in clinical diagnostics," *Mol Aspects Med*, 27(2-3): 160-75 (2006).

Lepkowicz, R.S., et al., "Nature of the electronic transitions in thiacarbocyanines with a long polymethine chain," *Chemical Physics*, 305: 259-270 (2004).

Lesnik, E.A., et al., "Evaluation of pyrimidine PNA binding to ssDNA targets from nonequilibrium melting experiments," *Nucleic Acids Res*, 25(3): 568-74 (1997).

Letertre, C., et al., "Evaluation of the performance of LNA and MGB probes in 5'-nuclease PCR assays," *Mol Cell Probes*, 17(6): 307-11 (2003).

Lewis, M.R., et al., "Radiometal-labeled peptide-PNA conjugates for targeting bcl-2 expression: preparation, characterization, and in vitro mRNA binding," *Bioconjug Chem*, 13(6): 1176-80 (2002).

Li, Y., T. Jin, and K. Liu, "Synthesis and binding affinity of a chiral PNA analogue," *Nucleosides Nucleotides Nucleic Acids*, 20(9): 1705-21 (2001).

Lifanov, Y.I., et al., "Cis-Trans Isomerization of Polymethine Dyes in the case of Pulsed Photoexcitation," *V. I. Vernadskii Institute of Geochemistry and Analytical Chemistry*, p. 766-8 (1973).

Lim, I.-I.S., et al., "Adsorption of Cyanine Dyes on Gold Nanoparticles and Formation of J-Aggregates in the Nanoparticle Assembly," *J. Phys. Chem. B*, 110(13): 6673-6682 (2006).

Lisgarten, J.N., et al., "The antimalarial and cytotoxic drug cryptolepine intercalates into DNA at cytosine-cytosine sites," *Nature Structural Biology*, 9(1):57-60 (Jan. 2002).

Liu, B., et al., "Toward synthetic transcription activators: recruitment of transcription factors to DNA by a PNA-peptide chimera," *J Am Chem Soc*, 124(9): 1838-9 (2002).

Liu, B., et al., "Transcription activation by a PNA-peptide chimera in a mammalian cell extract," *Chem Biol*, 10(10): 909-16 (2003).

Liu, F., et al., "The pH-Induced Emission Switching and Interesting DNA-Binding Properties of a Noval Dinuclear Ruthenium(II) Complex," *Inorg. Chem.*, 43(5):1799-1806 (2004).

Liu, J., et al., "PNA-DNA hybridization study using labeled streptavidin by voltammetry and surface plasmon fluorescence spectroscopy," *Anal Chem*, 78(2): 470-6 (2006).

Liu, Y., et al., "Efficient and Isoform-Selective Inhibition of Cellular Gene Expression by Peptide Nucleic Acids," *Biochemistry*, 43(7): 1921-1927 (2004).

Ljungstrom, T., H. Knudsen, and P.E. Nielsen, "Cellular uptake of adamantyl conjugated peptide nucleic acids," *Bioconjug Chem*, 10(6): 965-72 (1999).

Lohse, J., et al., "Double duplex invasion by peptide nucleic acid: a general principle for sequence-specific targeting of double-stranded DNA," *Proc Natl Acad Sci U S A*, 96(21): 11804-8 (1999).

Lomakin, A. and M.D. Frank-Kamenetskii, "A theoretical analysis of specificity of nucleic acid interactions with oligonucleotides and peptide nucleic acids (PNAs)," *J Mol Biol*, 276(1): 57-70 (1998).

Longin, A., et al., "Comparison of anti-fading agents used in fluorescence microscopy: image analysis and laser confocal microscopy study," *J Histochem Cytochem*, 41(12): 1833-40 (1993).

Lonkar, P., "Pyrrolidine and Piperidine Nucleic Acids: Novel Class of PNA Analogues, in Division of Organic Chemistry," *University of Pune*: Pune, India, p. 1-302 (2004).

Lonkar, P.S. and V.A. Kumar, "Design and synthesis of conformationally frozen peptide nucleic acid backbone: chiral piperidine PNA as a hexitol nucleic acid surrogate," *Bioorg Med Chem Lett*, 14(9): 2147-9 (2004).

Lonkar, P.S., et al., "Constrained flexibility in PNA: DNA binding studies with bridged aminopropylglycyl PNA," *Nucleosides Nucleotides Nucleic Acids*, 20(4-7): 1197-200 (2001).

Lorente, C. and A.H. Thomas, "Photophysics and photochemistry of pterins in aqueous solution," *Acc Chem Res*, 39(6): 395-402 (2006).

Losytskyy, M.Y., et al., "Davydov Splitting in Spectra of Cyanine Dye J-Aggregates, Formed on the Polynucleotides," *Journal of Fluorescence*, 12(1): 109-12 (2002).

Lovrinovic, M., et al., "Synthesis of protein-nucleic acid conjugates by expressed protein ligation," *Chem Commun (Camb)*, (7): 822-3 (2003).

Lu, F., et al., "Study on the interaction of bovine serum albumin with acid cyanine 5R and its application in analysis," *Biochem Cell Biol*, 84(1): 1-8 (2006).

Luedtke, N.W., et al., "RNA-Ligand Interactions: Affinity and Specificity of Aminoglycoside Dimers and Acridine Conjugates to the HIV-1 Rev Response Element," *Biochemistry*, 42(39):11391-11403 (Oct. 2003).

Lukeman, P.S., A. C. Mittal, and N. C. Seeman, "Two dimensional PNA/DNA arrays: estimating the helicity of unusual nucleic acid polymers," *Chem Commun (Camb)*, (15): 1694-5 (2004).

Luminex Corportation, "Sample protocol for carbodiimide coupling of amine-modified oligonucleotides to xMap carboxylated microspheres," (Jan. 2006).

Lundin, K.E., et al., "Biological activity and biotechnological aspects of peptide nucleic acid," *Adv Genet*, 56: 1-51 (2006).

Lundin, K.E., et al., "Cooperative strand invasion of supercoiled plasmid DNA by mixed linear PNA and PNA-peptide chimeras," *Biomol Eng*, 21(2): 51-9 (2004).

Lundin, K.E., et al., "Increased stability and specificity through combined hybridization of peptide nucleic acid (PNA) and locked nucleic acid (LNA) to supercoiled plasmids for PNA-anchored "Bioplex" formation," *Biomol Eng*, 22(5-6): 185-92 (2005).

Ma, D. and Che, C., "A Bifunctional Platinum(II) Complex Capable of Intercalation and Hydrogen-Bonding Interactions with DNA: Binding Studies and Cytotoxicity," *Chem. Eur. J.*, 9:6133-6144 (2003).

Ma, Z. and J.S. Taylor, "PNA-based RNA-triggered drug-releasing system," *Bioconjug Chem*, 14(3): 679-83 (2003).

Macanovic, A., et al., "Impedance-based detection of DNA sequences using a silicon transducer with PNA as the probe layer," *Nucleic Acids Res*, 32(2): e20 (2004).

Maier, M.A., et al., "Evaluation of basic amphipathic peptides for cellular delivery of antisense peptide nucleic acids," *J Med Chem*, 49(8): 2534-42 (2006).

Maiti, S., et al., "Hoechst 33258 binds to G-quadruplex in the promoter region of human c-myc," *Biochemical and Biophysical Research Communications*, 310:505-512 (2003).

Marin, V., et al., "Effect of LNA modifications on small molecule binding to nucleic acids," *J Biomol Struct Dyn*, 21(6): 841-50 (2004).

Marin, V.L. and B.A. Armitage, "Hybridization of complementary and homologous peptide nucleic acid oligomers to a guanine quadruplex-forming RNA," *Biochemistry*, 45(6): 1745-54 (2006).

Marin, V.L. and B.A. Armitage, "RNA guanine quadruplex invasion by complementary and homologous PNA probes," *J Am Chem Soc*, 127(22): 8032-3 (2005).

Marques, B.F. and J.W. Schneider, "Sequence-specific binding of DNA to liposomes containing di-alkyl peptide nucleic acid (PNA) amphiphiles," *Langmuir*, 21(6): 2488-94 (2005).

Mason, S.J. and S. Balasubramanian, "Solid-phase catch, activate, and release synthesis of cyanine dyes," *Org Lett*, 4(24): 4261-4 (2002).

Masuko, M., "Hybridization of an immobilized PNA probe with its complementary oligodeoxyribonucleotide on the surface of silica glass," *Nucleic Acids Res Suppl*, (3): 145-6 (2003).

Mateo-Marti, E., et al., "Self-assembled monolayers of peptide nucleic acids on gold surfaces: a spectroscopic study," *Langmuir*, 21(21): 9510-7 (2005).

Matselyukh, B.P., et al., "Interaction of cyanine dyes with nucleic acids: XXXI. Using of polymethine cyanine dyes for the visualization of DNA in agarose gels," *J Biochem Biophys Methods*, 57(1): 35-43 (2003).

Matysiak, S., et al., "Automating Parallel Peptide Synthesis for the Production of PNA Library Arrays," *BioTechniques*, 31:896-904 (Oct. 2001).

Mayfield, L.D. and Corey D.R., "Automated Synthesis of Peptide Nucleic Acids and Peptide Nucleic Acid—Peptide Conjugates," *Analytical Biochemistry*, 268:401-404 (1999).

Mayhood, T., et al., "Inhibition of Tat-mediated transactivation of HIV-1 LTR transcription by polyamide nucleic acid targeted to TAR hairpin element," *Biochemistry*, 39(38): 11532-9 (2000).

Mazerski, J. and Muchewicz, K., "The intercalation of imidazoacridinones into DNA inducesconformational changes in their side chain," *Acta Biochimica Polonica*, 47(1):65-78 (2000).

McCairn, M.C., et al., "Solid-phase PNA synthesis and in situ scintillation proximity assay for the detection of PNA-DNA hybridization," *J Comb Chem*, 8(1): 1-3 (2006).

McTigue, P.M., et al., "Sequence-dependent thermodynamic parameters for locked nucleic acid (LNA)-DNA duplex formation," *Biochemistry*, 43(18): 5388-405 (2004).

Mearini, G., P.E. Nielsen, and F.O. Fackelmayer, "Localization and dynamics of small circular DNA in live mammalian nuclei," *Nucleic Acids Res*, 32(8): 2642-51 (2004).

Meier, C. and J.W. Engels, "Peptide Nucleic Acids (PNAs)-Unusual Properties of Nonionic Oligonucleotide Analogues," *Angew. Chem. Int. Ed. Engl.*, 31(8): 1008-10 (1992).

Meldgaard, M., et al., "3'-C-Branched LNA-type nucleosides locked in an N-type furanose ring conformation: synthesis, incorporation into oligodeoxynucleotides, and hybridization studies," *J Org Chem*, 69(19): 6310-22 (2004).

Mier, W., et al., "Peptide-PNA conjugates: targeted transport of antisense therapeutics into tumors," *Angew Chem Int Ed Engl* 42(17): 1968-71 (2003).

Mikelsons, L., et al., "Experimental and theoretical study of the interaction of single-strandedDNA homopolymers and a monomethine cyanine dye: nature of specific binding," *Photochem Photobiol Sci*, 4(10): 798-802 (2005).

Mikheikin, A.L., et al., "Binding of symmetrical cyanine dyes into the DNA minor groove," *J Biomol Struct Dyn*, 18(1): 59-72 (2000).

Milano, M.T., et al., "Migration of Electrons and Holes in Crystalline d(CGATCG)-Anthracycline Complexes X-Irradiated at 4 K," *Radiation Research*, 150:101-114 (1998).

Mishra, A., et al., "Cyanines during the 1990s: A Review," *Chem Rev*, 100(6): 1973-2011 (2000).

Mizuta, M., et al., "Properties of ferrocene-polyamide compounds as redox active DNA binding molecules toward the SNPs detection," *Nucleic Acids Symp Ser (Oxf)*, (48): 237-8 (2004).

Modi, S., et al., "The PNA-DNA hybrid I-motif: implications for sugar-sugar contacts in i-motif tetramerization," *Nucleic Acids Res*, 34(16): 4354-63 (2006).

Mokhir, A., et al., "Synthesis and DNA binding properties of dioxime-peptide nucleic acids," *Bioorg Med Chem Lett*, 14(11): 2927-30 (2004).

Mokhir, A., et al., "Synthesis and DNA binding properties of terminally modified peptide nucleic acids," *Bioorg Med Chem Lett*, 13(15): 2489-92 (2003).

Mokhir, A., R. Kramer, and H. Wolf, "Zn2+-dependent peptide nucleic acids probes," *J Am Chem Soc*, 126(20): 6208-9 (2004).

Mokhir, A., R.et al., "Peptide nucleic acid-metal complex conjugates: facile modulation of PNA-DNA duplex stability," *Bioorg Med Chem Lett*, 13(8): 1399-401 (2003).

Mollegaard, N. E., et al., "Peptide nucleic acid.DNA strand displacement loops as artificial transcription promoters," *Proc Natl Acad Sci U S A*, 91(9): 3892-5 (1994).

Mollegaard, N. E., et al., "Quinoxaline antibiotics enhance peptide nucleic acid binding to double-stranded DNA," *Biochemistry*, 39(31): 9502-7 (2000).

Mologni, L., et al., "Additive antisense effects of different PNAs on the in vitro translation of the PML/RARalpha gene," *Nucleic Acids Res*, 26(8): 1934-8 (1998).

Mologni, L., P.E. Nielsen, and C. Gambacorti-Passerini, "In vitro transcriptional and translational block of the bcl-2 gene operated by peptide nucleic acid," *Biochem Biophys Res Commun*, 264(2): 537-43 (1999).

Morozkin, E.S., et al., "Fluorometric quantification of RNA and DNA in solutions containing both nucleic acids," *Analytical Biochemistry*, 322:48-50 (2003).

Mueller, S.O. and Stopper, Helga, "Characterization of the genotoxicity of anthraquinones in mammalian cells," *Biochimica et Biophysica Acta*, 1428:406-414 (1999).

Murakami, T., et al., "A novel method for detecting HIV-1 by non-radioactive in situ hybridization: application of a peptide nucleic acid probe and catalysed signal amplification," *J Pathol*, 194(1): 130-5 (2001).

Myers, M.C., et al., "Peptide nucleic acids with a flexible secondary amine in the backbone maintain oligonucleotide binding affinity," *Org Lett*, 6(25): 4699-702 (2004).

Myers, M.C., et al., "A cyclopentane conformational restraint for a peptide nucleic acid: design, asymmetric synthesis, and improved binding affinity to DNA and RNA," *Org Lett*, 5(15): 2695-8 (2003).

Ng, P.S., "Alternative nucleic acid analogues for programmable assembly: hybridization of LNA to PNA," *Nano Lett*, 5(1): 107-11 (2005).

Nguyen, B., et al., "Strong Binding in the DNA Minor Groove by an Aromatic Diamidine with a Shape That Does Not Match the Curvature of the Groove," *J. Am. Chem. Soc.*, 124:13680-13681 (2002).

Nielsen, C.B., et al., "NMR Structure Determination of a Modified DNA Oligonucleotide Containing a New Intercalating Nucleic Acid," *Bioconjugate Chem.*, 15:260-269 (2004).

Nielsen, J.T., P.C. Stein, and M. Petersen, "NMR structure of an alpha-L-LNA:RNA hybrid: structural implications for RNase H recognition," *Nucleic Acids Res*, 31(20): 5858-67 (2003).

Nielsen, K.E., et al., "NMR studies of fully modified locked nucleic acid (LNA) hybrids: solution structure of an LNA:RNA hybrid and characterization of an LNA:DNA hybrid," *Bioconjug Chem*, 15(3): 449-57 (2004).

Nielsen, K.E., et al., "Solution structure of an LNA hybridized to DNA: NMR study of the d(CT(L)GCT(L)T(L)CT(L)GC):d(GCAGAAGCAG) duplex containing four locked nucleotides," *Bioconjug Chem*, 11(2): 228-38 (2000).

Nielsen, K.M., et al., "alpha-L-LNA (alpha-L-ribo configured locked nucleic acid) recognition of DNA: an NMR spectroscopic study," *Chemistry*, 8(13): 3001-9 (2002).

Nielsen, P., "Targeting structured nucleic acids with antisense agents," *Drug Discov Today*, 8(10): 440 (2003).

Nielsen, P.E. and Egholm, M., "Strand displacement recognition of mixed adenine-cytosine sequences in double stranded DNA by thymine-guanine PNA (peptide nucleic acid)," *Bioorganic & Medicinal Chemistry*, 9: 2429-34 (2001).

Nielsen, P.E., "Peptide nucleic acid: a versatile tool in genetic diagnostics and molecular biology," *Curr Opin Biotechnol*, 12(1): 16-20 (2001).

Nielsen, P.E., "Targeting double stranded DNA with peptide nucleic acid (PNA)," *Curr Med Chem*, 8(5): 545-50 (2001).

Nielsen, P.E., "The many faces of PNA," *Letters in Peptide Science*, 10(3-4): 135-147 (2003).

Nielsen, P.E., "Applications of peptide nucleic acids," *Curr Opin Biotechnol*, 10(1): 71-5 (1999).

Nielsen, P.E., et al., "Evidence for (PNA)2/DNA triplex structure upon binding of PNA to dsDNA by strand displacement," *J Mol Recognit*, 7(3): 165-70 (1994).

Nielsen, P.E., et al., "Extended target sequence specificity of PNA-minor-groove binder conjugates," *Chembiochem*, 6(1): 66-8 (2005).

Nielsen, P.E., et al., "Sequence-Selective Recognition of DNA by Strand Displacement with a Thymine-Substitute Polyamide," *Science*, 254:1497-1500 (Dec. 1991).

Nielsen, P.E., et al., "Sequence-specific transcription arrest by peptide nucleic acid bound to the DNA template strand," *Gene*, 149(1): 139-45 (1994).

Nielsen, P.E., "Peptide Nucleic Acid. A Molecule with Two Identities," *Acc. Chem. Res.*, 32(7): 624-630 (1999).

Nielsen, P.E., "Peptide nucleic acids as therapeutic agents," *Curr Opin Struct Biol*, 9(3): 353-7 (1999).

Nielsen, P.E., "Systemic delivery: the last hurdle?" *Gene Ther*, 12(12): 956-7 (2005).

Ninomiya, K., et al., "In situ chemical aminoacylation with amino acid thioesters linked to a peptide nucleic acid," *J Am Chem Soc*, 126(49): 15984-9 (2004).

Nojima, T., et al., "Detection of DNA hybridization by use of a lanthanide fluorescent intercalator that specifically binds to double stranded DNA," *Nucleic Acids Research Supplement*(1): 105-106 (2001).

Norden, B. and F. Tjerneld, "Optical Studies on Complexes between DNA and Pseudoisocyanine," *Biophysical Chemistry*, 6(1): 31-45 (1977).

Norton, J.C., et al., Targeting peptide nucleic acid-protein conjugates to structural features within duplex DNA, *Bioorg Med Chem*, 3(4): 437-45 (1995).

Norton, J.C., et al., "Inhibition of human telomerase activity by peptide nucleic acids," *Nat Biotechnol*, 14(5): 615-9 (1996).

Noukakis, D., et al., "Photophysics of a Thiacarbocyanine Dye in Organic Solvents," *J. Phys. Chem.*, 99(31): 11860-11866 (1995).

Novopashina, D., et al., "Conjugates of Oligo (2'-O-Methylribonucleotides) with Minor Groove Binders as New Sequence-Specific Agents Recognizing Both Grooves of Double-Stranded DNA," *Nucleosides, Nucleotides & Nucleic Acids*, 22(5-8):1179-1182 (2003).

Nulf, C.J. and D. Corey, "Intracellular inhibition of hepatitis C virus (HCV) internal ribosomal entry site (IRES)-dependent translation by peptide nucleic acids (PNAs) and locked nucleic acids (LNAs)," *Nucleic Acids Res*, 32(13): 3792-8 (2004).

Nulf, C.J. and D.R. Corey, "DNA assembly using bis-peptide nucleic acids (bisPNAs)," *Nucleic Acids Res*, 30(13): 2782-9 (2002).

Núñez, M.E., et al., "Long-Range Guanine Oxidation in DNA Restriction Fragments by a Triplex-Directed Naphthalene Diimide Intercalator," *Biochemistry*, 39:6190-6199 (2000).

Nygren, J., N. Svanvik, and M. Kubista, "The interactions between the fluorescent dye thiazole orange and DNA," *Biopolymers*, 46(1): 39-51 (1998).

Ogul'chansky, T.Y., et al., "Interaction of cyanine dyes with nucleic acids. XVIII. Formation of the carbocyanine dye J-aggregates in nucleic acid grooves," *Elsevier Science B.V.*, 57(13): 2705-2715 (2001).

Ogul'chansky, T., et al., "Interaction of cyanine dyes with nucleic acids. XVII. Towards an aggregation of cyanine dyes in solutions as a factor facilitating nucleic acid detection," *Spectrochim Acta A Mol Biomol Spectrosc*, 56(4): 805-14 (2000).

Ogul'chansky, T., et al., "Interactions of cyanine dyes with nucleic acids. XXIV. Aggregation of monomethine cyanine dyes in presence of DNA and its manifestation in absorption and fluorescence spectra," *Spectrochim Acta A Mol Biomol Spectrosc*, 57(7): 1525-32 (2001).

Ohtsuki, T., et al., "RNA isolation using immobilized PNA," *Nucleic Acids Symp Ser (Oxf)*, (49): 263-4 (2005).

Okamoto, A., et al., "Site-specific discrimination of Cytosine and 5-methylcytosine in duplex DNA by Peptide nucleic acids," *J Am Chem Soc*, 124(35): 10262-3 (2002).

Oliveira, K., et al., "Differentiation of *Candida albicans* and *Candida dubliniensis* by fluorescent in situ hybridization with peptide nucleic acid probes," *J Clin Microbiol*, 39(11): 4138-41 (2001).

Oliveira, K., et al., "Direct identification of *Staphylococcus aureus* from positive blood culture bottles," *J Clin Microbiol*, 41(2): 889-91 (2003).

Olsen, A.G., et al., "A novel PNA-monomer for recognition of thymine in triple-helix structures," *Nucleosides Nucleotides Nucleic Acids*, 22(5-8): 1331-3 (2003).

Olsen, A.G., et al., "Synthesis and evaluation of a conformationally constrained pyridazinone PNA-monomer for recognition of thymine in triple-helix structures," *Bioorg Med Chem Lett*, 14(6): 1551-4 (2004).

Önfelt, B., et al., "Cell studies of the DNA bis-intercalator $\Delta$-$\Delta[\mu\text{-C4(cpdppz)}_{2\Delta}\text{(phen)}_4\text{Ru}_2]^{4+}$: toxic effects and properties as a light emitting DNA probe in V79 Chinese hamster cells," *Mutagenesis*, 17(4):317-320 (2002).

Önfelt, B., et al., "Enantioselective DNA Threading Dynamics by Phenazine-Linked $[\text{Ru(phen)}_2\text{dppz}]^{2+}$ Dimers," *J. Am. Chem. Soc.*, 123:3630-3637 (2001).

Ootsubo, M., et al., "Seven-hour fluorescence in situ hybridization technique for enumeration of Enterobacteriaceae in food and environmental water sample," *J Appl Microbiol*, 95(6): 1182-90 (2003).

Osiadacz, J., et al., "Sequence-Selectivity of 5,11-Dimethyl-5H-indolo[2,3-b]quinoline Binding to DNA. Footprinting and Molecular Modeling Studies," *Bioorganic & Medicinal Chemistry*, 8:937-943 (2000).

Ostaszewski, R., et al., "The Synthesis of a New Type of Anthracene DNA Intercalator," *Bioorganic & Medicinal Chemistry Letters*, 8:2995-2996 (1998).

Ouameur, A. A., et al., "Thallium-DNA Complexes in Aqueous Solution. Major or Minor groove Binding," *J. Biomolecular Structure & Dynamics*, 20(4):561-565 (2003).

Owczarzy, R., et al., "Predicting sequence-dependent melting stability of short duplex DNA oligomers," *Biopolymers*, 44(3): 217-39 (1997).

Ozkan, D., et al, "DNA and PNA sensing on mercury and carbon electrodes by using methylene blue as an electrochemical label," *Bioelectrochemistry*, 58(1): 119-26 (2002).

Pack, P. et al., "Tetravalent Miniantibodies with High Avidity Assembling in *Escherichia coli*," *J. Mol. Biol.*, 246:28-34 (1995).

Papadopoulou, M.V., et al., "4-[3-(2-Nitro-1-imidazolyl)propylamino]-7-chloroquinoline Hydrochloride (NLCQ-1), A Novel Bioreductive Agent as Radiosensitizer In Vitro and In Vivo: Comparison With Tirapazamine," *Oncology Research*, 12:325-333 (2000).

Pardridge, W.M., R.J. Boado, and Y.S. Kang, "Vector-mediated delivery of a polyamide ("peptide") nucleic acid analogue through the blood-brain barrier in vivo," *Proc Natl Acad Sci U S A*, 92(12): 5592-6 (1995).

Paroo, Z. and D.R. Corey, "Challenges for RNAi in vivo," *Trends Biotechnol*, 22(8): 390-4 (2004).

Paroo, Z. and D.R. Corey, "Imaging gene expression using oligonucleotides and peptide nucleic acids," *J Cell Biochem*, 90(3): 437-42 (2003).

Pasternack, R.F., et al., "Aggregation kinetics of extended porphyrin and cyanine dye assemblies," *Biophys J*, 79(1): 550-60 (2000).

Patel, D.J., et al., "Structure, Recognition and Adaptive Binding in RNA Aptamer Complexes," *J. Mol. Biol.*, 272:645-664 (1997).

Patolsky, F., et al., "Amplified DNA Detection by Electrogenerated Biochemiluminescence and by the Catalyzed Precipitation of an Insoluble Product on Electrodes in the Presence of the Doxorubicin Intercalator," Agnew Chem. Int. Ed., 41(18):3398-3402 (2002).

Patzel, V., et al., "A theoretical approach to select effective antisense oligodeoxyribonucleotides at high statistical probability," *Nucleic Acids Res*, 27(22): 4328-34 (1999).

Peano, C., et al., "Development of a peptide nucleic acid polymerase chain reaction clamping assay for semiquantitative evaluation of genetically modified organism content in food," *Anal Biochem*, 344(2): 174-82 (2005).

Peffer, N.J., et al., "Strand-invasion of duplex DNA by peptide nucleic acid oligomers," *Proc Natl Acad Sci U S A*, 90(22): 10648-52 (1993).

Pellestor, F., et al., "The Use of Peptide Nucleic Acids for In Situ Identification of Human Chromosomes," *Journal of Histochemistry & Cytochemistry*, 53(3): 395-400 (2005).

Pelley, R., et al., "A phase II pharmacodynamic study of pyrazoloacridine in patients with metastatic colorectal cancer," *Cancer Chemother Pharmacol*, 46:251-254 (2000).

Pelton, J.G. and D.E. Wemmer, "Structural modeling of the distamycin A-d(CGCGAATTCGCG)2 complex using 2D NMR and molecular mechanics," *Biochemistry* 27(21): 8088-96 (1988).

Perrin, L.C., et al., "DNA targeted platinum complexes: synthesis, cytotoxicity and DNA interactions of cis-dichloroplatinum(II) complexes tethered to phenazine-1-carboxamides," *Journal of Inorganic Biochemistry*, 81:111-117 (2000).

Perry-O'Keefe, H., et al., "Filter-based PNA in situ hybridization for rapid detection, identification and enumeration of specific microorganisms," *J Appl Microbiol*, 90(2): 180-9 (2001).

Perry-O'Keefe, H., et al., "Identification of indicator microorganisms using a standardized PNA FISH method," *J Microbiol Methods*, 47(3): 281-92 (2001).

Perry-O'Keefe, H., et al., "Peptide nucleic acid pre-gel hybridization: an alternative to southern hybridization," *Proc Natl Acad Sci U S A*, 93(25): 14670-5 (1996).

Petersen, K.H., O. Buchardt, and P.E. Nielsen, "Synthesis and Oligomerization of $N^A$(delta)-Boc-$N^A$(alpha)-(thymin-1-ylacetyl)ornithine," *Bioorganic & Medicinal Chemistry Letters*, 6(7): 793-796 (1996).

Petersen, M. and Wengel, J., "LNA: a versatile tool for therapeutics and genomics," *TRENDS in Biotechnology*, 21(2):74-81 (Feb. 2003).

Petersen, M., et al., "alpha-L-LNA (alpha-I-ribo configured locked nucleic acid) recognition of RNA. A study by NMR spectroscopy and molecular dynamics simulations," *J Am Chem Soc*, 123(30): 7431-2 (2001).

Petersen, M., et al., "Locked nucleic acid (LNA) recognition of RNA: NMR solution structures of LNA:RNA hybrids," *J Am Chem Soc*, 124(21): 5974-82 (2002).

Petersen, M., et al., "Structural characterization of LNA and alpha-L-LNA hybridized to RNA," *Nucleosides Nucleotides Nucleic Acids*, 22(5-8): 1691-3 (2003).

Petersen, M., et al., "The conformations of locked nucleic acids (LNA)," *J Mol Recognit*, 13(1): 44-53 (2000).

Peterson, A.W., et al., "Hybridization of mismatched or partially matched DNA at surfaces," *J Am Chem Soc*, 124(49): 14601-7 (2002).

Peterson, A.W., et al., "The effect of surface probe density on DNA hybridization," *Nucleic Acids Res*, 29(24): 5163-8 (2001).

Petersson, B., et al., "Crystal structure of a partly self-complementary peptide nucleic acid (PNA) oligomer showing a duplex-triplex network," *J Am Chem Soc*, 127(5): 1424-30 (2005).

Petraccone, L., et al., "Targeting duplex DNA with DNA-PNA chimeras? Physico-chemical characterization of a triplex DNA-PNA/DNA/DNA," *Biopolymers*, 73(4): 434-42 (2004).

Petri, V. and M. Brenowitz, "Quantitative nucleic acids footprinting: thermodynamic and kinetic approaches," *Curr Opin Biotechnol*, 8(1): 36-44 (1997).

Petrov, N. K., et al., "Photophysical Properties of 3,3'-Diethylthiacarbocyanine Iodide in Binary Mixtures," *Journal of Physical Chemistry A*, 107(33): 6341-4 (2003).

Peyman, A., et al., "PHONA—PNA Co-Oligomers: Nucleic Acid Mimetics with Interesting Properties," *Angew. Chem. Int. Ed. Engl.*, 36(24): 2809-12 (1997).

Peyratout, C., E. Donath, and L. Daehne, "Electrostatic interactions of cationic dyes with negatively charged polyelectrolytes in aqueous solution," *Journal of Photochemistry and Photobiology A: Chemistry*, 142: 51-57 (2001).

Pieck, J.C., et al., "PNA-based reagents for the direct and site-specific synthesis of thymine dimer lesions in genomic DNA," *J Am Chem Soc*, 128(5): 1404-5 (2006).

*PNA ISH Detection Kit*, DakoCytomation: Denmark. p. 1-22.

Pokorski, J.K., et al., "(S,S)-trans-cyclopentane-constrained peptide nucleic acids. a general backbone modification that improves binding affinity and sequence specificity," *J Am Chem Soc*, 126(46): 15067-73 (2004).

Ponterini, G. and F. Momicchioli, "Trans-cis photoisomerization mechanism of carbocyanines: experimental check of theoretical models," *Chemical Physics*, 151(1): 111-26 (1991).

Pooga, M. and U. Langel, "Targeting of cancer-related proteins with PNA oligomers," *Curr Cancer Drug Targets*, 1(3): 231-9 (2001).

Poopeiko, N. E., et al., "xylo-configured oligonucleotides (XNA, xylo nucleic acids): synthesis and hybridization studies," *Nucleosides Nucleotides Nucleic Acids*, 22(5-8): 1147-9 (2003).

Popescu, D.L., T.J. Parolin, and C. Achim, "Metal incorporation in modified PNA duplexes," *J Am Chem Soc*, 125(21): 6354-5 (2003).

Praseuth, D., et al., "Peptide nucleic acids directed to the promoter of the alpha-chain of the interleukin-2 receptor," *Biochim Biophys Acta*, 1309(3): 226-38 (1996).

Prento, P. and Lyon, H.O., "Methyl green-pyronin Y straining of nucleic acids: studies on the effects of staining time, dye composition and diffusion rates," *Biotechnic & Histochemistry*, 78(1):27-33 (2003).

Prescott, A.M. and C.R. Fricker, "Use of PNA oligonucleotides for the in situ detection of *Escherichia coli* in water," *Mol Cell Probes*, 13(4): 261-8 (1999).

Price, M.A. and T.D. Tullius, "Using hydroxyl radical to probe DNA structure," *Methods Enzymol*, 212: 194-219 (1992).

Pronkin, P.G., et al., "The Study of cis—trans Equilibrium and Complexation with DNA of meso-Substituted Carbocyanine Dyes," *High Energy Chemistry*, 39(4): 237-43 (2005).

Protozanova, E., et al., "Pseudocomplementary PNAs as selective modifiers of protein activity on duplex DNA: the case of type IIs restriction enzymes," *Nucleic Acids Res*, 31(14): 3929-35 (2003).

Protozanova, E., et al., "Tailoring the activity of restriction endonuclease PleI by PNA-induced DNA looping," *EMBO Rep*, 3(10): 956-61 (2002).

Proudfoot, E.M., et al., "Probing Site Specificity of DNA Binding Metallointercalators by NMR Spectroscopy and Molecular Modeling," *Biochemistry*, 40:4867-4878 (2001).

Pućkowska, A., et al., "Aromatic analogues of DNA minor groove binders—synthesis and biological evaluation," *European Journal of Medicinal Chemistry*, 39:99-105 (2004).

Puschl, A., et al., "Peptide Nucleic Acids (PNAs) with a Functional Backbone," *Tetrahedron Letters*, 39(26): 4707-4710 (1998).

Puschl, A., et al., "Synthesis of pyrrolidinone PNA: a novel conformationally restricted PNA analogue," *J Org Chem*, 66(3): 707-12 (2001).

Rajeev, K.G., et al., "High-affinity peptide nucleic acid oligomers containing tricyclic cytosine analogues," *Org Lett*, 4(25): 4395-8 (2002).

Rajwanshi, V.K., et al., "High-affinity nucleic acid recognition using 'LNA' (locked nucleic acid, beta-D-ribo configured LNA), 'xylo-LNA' (beta-D-xylo configured LNA) or 'alpha-L-LNA' (alpha-L-ribo configured LNA)," *Chem. Commun.*, (20): 2073-2074 (1999).

Rajwanshi, V.K., et al., "LNA stereoisomers: xylo-LNA (beta-D-xylo configured locked nucleic acid) and alpha-L-LNA (alpha-L-ribo configured locked nucleic acid," *Chem. Commun.*, (15): 1395-1396 (1999).

Rajwanshi, V.K., et al., "The Eight Stereoisomers of LNA (Locked Nucleic Acid): A Remarkable Family of Strong RNA Binding Molecules," *Angew Chem Int Ed Engl*, 39(9): 1656-1659 (2000).

Ramaiah, D., et al., "Enzymatic reaction with unnatural substrates: DNA photolyase (*Escherichia coli*) recognizes and reverses thymine [2+2] dimers in the DNAa strand of a DNA/PNA hybrid duplex," *Proc Natl Acad Sci U S A*, 95(22): 12902-5 (1998).

Ranasinghe, R.T. and T. Brown, "Fluorescence based strategies for genetic analysis," *Chem Commun (Camb)*, (44): 5487-502 (2005).

Randazzo, A., et al., "NMR solution structure of a parallel LNA quadruplex," *Nucleic Acids Res*, 32(10): 3083-92 (2004).

Randolph, J.B. and A.S. Waggoner, "Stability, specificity and fluorescence brightness of multiply-labeled fluorescent DNA probes," *Nucleic Acids Res*, 25(14): 2923-9 (1997).

Rasmussen, F.W., et al., "Evaluation of transfection protocols for unmodified and modified peptide nucleic acid (PNA) oligomers," *Oligonucleotides*, 16(1): 43-57 (2006).

Rasmussen, H., et al., "Crystal structure of a peptide nucleic acid (PNA) duplex at 1.7 A resolution," *Nat Struct Biol*, 4(2): 98-101 (1997).

Rasmussen, H., et al., "The influence of a chiral amino acid on the helical handedness of PNA in solution and in crystals," *J Biomol Struct Dyn*, 21(4): 495-502 (2004).

Ratilainen, T., et al., "Hybridization of peptide nucleic acid," *Biochemistry*, 37(35): 12331-42 (1998).

Ratilainen, T., et al., "Thermodynamics of sequence-specific binding of PNA to DNA," *Biochemistry*, 39(26): 7781-91 (2000).

Ray, A. and Norden, B., "Peptide nucleic acid (PNA): its medical and biotechnical applications and promise for the future," *The FASEB Journal*, 14:1041-1060 (Jun. 2000).

Reddy, P., A.N., et al., "Metal-assisted light-induced DNA cleavage activity of 2-(methylthio)phenylsalicylaldimine Schiff base copper(II) complexes having planar heterocyclic bases," *Journal of Inorganic Biochemistry*, 98:377-386 (2004).

Reddy, P., et al., "Sequence Selective Recognition in the Minor Groove of dsDNA by Pyrrole, Imidazole-Substituted Bisbenzimidazole Conjugates," *J. Am. Chem. Soc.*, 125:7843-7848 (2003).

Řeha, D., et al. "Intercalators. 1. Nature of Stacking Interactions between Intercalators (Ethidium, Daunomycin, Ellipticine, and 4',6-Diaminide-2-phenylindole) and DNA Base Pairs. Ab Initio Quantum Chemical, Density Function. Theory, and Empirical Potential Study," *J. Am. Chem. Soc.*, 124:3366-3376 (2002).

Renneberg, D., and Dervan, P.., "Imidazopyridine/Pyrrole and Hydroxybenzimidazole/Pyrrole Pairs for DNA Minor Groove Recognition," *J. Am. Chem. Soc.*, 125:5707-5716 (2003).

Rentsch, S.K., D. Fassler, and P. Hampe, "Picosecond Time-Resolved Spectroscopic Studies of a Monomer-Dimer System of 3,3'-Diethyl Thiacarbocyanine Iodide in Aqueous Solution," *Chemical Physics Letters*, 89(3): 249-53 (1982).

Rigby, S., et al., "Fluorescence in situ hybridization with peptide nucleic acid probes for rapid identification of Candida albicans directly from blood culture bottles," *J Clin Microbiol*, 40(6): 2182-6 (2002).

Rippe, K. and T.M. Jovin, "Parallel-stranded duplex DNA" *Methods Enzymol*, 211: 199-220 (1992).

Robaczewska, M., et al., "Sequence-specific inhibition of duck hepatitis B virus reverse transcription by peptide nucleic acids (PNA)," *J Hepatol*, 42(2): 180-7 (2005).

Robertson, K.L., et al., "Fluorescent PNA probes as hybridization labels for biological RNA," *Biochemistry*, 45(19): 6066-74 (2006).

Rockenbauer, E., et al., "SNP genotyping using microsphere-linked PNA and flow cytometric detection," *Cytometry A*, 64(2): 80-6 (2005).

Rogers, F.A., et al., "Site-directed recombination via bifunctional PNA-DNA conjugates," *Proc Natl Acad Sci U S A*, 99(26): 16695-700 (2002).

Rose, D.J., "Characterization of antisense binding properties of peptide nucleic acids by capillary gel electrophoresis," *Anal Chem*, 65(24): 3545-9 (1993).

Rosenbaum, D.M. and D.R. Liu, "Efficient and sequence-specific DNA-templated polymerization of peptide nucleic acid aldehydes," *J Am. Chem Soc*, 125(46): 13924-5 (2003).

Ross, G.F., et al., "Synthesis of trifunctional PNA-benzophenone derivatives for mitochondrial targeting, selective DNA binding, and photo-cross-linking," *Bioconjug Chem*, 14(5): 962-6 (2003).

Rosu, F., et al., "Determination of affinity, stoichiometry and sequence selectivity of minor groove binder complexes with double-stranded oligodeoxynucleotides by electrospray ionization mass spectrometry," *Nucleic Acids Res*, 30(16): e82 (2002).

Rulliere, C., "Laser Action and Photoisomerisation of 3,3'-Diethyl Oxadicarrocyanine Iodide (DODCI): Influence of Temperature and Concentration," *Chemical Physics Letters*, 43(2): 303-8 (1976).

Running, J.A. and Urdea, M.S., "A Procedure for Productive Coupling of Synthetic Oligonucleotides to Polystyrene Microtiter Wells for Hybridization Capture," *Bio Techniques*, 8(3):276-277 (1990).

Rye, H.S. and A.N. Glazer, "Interaction of dimeric intercalating dyes with single-stranded DNA," *Nucleic Acids Res*, 23(7): 1215-22 (1995).

Sagawa, T., H. Tobata, and H. Ihara, "Exciton interactions in cyanine dye—hyaluronic acid (HA) complex: reversible and biphasic molecular switching of chromophores induced by random coil-to-double-helix phase transition of HA," *Chem Commun (Camb)*, (18): 2090-1 (2004).

Sajewicz, W. and Dlugosz, A., "Cytotoxicity of some Potential DNA Intercalators (Carbazole, Acridine and Anthracene Derivatives) Evaluated through Neutrophil Chemiluminescence," *J. Appl. Toxicol.*, 20:305-312 (2000).

Sambrook, J., et al., "Molecular Cloning: A Laboratory Manual," 2d ed., Cold Spring Harbor Press, (1989).

Sanchez-Galvez, A., et al., "Ultrafast Radiationless Deactivation of Organic Dyes: Evidence for a Two-State Two-Mode Pathway in Polymethine Cyanines," *J. Am. Chem. Soc.*, 122(12): 2911-2924 (2000).

Sanford, D.G. and B.D. Stollar, "Assay of anti-DNA antibodies," *Methods Enzymol*, 212: 355-71 (1992).

Sano, S., et al., "A PNA-DNA hybridization chip approach for the detection of beta-secretase activity," *Bioorg Med Chem Lett*, 16(3): 503-6 (2006).

Sato, H., et al., "Synthesis and Conformation Control of Peptide Ribonucleic Acid (PRNA) Containing 5'-Amino-5'- deoxyribopyrimidine and 5'-Amino-5'-deoxyribopurinenucleosides," *Journal of Bioactive and Compatible Polymers*, 19: 65-79 (2004).

Sato, H., et al., "Picosecond Study of Energy Transfer Between Rhodamine 6G and 3,3'-Diethylthiacarbocyanine Iodide in the Premicellar Region: Forster Mechanism with Increased Local Concentration," *Chemical Physics Letters*, 71(2): 326-9 (1980).

Sauerwein, B. and G.B. Schuster, "External Iodine Atoms Influence over the Intersystem Crossing Rate of a Cyanine Iodide Ion Pair in Benzene Solution," *J. Phys. Chem.*, 95: 1903-1906 (1991).

Sazani, P., et al., "Effects of base modifications on antisense properties of 2'-O-methoxyethyl and PNA oligonucleotides," *Antisense Nucleic Acid Drug Dev*, 13(3): 119-28 (2003).

Sazani, P., et al., "Systemically delivered antisense oligomers upregulate gene expression in mouse tissues," *Nat Biotechnol*, 20(12): 1228-33 (2002).

Sazani, P., et al., "Nuclear antisense effects of neutral, anionic and cationic oligonucleotide analogs," *Nucleic Acids Res*, 29(19): 3965-74 (2001).

Scarfi, S., et al., "Synthesis, uptake, and intracellular metabolism of a hydrophobic tetrapeptide-peptide nucleic acid (PNA)-biotin molecule," *Biochem Biophys Res Commun*, 236(2): 323-6 (1997).

Schaberle, F.A., et al., "Spectroscopic studies of the interaction of bichromophoric cyanine dyes with DNA. Effect of ionic strength," *Biochimica et Biophysica Acta*, 1621:183-191 (2003).

Schatz, P., et al., "Novel method for high throughput DNA methylation marker evaluation using PNA-probe library hybridization and MALDI-TOF detection," *Nucleic Acids Res*, 34(8): e59 (2006).

Scheblykin, I.G., et al., "Dimensionality and temperature dependence of the radiative lifetime of J-aggregates with Davydov splitting of the exciton band," *Chemical Physics Letters*, 316(1): 37-44 (2000).

Scheblykin, I.G., et al., "Non-coherent exciton migration in J-aggregates of the dye THIATS: exciton-exciton annihilation and fluorescence depolarization," *Chemical Physical Letters*, 298(4-6): 341-350 (1998).

Schmid, I., et al., "Simultaneous flow cytometric analysis of two cell surface markers, telomere length, and DNA content," *Cytometry*, 49(3): 96-105 (2002).

Schulz, G.E. and Schirmer, R.H., "Principles of Protein Structure: Springer Advanced Texts in Chemistry," Springer-Verlag, New York (1979).

Schutz, R., et al., "Olefinic Peptide Nucleic Acids (OPAs): New Aspects of the Molecular Recognition of DNA by PNA," *Angew Chem Int Ed Engl*, 39(7): 1250-1253 (2000).

Schwarz, F.P., et al., "Thermodynamic comparison of PNA/DNA and DNA/DNA hybridization reactions at ambient temperature," *Nucleic Acids Res*, 27(24): 4792-800 (1999).

Seeger, C., et al., "PNA-mediated purification of PCR amplifiable human genomic DNA from whole blood," *Biotechniques*, 23(3): 512-7 (1997).

Seifert, J.L., et al., "Spontaneous Assembly of Helical Cyanine Dye Aggregates on DNA Nanotemplates," *J. Am. Chem. Soc.*, 121(13): 2987-2995 (1999).

Sen, A. and P.E. Nielsen, "Unique properties of purine/pyrimidine asymmetric PNA.DNA duplexes: differential stabilization of PNA.DNA duplexes by purines in the PNA strand," *Biophys J*, 90(4): 1329-37 (2006).

Sen, S. and L. Nilsson, "MD simulations of homomorphous PNA, DNA, and RNA single strands: characterization and comparison of conformations and dynamics," *J Am Chem Soc*, 123(30): 7414-22 (2001).

Sforza, S., et al., "Role of chirality and optical purity in nucleic acid recognition by PNA and PNA analogs," *Chirality*, 14(7): 591-8 (2002).

Sforza, S., et al., "Chiral Peptide Nucleic Acids (PNAs): Helix Handedness and DNA Recognition," *Eur. J. Org. Chem.*, 1999(1): 197-204 (1999).

Sforza, S., et al., "Direction control in DNA binding of chiral D-lysine-based peptide nucleic acid (PNA) probed by electrospray mass spectrometry," *Chem Commun (Camb)*, 9: 1102-3 (2003).

Sforza, S., et al., "DNA Binding of a D-Lysine-Based Chiral PNA: Direction Control and Mismatch Recognition," *Eur. J. Org. Chem.*, 16: 2821-2965 (2000).

Sforza, S., et al., "Fast, Solid-Phase Synthesis of Chiral Peptide Nucleic Acids with a High Optical Purity by a Submonomeric Strategy," *Eur. J. Org. Chem.*, 6: 2905-13 (2003).

Sforza, S., et al., "Unconventional method based on circular dichroism to detect peanut DNA in food by means of a PNA probe and a cyanine dye," *Chirality*, 17(9): 515-21 (2005).

Shah, B.K. and D.C. Neckers, "Anthanthrene Derivatives as Blue Emitting Materials for Organic Light-Emitting Diode Applications," *Chem. Mater.*, 18(3): 603-608 (2006).

Shakeel, S., et al., "Peptide nucleic acid (PNA)—a review," *Journal of Chemical Technology and Biotechnology*, 81(6): 892-899 (2006).

Shammas, M., et al., "Telomerase inhibition by peptide nucleic acids reverses 'immortality' of transformed human cells," *Oncogene*, 18(46): 6191-200 (1999).

Sharon, J. and Givol, D., "Preparation of Fv Fragment from the Mouse Myeloma XRPC-25 Immunoglobulin Possessing Anti-Dinitrophenyl Activity," *Biochemistry*, 15(7):1591-1594 (1976).

Shi, L., B. Hernandez, and M. Selke, "Singlet oxygen generation from water-soluble quantum dot-organic dye nanocomposites," *J Am Chem Soc*, 128(19): 6278-9 (2006).

Shi, N., R.J. Boado, and W.M. Pardridge, "Antisense imaging of gene expression in the brain in vivo," *Proc Natl Acad Sci U S A*, 97(26): 14709-14 (2000).

Shim, Y., et al., "Relative DNA binding affinity of helix 3 homeodomain analogues, major groove binders, can be rapidly screened by displacement of prebound ethidium bromide. A comparative study," *Org. Biomol. Chem.*, 2:915-921 (2004).

Shiraishi, T., N. Bendifallah, and P.E. Nielsen, "Cellular delivery of polyheteroaromate-peptide nucleic acid conjugates mediated by cationic lipids." *Bioconjug Chem*, 17(1): 189-94 (2006).

Silverman, A.P., et al., "2.4-Å Crystal Structure of the Asymmetric Platinum Complex {Pt(ammine)(cyclohexylamine)}$^{2+}$ Bound to a Dodecamer DNA Duplex," *Journal of Biological Chemistry*, 277(51):49743-49749 (2002).

Simeonov, A. and T.T. Nikiforov, "Single nucleotide polymorphism genotyping using short, fluorescently labeled locked nucleic acid (LNA) probes and fluorescence polarization detection," *Nucleic Acids Res*, 30(17): e91 (2002).

Sims, P.J., et al., "Studies on the mechanism by which cyanine dyes measure membrane potential in red blood cells and phosphatidylcholine vesicles," *Biochemistry*, 13(16): 3315-30 (1974).

Singh, S.K. and J. Wengel, "Universality of LNA-mediated high-affinity nucleic acid recognition," *Chem. Commun.*, (12): 1247-8 (1998).

Singh, S.K., et al., "LNA (locked nucleic acids): synthesis and high-affinity nucleic acid recognition," *Chem. Commun.*, (4): 455-456 (1998).

Singh, S.K., R. Kumar, and J. Wengel, "Synthesis of 2'-Amino-LNA: A Novel Conformationally Restricted High-Affinity Oligonucleotide Analogue with a Handle," *J. Org. Chem.*, 63(26): 10035-10039 (1998).

Skerra, A., "Engineered protein scaffolds for molecular recognition," *J. Mol. Recognit.*, 13:167-187 (2000).

Slaitas, A. and E. Yeheskiely, "A Novel N-(Pyrrolidinyl-2-methyl)glycine-Based PNA with a Strong Preference for RNA over DNA," *Eur. J. Org. Chem.*, 2002(14): 2391-2399 (2002).

Slavnova, T.D., A.K. Chibisov, and H. Gorner, "Photoprocesses of Thiacarbocyanine Monomers, Dimers, and Aggregates Bound to Polyanions," *J. Phys. Chem. A*, 106(46): 10985-10990 (2002).

Smith, J.O., D.A. Olson, and B.A. Armitage, "Molecular Recognition of PNA-Containing Hybrids: Spontaneous Assembly of Helical Cyanine Dye Aggregates on PNA Templates," *J. Am. Chem. Soc.*, 121(12): 2686-2695 (1999).

Smolina, I.V., V.V. Demidov, and M.D. Frank-Kamenetskii, "Pausing of DNA polymerases on duplex DNA templates due to ligand binding in vitro," *J Mol Biol*, 326(4): 1113-25 (2003).

Smulevitch, S.V., et al., "Enhancement of strand invasion by oligonucleotides through manipulation of backbone charge," *Nat Biotechnol*, 14(13): 1700-4 (1996).

Soliva, R., et al., "Molecular Dynamics Simulations of PNA-DNA and PNA-RNA Duplexes in Aqueous Solution," *J. Am. Chem. Soc.*, 122(25): 5997-6008 (2000).

Song, J.Y., et al., "Diagnosis of HNF-1alpha mutations on a PNA zip-code microarray by single base extension," *Nucleic Acids Res*, 33(2): e19 (2005).

Song, L., et al., "Photobleaching kinetics of fluorescein in quantitative fluorescence microscopy," *Biophys J*, 68(6): 2588-600 (1995).

Sorensen, M.D., et al., "Branched oligonucleotides containing bicyclic nucleotides as branching points and DNA or LNA as triplex forming branch," *Bioorg Med Chem Lett*, 10(16): 1853-6 (2000).

Sorensen, M.D., et al., "Alpha-L-ribo-configured locked nucleic acid (alpha-L-LNA): synthesis and properties," *J Am Chem Soc*, 124(10): 2164-76 (2002).

Sovenyhazy, K.M., et al., "Spectroscopic studies of the multiple binding modes of a trimethine-bridged cyanine dye with DNA," *Nucleic Acids Research*, 31(10):2561-2569 (2003).

Stefano, K. and Hyldig-Nielsen, J.J., "Diagnostic Applications of PNA Oligomers," *Diagnostic Gene Detection and Quantification Technologies*, Chapter 1.2:19-39 (Minden ed., 1997).

Stender, H., et al., "Combination of ATP-bioluminescence and PNA probes allows rapid total counts and identification of specific microorganisms in mixed populations," *J Microbiol Methods*, 46(1): 69-75 (2001).

Stender, H., et al., "Direct detection and identification of *Mycobacterium tuberculosis* in smear-positive sputum samples by fluorescence in situ hybridization (FISH) using peptide nucleic acid (PNA) probes," *Int J Tuberc Lung Dis*, 3(9): 830-7 (1999).

Stender, H., et al., "Fluorescence In situ hybridization assay using peptide nucleic acid probes for differentiation between tuberculous and nontuberculous mycobacterium species in smears of mycobacterium cultures," *J Clin Microbiol*, 37(9): 2760-5 (1999).

Stender, H., et al., "Identification of Dekkera bruxellensis (brettanomyces) from wine by fluorescence in situ hybridization using peptide nucleic acid probes," *Applied and Environmental Microbiology*, 67(2): 938-41 (2001).

Stender, H., et al., "Rapid detection, identification, and enumeration of *Pseudomonas aeruginosa* in bottled water using peptide nucleic acid probes," *J Microbiol Methods*, 42(3): 245-53 (2000).

Stender, H., et al., "Rapid detection, identification, and enumeration of *Escherichia coli* by fluorescence in situ hybridization using an array scanner," *J Microbiol Methods*, 45(1): 31-9 (2001).

Stock, R.P., et al., "Inhibition of gene expression in Entamoeba histolytica with antisense peptide nucleic acid oligomers," *Nat Biotechnol*, 19(3): 231-4 (2001).

Sugimoto, N., "Beyond the Watson-Crick double helix: design of functional nucleic acids in silico, in tube, and in cell," *Nucleic Acids Res Suppl*, (3): 211-2 (2003).

Sugimoto, N., et al., "Stabilization factors affecting duplex formation of peptide nucleic acid with DNA," *Biochemistry*, 40(29): 8444-51 (2001).

Sun, B.W., et al., "Sequence and pH effects of LNA-containing triple helix-forming oligonucleotides: physical chemistry, biochemistry, and modeling studies," *Biochemistry*, 43(14): 4160-9 (2004).

Sun, J.Y., et al., "Immune responses to adeno-associated virus and its recombinant vectors," *Gene Ther*, 10(11): 964-76 (2003).

Svanvik, N., et al., "Detection of PCR products in real time using light-up probes," *Anal Biochem*, 287(1): 179-82 (2000).

Svanvik, N., et al., "Light-up probes: thiazole orange-conjugated peptide nucleic acid for detection of target nucleic acid in homogeneous solution," *Anal Biochem*, 281(1): 26-35 (2000).

Svanvik, N., et al., "Free-probe fluorescence of light-up probes," *J Am Chem Soc*, 123(5): 803-9 (2001).

Svoboda, J. and B. Konig, "Templated photochemistry: toward catalysts enhancing the efficiency and selectivity of photoreactions in homogeneous solutions," *Chem Rev*, 106(12): 5413-30 (2006).

Tackett, A.J., D.R. Corey, and K.D. Raney, "Non-Watson-Crick interactions between PNA and DNA inhibit the ATPase activity of bacteriophage T4 Dda helicase," *Nucleic Acids Res*, 30(4): 950-7 (2002).

Takenaka, S., et al., "An anthracene derivative carrying ferrocenyl moieties at its 9 and 10 positions as a new electrochemically active threading intercalator," *Nucleic Acids Research Supplement*, (2): 291-292 (2002).

Tanious, F.A., et al., "DNA Sequence Dependent Monomer-Dimer Binding Modulation of Asymmetric Benzimidazole Derivatives," *J. Am. Chem. Soc.*, 126:143-153 (2004).

Tarasov, S.G., et al., "Bisimidazoacridones: 2. Steady-state and Time-resolved Fluorescence Studies of Their Diverse Interactions with DNA," *Photochemistry and Photobiology*, 78(4):313-322 (2003).

Tatikolov, A.S. and S.M. Costa, "Complexation of polymethine dyes with human serum albumin: a spectroscopic study," *Biophys Chem*, 107(1): 33-49 (2004).

Tatikolov, A.S. and S.M. Costa, "Photophysics and photochemistry of hydrophilic cyanine dyes in normal and reverse micelles," *Photochem Photobiol Sci*, 1(3): 211-8 (2002).

Tawar, U., et al., "Minor Groove Binding DNA Ligands with Expanded A/T Sequence Length Recognition, Selective Binding to Bent DNA Regions and Enhanced Fluorescent Properties," *Biochemistry*, 42:13339-13346 (2003).

Tedeschi, T., et al., "Lysine-based peptide nucleic acids (PNAs) with strong chiral constraint: control of helix handedness and DNA binding by chirality," *Chirality*, 17 Suppl: S196-204 (2005).

Tedeschi, T., et al., "Racemization of chiral PNAs during solid-phase synthesis: effect of the coupling conditions on enantiomeric purity," *Tetrahedron: Asymmetry*, 13(15): 1629-1636 (2002).

Tedeschi, T., et al., "Synthesis of new chiral PNAs bearing a dipeptide-mimic monomer with two lysine-derived stereogenic centres," *Tetrahedron Letters*, 46(48): 8395-8399 (2005).

Tempest, P.R., et al., "Reshaping A Human Monoclonal Antibody to Inhibit Human Respiratory Syncytial Virus Infection In Vivo," *Biotechnology*, 9:266-271 (1991).

Tian, H. and S. Yang, "Intramolecular triplet energy transfer in multichromophoric dyes and its influence on the photostability," *Journal of Photochemistry and Photobiology C: Photochemistry Reviews*, 3(1): 67-76 (2002).

Tijssen, P. "Practice and Theory of Enzyme Immunoassays," www.elsevier.com, 576 pages (1985).

Tok, J., and Fenker, J., "Novel Synthesis and RNA-Binding Properties of Aminoglycoside Dimers Conjugated Via a Naphthalene Diimide-based Intercalator," *Bioorganic & Medicinal Chemistry Letters*, 11:2987-2991 (2001).

Tolstrup, N., et al., "OligoDesign: Optimal design of LNA (locked nucleic acid) oligonucleotide capture probes for gene expression profiling," *Nucleic Acids Res*, 31(13): 3758-62 (2003).

Tolun, G., and Myers, R.S., "A real-time DNase assay (ReDA) based on PicoGreen® fluorescence," *Nucleic Acids Research*, 31(18): 1-6 (2003).

Tomac, S., et al., "Ionic Effects on the Stability and Conformation of Peptide Nucleic Acid Complexes," *J. Am. Chem. Soc.*, 118(24): 5544-5552 (1996).

Tomlinson, A., et al. "A structural model for cyanine dyes templated into the minor groove of DNA," *Chemical Physics*, 325: 36-47 (2006).

Tonelli, R., et al., "Antigene peptide nucleic acid specifically inhibits MYCN expression in human neuroblastoma cells leading to cell growth inhibition and apoptosis," *Molecular Cancer Therapeutics*, 4(5): 779-786 (2005).

Torres, M.J., et al., "Improved real-time PCR for rapid detection of rifampin and isoniazid resistance in *Mycoabcterium tuberculosis* clinical isolates," *Diagn. Microbiol. Infect. Dis.*, 45:207-212 (2003).

Toshima, K., et al., "2-Phenylquinoline-Carbohydrate Hybrids: Molecular Design, Chemical Synthesis, and Evaluation of a New Family of Light-Activatable DNA-Cleaving Agents," *Angew. Chem. Int. Ed.*, 38(24):3733-3735 (1999).

Turro, N.J., et al., "Reactivity and Intersystem Crossing of Singlet Methylene in Solution," *J. Am. Chem. Soc.*, 109(7): 2101-2107 (1987).

Ugozzoli, L.A., et al., "Real-time genotyping with oligonucleotide probes containing locked nucleic acids," *Anal Biochem*, 324(1): 143-52 (2004).

Uhlmann, E., et al., "PNA: Synthetic Polyamide Nucleic Acids with Unusual Binding Properties," *Angew. Chem. Int. Ed. Engl.*, 37(20): 2796-2823 (1998).

Valyukh, I.V., et al., "Spectroscopic Studies of α, γ-Disubstituted Trimethine Cyanine: New Fluorescent Dye for Nucleic Acids," *Journal of Fluorescence*, 12(1): 105-7 (2002).

Varadarajan, S., et al., "DNA Damage and Cytotoxicity Induced by Minor Groove Binding Methyl Sulfonate Esters," *Biochemistry*, 42:14318-14327 (2003).

Vauthey, E., "Isomerisation dynamics of a thiacarbocyanine dye in different electronic states and in different classes of solvents," *Chemical Physics*, 196(3): 569-582 (1995).

Vesperinas, A., et al., "Photoinduced phase separation," *J Am Chem Soc*, 128(5): 1468-9 (2006).

Vester, B. and J. Wengel, "LNA (locked nucleic acid): high-affinity targeting of complementary RNA and DNA," *Biochemistry*, 43(42): 13233-41 (2004).

Vinogradov, A.M. and V.A. Kuz'min, "Photoisomerization of Symmetrical Carbocyanine Dyes from Higher Excited States," *Institute of Chemical Physics*, p. 2419-20 (1978).

Vinogradov, A.M., et al., "The effect of anionic, cationic and neutral surfactants on the photophysics and isomerization of 3,3'-diethylthiacarbocyanine," *Phys. Chem. Chem. Phys*, 3: 4325-4332 (2001).

Viola, G., et al., "Indolo[2,3-b]-Quinolizinium Bromide: An Efficient Intercalator with DNA-Photodamaging Properties," ChemBioChem, 3:550-558 (2002).

Vlaspolder, F., P. Singer, and C. Roggeveen, "Diagnostic value of an amplification method (Gen-Probe) compared with that of culture for diagnosis of tuberculosis," *J Clin Microbiol*, 33(10): 2699-703 (1995).

Vollmer, J., et al., "Modulation of CpG oligodeoxynucleotide-mediated immune stimulation by locked nucleic acid (LNA)," *Oligonucleotides*, 14(1): 23-31 (2004).

Vranken, N., et al., "The Influence of Meso-Substitution on the Photophysical Behavior of Some Thiacarbocyanine Dyes in Dilute Solution," *J. Phys. Chem. A*, 105(45): 10196-10203 (2001).

Wagner, S.J., "Virus Inactivation in Blood Components by Photoactive Phenothiazine Dyes," *Transfusion Medicine Reviews*, 16(1):61-66 (Jan. 2002).

Wainwright, M. and J.E. Kristiansen, "Quinoline and cyanine dyes—putative anti-MRSA drugs," *Int J Antimicrob Agents*, 22(5): 479-86 (2003).

Wakelin, L., P.G., et al., "Bisintercalating Threading Diacridines: Relationships between DNA Binding, Cytotoxicity, and Cell Cycle Arrest," *J. Med. Chem.*, 46:5790-5802 (2003).

Wan, C., et al., "Femtosecond dynamics of DNA-mediated electron transfer," *Proc Natl Acad Sci U S A*, 96(11): 6014-9 (1999).

Wang, L., et al., "Specific molecular recognition of mixed nucleic acid sequences: an aromatic dication that binds in the DNA minor groove as a dimmer," *Proc Natl Acad Sci U S A*, 97(1): 12-6 (2000).

Wang, M. and Armitage, B.A., "Colorimetric Detection of PNA-DNA Hybridization Using Cyanine Dyes," *Methods in Molecular Biology, Peptide Nucleic Acids: Methods and Protocols*, Humana Press Inc., Totowa, NJ, 208:131-142 (2002).

Wang, M., et al., "DNA-Templated Formation of a Helical Cyanine Dye J-Aggregate," *J. Am. Chem. Soc.*, 122(41): 9977-9986 (2000).

Wang, M., I. Dilek, and B.A. Armitage, "Electrostatic Contributions to Cyanine Dye Aggregation on Peptide Nucleic Acid Templates," *Langmuir*, 19(16): 6449-6455 (2003).

Wang, S., et al., "Electrochemical determination of interaction parameters for DNA and mitoxantrone in an irreversible redox process," *Biophysical Chemistry*, 104:239-248 (2003).

Wang, Z., et al., "A temperature-dependent interaction of neutral red with calf thymus DNA," *Spectrochimica Acta Part A*, 59:949-956 (2003).

Ward, E.S., et al. "Binding activities of a repertoire of single immunoglobulin variable domains secreted from *Escherichia coli*," *Nature*, 341:544-546 (Oct. 1989).

Weicherding, D., et al., "Femtosecond time-resolved guanine oxidation in acridine modified alanyl peptide nucleic acids," *Bioorg Med Chem Lett*, 14(7): 1629-32 (2004).

Weiler, J., et al., "Hybridisation based DNA screening on peptide nucleic acid (PNA) oligomer arrays," *Nucleic Acids Res*, 25(14): 2792-9 (1997).

Wengel, J., et al., "LNA and alpha-L-LNA: towards therapeutic applications," *Nucleosides Nucleotides Nucleic Acids*, 22(5-8): 601-4 (2003).

Wengel, J., et al., "LNA (locked nucleic acid) and the diastereoisomeric alpha-L-LNA: conformational tuning and high-affinity recognition of DNA/RNA targets," *Nucleosides Nucleotides Nucleic Acids*, 20(4-7): 389-96 (2001).

Wengel, J., "Synthesis of 3'-C- and 4'-C-Branched Oligodeoxynucleotides and the Development of Locked Nucleic Acid (LNA)," *Acc Chem Res*, 32(4): 301-310 (1999).

West, W. and S. Pearce, "The Dimeric State of Cyanine Dyes," *The Journal of Physical Chemistry*, 69(6): 1894-1903 (1965).

Wilds, C.J., et al., "Direct observation of a cytosine analogue that forms five hydrogen bonds to guanosine: guanidino G-clamp," *Angew Chem Int Ed Engl*, 41(1): 115-7 (2002).

Wilhelmsson, L. M., et al., "Genetic screening using the colour change of a PNA-DNA hybrid-binding cyanine dye," *Nucleic Acids Research*, 30(2 e3): 1-4 (2002).

Wilson, D.A., et al., "Multicenter evaluation of a *Candida albicans* peptide nucleic acid fluorescent in situ hybridization probe for characterization of yeast isolates from blood cultures," *J Clin Microbiol*, 43(6): 2909-12 (2005).

Wolf, Y., et al., "Structural requirements for cellular uptake and antisense activity of peptide nucleic acids conjugated with various peptides," *Biochemistry*, 45(50): 14944-54 (2006).

Wong, L.S. and Gooding, J.J., "Electronic Detection of Target Nucleic Acids by a 2,6-Disulfonic Acid Anthraquinone Intercalator," *Anal. Chem.*, 75:3845-3852 (2003).

Wong, M., et al., "Oxazole yellow homodimer YOYO-1-labeled DNA: a Fluorescent complex that can be used to assess structural changes in DNA following information and cellular delivery of cationic lipid DNA complexes," *Biochimica et Biophysica Acta*, 1527:61-72 (2001).

Woods, C.R., et al., "Synthesis and DNA Binding Properties of Iminodiacetic Acid-Linked Polyamides: Characterization of Cooperative Extended 2:1 Side-by-Side Parallel Binding," *J. Am. Chem. Soc.*, 124:10676-10682 (2002).

Woods, C.R., et al., "Synthesis and DNA Binding Properties of Saturated Distamycin Analogues," *Bioorganic & Medicinal Chemistry Letters*, 12:2647-2650 (2002).

Worden, A.Z. and B.J. Binder, "Growth Regulation of rRNA Content in *Prochlorococcus* and *Synechococcus* (Marine Cyanobacteria) Measured by Whole-Cell Hybridization of rRNA-targeted Peptide Nucleic Acids," *J. Phycol.*, 39(3): 527-534 (2003).

Worden, A.Z., et al., "In situ hybridization of *Prochlorococcus* and *Synechococcus* (marine cyanobacteria) spp. with RRNA-targeted peptide nucleic acid probes," *Appl Environ Microbiol*, 66(1): 284-9 (2000).

Xi, C., et al., "Use of DNA and Peptide Nucleic Acid Molecular Beacons for Detection and Quantification of rRNA in Solution and in Whole Cells," *Applied and Environmental Microbiology*, 69(9): 5673-5678 (2003).

Xiao, Y., et al., "Electrocatalytic intercalator-induced winding of double-stranded DNA with polyaniline," *Chem. Commun.*,7:1540-1541 (2003).

Xu, H., et al., "Multiplexed SNP genotyping using the Qbead™ system: a quantum dot-encoded microsphere-based assay," *Nuc. Acids Res.*, 31(8:e43): 1-10 (2003).

Xu, Q.H., et al., "Time-resolved energy transfer in DNA sequence detection using water-soluble conjugated polymers: the role of electrostatic and hydrophobic interactions," *Proc Natl Acad Sci U S A*, 101(32): 11634-9 (2004).

Yamana, K., et al., "Electrochemical detection of single-base mismatches in DNA by a redox-active intercalator conjugated oligonucleotide," *Nucleic Acids Research Supplement*, (3): 89-90 (2003).

Yang, C., et al., "Handling and detection of 0.8 amol of a near-infrared cyanine dye by capillary electrophoresis with laser-induced fluorescence detection," *J Chromatogr A*, 979(1-2): 307-14 (2002).

Yang, X., et al., "DNA binding studies of a solvatochromic fluorescence probe 3-methoxybenzanthrone," *Spectrochimica Acta Part A*, 55:2719-2727 (1999).

Yao, D., et al., "Surface density dependence of PCR amplicon hybridization on PNA/DNA probe layers," *Biophys J*, 88(4): 2745-51 (2005).

Yarmoluk, S., et al., "Influence of the Aggregation of Homo-N-Mer Cyanine Dyes on the Nucleic Acids Detection Sensitivity," *Journal of Fluorescence*, 12(2): 155-7 (2002).

Yarmoluk, S.M. et al., "Interaction of cyanine dyes with nucleic acids XXVI. Intercalation of the trimethine cyanine dye Cyan 2 intor double-stranded DNA: study by spectral luminescence methods," *Spectrochimica Acta Part A*, 58: 3223-32 (2002).

Yarmoluk, S.M., et al, "Interaction of cyanine dyes with nucleic acids—XXVII: synthesis and spectral properties of novel homodi- and homotrimeric monomethine cyanine dyes," *Dyes and Pigments*, 50(1): 21-28 (2001).

Yarmoluk, S.M., et al., "Interaction of cyanine dyes with nucleic acids. Part 19: new method for the covalent labeling of oligonucleotides with pyrylium cyanine dyes," *Bioorg Med Chem Lett*, 10(19): 2201-4 (2000).

Yarmoluk, S.M., et al., "Interaction of cyanine dyes with nucleic acids. XII.beta-substituted carbocyanines as possible fluorescent probes for nucleic acids detection," *Bioorg Med Chem Lett*, 9(12): 1677-8 (1999).

Yarmoluk, S.M., et al., "Interaction of cyanine dyes with nucleic acids. XXI. Arguments for half-intercalation model of interaction," *Biopolymers*, 62(4): 219-27 (2001).

Yarmoluk, S.M., et al., "Interaction of cyanine dyes with nucleic acids. XX. New methods for the preparation of fluorescent probes based on benzothiavol-4-[2,6-dimethylpyridinium] cyanine dyes," *Dyes and Pigments*, 48(3): 165-172 (2001).

Yarmoluk, S.M., et al., "Proteins and cyanine dyes. Part III. Synthesis and spectroscopic studies of benzothiazolo-4[1,2,6-trimethylpyridinium] monomethine cyanine dyes for fluorescent detection of bovine serum albumin in solutions," *Dyes and Pigments*, 51(1): 41-9 (2001).

Yarmoluk, S.M., et al., "Interaction of cyanine dyes with nucleic acids XXVI. Intercalation of the trimethine cyanine dye Cyan 2 into double-stranded DNA: study by spectral luminescence methods" *Spectrochimica Acta Part A*, 58: 3223-32 (2002).

Ye, S., et al., "Simultaneous detection of multiple single nucleotide polymorphism by single-strand-specific nuclease and PNA probe," *Nucleic Acids Res Suppl*, 3: 185-6 (2003).

Ye, Y., et al., "Multivalent carbocyanine molecular probes: synthesis and applications," *Bioconjug Chem*, 16(1): 51-61 (2005).

Yukruk, F., et al., "Water-soluble green perylenediimide (PDI) dyes as potential sensitizers for photodynamic therapy," *Org Lett*, 7(14): 2885-7 (2005).

Zelder, F.H., A.A. Mokhir, and R. Kramer, "Sequence selective hydrolysis of linear DNA using conjugates of Zr(IV) complexes and peptide nucleic acids," *Inorg Chem*, 42(26): 8618-20 (2003).

Zelphati, O., et al., "PNA-dependent gene chemistry: stable coupling of peptides and oligonucleotides to plasmid DNA," *Biotechniques*, 28(2): 304-10, 312-4, 316 (2000).

Zeng, Z., et al., "Fluorescence energy-transfer cyanine heterodimers with high affinity for double-stranded DNA. II. Applications to multiplex restriction fragment sizing," *Anal Biochem*, 231(1): 256-60 (1995).

Zerbi, P., et al., "Amplified in situ hybridization with peptide nucleic acid probes for differentiation of *Mycobacterium tuberculosis* complex and nontuberculous Mycobacterium species on formalin-fixed, paraffin-embedded archival biopsy and autopsy samples," *Am J Clin Pathol*, 116(5): 770-5 (2001).

Zhang, L., J. Min, and L. Zhang, "Studies on the synthesis and properties of new PNA analogs consisting of L- and D-lysine backbones," *Bioorg Med Chem Lett*, 9(20): 2903-8 (1999).

Zhang, P., et al., "Peptide Nucleic Acid—DNA Duplexes Containing the Universal Base 3-Nitropyrrole," *Methods*, 23(2): 132-140 (2001).

Zhang, X., C.G. Simmons, and D.R. Corey, "Liver cell specific targeting of peptide nucleic acid oligomers," *Bioorg Med Chem Lett*, 11(10): 1269-72 (2001).

Zhang, X., T. Ishihara, and D.R. Corey, "Strand invasion by mixed base PNAs and a PNA-peptide chimera," *Nucleic Acids Res*, 28(17): 3332-8 (2000).

Zheng, H., et al., "Dye-binding protein assay using a long-wave-absorbing cyanine probe," *Anal Biochem*, 318(1): 86-90 (2003).

Zhilina, Z.V., et al., "PNA-nitrogen mustard conjugates are effective suppressors of HER-2/neu and biological tools for recognition of PNA/DNA interactions," *Bioconjug Chem*, 17(1): 214-22 (2006).

Zhou, P., et al., "Novel binding and efficient cellular uptake of guanidine-based peptide nucleic acids (GPNA)," *J Am Chem Soc*, 125(23): 6878-9 (2003).

Zhou, P., et al., "Synthesis of cell-permeable peptide nucleic acids and characterization of their hybridization and uptake properties," *Bioorg Med Chem Lett*, 16(18): 4931-5 (2006).

Zhou, P., "Synthesis and Properties of Guanidine-based Peptide Nucleic Acid," Department of Chemistry, Carnegie Mellon University, Powerpoint Presentation.

Zhu, C.Q., et al., "Determination of nucleic acids by near-infrared fluorescence quenching of hydrophobic thiacyanine dye in the presence of Triton X-100," *Anal Sci*, 20(6): 945-9 (2004).

Zhu, C.Q., et al., "Fluorescence enhancement method for the determination of nucleic acids using cationic cyanine as a fluorescence probe," *Analyst*, 129(3): 254-8 (2004).

Zielinski, J., et al., "In vivo identification of ribonucleoprotein-RNA interactions," *Proc Natl Acad Sci U S A*, 103(5): 1557-62 (2006).

Zipper, H., et al., "Investigations on DNA intercalation and surface binding by SYBR Green I, its structure determination and methodological implications," *Nucleic Acids Res*, 32(12): e103 (2004).

Bartlett, J.A. and G.L. Indig, "Effect of self-association and protein binding on the photochemical reactivity of triarylmethanes. Implications of noncovalent interactions on the competition between photosensitization mechanisms type I and type II," *Photochem Photobiol*, 70(4): 490-8 (1999).

Betts, L., et al., "A nucleic acid triple helix formed by a peptide nucleic acid-DNA complex," *Science*, 270(5243): 1838-41 (1995).

Biver, T., et al., "Cyanine dyes as intercalating agents: kinetic and thermodynamic studies on the DNA/Cyan40 and DNA/CCyan2 systems," *Biophys J*, 89(1): 374-83 (2005).

de la Torre, B.G. and R. Eritja, "Synthesis of labelled PNA oligomers by a post-synthetic modification approach," *Bioorg Med Chem Lett*, 13(3): 391-3 (2003).

Demidov, V.V., et al., "Peptide nucleic acid-assisted topological labeling of duplex DNA," *Methods*, 23(2): 123-31 (2001).

Dragulescu-Andrasi, A., et al., "Cell-permeable GPNA with appropriate backbone stereochemistry and spacing binds sequence-specifically to RNA," *With Supporting Information Chem Commun (Camb)*, (2): 244-6 (2005).

Dragulescu-Andrasi, A., et al., Cell-permeable GPNA containing appropriate backbone stereochemistry and spacing binds sequence-specifically to RNA, *Chem Commun, Supplementary Material (ESI) For Chemical Communications, The Royal Society of Chemistry* 2005, 5 pages.

Gambari, R., "Peptide-nucleic acids (PNAs): a tool for the development of gene expression modifiers," *Curr Pharm Des.*, 7(17): 1839-62 (2001).

Gaylord, B.S., A.J. Heeger, and G.C. Bazan, "DNA detection using water-soluble conjugated polymers and peptide nucleic acid probes," *Proc Natl Acad Sci U S A*, 99(17): 10954-7 (2002).

Kuhn, H., et al., "PNA beacons for duplex DNA," *Antisense Nucleic Acid Drug Dev*, 11(4): 265-70 (2001).

Kumar, R., et al., "The first analogues of LNA (locked nucleic acids): phosphorothioate-LNA and 2'-thio-LNA," *Bioorg Med Chem Lett*, 8(16): 2219-22 (1998).

Nielsen, P.E., et al., "Sequence specific inhibition of DNA restriction enzyme cleavage by PNA," *Nucleic Acids Res*, 21(2): 197-200 (1993).

Petersen, K., et al., "Short PNA molecular beacons for real-time PCR allelic discrimination of single nucleotide polymorphisms," *Mol Cell Probes*, 18(2): 117-22 (2004).

Pokorski, J.K., M.C. Myers, and D.H. Appella, "Cyclopropane PNA: observable triplex melting in a PNA constrained with a 3-membered ring," *Tetrahedron Letters*, 46(6): 915-7 (2005).

Rao, K.E. and J.W. Lown, "Molecular recognition between ligands and nucleic acids: DNA binding characteristics of analogues of Hoechst 33258 designed to exhibit altered base and sequence recognition," *Chem Res Toxicol*, 4(6): 661-9 (1991).

Ren, B., et al, "Straightforward detection of SNPs in double-stranded DNA by using exonuclease III/nuclease S1/PNA system," *Nucleic Acids Res*, 32(4): e42 (2004).

Senamaud-Beaufort, et al., "Short pyrimidine stretches containing mixed base PNAs are versatile tools to induce translation elongation arrest and truncated protein synthesis," *Oligonucleotides*, 13(6): 465-78 (2003).

Sharma, N. K. and K.N. Ganesh, "Expanding the repertoire of pyrrolidyl PNA analogues for DNA/RNA hybridization selectivity: aminoethylpyrrolidinone PNA (aepone-PNA)," *Chem Commun (Camb)*, 2003(19): 2484-5.

Shields, G.C., et al. "Additions and Corrections," *J. Am. Chem. Soc.*, 121(7): 1625-6 (1999).

Shiraishi, T., S. Pankratova, and P.E. Nielsen, "Calcium ions effectively enhance the effect of antisense peptide nucleic acids conjugated to cationic tat and oligoarginine peptides," *Chem Biol*, 12(8): 923-9 (2005).

Sybesma, W., et al., "Non-Disruptive PNA-Fish Protocol for Formalin-Fixed and Paraffin-Embedded Tissue Sections," *BioTechniques*, 31: 472-476 (2001).

"Telomere PNA Kit/FITC for Flow Cytometry," *Dako: Denmark*, p. 1-11.

Trawick, B.N., A.T. Daniher, and J.K. Bashkin, "Inorganic Mimics of Ribonucleases and Ribozymes: From Random Cleavage to Sequence-Specific Chemistry to Catalytic Antisense Drugs," *Chem Rev*, 98(3): 939-960 (1998).

Tyler, B.M., et al., "Peptide nucleic acids targeted to the neurotensin receptor and administered i.p. cross the blood-brain barrier and specifically reduce gene expression," *Proc. Natl Acad Sci U S A*, 96(12): 7053-8 (1999).

Yunus, W.M.M. and C.K. Sheng, "Photodegradation Study of Methylene Blue (MB) Trapped in Poly (methyl Methacrylate) (PMMA) Matrix," *Suranaree J. Sci. Technol.*, 11(2): 138-142 (2004).

Letter dated Sep. 3, 2008 from Canadian associate citing references.

Preliminary Report on Patentability in related PCT Application No. PCT/US2008/054371.

International Search Report for PCT Application No. PCT/US07/04814.

DeAngelis, D., "Why FRET Over Genomics," *Physiol. Genomics*, 1:93-99 (1999).

Ogul'chansky, T., et al., "Interaction of cyanine dyes with nucleic acids. XVIII. Formation of the carbocyanine dye J-aggregates in nucleic acid grooves," *Spectrochimica Acta Part A*, 57:2705-2715 (2001).

Roberts, E., et al., "Selective Dequenching by Photobleaching Increases Fluorescence Probe Visibility," *J. of Fluorescence*, 13(6):513-517 (2003).

Baeumner, et al., "A Universal Nucleic Acid Sequence Biosensor with Nanomolar Detection Limits," *Anal. Chem.*, 76(4):888-894 (2004).

Komiyama, et al., "PNA for One-Base Differentiating Protection of DNA from Nuclease and its Use for SNPs Detection," *J Am Chem Soc*, 125:3758-3762 (2003).

Lartia, et al., "New Cyanine-Oligonucleotide Conjugates: Relationships between Chemical Structures and Properties," *Chem. Eur. J.*, 12:2270-2281 (2006).

Sforza, S., et al., "Unconventional Method Based on Circular Dichroism to Detect Peanut DNA in Food by Means of a PNA Probe and a Cyanine Dye," *Chirality*, 17:515-521 (2005).

Wang, M. et al., "Colorimetric Detection of PNA-DNA Hybridization Using Cyanine Dyes," *Methods Mol. Biol.*, 208:131-142 (2002).

Supplementary European Search Report in European Patent Application No. 07751566.6 dated Mar. 11, 2010.

\* cited by examiner

METHODS AND COMPOSITIONS FOR RAPID LIGHT-ACTIVATED ISOLATION AND DETECTION OF ANALYTES

RELATED APPLICATIONS

The present patent document claims the benefit of the filing date under 35 U.S.C. §119(e) of Provisional U.S. Patent Application Ser. No. 60/903,116, filed Feb. 23, 2007, which is hereby incorporated by reference.

FIELD

The present invention relates to the field of diagnostics. More particularly, the invention disclosed herein is directed to methods, compositions, and kits for detecting nucleic acids, polynucleotides, pathogens, toxins, or other agents or factors that are desirably detected or measured.

BACKGROUND

There is a great need to detect and quantify various molecular species, such as polynucleotides, polypeptides, carbohydrates, lipids, and small molecules. For example, current methods of detecting a polynucleotide, such as those associated with pathogens, pathogen infection, human genes associated with diseases and disorders, altered physiology or physiological conditions, genetically modified organisms (GMOs, i.e., organisms with transgenic DNA), biowarfare agents, veterinary applications, and agricultural applications presently rely on complex methods, such as the polymerase chain reaction (PCR), nucleic acid sequence-based amplification (NASBA), transcription-mediated amplification (TMA), or branched DNA (bDNA). These methods require skilled personnel and specialized equipment. Further, the methods are generally incapable of determining the presence or quantity of polynucleotides in crude cell and tissue extracts.

There are similar difficulties in the existing immunoassays for detecting antigens. For example, antigens associated with blood coagulation disorders (e.g., F 1+2; Dade Behring, Bannockburn, Ill.), hepatitis infection (e.g., hepatitis B surface antigen; Abbott Laboratories, Abbott Park, Ill.), cancer-detection (e.g., gastrointestinal stromal tumor-specific antigens; Ventana Medical Systems, Inc., Tucson, Ariz.); acute pancreatitis (e.g., pancreatic elastase; Schebo-Biotech AG, Giessen, Germany), prostate cancer (e.g., PSA; Beckman-Coulter, Inc., Fullerton, Calif.), and the like are all based on multi-step ELISA immunoassays that require skilled personnel and specialized equipment to run.

Accordingly, there is a great need for a convenient, fast and economical method of detection, identification, and quantification of various molecules, such as polynucleotides and proteins, including polypeptides, peptides, and antigens. Reducing the complexity and increasing the reliability of such tests are among the features that would be desirably improved.

SUMMARY

The present invention relates to novel methods for isolating a target molecule from a sample suspected of containing the target molecule. The methods of the present invention utilize solid substrates as a means for capturing, separating, and releasing target molecules, such as chemical or biological compounds. The present invention is specifically related to novel approaches for capturing, separating and releasing such target molecules.

In particular embodiments of the invention, the target molecule of interest is captured by indirectly immobilizing the target molecule to a solid support via the formation of one or more "intermediary" or "bridging" light reactive complex comprising two complementary polynucleotide molecules, at least one of which is a nucleic acid analog polynucleotide, such as a PNA polynucleotide, that is capable of forming a light reactive complex with the light reactive dye.

The formation of the light reactive complex occurs under highly favorable ambient light and temperature conditions, and may even occur in the dark. Surprisingly, the formation of the light reactive complex is not negatively impacted by even ambient light. In addition, the disassociation of the light reactive complex from the solid substrate is facilitated by similarly advantageous conditions of ambient light and temperature, over time periods of brief duration (less than 2 hours, less than 1 hour, less than 30 minutes or less than 5 minutes), allowing the method to be performed without equipment typically required, for example, for nucleic acid hybridization and melting conditions used in polymerase chain reaction methods or hybridization reaction methods, while still achieving an acceptable level of high degree of specificity and sensitivity. The methods of the present invention may therefore be advantageously used, for example, in the field outside controlled laboratory conditions, for the detection and analysis of a multiplicity of compounds or biological agents.

In one aspect, the present invention relates to methods for capturing a target molecule, by combining
 (i) a polynucleotide linked to target molecule,
 (ii) a nucleic acid analog that is complementary to the polynucleotide and is bound, directly or indirectly, to a solid substrate, and
 (iii) a light reactive dye, to form a light reactive complex bound to the solid substrate, which can then be separated, based on a property of the solid substrate, as a unit, to thereby isolate the target polynucleotide.

In one embodiment of the present invention, the methods of the present invention are used to isolate a target molecule that is a polynucleotide, such as a DNA or RNA molecule, by means of a direct interaction between a target polynucleotide and a capture nucleic acid analog polynucleotide that is complementary to the target polynucleotide or a portion thereof and is immobilized on a solid substrate. In accordance with such embodiments, the methods of the invention comprise the step of combining the following components:
 (i) a sample suspected of containing the target polynucleotide;
 (ii) a first nucleic acid analog immobilized to a solid substrate, wherein the first nucleic acid analog is complementary to a portion of the target polynucleotide; and
 (iii) a first light reactive dye, to form, if the target polynucleotide is present in the sample, a light reactive complex comprising the target polynucleotide, the first nucleic acid analog, and the light reactive dye, followed by the step of separating, based on a property of the solid substrate, the solid substrate and the light reactive complex, as a unit, to thereby isolate the target polynucleotide from the sample.

In another embodiment, the methods of the present invention are used to isolate a target molecule that is a polynucleotide, such as a DNA or RNA molecule, by means of an indirect interaction between a target molecule and a capture polynucleotide immobilized on a solid substrate. In these embodiments, various intermediary constructs are used to link the target molecule with a capture polynucleotide immobilized to a solid support. The intermediary constructs are designed so as to provide at least one pair of complementary polynucleotides, at least one polynucleotide of which is a nucleic acid analog, such as, for example, a PNA polynucleotide, a LNA polynucleotide, or morpholino polynucleotide, that can associate with a light reactive dye to form a light reactive complex.

In one embodiment, illustrating an indirect interaction between a target molecule and a capture nucleic acid analog polynucleotide immobilized on a solid substrate, the present invention relates to a method of isolating a target molecule from a sample suspected of containing the target molecule, comprising the step of combining the following:
 (i) a sample suspected of containing a target molecule;
 (ii) a bound polynucleotide immobilized on a solid substrate;
 (ii) a chimeric molecule comprising (1) a bridging polynucleotide complementary to the bound polynucleotide, and (2) a target component capable of binding to a portion of the target molecule; and
 (iv) a light reactive dye.

In this particular embodiment, the target component binds to the target molecule, if present, and the target component is linked to a bridging polynucleotide (the target component and the bridging polynucleotide are collectively referred to as the "chimeric molecule"). The bridging polynucleotide is complementary to another polynucleotide that is complexed with the bound polynucleotide immobilized on the solid substrate. At least one of (a) the bridging polynucleotide of the chimeric molecule or (b) the bound polynucleotide immobilized on the solid substrate, is a nucleic acid analog polynucleotide, which nucleic acid analog polynucleotide associates with its complementary polynucleotide and the light reactive dye to form a light reactive complex immobilized on a solid substrate. Thus, the indirect interaction requires at least one complementary pair of polynucleotides that can associate with the light reactive dye to form a light reactive complex.

In yet another embodiment, illustrating another indirect interaction between a target molecule and a capture nucleic acid analog polynucleotide immobilized on a solid substrate, the present invention relates to a method of isolating a target molecule from a sample suspected of containing the target molecule, comprising the step of combining the following:
 (i) a sample suspected of containing a target molecule,
 (ii) a bound polynucleotide immobilized on a solid substrate,
 (iii) an intermediary binding polynucleotide having a first binding region complementary to the bound polynucleotide and a second binding region,
 (iv) a chimeric molecule comprising (1) a bridging polynucleotide complementary to the second binding region of the intermediary binding polynucleotide, and (2) a target component capable of specifically binding to the target molecule, and
 (v) a light reactive dye.

In this embodiment, the target component binds to the target molecule, if present, and the target component is linked to a bridging polynucleotide. In contrast to the embodiment described in the preceding paragraph (where the bridging polynucleotide forms a complex directly with the bound polynucleotide immobilized on the solid substrate), this embodiment contemplates the use of an intermediary binding polynucleotide, having a first binding region complementary to the bound polynucleotide immobilized on the solid substrate, and a second binding region that is complementary to the bridging polynucleotide of the chimeric molecule to which the target component is linked. In this construct, there are at least two regions of complementarity between separate polynucleotides: the first region of complementarity is between the bound polynucleotide and the first binding region of the intermediary binding polynucleotide; the second region of complementarity is between the bridging polynucleotide and the second binding region of the intermediary binding polynucleotide. Either one or both of these regions may form a light reactive complex with a light reactive dye, provided that at least one of the complementary pair of polynucleotide is a nucleic acid analog, such as, for example, a PNA polynucleotide, an LNA polynucleotide, or a morpholino polynucleotide, which nucleic acid analog polynucleotide can associate with its complementary polynucleotide.

In another aspect, the methods of the present invention include the step of separating the solid substrate (to which the target molecule is directly or indirectly attached) from the mixture, to thereby isolate the target molecule. In typical applications, the target molecule will originate from a heterogeneous mixture, such as a blood sample, a water sample, a tissue sample, etc., which comprises various contaminants mixed together with the target molecule of interest. The methods of the present invention are particularly useful in separating a target molecule from such a heterogeneous mixture. Thus, in one embodiment of the invention, the target molecule, immobilized to the solid substrate via at least one light reactive complex, is isolated, based on a property of the solid substrate, from a mixture, to thereby isolate the target polynucleotide from the sample.

In yet another aspect of the present invention, the target molecule, captured via formation of a light reactive complex between complementary polynucleotides immobilized to a solid substrate, is released from the light reactive complex.

In one embodiment, the present invention optionally includes the step of exposing the light reactive complex, formed as described above, to light, to thereby elute the target molecule from the solid substrate into the eluant to provide a purified target molecule.

In yet another embodiment, the present invention relates to a method of making a nucleic acid diagnostic kit comprising the step of combining, in a packaged combination, (i) an immobilized nucleic acid analog bound to a solid substrate, wherein the nucleic acid analog is complementary to a portion of a target polynucleotide; and (ii) a light reactive dye in a container, wherein the light reactive dye is capable of forming a light reactive complex with the target polynucleotide and a complementary nucleic acid analog.

In yet another embodiment, the invention relates to a method comprising the step of combining (i) a sample that may or may not contain a target molecule; (ii) an immobilized polynucleotide bound to a solid substrate; (iii) a bridging complex comprising (1) a polynucleotide portion complementary to the immobilized polynucleotide, wherein at least one of the immobilized polynucleotide and the polynucleotide portion of the bridging complex is a nucleic acid analog polynucleotide, and (2) a target-specific portion capable of binding to the target molecule, wherein the bridging complex comprises one or more molecules complexed together; and (iv) a light reactive dye capable of forming a light reactive complex with the immobilized polynucleotide and the complementary polynucleotide portion of the bridging complex.

In further embodiment, the invention relates to a method for making a nucleic acid diagnostic kit comprising the step of combining, in a packaged combination, (i) an immobilized polynucleotide bound to a solid substrate; and (ii) a container comprising at least one of: a bridging complex comprising (1) a polynucleotide portion complementary to the immobilized polynucleotide, wherein at least one of the immobilized polynucleotide and the polynucleotide portion of the bridging complex is a nucleic acid analog polynucleotide, and (2) a target-specific portion capable of binding to the target molecule, wherein the bridging complex comprises one or more molecules complexed together; and a light reactive dye capable of forming a light reactive complex with the immobilized polynucleotide and the complementary polynucleotide portion of the bridging complex.

DETAILED DESCRIPTION

Figure 1:
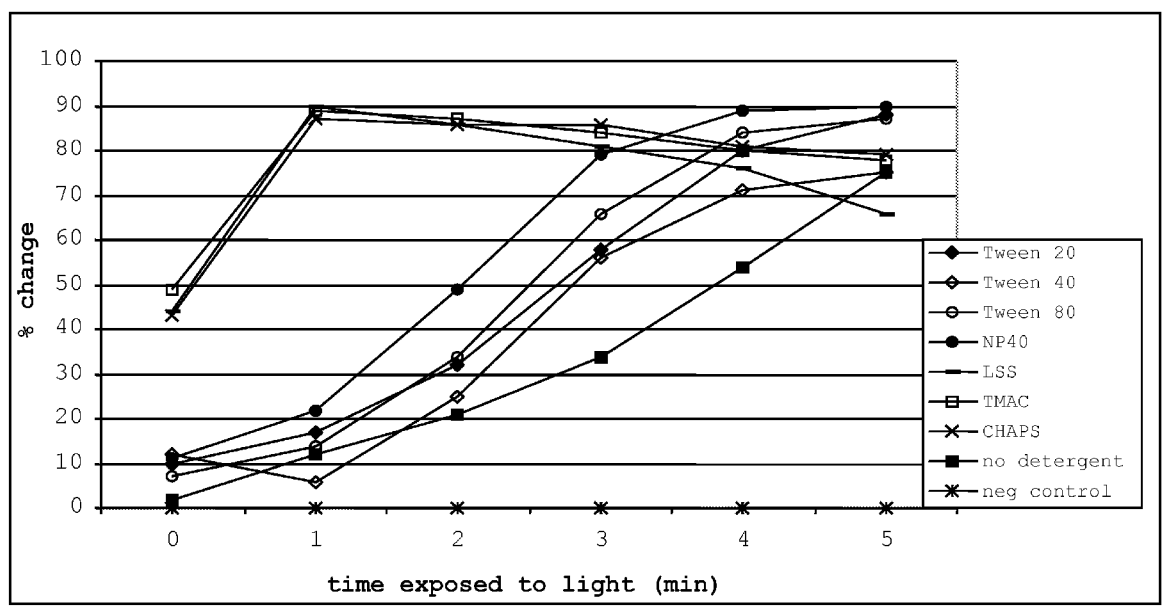
FIG. 1 depicts the percent change in fluorescence intensity as a function of time exposed to light in mixtures that include 3,3' diethylthiacarbocyanine iodide dye, ncPNA, target polynucleotide, and one of a series of surfactants.

The present invention provides methods, compositions and kits for determining the presence or amount of a target molecule by using nucleic acid analogs and a dye in the context of a reaction mixture that has a characteristic optical property. The target molecule can be any macromolecule or small molecule, as further detailed below. Even when the target molecule is a polynucleotide, the nucleic acid analogs used in the present invention may or may not include a sequence that is complementary to a segment or moiety of the target molecule. The present invention, generally speaking, relates to the presence in a reaction mixture of a hybrid nucleic acid molecule that includes the nucleic acid analog if the target molecule is present; and if so, then the optical property of the reaction mixture changes, thereby indicating the presence of the target molecule.

I. GENERAL TECHNIQUES

The practice of the present invention employs, unless otherwise indicated, conventional techniques of molecular biology (including recombinant techniques), microbiology, cell biology, biochemistry, immunology, protein kinetics, and mass spectroscopy, which are within the skill of the art. Such techniques are explained fully in the literature, such as, Sambrook et al., MOLECULAR CLONING: A LABORATORY MANUAL (2d ed., Cold Spring Harbor Press 2000); CELL BIOLOGY: A LABORATORY NOTEBOOK (J. E. Cellis, ed., Academic Press 1998); ANIMAL CELL CULTURE (R. I. Freshney, ed., 1987); METHODS IN ENZYMOLOGY (a series of volumes directed at enzymology protocols that is published by Academic Press, Inc.); HANDBOOK OF EXPERIMENTAL IMMUNOLOGY (D. M. Weir and C. C. Blackwell, eds.); PCR: THE POLYMERASE CHAIN REACTION (Mullis et al., eds., 1994); and the like. Furthermore, procedures employing commercially available assay kits and reagents typically are used according to manufacturer-defined protocols, unless otherwise noted.

II. DEFINITIONS

The term "target molecule" generally refers to a molecule having a nucleic acid sequence or an antigenic determinant or a carbohydrate that is detected using the methods, compositions, or kits disclosed herein. A target molecule can be a macromolecule or a small molecule as those terms are used in the art. In particular, a macromolecule is a polynucleotide, a polypeptide, a carbohydrate, a lipid, or a combination of one or more of these. As a general rule, the molecular mass of a macromolecule is at least about 300 Daltons and can be millions of Daltons. A small molecule is an organic compound having a molecular weight of up to about 300 Daltons.

The term "target nucleic acid sequence" refers to the nucleic acid sequence of a target polynucleotide that hybridizes to a nucleic acid analog or the nucleic acid sequence of an intermediary polynucleotide in a sequence specific manner, for the purpose of detecting the target polynucleotide using the methods, compositions or kits disclosed herein. All or part of the target polynucleotide or intermediary polynucleotide which is at least partially hybridized with the target polynucleotide may form a hybrid with a nucleic acid analog by sequence-specific hybridization, albeit some mismatch may exist depending on the conditions of the reaction mixture. The binding could be by way of Watson-Crick hybridization or sequence specific binding modes yet undescribed. The target nucleic acid sequence may be of any length. In certain instances, the target nucleic acid sequence is preferably less than about 1000 bases, less than about 500 bases, less than about 100 bases, less than about 40 bases, or less than about 24 bases. In other embodiments, the target nucleic acid sequence is greater than about 4, about 5, about 6, about 7, about 8, about 9, about 10, about 12, about 14, about 16, about 18, about 20, about 25, about 30, about 35, about 40, about 45, or about 50 bases in length. In yet other embodiments, the target nucleic acid sequence is preferably greater than about 4 bases and less than about 24 bases in length. In certain embodiments, the target nucleic acid sequence is about 4, about 6, about 8, about 10, about 12, about 14, about 16, about 18, about 20, about 22, or about 24 bases in length. The target nucleic acid sequence may include a protein coding sequence and/or a non-coding sequence (e.g., intergenic spacer sequences regulatory sequences, introns, and the like).

The term "polynucleotide" refers to a polymeric form of nucleotides or nucleotide analogs of any length, either deoxyribonucleotides or ribonucleotides, or analogs thereof, or mixtures thereof. Polynucleotides may be single-stranded, double-stranded, triple-stranded, or multi-stranded to yet greater degrees. The following are non-limiting examples of polynucleotides: a gene or gene fragment, exons, introns, messenger RNA (mRNA), transfer RNA, ribosomal RNA, armored RNA, ribozymes, cDNA, recombinant polynucleotides, branched polynucleotides, plasmids, vectors, nucleic acid probes, primers, amplified DNA, and synthesized DNA. A polynucleotide may contain modified bases, including those that include, without limitation, a methylation, deamination, thiolation, and/or acetylation. The sequence of nucleotides of a polynucleotide may be interrupted by non-nucleotide components, and may include one or more nucleic acid analogs. A polynucleotide may be further modified before or after polymerization, such as by conjugation with a labeling component. The polynucleotide may be an amplified region of a longer sequence of nucleotides. A polynucleotide may be a peptide nucleic acid (PNA) or a chiral PNA or an achiral PNA, among other nucleic acid analogs.

The term "target polynucleotide" refers to a polynucleotide that includes a target nucleic acid sequence. The target polynucleotide may be of any length. In certain instances, the target polynucleotide is preferably less than about 1000 bases, less than about 500 bases, less than about 100 bases, less than about 40 bases, or less than about 24 bases. In other embodiments, the target polynucleotide is preferably greater than about 8, about 9, about 10, about 12, about 14, about 16, about 18, about 20, about 25, about 30, about 35, about 40, about 45, about 50, about 75, about 100, about 150, about 200, about 250, about 300, about 350, about 400, about 450, about 500, or about 1000 bases in length. In yet other embodiments, the target polynucleotide is preferably greater than about 20 bases and less than about 1000 bases in length; more preferably, greater than about 20 and less than about 500; even more preferably, greater than about 20 and less than about 400 bases in length. In certain embodiments, the target polynucleotide is about 50, about 100, about 150, about 200, about 250, about 300, about 350, about 400, about 450, about 500, or about 1000 bases in length. Other lengths are also contemplated. For example, the target polynucleotide may be from 2 to 5 kb in length.

Figure 6A:
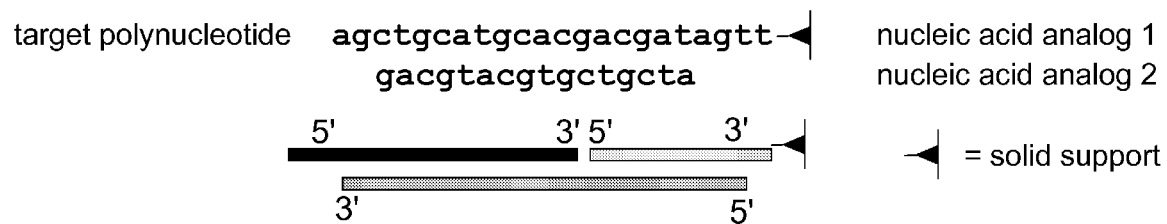
FIGS. 6A-B depict different schemes of capturing and detecting polynucleotide targets, either on a solid substrate or in a liquid.
Figure 6B:
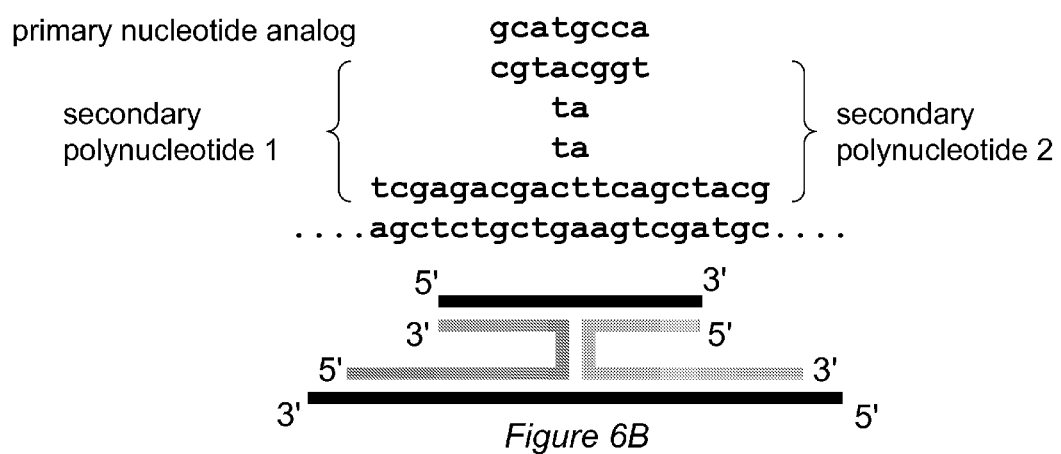

The term "intermediary polynucleotide" refers to a polynucleotide used in an indirect hybridization method for detecting a target polynucleotide. The intermediary polynucleotide includes a portion that is complementary to a target polynucleotide and another portion that is complementary to a nucleic acid or a nucleic acid analog. One example of such intermediary polynucleotide is shown in FIG. 6A. In another embodiment, the intermediary polynucleotide may be employed as a pair. An example of such intermediary polynucleotide is shown in FIG. 6B. Each of the pair of intermediary polynucleotides includes, in the following order, (1) a first segment that is complementary to contiguous segments, respectively, of the target polynucleotide, (2) a second segment that is the complement of the analogous portion of the other intermediary polynucleotide, and (3) a third segment that is complementary to contiguous segments of a nucleic acid, which may or may not be a nucleic acid analog.

"Armored RNA™" refers to an RNA that is ribonuclease resistant due to the encapsidation of the RNA by bacteriophage proteins. "Armored RNA™" is further described, for example, in U.S. Pat. Nos. 6,399,307; 6,214,982; 5,939,262; 5,919,625; and 5,677,124.

The term "nucleic acid analog" refers to any molecule that is described in part by a sequence of bases, as is commonly done for DNA or RNA, which molecule has one or more bases that differ from conventional guanine, thymine, adenosine, cytosine, or uracil, and/or having one or more differences from the conventional phosphoribose of an RNA backbone or the conventional phosphodeoxyribose of a DNA backbone at one or more bases. The nucleic acid analog is preferably greater than about 4 bases in length and less than about 24 bases in length, excluding linkers, amino acids and labels. In other embodiments, the nucleic acid analog may be from about 5 to about 100, from about 8 to about 60, or from about 10 to about 20 bases in length. In another embodiment, the nucleic acid analog is about 6, about 8 about 10, about 12, about 14, about 18, about 22, about 26, about 30, about 35, about 40, or about 45 bases in length, excluding linkers, amino acids and labels. In other embodiments, the target nucleic acid can be at least 4, at least 5, at least 6, at least 7, at least 8, at least 9, at least 10, at least 12, at least 14, at least 15, at least 18, at least 20, at least 25, at least 30, at least 35, at least 40, at least 45, or at least 50 bases in length. Nucleic acid analogs can be chimeric by having a specific type of nucleic acid analog nucleoside in combination with another nucleic acid analog nucleoside, and/or one or more conventional DNA nucleosides or RNA nucleosides.

Exemplary phosphorous modifications useful in creating nucleic acid analogs include chiral phosphorothioate (bridging and non-bridging), phosphorodithioate, chiral methyl phosphonate, chiral phosphoramidate, chiral phosphate trimester, chiral boranophosphate, and chiral phosphoroselenoate. Exemplary linkage modifications include methylenemethylimino (MMI), 3'-amide, 3' achiral phosphoramidate, 3' archiral methylene phosphonate, thioformacetal, and thioethyl ether modifications. Exemplary sugar modifications include 2'-fluoro, 2'-O-methyl, 2'-O-(3-amino)propyl, 2'-O-(2-methoxy)ethyl, 2'-O-2-(N,N-dimethylaminooxy)ethyl (DMAOE), 2'-O-2-[2-(N,N-dimethylamino)ethyloxy]ethyl (DMAEOE), and 2'-O—N,N-dimethylacetamidyl. Classes of analog nucleotides having sugar modifications include N-morpholinophosphordiamidate (Morpholinos); hexose nucleic acid (HNA); threose nucleic acid (TNA), such as those disclosed in Chaput et al., AMER. CHEM. SOC., 125: 856-857 (2003); cyclohexene nucleic acid (CeNA); locked nucleic acid (LNA), having methylene bridges between the 2'-O and 4'-C on the ribofuranose ring of some or all individual nucleotides of a polynucleotide (which methylene bridges function to restrict the flexibility of the polynucleotide and are associated with enhanced stability and hybridization characteristics), such as those disclosed in TRENDS IN BIOTECHNOLOGY 21:74-81 (2003); and tricycle-deoxyribose nucleic acid (tcDNA) modifications. Preferred base modifications include 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clamp, 2,6-diamino purine, and 2,6-diamino thiouracil. A preferred connection modification is an α-deoxyribofuranosyl. Preferred sugar replacement modifications include production of a peptide nucleic acid (PNA) or a chiral PNA or an achiral PNA. Other exemplary nucleic acid analogs include sequence-specific DNA binding minor groove ligands, such as polyamides (containing imidazole (Im), pyrrole (Py), and hydroxypyrrole (Hp)). Nucleic acid analogs can be chimeric, and have multiple different modifications, and can include non-nucleic acid analogs, such as linkers, as are known in the art. Polynucleotides that include analog nucleotides are described as to sequence with respect to its non-modified analog as identified in the accompanying Sequence Listing, with further description of which, if not all, included nucleotides are modified.

The term "photochemical reaction" refers to a reaction that can occur when electromagnetic radiation interacts with matter and initiates the production of new chemical species. Absorption of electromagnetic radiation, typically in the region of the electromagnetic spectrum which ranges from approximately 180 nanometers in the ultraviolet to 800 nanometers in the near infrared, initiate electronic transitions in the absorbing species and result in a temporary change in its electronic structure. This electronically excited species may reemit the energy absorbed via radiationless decay, fluorescent emission, or phosphorescent emission resulting in no change to the original absorber. Alternatively, the electronically activated species can undergo an irreversible electronic change creating a new product molecule or molecules. Also, the electronically excited species can interact with a second molecule with different chemical structure in the sample causing changes in that molecule's electronic structure which in turn can cause reversible or irreversible changes to the second molecule. Products of these photochemically induced reactions can in turn react with other chemically distinct molecules in the sample to initiate other chemical reactions.

The term "reaction mixture" refers to the mixture of at least the following when the polynucleotide is the complement of a target nucleic acid sequence of the target molecule, which, in this case, would be a target polynucleotide: (1) a target polynucleotide; (2) a polynucleotide; and (3) a dye. Alternatively, when the polynucleotide and its complement are unrelated to the target molecule, and instead are attached to a target binding component as part of the reporter complex, the reaction mixture comprises: (1) a target molecule; (2) a target binding component; and (3) a dye.

The term "peptide nucleic acid," or "PNA," includes any nucleic acid analog in which the deoxyribose phosphate backbone of a nucleic acid has been replaced by a synthetic peptide-like backbone, including, for example, n-(2-aminoethyl)-glycine units, such as, without limitation, those disclosed in U.S. Pat. Nos. 5,786,461; 6,357,163; 6,107,470; 5,773,571; 6,441,130, 6,451,968; 6,228,982; 5,641,625; 5,766,855; 5,736,336; 5,719,262; 5,714,331; 5,719,262; and 6,414,112. The purine and pyrimidine bases may be attached by any covalent linkage, including, for example, methylene carbonyl linkages. As used herein, PNA molecules can have additional atoms between the PNA backbone and nucleobase. These analogs include, for example, D-lysine chains, cyclic structures, such as cyclopentane or pyrrolidine rings, and/or chiral substituents, including PNA molecules described in U.S. Pat. No. 6,403,763, U.S. Patent Application US 2003/0162699, and U.S. Patent Application US 2003/0157500. The PNA backbone may include substitutions or extensions in the peptide backbone. PNAs may include peptide-based nucleic acid mimics (PENAMS), such as those disclosed, for example, in U.S. Pat. No. 5,705,333, atoms having unusual chiral centers, such as D-chiral centers and quasi-chiral centers, and atom substitutions in the PNA backbone.

The term "chiral PNA" or "cPNA" refers to a chiral PNA molecule in which at least a portion of the peptide backbone has been modified to include a proline or modified proline side-chain that includes the backbone nitrogen and α-carbon. Non-limiting examples of chiral PNA molecules include those that are disclosed at, for example, U.S. Pat. No. 6,403,763, U.S. Patent Applications US 2003/0162699 and US 2003/0157500.

The term "achiral PNA" or "non-chiral PNA" or "ncPNA" refers to a PNA molecule in which no portion of the peptide backbone has been modified to include a proline or modified proline side chain that includes the backbone nitrogen and α-carbon.

The term "non-PNA nucleic acid analog" refers to a nucleic acid analog in which the backbone is not made up of n-(2-amino-ethyl)-glycine subunits.

The term "locked nucleic acid" or "LNA" refers to a bicyclic nucleic acid in which at least one ribonucleoside is linked between the 2'-oxygen and the 4'-carbon with a methylene group. Non-limiting examples of LNAs are disclosed in TRENDS IN BIOTECHNOLOGY 71:74-81 (2003).

The term "morpholino nucleic acid" or "MNA" refers to a nucleic acid analog in which each backbone monomer is a substituted or unsubstituted six-membered morpholino ring. The morpholino rings are linked by non-ionic phosphorodiamidate linkages. Non-limiting examples of MNAs include those described in U.S. Pat. No. 5,034,506.

The term "threose nucleic acid" or "TNA" refers to a nucleic acid in which the sugar-phosphate backbone is a four-carbon sugar threose in place of the five-carbon sugar ribose.

The term "metal linked nucleic acid" or "MLNA" refers to a nucleic acid sequence in which at least a portion of the ribose phosphate backbone is modified with a transition metal. Non-limiting examples of MLNAs include those MLNAs disclosed at the website of the Wilker Research Group, Purdue University website.

The terms "nucleic acid analog/polynucleotide hybrid" and "polynucleotide/nucleic acid analog hybrid" and "P/TP hybrid" are synonymous and refer to a nucleic acid analog and target polynucleotide hybridized in a sequence-specific manner. Non-limiting examples of nucleic acid analog/polynucleotide hybrids include nucleic acid analog/polynucleotide duplexes and triplexes.

The terms "PNA/polynucleotide hybrid" and "polynucleotide/PNA hybrid" are synonymous and refer to a PNA and polynucleotide hybridized in a sequence-specific manner. Non-limiting examples of PNA/polynucleotide hybrids include PNA/polynucleotide duplexes and triplexes. The PNA may be chiral or non-chiral.

By "complementary" it is meant that a single-stranded nucleic acid analog has the ability to bind a polynucleotide in a base-specific manner. The nucleic acid analog may be synthesized to bind a target polynucleotide, such as a full-length polynucleotide strand or a part thereof. A nucleic acid analog that is "complementary" may have one or more single base-pair mismatches, additions, and/or deletions, but is still capable of hybridizing to the target polynucleotide under the selected hybridization or association conditions. In one embodiment, complementary sequences may hybridize through Watson-Crick base pairing (A-T or A-U and C-G or alternatively pairing with inosine). In a further embodiment, complementary sequences may hybridize through Hoogstein base pairing. In alternative embodiment, complementary sequences may hybridize through formation of a unique dye-PNA-DNA composite. In other words, the dye may function as an accelerator for DNA duplex formation.

The term "hybrid" refers to an association between a dye, nucleic acid analog and a target polynucleotide in a manner that forms a complex and permits detecting a change in an optical property when specific binding occurs versus when specific binding does not occur. It is not known what physical or structural relationship occurs between the dye, nucleic acid analog and the target polypeptide in the hybrid. Without being bound by a particular theory, formation of a duplex, triplex, Watson-Crick base pairing, Hoogstein base pairing, or any other yet undefined binding or association is contemplated herein. As such, the term "hybrid" is not limited to any particular physical or structural relationship between the elements of the hybrid.

By "exactly complementary", it is meant that the single-stranded nucleic acid analog has the ability to hybridize to a target nucleic acid sequence without base mismatches. A nucleic acid analog is not exactly complementary to a target polynucleotide if there is a single base-pair mismatch between the nucleic acid analog and the target polynucleotide.

The term "rate" refers to a change (e.g., of a property of a composition or compound). A rate may be described in terms of a specific rate constant. A rate may be determined by making measurements over a period of time. A rate may be described by making measurements, determined by measurements at two different time points in a process or by making measurements at least three, at least four, or at least five, timepoints. A rate may be determined based on a single measurement and a known quantity, such as a previously known or calculated quantity. A rate may be expressed in quantitative or qualitative terms (e.g., a change is "fast" or "slow"). A rate may be determined by comparing a property or compound to a reference value, or by observation of changes in a given property or compound over time, using standard methods.

As used herein, the term "relative rate" refers to the rate of one process compared to the rate of another process. A "relative rate" may be approximate (e.g., the rate of one process may be "faster" or "slower" than the rate of another process) or quantitative (e.g., comparing measured rate constants of two processes).

As used herein, the term "dye" refers to a first compound that has a measurable optical property or that may be converted to a second compound with a measurable optical property. Preferred dyes include those where the measurable optical property thereof differs in comparison to that of the second compound. Measurable optical properties include, but are not limited to color, absorbance, percent transmittance, fluorescence, reflectance, chemiluminescence, and infrared (IR) spectrum measurements. The dye may exhibit the optical property under certain conditions, such as binding or forming a complex or otherwise being in contact with a target polynucleotide/nucleic acid analog hybrid or, or not binding or forming a complex or otherwise being in contact with a target polynucleotide/nucleic acid analog hybrid.

The term "light reactive dye" means a dye that reacts to light exposure, such that when the light reactive dye is associated in a complex with complementary polynucleotides, at least one of which is a nucleic acid analog, such as a PNA molecule, the light reactive dye confers a property on the complex that, in response to exposure of the complex to light, results in the disassociation of the complex and a corresponding change in optical property of the light reactive dye. In some embodiments, the complementary polynucleotides of the complex may comprise nucleic acid analog and a standard nucleic acid. In other embodiments, the complex may comprise two nucleic acid analogs. Complexes formed between the light reactive dye and complementary polynucleotides comprising at least one nucleic acid analog polynucleotide are referred to herein as "light reactive complexes."

A "hybrid catalyst" refers to a hybrid molecule that is capable of promoting the photodegradation of a dye. The following examples are usefully employed in the present invention: nucleic acid-nucleic acid hybrids, nucleic acid analog-nucleic acid hybrids, nucleic acid analog-nucleic acid analog hybrids. The present invention establishes reaction conditions by which the nucleic acid-nucleic acid hybrids present in any cell lysate, for example, contribute minimally to the catalytic function assigned to any of these hybrids. The same conditions that minimize the ability of the nucleic acid-nucleic acid hybrids to change an optical property also tend to potentiate the activity of the nucleic acid-nucleic acid analog hybrids.

"Sample" refers to a liquid sample of any type (e.g., blood, serum, water, urine, fecal matter, sputum, or lysate or extract of a solid sample), a solid sample of any type (e.g., cells, food, ice, dirt, grain, or material acquired from a surface), an airborne sample of any type, and/or a material embedded in a gel material and/or any solid-phase material, such as agarose, acrylamide, or gelatin.

The term "pathogen" refers to any agent causing a disease, disorder and/or pathological condition and/or symptoms. By way of example, the pathogen may be an organism (or its associated toxin) found in nature, or created in a laboratory, that causes disease in or development of a pathological condition or symptom in, incapacitates, debilitates and/or kills an organism. Pathogens include, but are not limited to, viruses, bacteria, fungi, eukaryotes, and/or prokaryotes; and may function as biological weapons agents, or vectors of infectious diseases; and may spread via water, as in water-borne pathogens, food, as in food pathogens, air or direct skin contact.

The term "biological weapons agent" refers to any organism (or its associated toxin) found in nature or created in the laboratory that is used for the primary purpose of causing disease in, incapacitating, or killing another living organism. Examples of biological weapons agents include, but are not limited to, pathogenic bacteria, fungi, protozoa, rickettsiae, and viruses. The target of a biological weapons agent includes any of humans, animals, and plants, as well as sub-populations thereof.

As used herein, the term "infection" refers to the presence of a pathogen in or on a host. The infection may be dormant or virulent. In one embodiment, the presence of the pathogen is indicated by an alteration in host polynucleotide and/or polypeptide expression. Infection may occur through such routes including, but not limited to, airborne droplets, direct contact, animal or insect vectors, and contaminated food or drink.

As used herein, the term "host-response polynucleotide" refers to a polynucleotide that is altered, or a polynucleotide for which the expression is altered, in a host in response to a stimulus, such as infection, and/or contact by a pathogen.

The term "host" as used herein refers to humans, animals, and plants. The animal may be a mammal. Examples of mammals include, non-human primates, farm animals, sport animals, mice, and rats. Examples of plants include, but are not limited to, dicot or monocot agricultural crops.

As used herein, the term "alkyl," "alkenyl," and "alkynyl" refer to straight-chain, branched-chain and cyclic monovalent substituents, and can be substituted or unsubstituted. Examples include methyl, ethyl, isobutyl, cyclohexyl, cyclopentylethyl, 2-propenyl, 3-butynyl, and the like. Typically, the alkyl, alkenyl and alkynyl substituents contain $C_{1-10}$ (alkyl) or $C_{2-10}$ (alkenyl or alkynyl). Preferably they contain $C_{1-6}$ (lower alkyl) or $C_{2-6}$ (lower alkenyl or lower alkynyl). Examples of alkyl groups include propyl, tert-butyl, and cycloalkyls such as cyclopropyl, cyclobutyl, cyclopentyl, cyclohexyl, and cycloheptyl groups. Examples of alkenyl groups include allyl, crotyl, 2-pentenyl, 3-hexenyl, 2-cyclopentenyl, 2-cyclohexenyl, 2-cyclopentenylmethyl, and 2-cyclohexenylmethyl groups.

As used herein, the terms "heteroalkyl," "heteroalkenyl," and "heteroalkynyl" are similarly defined but may contain one or more O, S or N heteroatoms or combinations thereof within the backbone residue; collectively, the aforementioned terms having the "hetero-" prefix are referred to as "hetero forms."

As used herein, "acyl" encompasses the definitions of alkyl, alkenyl, alkynyl, each of which is coupled to an additional residue through a carbonyl group. Heteroacyl includes the related heteroforms.

"Aromatic" moiety or "aryl" moiety refers to a monocyclic or fused bicyclic moiety such as phenyl or naphthyl; "heteroaryl" refers to monocyclic or fused bicyclic ring systems containing one or more heteroatoms selected from O, S and N. The inclusion of a heteroatom permits inclusion of 5-membered rings as well as 6-membered rings. Thus, typical aryl/heteroaryl systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl, and the like. Because tautomers are theoretically possible, phthalimido is also considered aromatic. Any monocyclic or fused ring bicyclic system that has the characteristics of aromaticity in terms of electron distribution throughout the ring system is included in this definition. Typically, the ring systems contain 5- to 12-ring-member atoms.

Similarly, "arylalkyl" and "heteroarylalkyl" refer to aryl and heteroaryl systems that are coupled to another residue through a carbon chain, including those carbon chains that are substituted or unsubstituted, saturated or unsaturated, typically having one to eight carbon atoms, including hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

As used herein, the term "halogen" and "halo" are used interchangeably and refer to one or more substituents including fluorine, chlorine, bromine, iodine, and astatine.

Examples of substituted hydroxyl and thiol groups include substituted alkyloxy or alkylthio (e.g., $C_{1-10}$ alkyl), such as methyl, ethyl, propyl, isopropyl, butyl, isobutyl, sec-butyl, tert-butyl, pentyl, cyclopropyl, cyclobutyl, cyclopentyl, cyclohexyl, and cycloheptyl, a substituted arylalkyloxy or arylalkylthio (e.g., phenyl-$C_{1-4}$ alkyl, benzyl, or phenethyl). Where there are two adjacent hydroxyl or thiol substituents, the heteroatoms may be connected via an alkylene group such as $O(CH_2)_nO$ and $S(CH_2)_nS$ (where n=1-5).

Examples of substituted hydroxyl groups also include optionally substituted $C_{2-4}$ alkanoyl (e.g., acetyl, propionyl, butyryl or isobutyryl), $C_{1-4}$ alkylsulfonyl (e.g., methanesulfonyl or ethanesulfonyl) and a substituted aromatic and heteroaryl carbonyl group, including benzoyl and pyridinecarbonyl.

Substituents on substituted amino groups may bind to each other to form a cyclic amino group (e.g., 5- to 6-membered cyclic amino, etc., such as tetrahydropyrrole, piperazine, piperidine, pyrrolidine, morpholine, thiomorpholine, pyrrole or imidazole). The cyclic amino group may have a substituent, and examples of the substituents include halogen, nitro, cyano, hydroxy group, thiol group, amino group, carboxyl group, an optionally halogenated $C_{1-4}$ alkyl, an optionally halogenated $C_{1-4}$ alkoxy (e.g., methoxy, ethoxy, trifluoromethoxy, trifluoroethoxy, etc.), $C_{2-4}$ alkanoyl (e.g., acetyl or propionyl), and $C_{1-4}$ alkylsulfonyl (e.g., methanesulfonyl or ethanesulfonyl).

An amino group may also be substituted once or twice (to form a secondary or tertiary amine) with a group such as an optionally substituted alkyl group including $C_{1-10}$ alkyl (e.g., methyl or ethyl propyl); an optionally substituted alkenyl group, such as allyl, crotyl, 2-pentenyl, 3-hexenyl, and the like, or an optionally substituted cycloalkyl group such as cyclopropyl, cyclobutyl, cyclopentyl, cyclohexyl or cycloheptyl. In certain cases, these groups are $C_{1-6}$ alkyl, $C_{2-6}$ alkenyl, or cycloalkyl groups. The amine group may also be optionally substituted with an aromatic or heteroaromatic group, aralkyl (e.g., phenyl $C_{1-4}$ alkyl) or heteroalkyl, for example, phenyl, pyridine, phenylmethyl (benzyl), phenethyl, pyridinylmethyl, or pyridinylmethyl. The heteroaromatic group may be a 5- or 6-membered ring containing 1-4 heteroatoms.

An amino group may be substituted with an optionally substituted $C_{2-4}$ alkanoyl (e.g., acetyl, propionyl, butyryl, and isobutyryl), or a $C_{1-4}$ alkylsulfonyl (e.g., methanesulfonyl or ethanesulfonyl), or a carbonyl- or sulfonyl-substituted aromatic or heteroaromatic ring (e.g., benzenesulfonyl, benzoyl, pyridinesulfonyl and pyridinecarbonyl). The heteroaromatics are as defined above.

Examples of carbonyl groups, sulfinyl groups, or sulfonyl groups include substituted or unsubstituted forms of such groups formed from various hydrocarbyls, such as alkyl, alkenyl and 5- to 6-membered monocyclic aromatic group (e.g., phenyl and pyridyl), as defined above.

The term "salt" is meant to include salts of the active compounds from any acid or base known in the art, as appropriate to the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include (1) any halogen; (2) those derived from an inorganic acid, such as hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acid, or the like; and those derived from relatively nontoxic organic acids, such as acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids, including arginate and the like, and salts of organic acids, including glucuronic or galacturonic acid and the like (see, for example, S. M. Berge et al., J. PHARMA. SCI. 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents. Otherwise, however, the salts are equivalent to the parent form of the compound for the purposes of the present invention.

As used herein, the term "target binding component" refers to a molecule capable of interacting with a target molecule. Target binding components having limited cross-reactivity are generally preferred. In certain embodiments, suitable target binding components include, for example: lectins; receptors; antibodies, including monoclonal antibodies, polyclonal antibodies, and derivatives or analogs thereof, including without limitation, Fv fragments, single chain Fv (scFv) fragments, Fab' fragments, F(ab')$_2$ fragments, single domain antibodies, camelized antibodies and fragments thereof, humanized antibodies and fragments thereof, and multivalent versions of the foregoing. Multivalent versions of target binding components include without limitation: monospecific or bispecific antibodies, such as disulfide stabilized Fv fragments, scFv tandems ((scFV)$_2$ fragments), diabodies, tribodies or tetrabodies, which typically are covalently linked or otherwise stabilized (i.e., leucine zipper or helix stabilized) scFv fragments. Other binding reagents include, for example, template imprinted materials (such as those of U.S. Pat. No. 6,131,580), and organic or inorganic binding elements. In certain embodiments, a target binding component specifically interacts with a single identifying unit of the target molecule, such as an epitope or a sugar or a ligand. In other embodiments, a target binding component may interact with several structurally related epitopes or sugars or ligands.

The term "reporter complex" refers to a first reporter nucleotide sequence, a second reporter nucleotide sequence, and a dye. The first reporter nucleotide sequence and second reporter nucleotide sequence can be covalently bonded together, or not covalently bonded together.

The term "modified target binding component" refers to a target binding component that is covalently modified by at least one component of the reporter complex.

The term "target binding complex" refers to the modified target binding component and the remaining components of the reporter complex.

The term "bridging complex" refers to one or more molecules that link the solid substrate to a target specific portion that binds to a desired target molecule.

The term "antibody" refers to an immunoglobulin, derivatives thereof that maintain specific binding ability, and proteins having a binding domain that is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In certain embodiments, antibodies used with the methods and compositions described herein are derivatives of the IgG class.

The term "antibody fragment" refers to any derivative of an antibody that is less than full-length. In certain embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially produced synthetically. The antibody fragment may optionally be a single chain antibody fragment. Alternatively, the fragment may comprise multiple chains that are linked together, for instance, by disulfide linkages. The fragment may also optionally be a multimolecular complex. A functional antibody fragment will typically comprise at least about 50 amino acids and more typically will comprise at least about 200 amino acids.

As used herein, the term "array" refers to a set of target binding components immobilized onto one or more substrates so that each target binding component is at a known location. Alternatively, the set of target binding components may be in solution, respectively in different receptacles of a microtiter dish, and therefore, located at known locations. In one embodiment, a set of target binding components is immobilized onto a surface in a spatially addressable manner so that each individual target binding component is located at different and identifiable location on the substrate.

The term "camelized antibody" refers to an antibody or variant thereof that has been modified to increase its solubility and/or reduce aggregation or precipitation, similar to that found in a camelid. Camelids produce heavy-chain antibodies consisting only of a pair of heavy chains wherein the antigen binding site comprises the N-terminal variable region or VEH (variable domain of a heavy chain antibody). The VHH domain comprises an increased number of hydrophilic amino acid residues that enhance the solubility of a VHH domain as compared to a VH region from noncamelid antibodies. Camelization of an antibody or variant thereof preferably involves replacing one or more amino acid residues of a non-camelid antibody with corresponding amino residues from a camelid antibody.

The term "chemical handle" refers to a component that may be attached to a target binding complex as described herein so as to facilitate the isolation, immobilization, identification, detection and/or increased solubility of the target binding complex. Suitable chemical handles include, for example, a polypeptide, a polynucleotide, a carbohydrate, a polymer, or a chemical moiety, and combinations or variants thereof.

The term "diabodies" refers to dimeric scFvs. The components of diabodies preferably have shorter peptide linkers than most scFvs and they show a preference for associating as dimers. The term diabody is intended to encompass both bivalent (i.e., a dimer of two scFvs having the same specificity) and bispecific (i.e., a dimer of two scFvs having different specificities) molecules. Methods for preparing diabodies are known in the art. See, e.g., EP 404097 and WO 93/11161.

As used herein, the term "epitope" refers to a physical structure on a molecule that interacts with a target binding component. In exemplary embodiments, epitope refers to a desired region on a target molecule that specifically interacts with a target binding component.

The term "Fab" refers to an antibody fragment that is substantially equivalent to that obtained by (1) digestion of immunoglobulin (typically IgG) with the enzyme papain or (2) reduction of the disulfide bridge or bridges joining the two heavy chain pieces in the F(ab')$_2$ fragment. The heavy chain segment of the Fab fragment is the Fd piece. Such fragments may be enzymatically or chemically produced by fragmentation of an intact antibody, recombinantly produced from a gene encoding the partial antibody sequence, or wholly or partially synthetically produced. Methods for preparing Fab fragments are known in the art. See, e.g., Tijssen, PRACTICE AND THEORY OF ENZYME IMMUNOASSAYS (Elsevier, Amsterdam, 1985).

The term "F(ab')$_2$" refers to an antibody fragment that is substantially equivalent to a fragment obtained by digestion of an immunoglobulin (typically IgG) with the enzyme pepsin at pH 4.4. Such fragments may be enzymatically or chemically produced by fragmentation of an intact antibody, recombinantly produced from a gene encoding the partial antibody sequence, or wholly or partially synthetically produced.

The term "Fv" refers to an antibody fragment that consists of one VH and one VL domain held together by noncovalent interactions. The term "dsFv" is used herein to refer to an Fv with an engineered intermolecular disulfide bond to stabilize the VH-VL pair. Methods for preparing Fv fragments are known in the art. See, e.g., Moore et al., U.S. Pat. No. 4,462,334; Hochman et al., BIOCHEMISTRY 12:1130 (1973); Sharon et al., BIOCHEMISTRY 15:1591 (1976); and Ehrlch et al., U.S. Pat. No. 4,355,023.

The term "immunogen" refers to compounds that are used to elicit an immune response in a human or an animal, and is used as such herein. Many techniques used to produce a desired target binding component, such as the phage display methods described below, do not rely wholly, or even in part, on immunizations. Nevertheless, these methods use compounds containing an "epitope," as defined above, to select for and clonally expand a population of target binding components specific to the "epitope." These in vitro methods mimic the selection and clonal expansion of immune cells in vivo. Therefore, the compounds containing the "epitope" that is used to clonally expand a desired population of phage and the like in vitro are embraced within the definition of "immunogens." Similarly, the terms "hapten" and "carrier" have specific meaning in relation to standard immunization protocols. In that context, and as used herein, a "hapten" is preferably a small molecule that contains an epitope, but is incapable of serving as an immunogen by itself. Therefore, to elicit an immune response to the hapten, the hapten is preferably conjugated with a larger carrier, such as bovine serum albumin or keyhole limpet hemocyanin, to produce an immunogen. An immune response would recognize the epitope on the hapten, but would not recognize any epitopes that may be on the carrier.

In the in vitro methods described herein for preparing the desired binding reagents, traditional "haptens" and "carriers" typically have their counterpart in epitope-containing compounds affixed to suitable substrates or surfaces, such as beads and tissue culture plates.

The terms "single-chain Fvs" and "scFvs" refers to recombinant antibody fragments consisting of only the variable light chain (VL) and variable heavy chain (VH) covalently connected to one another by a polypeptide linker. Either VL or VH may be the $NH_2$-terminal domain. The polypeptide linker may be of variable length and composition so long as the two variable domains are bridged without function-defeating steric interference. In exemplary embodiments, the linkers are comprised primarily of stretches of glycine and serine residues with some glutamic acid or lysine residues interspersed for solubility. Methods for preparing scFvs are known in the art. See, e.g., PCT/TJS/87/02208 and U.S. Pat. No. 4,704,692.

The term "single domain antibody" or Fd refers to an antibody fragment comprising a VH domain that interacts with a given antigen. An Fd does not contain a VL domain, but may contain other antigen-binding domains known to exist in antibodies, such as the kappa and lambda domains. Methods for preparing Fds are known in the art. See, e.g., Ward et al., NATURE 341:644-646 (1989) and EP 0368684.

The term "single chain antibody" refers to an antibody fragment that comprises variable regions of the light and heavy chains joined by a flexible linker moiety. Methods for preparing single chain antibodies are known in the art. See, for example, U.S. Pat. No. 4,946,778 to Ladner et al.

The term "triabody" refers to trivalent constructs comprising 3 scFv's, and thus comprising 3 variable domains (see, e.g., Iliades et al., FEBS LETT. 409(3):437-41 (1997)). This term also refers to molecules that comprise three variable domains having the same specificity, or three variable domains wherein two or more of the variable domains have different specificities.

The term "tetrabody" refers to engineered antibody constructs comprising four variable domains (see, e.g., Pack et al., J. MOL. BIOL. 246:28-34 (1995) and Coloma and Morrison, NAT. BIOTECHNOL. 15:159-63 (1997)). This term also refers to molecules that comprise four variable domains having the same specificity, or four variable domains wherein two or more of the variable domains have different specificities.

The term "VH" refers to a heavy chain variable region of an antibody.

The term "VL" refers to a light chain variable region of an antibody.

The term "optical property" refers to an intrinsic property of a material that can be observed when the material interacts with electromagnetic radiation in the region of the electromagnetic spectrum that ranges from approximately 180 nanometers in the ultraviolet to 40 micrometers in the infrared. Observable optical properties include, but are not limited to absorption of specific wavelengths of electromagnetic radiation, or absorption of specific wavelengths of electromagnetic radiation followed by emission at other specific wavelengths. Measuring such optical properties is well known in the art and uses commercially-available UV-VIS spectrometers and fluorophotometers. In the particular case of chiral molecules, the absorption of polarized electromagnetic radiation may also be measured by techniques such as Polarimetry and Circular Dichroism.

The term "observing" means detecting a change in a property or value, either directly or indirectly, by means of visual observation, instrumentation, or receipt of data. As used herein, the terms "observing" and "detecting" are synonymous.

Observable optical properties can also include chemical changes that happen to the sample when it absorbs electromagnetic radiation. Absorption of electromagnetic radiation may initiate an electronic rearrangement in the absorbing species and result in a change in its chemical reactivity or structure, or this electronically-activated species may interact with another molecule in the sample causing its structure or reactivity to change. In either of these cases, changes could occur in the absorption or emission spectra of the sample. Also, such changes could result in the appearance or disappearance of one of the materials in the reaction mixture. Such changes could therefore be measured by any of the aforementioned photometric methods.

III. FURTHER SUMMARIZATION OF THE EMBODIMENTS

The present invention relates in a first embodiment to a method of detecting a target polynucleotide in a sample. Preferably, the method includes producing a reaction mixture comprising a sample that may or may not contain a target polynucleotide, a nucleic acid or a nucleic acid analog that is immobilized to a solid substrate and which is complementary to a portion of the target polynucleotide, and a light reactive dye capable of forming a light reactive complex with the target polynucleotide, if present in the sample, and a complementary nucleic acid analog. Preferably, the nucleic acid or the nucleic acid analog is at least partially complementary to a segment of the target polynucleotide. The method may further include the step of isolating the solid substrate based on a property of the solid substrate. The method may further comprise the step of washing the solid substrate with a wash solution comprising the light reactive dye. Another step of the method may involve exposing the reaction mixture, including the solid substrate to a light under conditions sufficient to elute the target polynucleotide from the solid substrate. The light also may serve to activate the reaction that causes the change in the optical property of the reaction mixture. Yet another aspect of the method involves observing the optical property of the reaction mixture at least once after exposure to the light. Preferably, the reaction mixture has an optical property that changes in response to the light exposure if the first nucleic acid or first nucleic acid analog and the target polynucleotide are present therein, and wherein the dye is the compound of formula (I), or a salt or ester thereof, as described elsewhere in this specification. The present invention further provides for correlating the detecting of the target polynucleotide with the resultant change in the optical property of the reaction mixture.

Although applicants are not asserting any particular theory or mechanism by which the method set forth here works, evidence has been gained regarding the chemical reaction of oxidation that appears to be associated with at least one of the dyes usefully employed in the diagnostic test. Accordingly, the change in the optical property noted as a reporter of certain recognition-based activity of nucleic acids and binding pair type molecules correlates with a chemical change in the dye. Other mechanisms may be in play in the alternative or in addition. Suffice to say that when the aforementioned components of a reaction mixture are combined followed by a light exposure for activation, the optical property is commonly seen with a wide number of cyanine dyes.

A part of the present invention is the observation of the reaction mixture to determine whether the optical property has changed. Preferably, one will observe the reaction mixture at least twice.

In one embodiment, the optical property includes a first optical property that diminishes after exposure to the light and a second optical property that increases after exposure to the light. Typically, the property that diminishes is inherent to the reaction mixture, and reliably occurs to the extent that the reaction mixture includes a nucleic acid hybrid and dye, where the nucleic acid hybrid is composed of any pair-wise combination of a nucleic acids and nucleic acid analogs. Upon the diminishing optical property, the reaction mixture, contained in a vessel, further comprises a substance that delivers the second optical property; alternatively, the second optical property is contributed by a substance applied to the vessel itself, for example. The substance that contributes this second optical property may or may not be a soluble dye.

In another embodiment, the reaction mixture includes a detergent. The detergent has multiple functions, including stabilizing the dye, apparently, and lysing cells for study. Where a sample includes intact cells prior to being in contact with the detergent, the cell lyses and renders its genetic material, for example, available for study.

The reaction mixture in a further embodiment is directed at a reaction mixture that includes an achiral peptide nucleic acid. A similarly preferred alternative are those reaction mixtures that include a chiral peptide nucleic acid.

In another embodiment, the length of the target polynucleotide is greater than about 50 bases.

In yet another embodiment, the reaction mixture further comprises a second nucleic acid, wherein at least a portion of the second nucleic acid is complementary to a portion of the first nucleic acid that is not complementary to the target polynucleotide. This reaction mixture further comprises a third nucleic acid, and wherein one portion of the third nucleic acid is complementary to a portion of the target polynucleotide that is not complementary to the first nucleic acid and wherein another portion of the third nucleic acid is complementary to a portion of the second nucleic acid that is not complementary to the first nucleic acid. Preferably, the first part and the second part of the nucleic acid analog do not overlap.

The nucleic acid analog used in the context of the present invention is greater than about 4 bases in length and less than about 24 bases in length. In another embodiment, the nucleic acid analog is about 12 nucleic acid bases in length. In a further embodiment, the nucleic acid analog is 17 nucleic acid bases in length.

The present method also includes immobilizing the target polynucleotide and the nucleic acid analog on a solid substrate. In a preferred aspect, the nucleic acid analog is attached to a solid substrate.

In additional embodiment, the present method includes immobilizing and releasing the target polynucleotide and the nucleic acid analog from a solid substrate, as described in more detail in Section V below. In one aspect, the nucleic acid analog is attached to a solid substrate.

In one embodiment, the dye is a compound of formula (I), wherein $R_1$, $R_2$, and $R_3$ are hydrogen or hydrophobic alkyls, $R_4$ through $R_{13}$ are hydrogen, and Y is sulfur. In a second embodiment, the dye is of formula (I), wherein n is 1. More preferably, the dye is of formula (I), wherein n is 1; and wherein Y is sulfur or —$CR_{12}$=$CR_{13}$—. Even more preferably, the dye is of formula (I), wherein n is 1; wherein Y is sulfur or —$CR_{12}$=$CR_{13}$—; and wherein $R_1$ and $R_2$ are each independently selected from the group consisting of alkyl and alkenyl.

Yet another embodiment relates to a method of detecting a target polynucleotide in a sample, which includes producing a reaction mixture comprising the sample, a nucleic acid analog that is complementary to a target nucleic acid sequence of the target polynucleotide, and a dye; exposing the reaction mixture to a light; and observing the absorbance of the reaction mixture at least once. Preferably, the reaction mixture has an absorbance that changes if the target polynucleotide and the nucleic acid analog form a hybrid therein. Also preferably, the dye is the compound of formula (I), as set forth elsewhere in this specification. This embodiment further includes correlating the detecting of the target polynucleotide with the resultant change in the optical property of the reaction mixture. What is observed is the potential change in the optical property of the reaction mixture, which correlates with a chemical change in the dye.

The present invention also relates to a composition that includes a surfactant and a dye according to formula (I) or formula (II) or formula (III), or a salt thereof, as set forth elsewhere here.

The inventive composition can further include a nucleic acid analog; or target polynucleotide.

Yet another embodiment is a kit for detecting a target polynucleotide, which includes one or more nucleic acid analogs at least partially complementary to a target nucleic acid sequence of said target polynucleotide; one or more dyes; one or more surfactants; and instructions that relate to the method set forth herein above.

Another embodiment is a reporter complex that includes a first polynucleotide, a second polynucleotide, and a dye, wherein the first polynucleotide and the second polynucleotide form a hybrid and the reporter complex has an optical property that changes in response to exposure to a light stimulus. The hybrid used in the reporter is attached to a target binding component, which target binding component is selected from the group consisting of an antibody or fragment thereof, a lectin, or a receptor, among other selective binding agents. For example, aptamers, molecular imprints, and avimers may all be used in the context of the present invention. In a particularly preferred use, the polypeptide and the nucleic acid analog are immobilized on a solid substrate. In another embodiment, a second polynucleotide may be a nucleic acid analog. The second nucleic acid analog may be the same as or different from the first nucleic acid analog. The second nucleic acid analog may be bound to a solid substrate or may be in solution not be bound to a solid substrate. Alternatively, the reporter may be a single polynucleotide that forms a hairpin.

The present invention also relates to a method for detecting a target molecule in a sample, in which the target molecule and a target binding component bind one another with substantial specificity including combining the sample, the target binding component, a first polynucleotide, and a second polynucleotide in a reaction mixture in a vessel. Preferably, the first polynucleotide and second polynucleotide form a hybrid and are in contact with the target binding component. Also preferably, at least one of the target binding component, first polynucleotide, and second polynucleotide, or the target molecule are attached to a solid surface. The method also includes washing the reaction mixture; and combining the reaction mixture components that are immobilized on the solid substrate with dye, whereupon the reaction mixture has an optical property that changes if the sample includes the target molecule and it and the target binding component bind one another. A further aspect includes exposing the reaction mixture to light; and observing the optical property of the reaction mixture at least once. Again, this method is used with one of the dyes disclosed elsewhere, namely a compound of formula (I).

Another aspect of the present invention is a catalytic hybrid that includes two polynucleotides or a polynucleotide and a nucleic acid analog or two nucleic acid analogs that together form the hybrid, or a single polynucleotide or nucleic acid analog or chimeric structure that forms an internally complementary hairpin structure, wherein the hybrid catalyses a chemical reaction of a dye upon exposure to a light stimulus. The dye that the catalytic hybrid acts upon has been well-described here, namely a compound of formula (I).

For each of the methods disclosed here, the quantity of the target polynucleotide is determined by comparing the observed optical property as compared to a reference.

IV. METHODS OF DETECTING POLYNUCLEOTIDES

The present invention relates to methods, compositions and kits for determining the presence or amount of a target polynucleotide having a target nucleic acid sequence.

In one embodiment, (i) a sample for testing for the presence or amount of a target polynucleotide, (ii) a polynucleotide that binds a target nucleic acid sequence of the target polynucleotide in a sequence-specific manner, and (iii) a dye are combined to produce a reaction mixture that has an observable optical property that can change over time. If the target polynucleotide is present, then it and the polynucleotide will form a hybrid (referred to herein as the "P/TP" hybrid; if the polynucleotide is a nucleic acid analog, then the hybrid is referred to as a NAA/TP). The rate of change in the optical property of the mixture is preferably different in the presence and absence of the P/TP hybrid. In one aspect of the invention, a light stimulus is applied to the mixture. The light stimulus when so applied may serve to activate the reaction that results in a change in the optical property. The change in the optical property of the reaction mixture (i.e., the dye disappearing) does not occur in the absence of the light stimulus; the activation provided by the light stimulus is correlated with an increase in the rate of change of the optical property of the reaction mixture.

The rate of change in the optical property of the mixture is preferably compared to a reference value characteristic of the rate of change of the optical property in a similar mixture containing a known amount (which can be a zero amount) of the P/TP hybrid to determine a relative rate of change in the optical property. The relative rate of change in the optical property of the mixture is correlated with the presence or amount of the target polynucleotide in a sample to determine the presence or amount of target polynucleotide in the sample.

An alternative method substitutes the comparison of rates of change to an observation of the optical property after exposure of the reaction mixture to a light stimulus. One can conclude that the target polynucleotide is present to the extent that an observable change in the optical property occurs after the light stimulus exposure. One can also approximate the amount of the target polynucleotide that is present in the sample by comparing the optical property of the light-stimulus exposed reaction mixture after or upon a minimal or certain incubation time to a standard chart that displays the observable optical property as it will appear by the minimal or at the certain time. The standard chart is preferably generated by conducting the detection method with samples having known amounts of the target polynucleotide, memorializing the standard resultant state of optical property by, for example, taking color or black and white photographs of the mixtures after the minimal or at the certain time of incubation, and assembling the standard chart using the memorialized record of the state of the optical property of the mixture. Of course, one must take care that the memorialization as to quality (color) and/or quantity (intensity) is substantially accurate. Alternatively, the values of the standard chart can be generated by an equation.

A reference value can be a value characteristic of a property of a composition or compound having a known characteristic. For example, in various embodiments, a reference value can be determined using a mixture that does not contain an P/TP hybrid; contains a known amount of an P/TP hybrid; or is a reaction mixture from which one or more components (e.g., a nucleic acid analog, a target polynucleotide, or a dye) has been omitted, each of which are "controls" of the inventive method. In some instances, the reference value may be a known quantity or a measured quantity. Further nonlimiting examples of reference values include a value characteristic of an optical property of a mixture that has not been exposed to light stimulus, or, in an alternative embodiment, an optical property of a mixture that has been exposed to light stimulus. The aforementioned examples are for illustration and are not intended to limit the methods, and other examples will be apparent to the practitioner guided by this disclosure. It will be appreciated that a reference value may be, but need not necessarily be, empirically determined. For example, if it is known that the optical properties of a composition containing a dye do not change, or change minimally, in the absence of the P/TP hybrid, the reference value may be calculated or inferred and not measured. The reference value may be a constant. Although in some cases it may be convenient to assay a "control" sample concurrently with test samples, in certain embodiments of the method it is not necessary to do so. A reference value can be determined at one time point, and the value recorded for comparison at later time points as in the standard chart noted above. It will be understood that the aforementioned examples are for illustration and not limitation.

In one aspect, the reference value is characteristic of the rate of change in the optical property of a similar mixture containing no P/TP hybrid. In one embodiment, the reference value may be characterized by the optical property contributed by the dye prior to the combination of all the components in the mixture. Alternatively, the reference value can be external to the mixture, as in a color affixed to the vessel in which the reaction mixture is located. In another embodiment, the reference value may be characterized by the optical product of the reaction. For embodiments in which the mixture is exposed to light stimulus, the reference value may be characteristic of the optical property of the dye or mixture containing the dye prior to applying the light stimulus. It is not a requirement of the present invention that the reference value is necessarily determined by preparing one or more control samples that are included in separate mixtures and otherwise treated substantially identically as the experimental sample. In addition, it is understood that the reference value may be a constant.

The present invention is further directed to methods in which (i) a sample containing, or not containing, or possibly containing a target polynucleotide, (ii) a nucleic acid analog that binds a target nucleic acid sequence of the target polynucleotide in a sequence-specific manner, and (iii) a dye are preferably combined to form a mixture. A light stimulus is preferably applied and the intensity of an optical property of the mixture is observed. In one embodiment, the decrease in intensity of the mixture is correlated to the presence or amount of target polynucleotide in the sample. Alternative methods for observing the reaction include detection of the product of the photochemical reaction or detection of a previously hidden, masked or quenched component.

In certain embodiments, a dye preferably exhibits an initial color change when in the presence of a P/TP hybrid. Following the initial color change, the color of the mixture decreases until the mixture becomes substantially clear (i.e., lacks or nearly lacks color). The rate of the change in the optical property corresponding to the change of the mixture from the presence of a color to less color or the substantial lacking of color is preferably measured. The rate of change in the optical property can thereby be determined.

In still other methods, a sample and a non-PNA nucleic acid that is complementary to a target nucleic acid sequence in a target polynucleotide are combined with a dye to form a mixture. The mixture has a different optical property in the presence or absence of a P/TP hybrid. A change in the optical property of the mixture correlates to the presence of a target nucleic acid sequence.

In another embodiment of the invention, the time required to reach a specific change in an optical property is measured, and the percent change thereof is preferably calculated. Alternatively, the change in the optical property at a specific time point can also be measured, or merely observed where an approximate determination will suffice. For example, if the amount of target polynucleotide in a sample is known, the measured optical property at a specific time can be employed in assessing the relative amount of the target polynucleotide in a second sample of unknown target polypeptide content. By observing the optical property change at the specific time and comparing it to the characteristic of the known sample at the same point in the reaction the observer can conclude that the second sample contains a greater, about the same, or lesser amount or concentration of the target polypeptide as exists in the known sample. The amount or quantity of the target nucleic acid could thus be determined in a binary fashion, and the amount as well, albeit to an approximation or a comparative value of lesser or more.

A. Dyes

A group of related dyes are preferably used in the methods hereof to detect the presence or amount of a target polynucleotide.

In one embodiment, the preferred dye is a compound that is represented by the formula (I), or a salt or betaine thereof:

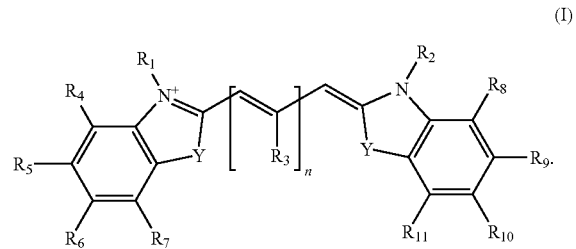

In formula (I), independently at each occurrence, $R_1$ and $R_2$ are each independently selected from hydrogen, alkyl, alkenyl, alkynyl, heteroalkyl, heteroalkenyl, heteroalkynyl, aryl, acyl, heteroacyl, heteroaryl, hydroxyl, alkoxy, carbonyl, sulfinyl, sulfonyl, and amino groups;

$R_3$ is selected from the group consisting of hydrogen, alkyl, alkenyl, alkynyl, aryl, heteroalkyl, heteroalkenyl, heteroalkynyl, aryl, acyl, heteroacyl, heteroaryl, aryl, alkyl, heteroarylalkyl, hydroxyl, alkoxy, halo, carbonyl, sulfinyl, sulfonyl, and amino groups;

$R_4$, $R_5$, $R_6$, $R_7$, $R_8$, $R_9$, $R_{10}$, $R_{11}$, $R_{12}$, and $R_{13}$ are each independently selected from the group consisting of hydrogen, halogen, alkyl, alkenyl, alkynyl, heteroalkyl, heteroalkenyl, heteroalkynyl, aryl, acyl, heteroacyl, heteroaryl, aryl, alkyl, heteroarylalkyl, hydroxyl, alkoxy, carbonyl, sulfinyl, sulfonyl; wherein n is 0, 1, 2, 3, 4, or 5; and Y is selected from the group consisting of —$C_{12}$=$CR_{13}$—, sulfur, nitrogen, and oxygen. In one embodiment, a dye is the compound of formula (I), wherein Y is —$C_{12}$=$CR_{13}$—, sulfur, or oxygen. In yet another embodiment, a dye is the compound of formula (I), wherein Y is sulfur; or wherein Y is $C_{12}$=$CR_{13}$—; or wherein Y is oxygen.

In another embodiment, the dye is preferably a compound that is represented by the formula (II), or a salt or ester thereof:

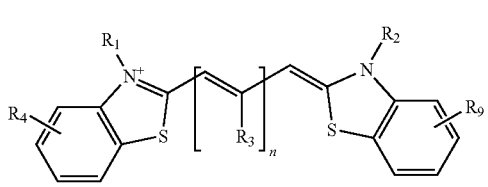

(II)

In formula (II), independently at each occurrence, $R_1$ and $R_2$ are each independently selected from $C_1$-$C_6$ alkyl, $C_2$-$C_6$ alkenyl, and $C_2$-$C_6$ alkynyl;

$R_3$ is selected from the group consisting of hydrogen, $C_1$-$C_6$ alkyl, $C_2$-$C_6$ alkenyl, and $C_2$-$C_6$ alkynyl, $C_6$-$C_{10}$ aryl, hydroxyl, alkoxy, carbonyl, sulfinyl, sulfonyl, and amino groups;

n is 1 or 2;

$R_4$ and $R_9$ are each independently selected from the group consisting of H, $C_1$-$C_6$ alkyl, $C_2$-$C_6$ alkenyl, $C_2$-$C_6$ alkynyl, $C_6$-$C_{10}$ aryl, hydroxyl, alkoxy, halo, carbonyl, sulfinyl, sulfonyl, and amino groups.

In a further embodiment, the dye is a compound that is represented by the formula (III), or a salt or ester thereof:

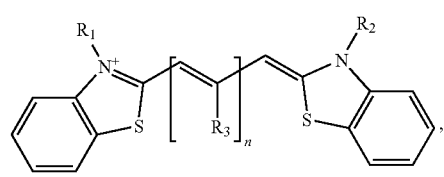

(III)

In formula (III), independently at each occurrence:

$R_1$ and $R_2$ are each independently selected from $C_1$-$C_6$ alkyl and $C_2$-$C_6$ alkenyl;

$R_3$ is selected from the group consisting of hydrogen and methyl;

n is 1 or 2.

In yet other embodiments, the dye is preferably selected from the following compounds:

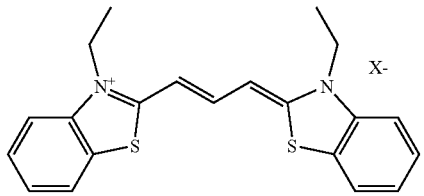

3,3'-Diethylthiacarbocyanine

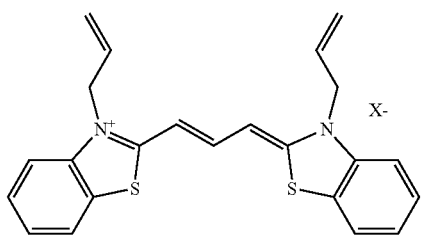

3,3'-Diallylthiacarbocyanine

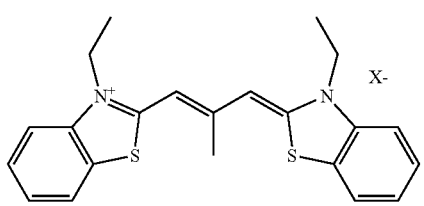

3,3'-Diethyl-9-methylthiacarbocyanine

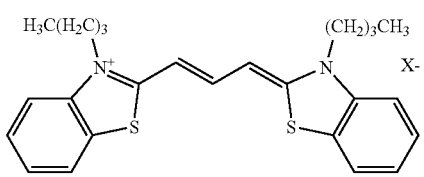

3,3'-Dibutylthiacarbocyanine

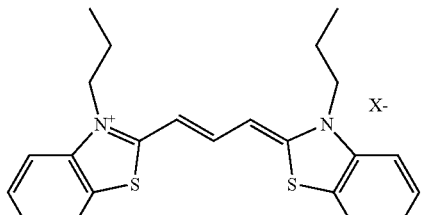

3,3'-Dipropylthiacarbocyanine

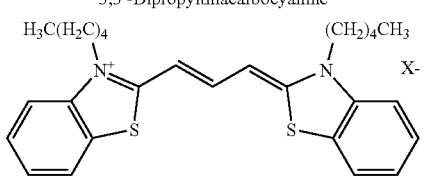

3,3'-Dipentylthiacarbocyanine

-continued

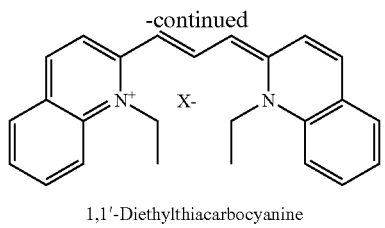

1,1'-Diethylthiacarbocyanine where X- is an anion. More preferably, the anion is a halogen; yet more preferably, the anion is iodide.

In one embodiment of formula (I, II, and III), n is 0.
In another embodiment of formula (I, II, and III), n is 1.
In another embodiment of formula (I, II, and III), n is 2.
In yet another embodiment of formula (I, II, and III), n is 3.

In one embodiment of formula (I, II, and III), $R_1$ and $R_2$ are each independently selected from group consisting of hydrogen, alkyl, alkenyl, alkynyl, heteroalkyl, heteroalkenyl, heteroalkynyl, aryl, and heteroaryl.

In another embodiment of formula (I, II, and III), $R_1$ and $R_2$ are each independently selected from group consisting of alkyl, alkenyl, alkynyl, heteroalkyl, heteroalkenyl, and heteroalkynyl.

In another embodiment of formula (I, II, and III), $R_1$ and $R_2$ are each independently selected from group consisting of alkyl, alkenyl, and alkynyl.

In another embodiment of formula (I, II, and III), $R_1$ and $R_2$ are each independently alkyl.

In one embodiment of formula (I, II, and III), $R_3$ is selected from the group consisting of hydrogen, alkyl, alkenyl, alkynyl, heteroalkyl, heteroalkenyl, and heteroalkynyl.

In one embodiment of formula (I, II, and III), $R_3$ is selected from the group consisting of alkyl, alkenyl, and alkynyl.

In one embodiment of formula (I, II, and III), $R_3$ is alkyl.

The compounds in the following list are within the scope of formulas (I-III. Nevertheless, because they did not perform optimally under the conditions described in Example 4, the dyes of this list are excluded from use in accordance with one aspect of the invention: 3,3'-Diethylthiacyanine; 3-Ethyl-9-methyl-3'-(3-sulfatobutyl) thiacarbocyanine; 3,3'-Dimethyloxacarbocyanine; 3-Carboxymethyl-3',9-diethyl-5,5'-dimethylthiacarbocyanine; 3,3'-Diethylthiadicarbocyanine; 3,3'-Diethylthiatricarbocyanine; 3,3'-Diethyloxacarbocyanine; 3,3'-Diethyloxadicarbocyanine; 3,3'-Dipropylthiadicarbocyanine; 3,3'-Dipropyloxacarbocyanine; 3,3'-Dihexyloxacarbocyanine; 3,3'-Diethyl-2,2'-oxathiacarbocyanine; 1,1'-Diethyl-2,2'-cyanine; 1,1'-Diethyl-2,4'-cyanine; 1,1'-Diethyl-4,4'-carbocyanine; 1,1'-Diethyl-3,3,3',3'-tetramethylindocarbocyanine; 1,1'-Dipropyl-3,3,3',3'-tetramethylindocarbocyanine; [5-[2-(3-Ethyl-3H-benzothiazol-2-ylidene)-ethylidene]-4-oxo-2-thioxo-thiazolidin-3-yl]-acetic acid; 1-Butyl-2-[3-(1-butyl-1H-benzo[cd]indol-2-ylidene)-propenyl]-benzo[cd]indolium; 5,6-Dichloro-2-[3-(5,6-dichloro-1,3-diethyl-1,3-dihydro-benzimidazol-2-ylidene)-propenyl]-1,3-diethyl-3H-benzimidazolium; 1,3,3-Trimethyl-2-(2-[2-phenylsulfanyl-3-[2-(1,3,3-trimethyl-1,3-dihydro-indol-2-ylidene)-ethylidene]-cyclohex-1-enyl)-vinyl)-3H-indolium; 4,5,4',5'-Dibenzo-3,3'-diethyl-9-methyl-thiacarbocyanine; and Thiazole orange.

Additionally, in accordance with another aspect of the invention 3,3'-diethylthiacarbocyanine iodide is also excluded from use with respect to the present invention.

Suitable dyes can be identified using any of a variety of screening methods. The suitability of a dye is a function of its ability to contribute an optical property to the reaction mixture, as described here, which optical property changes in response to and preferably, to the extent of the presence of a hybrid between either (1) a nucleic acid analog ("NAA") and a nucleic acid ("NA"), i.e., an NAA/NA; or (2) between two complementary NAs, i.e., a NA/NA. By way of example and not limitation, a NAA/NA, or a NA/NA, or a P/TP (collectively referred to as the "hybrid") is prepared for identifying suitable dyes. Preferably, the combination includes other components and is maintained in conditions to promote formation of the hybrid, using such components and conditions that are well known in the art. Suitable conditions and components are described herein. The candidate dye is then preferably added; more preferably, the candidate dye is added to separate aliquots of the combination, such that the dye is present in the separate aliquots at varying concentrations. Yet more preferably, a detergent, or a detergent and an alcohol, is added. The order of addition is not critical; the components can be added in any order. Once the reaction mixture is formed, a light stimulus is preferably applied, although not necessarily. The rate of change in the optical property over time is then determined. This rate is compared to a reference value characteristic of the rate of change in optical property of the reaction mixture in the absence of the hybrid. Example 4 illustrates one method for screening dyes for suitability for the inventive methods disclosed herein.

In certain embodiments, the reference value is characteristic of the absence of the target polynucleotide or the presence of the target polynucleotide, which can be single-stranded or double-stranded. In other embodiments, the reference value is characteristic of a non-zero concentration of the target polynucleotide. Preferably, the reference values employed include those characteristic of a zero and at least one non-zero concentration of the target polynucleotide, respectively.

In certain embodiments, the change in optical property can be the loss of intensity of the optical property. Dyes that contribute an optical property to the reaction mixture are particularly preferred, where the mixture exhibits a different rate of change in optical property over time compared to a reference value. The relative rate of change in the optical property of the mixture is correlated with the presence or amount of the target polynucleotide.

Alternatively, dyes that contribute an optical property to the reaction mixture, where the reaction mixture changes color in the presence of an NAA/NA hybrid, are preferably selected. Preferably, the nucleic acid analog used in the context of a color changing optical property is a non-PNA variety. Such nucleic acid analogs include, without limitation, an LNA, TNA, MLNA, and a morpholino nucleic acid.

B. Designing Nucleic Acid Analog Sequences

For use in the present invention, nucleic acid analogs may be designed to be complementary, but possibly including some mismatched bases, additions or deletions, or be exactly complementary to a nucleic acid target.

The sequence of the nucleic acid analogs or target polynucleotides may be designed in a variety of ways. By way of example and not limitation, the nucleic acid analogs or their respective complementary polynucleotides may be designed to have sequences based on known primers used for PCR-based amplification and detection of specific target sequences. The nucleic acid analog may also be designed to be complementary or exactly complementary to any target nucleic acid sequence of the target polynucleotide. Alternatively, the nucleic acid analog may be designed to have a one base mismatch or a two base mismatch. In certain embodiments, the sequence of the nucleic acid analog may be based on the sequence of PCR primers used to detect polynucleotides associated with pathogens, the presence of a pathogen in a host, a disease gene, a genetic condition, or a genetic change associated with a physiological change or condition. The nucleic acid analog may also be complementary or exactly complementary to all or part of the sequence encoding the active or functional domains of a protein and/or the intact protein and or non-coding sequences (e.g., regulatory sequences, introns etc).

One of skill in the art, guided by this disclosure, will recognize that in addition to nucleic acid analogs specifically listed herein, other nucleic acid analogs (including nucleic acid analogs discovered or developed in the future) may be used in the methods of invention. Nucleic acid analogs that form a P/TP hybrid under the assay conditions described herein are suitable for the present methods, and affect the rate of change in an optical property.

Exemplary nucleic acid sequences that can be used in the methods disclosed herein include but are not limited to those listed in Table 1. These and other sequences can be used with respect to target polynucleotides or nucleic acid analogs, and can be modified to include non-nucleic acids located at either terminus of the nucleic acid analog or anyplace in between the termini. Useful modifications include the addition of any natural or non-natural amino acid residues or a protein; amino acids may be present as single residues or present as a polypeptide; preferred amino acid residues include lysine and glycine. Preferred proteins that can be attached to such nucleic acid sequences include those that specifically bind a ligand; more preferred proteins include an antibody (specific for an antigen) and a ligand (specific for a sugar); a yet more preferred protein is biotin (specific for avidin or strepavidin). Other sequences include complementary sequences of those listed in Table 1.

TABLE 1

| Target | Sequence (5' to 3') | SEQ ID NO: |
|---|---|---|
| 35S CMV promotor | GATAGTGGGATTGTGCGT | 1 |
| Maize zein control | ACAGTTGCTGCA | 2 |
| Maize invertase | TGTATCACAAGG | 3 |
| Maize adh | CTCCGAGACCCT | 4 |
| Soy lectin | CTATTGTGACCT | 5 |
| Shiga-like toxin 1 | TCGTTGACTACT | 6 |
| Shiga-like toxin 2 | AACTGCTCCTGT | 7 |

Nucleic acid analogs can hybridize rapidly to target polynucleotides. PNA hybridization to polynucleotides, for example, is independent of salt concentration. See Demidov et al., BIOCHEM. PHARMACOL. 48:1310-3 (1994). PNAs are resistant to nuclease and protease attack, and bind to polynucleotides more specifically than conventional DNA probes. Short probes can be used with great sequence specificity (Ray and Norden, FASEB J. 14:1041-60 (2000)). Furthermore, PNA/polynucleotide hybrids have higher thermal stability than the corresponding DNA/polynucleotide hybrids, and the melting point of PNA/polynucleotide hybrids is relatively insensitive to ionic strength, showing equal thermal stability under low (<10 mM NaCl) and moderate (500 mM NaCl) salt concentrations. This ability of PNA/polynucleotide hybrids to form under low salt conditions is significant because the internal structure of dsRNA and rRNA is significantly destabilized at salt concentrations below 200 mM. Therefore, assay conditions can be chosen that favor the disruption of the target nucleic acid while still promoting formation of PNA:DNA hybrid molecules (Stefano and Hyldig-Nielsen, *Diagnostic Applications of PNA Oligomers*, in DIAGNOSTIC GENE DETECTION AND QUANTIFICATION TECHNOLOGIES 19-39 (Minden ed., 1997). PNA/polynucleotide hybridization is severely affected by base mismatches and PNA molecules can maintain sequence discrimination up to the level of a single mismatch.

ncPNA molecules may be purchased, for example, from Panagene (Korea), or synthesized by methods known in the art. In certain embodiments, the nucleic acid analogs can be a chiral PNA. ncPNA molecules can by synthesized, for example, according to the methods described in Mayfield and Corey ANAL BIOCHEM. 268(2):401-4 (1999), or Braasch et al, CURRENT PROTOCOLS IN NUCLEIC ACID CHEMISTRY. *Unit 4.11 Synthesis and Purification of Peptide Nucleic Acids*, pp. 14.11.11-14.11.18. John Wiley & Sons, New York. Chiral PNAs can be synthesized, for example, according to the methods disclosed by Kumar et al., ORG LETT. 3(9): 1269-72 (2001) or D'Costa et al., ORG LETT. 1(10): 1513-6 (1999).

In other embodiments, the nucleic acid analog includes one or more LNAs. LNAs may be purchased, for example, from Proligo (Boulder, Colo.). In still other embodiments, the nucleic acid analog is preferably a morpholino nucleic acid analog or a TNA. TNAs can be synthesized, for example, according to the methods disclosed by Chaput and Szostak, J. AM. CHEM. SOC. 125(31):9274-5 (2003). Morpholino nucleic acids can be purchased, for example, from Gene Tools (Philomath, Oreg.). A comparison between chiral PNA, LNA, morpholino nucleic acid analogs and non-chiral PNA analogs is disclosed in Example 3. The nucleic acid analogs produced reduced fluorescence intensities of the dye at various levels when compared to the negative control reaction.

C. Target Polynucleotides

The target polynucleotide may be any polynucleotide, including naturally occurring, synthetic, and amplified polynucleotides. Other types of polynucleotides may be single-stranded, double-stranded, triple-stranded, or yet greater degree multi-stranded. Non-limiting examples of target polynucleotides include DNA, RNA, regulatory RNA, mRNA, regulatory microRNA, siRNA, artificial RNA, chimeric RNA, and armored RNA. Other non-limiting examples of target polynucleotides include epigenomic DNA, epigenetic DNA, in vitro amplified DNA, and chimeric DNA. The target polynucleotide may contain single nucleotide polymorphisms (SNPs) that are identified or quantitated by the methods disclosed herein. The target polynucleotide can be a nucleic acid analog also.

D. Detergents

Any detergent can be usefully included with the reagents individually or with the reaction mixture. Indeed, the reaction mixture preferably includes detergent. The advantages of adding detergent to the reaction mixture were observed and are reported in Example 1 hereof. As can be seen in detail, the addition of detergent results in greater relative signal for test reaction mixtures as compared to negative control reaction mixtures. Furthermore, the addition of detergent reduces photobleaching of samples containing only dye and/or only dye and nucleic acid analog.

The detergent used in the context of the present invention, then, can be a cationic detergent, anionic detergent, nonionic detergent, or zwitterionic detergent. Non-limiting examples of cationic detergents include, for example, tetramethyl ammonium chloride (TMAC) (Sigma, St. Louis Mo.). Non-limiting examples of anionic detergents include N-lauroyl sarcosine sodium salt (LSS) and sodium dodecyl sulfate (SDS) (Sigma-Aldrich, St. Louis Mo.). Non-limiting examples of nonionic detergents include Tween® 20, Tween® 40, Tween® 80, NP40 (Tergitol®), Triton® X-100, Span® 20, and Span® 80 (Sigma, St. Louis Mo.). Non-limiting examples of zwitterionic detergents include 3-[(3-Cholamidopropyl)dimethylammonio]-1-propanesulfonate (CHAPS) (Sigma, St. Louis Mo.). The detergent is preferably included in the mixture itself and/or in the composition that includes the dye. Suitable concentration for the detergent ranges from about 0.01% to about 2%; more preferably from about 0.05% to about 1%; yet more preferably, about 0.05%, about 0.01%, about 0.5%, or about 1%.

E. Additional Additives

Other compounds that can be added to the reaction mixture include, but are not limited to, 1,4-diazabicyclo[2,2,2]octane (DABCO), p-phenylenediamine (PPD), n-propyl gallate (NPG), ascorbic acid, sodium azide, polyvinyl pyrrolidone (PVP), pwg-800, cyclodextran, and glycerol.

The reaction mixture can also incorporate other compounds and reagents. Examples of other compounds or reagents include Good's buffers, phosphate buffers, water, and alcohol. Suitable alcohols include butanol, methanol, and isopropanol. Alcohol is preferably included in a range of concentration of about 1% to about 15% on a v/v basis; more preferably, about 3%, about 5%, about 10%, or about 14% alcohol. DMSO can also be included, at concentrations of about 1% to about 12%; more preferably at about 10%.

F. Buffer Systems

Suitable buffers for the reaction mixture include: 50 mM KCl, 10 mM Tris HCl, and 0.1% Triton® X-100: blood lysis buffer (0.15 M NH$_4$Cl, 10 mM NaHCO$_3$, 0.1 mM EDTA pH 7.4); sucrose lysis buffer (0.32 M sucrose, 10 mM Tris, 1% Triton® X-100, 5 mM MgCl$_2$), 1×TE pH 7.0, 7.2, 7.4, 7.6, 7.8, 8.0, 8.5, 9.0, etc, phosphate-citrate buffers of 0.2M Na$_2$HPO$_4$ (from Teknova, catalogue # S0215) and 0.1M citric acid (from Teknova, catalogue # C2440) to a final pH of 4.0, 4.2, 4.4, 4.6 and 4.8, and 10 mM or 20 mM homopipes buffers pH of 4.0, 4.2, 4.4, 4.6, 4.8 and 5.0. Any of these buffers may also include 0.05% Tween® 80.

Other useful reaction solutions can include 0.5% Tween® 20 in 5 mM phosphate, adjusted to pH 5.5; 0.5% Tween® 40 with 5 mM phosphate, adjusted to pH 5.5; 0.5% NP40 with 5 mM phosphate, adjusted to pH 5.5; 0.05% lauryl sarcosine with 5 mM phosphate, adjusted to pH 5.5; or 5 mM phosphate, adjusted to pH 5.5, with 0.05% Tween® 80 and 14% methanol.

Various concentrations, pH, and combinations of the aforementioned compounds and reagents as well, but not limited to the above, can be usefully employed with the present invention. Target polynucleotides can be detected in samples that contain cells or tissues. The addition of a detergent preferably permeabilizes and/or lyses cells without requiring purification or separation of polynucleotides from other components of a sample. The target polynucleotide is preferably detected directly in the permeabilized cells or crude cell lysate; the target polynucleotide does not need to be additionally purified or isolated from the mixture.

The addition of alcohol to a reaction mixture containing the detergent further reduces the photobleaching of the dye in the absence of an NAA/NA hybrid, but does not reduce the change in absorbance or fluorescence of the reaction mixture when the NAA/NA hybrid is present. This aspect of the present invention is surprising because in the absence of detergent, the addition of alcohol slows the change in optical property. In certain embodiments, about 8-12% ethanol or about 12-15% methanol is added in tandem with a detergent.

An example showing the detection of a target polynucleotide from a detergent-treated bacterial sample will assist in describing the usefulness of both the method and the inclusion of surfactant. With reference to Example 2 and FIG. 3, individual buffer solutions, containing various detergents, were used to permeabilize and/or lyse bacterial cells. After 10 minutes incubation, 5 μl from detergent-treated bacterial cells were transferred to a buffer containing achiral PNA (a nucleic acid analog) and 3,3'-diethylthiacarbocyanine iodide dye, thus forming the test reaction mixture. Fluorescence intensity (535 nm excitation, 590 nm emission) of reactions was read at time zero. Reactions were exposed to light for one minute and re-read. This exposure-reading cycle was repeated to 10 minutes total exposure. For each detergent, the "percent change" in fluorescence intensity at each timepoint was calculated as per the formula: $100-[RFU_{TW}-RFU_{NC}]\times100$, where $RFU_{TW}$ is the measured fluorescence intensity of the test reaction mixture, and $RFU_{NC}$ is the measured fluorescence intensity of the negative control mixture (i.e., ncPNA, no target nucleic acid, dye, in buffer containing each type of detergent). Magnitude of percent changes corresponds to relative signal intensity (test reaction relative to negative control reaction mixtures) in the detection of the presence of the target nucleic acid sequence. A consistent positive percent change indicates a consistently stronger signal from the test reaction mixture as compared to the negative control mixture, indicating a consistent ability for the system to detect TP. Detergents increase the relative signal, allowing the easier detection of TP in a detergent-treated sample. The effect of some detergents is more dramatic than that of others. Notably, the presence of a target nucleic acid sequence can be determined from the detergent-treated cells, without requiring further purification of the target polynucleotide.

The presence or quantity of a target nucleic acid in the target polynucleotide may be detected in any group of cells or tissues. For example, the presence of a target nucleic acid can be detected in a tissue culture, cells, tissues or fluids obtained from an animal or plant. In other embodiments, the presence or absence of a target polynucleotide in any tissue or fluid can be determined. Non-limiting examples of such tissues or fluid include urine, blood, saliva, lacrimal fluid, inflammatory exudates, synovial fluid, abscess, emphysema or other infected fluid, cerebrospinal fluid, sweat, pulmonary secretions (sputum), seminal fluid, feces, and plant tissue. Cancer cells or other cells circulating in blood can be detected, or cells having different RNA expression levels. Other examples include detection of cell (animal or bacterial) transformation, or the absence of contamination in tissue cultures.

G. Light Stimulus

Light stimulus can be provided to a sample, nucleic acid analog, and dye mixture either concurrently with the production of the mixture or at a specified time after the production of the mixture. The light stimulus causes a different rate of change in an optical property of the mixture. The light stimulus may be in the visible spectrum or outside the visible spectrum. The light stimulus may be white light of a number of wavelengths. Alternatively, the light stimulus may be a specific wavelength or wavelengths, or range of wavelengths.

Light sources are known in the art. Different light sources result in different reaction rates because of differences in intensity or wavelength of the light sources. Examples of light sources include Xenon arc lamp (Ushio, #UXL-451-O), Sylvania dulux S9W CF9DS/blue and Sylvania Cool White T8-CW (OSRAM SYLVANIA, Danvers, Mass.), General Electric T8-C50 GE Lighting, Cleveland, Ohio), Osram F9TT/50K (OSRAM GmbH, Munich, Germany), and Fritz Aurora 50/50 (Fritz Industries, Inc., Mesquite, Tex.). Other light sources include light emitting diodes (LEDs) that produce a specific range of wavelengths, such as Jameco #183222 a 470 nm LED, Jameco #334473 a 505 nm LED, Jameco #183214 a 515 nm LED, or a white multiwavelength (420-700 nm) LED #LLW5210200. LEDs emit light at least one peak wavelength, and in certain embodiments can emit light at multiple peaks. In certain variations, the bandwidth of the LED can be as small as 1 nm, or as large as 20 nm. Other light sources include commercially available halogen light sources, such as halogen headlamps (NAPA Auto Parts, Atlanta, Ga.).

The light stimulus may also have a specific intensity. In certain variations, a 15-Watt light source at 555 nm produces between about 400 foot-candles and 2000 foot-candles of illumination. In other variations, the light stimulus is one or more LEDs, preferably it is a bank of LEDs, the power of which varies from 500 µW to 4000 µW/cm$^2$ at 3.5 inches away from the light.

For example, when performing the methods described herein, the light reactive complex may be exposed to light for a period of less than 2 hours. Alternatively, the light reactive complex may be exposed to light for a period of less than 1 hour. In yet other instances, the light reactive complex may be exposed to light for a period of less than 30 minutes. In further embodiments, the light reactive complex may be exposed to light for a period of less than 5 minutes. Other time periods are also contemplated.

Those of skill in the art will recognize that the optimal light stimulus may be determined without undue experimentation for a specific dye, or a specific nucleic acid analog, polynucleotide, and dye mixture. A single set of temperature and concentration conditions can be optimized for a specific mixture. A source of the light stimulus can also be optimized for illuminating a plurality of hybridizations.

H. Forming Alternative Target Polynucleotide/Nucleic Acid Analog Hybrids

Assays for detection of target polynucleotides can be carried out using a variety of hybridization, or association or complex formation schemes. In one format, the polynucleotide sequence may be identified by hybridization of a target polynucleotide directly to a nucleic acid analog to form a target polynucleotide/nucleic acid analog hybrid, which is described above. Here, we will present two additional schemes for detecting the target polynucleotide by means of a change in the optical property of the reaction mixture, as follows:

In one aspect, and as depicted in FIG. 6A, a nucleic acid analog 2 molecule hybridizes to a portion of a complementary target nucleic acid target sequence. The nucleic acid analog can then hybridize to a second nucleic acid analog 1 molecule that is preferably immobilized on a solid substrate, as depicted in FIG. 6A. This may be accomplished in a one-step or multistep process. In a one step process, the target polynucleotide and nucleic acid analogs are combined simultaneously. In a multistep process, the target polynucleotide and nucleic acid analogs are combined sequentially.

In another aspect, the presence of a target polynucleotide may be detected by forming a branched reaction crucifix form structure, an example of which is depicted in FIG. 6B. In this format, a target polynucleotide is hybridized to two intermediary polynucleotides 1 and 2 that are complementary to non-overlapping and contiguous portions of the target polynucleotide. The intermediary polynucleotides form a branched structure that also hybridizes to a primary nucleic acid analog. The target hybridizing regions of the intermediary polynucleotides may be designed to be too short for a dye to facilitate the color change reaction described herein with respect to the primary nucleic acid analog, but large enough to facilitate the color change reaction with respect to the primary nucleic acid analogs or target polynucleotides when hybridized/associated.

Without relying on any particular mechanism of action, the change of color or fluorescence of a dye has been found to depend on the length of the nucleic acid analog. The optical property contributed by the dye changes if the nucleic acid analog is at least about 10 bases long. Accordingly, by employing a sufficient short primary nucleic acid analog in the mixture, the rate of optical change of the reaction mixture may then be determined after the step of allowing hybridization or association or complex formation to occur. In the absence of the hybridization of the primary nucleic acid analog to the secondary polynucleotides, no substantial change in the optical property of the reaction mixture is observed. Unless the intermediary polynucleotides hydridize to the target polynucleotide and to the primary nucleic acid analog, the optical property of the reaction mixture remains substantially stable.

In one embodiment, the single nucleic acid analog is a universal nucleic acid analog that is used for all assays and optimized for effective changes in the optical property of a dye. The universal nucleic acid analog could be used for any target nucleic acid and the secondary sequences could be varied to be specific for a given target polynucleotide. This scheme can be adapted to a format using an immobilized nucleic acid analog. This universal sequence can be optimized for a given set of reaction conditions.

Figure 6C:
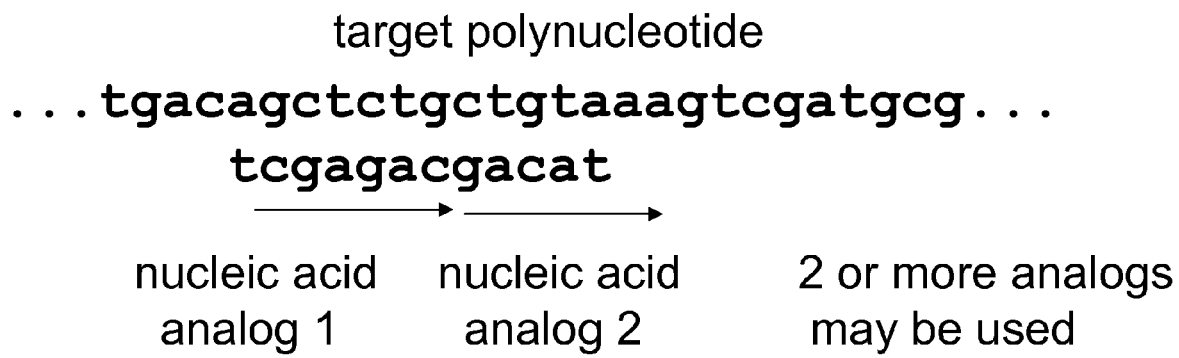
FIG. 6C-D depict means of detecting mutations using nucleic acid analogs.

In another format, multiple nucleic acid analogs or target polynucleotides form a P/TP hybrid with adjacent regions of a target polynucleotide. In this format, each nucleic acid analog is preferably too short for the reaction mixture's optical property to change, although it does change at the background rate; but multiple nucleic acid analogs that are complementary to contiguous segments of the target polynucleotide preferably provide a large enough region for a rate of change in the optical property to result. As depicted in FIG. 6C, a target polynucleotide as a single molecule may form a P/TP hybrid with two or more separate nucleic acid analogs that hybridize to adjacent sequences. SNPs can be identified using the two separate nucleic acid molecules when there is a single base mismatch between the target nucleic acid and one of the SNPs. If all the bases in one nucleic acid analog cannot hybridize as in FIG. 6D then a change in optical property may not be observed.

I. Hybridization Conditions

The methods disclosed herein detect SNPs at room temperature. As a result, stringent hybridization conditions do not need to be used. Although hybridization conditions can be modified or optimized, generally the hybridization conditions within a reasonable range do not affect the ability to detect a target polynucleotide according to the methods disclosed herein.

If hybridization controls are changed or optimized, the design and/or choice of hybridization conditions is governed by several parameters. These parameters include, but are not limited to, the degree of complementarity of the nucleic acid analog to the target polynucleotide, the length of the nucleic acid analog to be utilized and the target polynucleotide itself. Preferred hybridization conditions allow for one or more of the following: efficient hybridization of nucleic acid analogs to target polynucleotides, minimization of RNA or DNA secondary structure, minimization of RNA degradation and either discrimination of one or more base pair changes or inclusion of one or more base pair changes.

Hybridization reactions can be performed under conditions of different "stringency." Conditions that effect stringency of a hybridization reaction are widely known and published in the art. See, e.g., Sambrook et al. (2000), supra. Examples of relevant conditions include but are not limited to, salt concentrations, pH (buffers), and temperature. Hybridization conditions utilizing lower salt concentrations generally enhance DNA instability and PNA/polynucleotide stability. Examples of buffers that may be used include, but are not limited to, $Na_3PO_4$, $NaHSO_4$, $K_2HPO_4$, $K_2SO_4$, or $CaSO_4$. By way of example, the molarity of the buffers may range between about 10 mM and about 0.5 M and have a pH between about 4 to about 10, or between about 7 to about 10, such as about 7.0 or about 7.5. By way of example, $Na_3PO_4$ may be used at between about 0.5 mM and about 0.5 M, such as for example, 2.5 mM, and at a pH between about 4 to about 10 or between about 7 to about 10, such as about 7 or about 7.5.

Other buffer conditions include a 5 mM phosphate buffer, pH, 5.5 with 0.05% NP-40 (Tergitol®). Alternatively, the 0.05% NP-40 (Tergitol®) can be substituted with 0.05% Tween 80, optionally including about 10-14% methanol or about 8-12% ethanol. Examples of sample conditions include but are not limited to (in order of increasing stringency): incubation temperatures of about 25° C., about 37° C., about 50° C. and about 68° C.; buffer concentrations of 10×SSC, 6×SSC, 4×SSC, 1×SSC, 0.1×SSC (where SSC is 0.15 M NaCl and 15 mM of any buffer as described herein) and their equivalents using other buffer systems; formamide concentrations of 0%, 25%, 50%, and 75%; incubation times from about 5 minutes to about 24 hours; one, two, or more washing steps; wash incubation times of one, two, or 15 minutes; and wash solutions of 6×SSC, 1×SSC, 0.1×SSC, or deionized water. In one embodiment, hybridization and wash conditions are done at high stringency. By way of example, hybridization may be performed at high stringency using 50% formamide and 4×SSC followed by washes of 2×SSC/formamide at 50° C. and with 1×SSC.

Buffers may contain ions or other compounds, or different buffering capacity. Alternatively a component in the buffer may have a stabilization capacity; such as neomycin or other aminoglycosides, that stabilizes triplex DNA, (Arya et al; 2003) or naphthalene diamides that enhance triplex stability (Gianolio and McLaughlin, BIOORG. MED. CHEM. 9:2329-34 (2001)), or naphthylquinoline cyanogen (Keppler et al., FEBS LETT. 447:223-6 (1999)).

J. Mutation Detection

Figure 8:
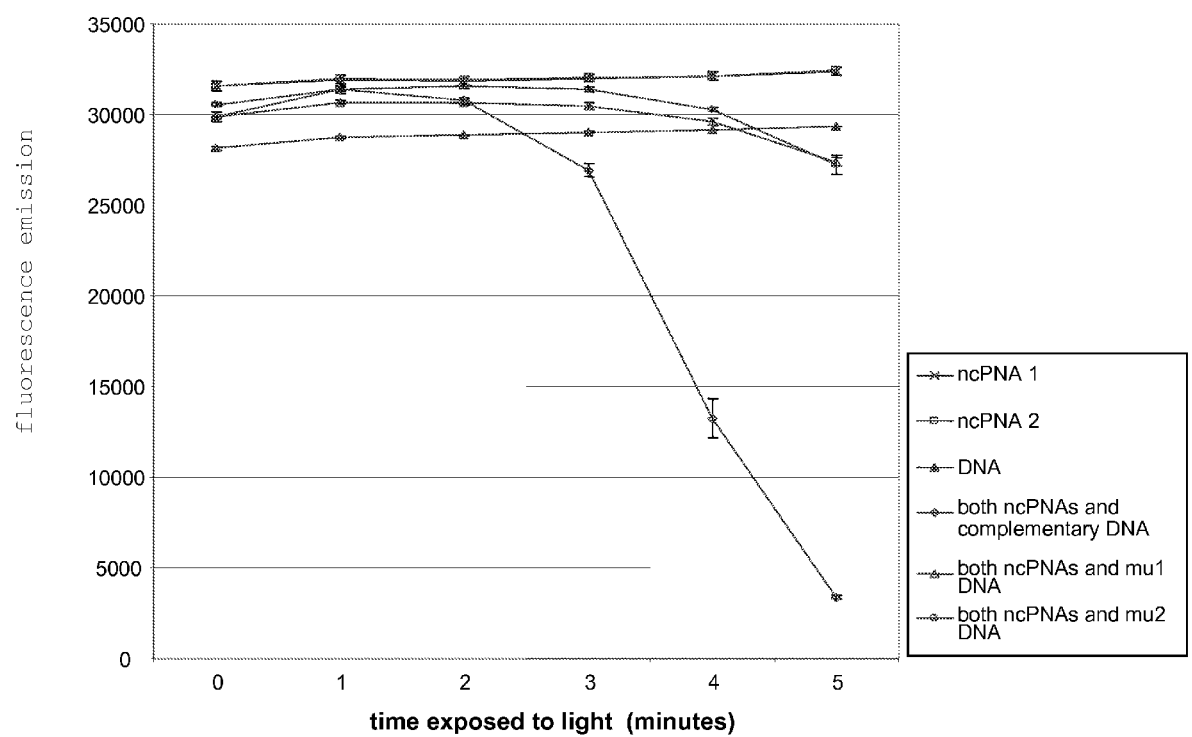
FIG. 8 depicts a series of single nucleotide polymorphisms detected by the methods disclosed herein.
Figure 9:
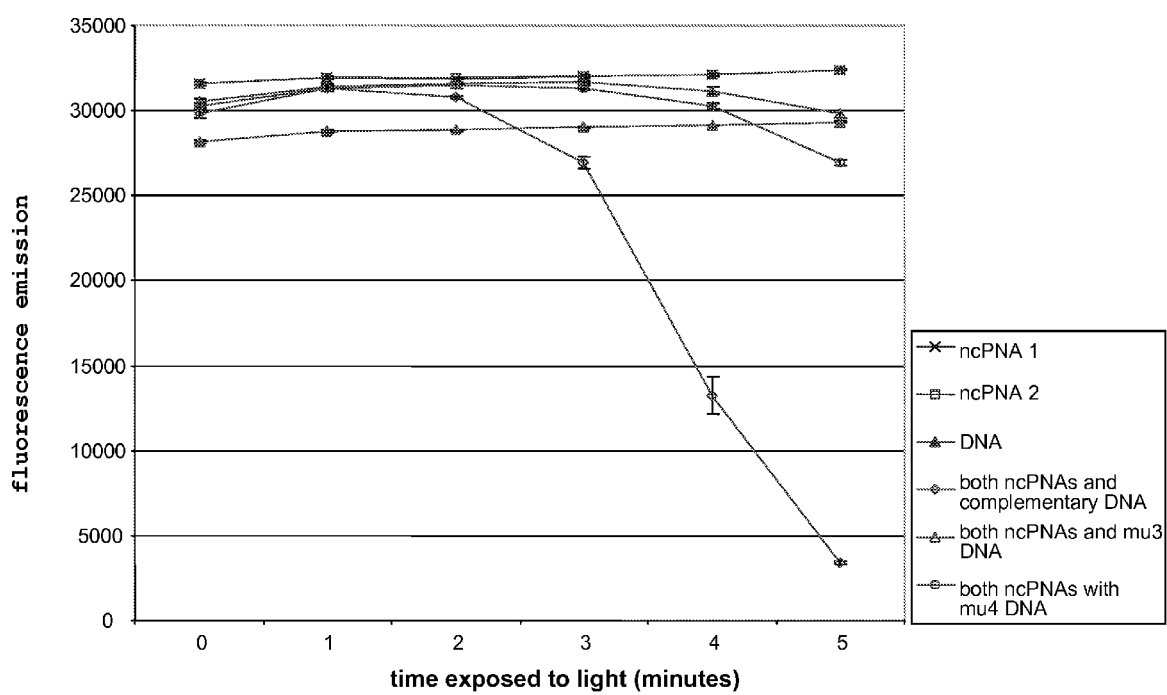
FIG. 9 depicts a series of two or more nucleotide polymorphisms detected by the methods disclosed herein.

In one embodiment, nucleic acid analogs can be used to distinguish between polynucleotides having an exactly complementary sequence and one with a single base mismatch. For example and without limitation, nucleic acid analogs for use in the inventive diagnostic method may be designed to detect single nucleotide polymorphisms (SNPs). Formation of the P/TP hybrid is affected by base mismatches. According to the methods of the present invention, upon the addition of a dye, a single base mismatch between a target sequence (e.g., SNP) and a nucleic acid analog results in a slower rate of change in optical property of the mixture compared to a nucleic acid analog that does not have the mismatch. Example 7 depicts detection of a series of mutant SNPs. Single base mismatches along a double-stranded DNA were detected. FIG. 8 depicts the detection of SNPs DNA molecules with single base-pair changes. FIG. 9 depicts detection of DNA molecules with a two or a four base-pair change. The identification of SNPs for diagnosis and other methods is well known in the art.

In another embodiment, the nucleic acid analog may be designed to detect the presence or amount of a class of organisms. By class of organisms, it is meant that all organisms have one or more sequences that are complementary to, or exactly complementary to, a nucleic acid analog sequence. Such classes of organisms can be distinguished from other organisms based on the complementarity to nucleic acid sequences.

In yet another embodiment, the nucleic acid analog has a purine content of less than about 60%, and has a maximum of 4 purine bases or three guanine bases in a row. Purine-rich nucleic acid analogs tend to aggregate and have low solubility in aqueous solutions. The nucleic acid analogs are preferably selected to minimize or avoid self-complementary sequences with inverse repeats, hairpins and palindromes because these types of structures are prone to aggregate.

Nucleic acid analogs may hybridize to target polynucleotides in either orientation, but an anti-parallel orientation is preferred. Anti-parallel is the preferred configuration for antisense and DNA hybridization-type applications. When the orientation of the nucleic acid analog is anti-parallel, the N-terminal of the nucleic acid analog is equivalent to the 5'-end of the DNA. Both N' and 5' are used herein.

K. Automated Devices

Certain automated devices that can activate the reactions, record the results and/or include the software to assist in interpretation of the results are also contemplated within this invention. The device is preferably fully automated and perform all reaction steps after sample addition. The device can be a handheld unit, a mobile unit or a stationary lab unit.

In certain aspects, the device preferably detects changes in absorbance. Fluorescence detection devices can have a light source for activating the dye and a light source for exciting the dye. The device determines the emission at a range of wavelengths. Alternatively, if the device detects absorbance, a first light source can activate the dye and a second light source can be used for absorbance measurements; alternatively, the instrument can use a single light source coupled with appropriate light filters. Possible test formats include but are not limited to, a test strip (e.g., nitrocellulose or nylon), beads (e.g., latex or polystyrene, 1-5 micron microparticles, ⅛" or ¼" molded or ground beads), capillary tubes, monofilament, plastic test tubes, or in micro wells on an etched surface or plastic form.

Once a sample is exposed to an activating light source and read, the data can be gathered and stored in the device. The device preferably automatically tracks and calculates the change in fluorescence and produces a read out indicating whether a sample does or does not contain the target polynucleotide, and/or determine the amount of the target polynucleotide. The testing format can, for example, be bar coded to provide the unit with predetermined information on the test that may be used to increase the accuracy of the calculations.

Changes in the concentration of the dye can also be determined by measuring the amount of light transmitted through the reaction cell during the reaction using a solid state photodiode sensor. This sensor produces a current proportional to the amount of light incident on it. This photocurrent can be converted to a measurable voltage with an operational amplifier configured to convert current to voltage. This voltage can be recorded as a function of time in order to monitor changes in dye concentration. Results can be expressed as voltage vs. time or converted to absorbance with the following formula, $$A_t = -\log(V_0/V_t)$$

Where $A_t$ is the absorbance at any time in the reaction, $V_0$ is the voltage produced by the photo detector when no dye is present in the cell, $V_t$ is the voltage produced by the photodetector at time t during the reaction. If the dye concentration is properly chosen, typically 9-18 uM for dye I, Beers Law is obeyed and absorbance is linearly related to concentration of absorbing species by the following equation, $$A=ebc$$

where A is absorbance, e is molar absorptivity ($M^{-1}$ $cm^{-1}$), b is the cell pathlength in cm, and c in the molar concentration (M) of the absorbing species. Absorbance changes vs. time can then be measured for samples and standards and the presence or absence of absorbing species can be inferred.

IV. METHOD FORMATS

The methods can be adapted to several different formats. Preferred formats include, without limitation, liquid-based formats, solid-substrate-based formats, and gel-based formats. It will be understood that various aspects of the formats can be combined.

A. Liquid-Based Formats

In one embodiment, the method for detecting a target polynucleotide is liquid-based. The sample containing the target polynucleotide, a nucleic acid analog that forms a hybrid, complex or association with a target nucleic acid sequence of the polynucleotide in a sequence specific manner, and the dye are preferably combined to produce a mixture in liquid solution. The mixture preferably has an optical property that can change over time. The rate of change in the optical property of the mixture is compared to a reference value characteristic of the rate of change in the optical property of a similar mixture containing a known amount of a P/TP hybrid and dye to determine a relative rate of change in the optical property. The relative rate of change in the optical property of the mixture correlates to the presence or amount of the specified polynucleotide in a sample, thereby determining the presence or amount of polynucleotide in the sample. The change in the optical property of the mixture containing a nucleic acid analog or, upon adding a further step for introducing a light stimulus, a decrease in intensity of an optical property can be observed in a liquid-based format or in a gel-based format or solid support format. The various methods disclosed herein may be performed in a liquid-based format.

The methods may also be conducted in any vessel, such as microfuge tubes, test tubes, and chips that hold a liquid by surface tension. The methods may also be conducted in multiwell plates or multiwell strips. The plates may contain any number of wells. In one format, 96-well plates are used. In another format, 384-well plates are used. Any type of plate having any number of wells can be used. The wells themselves may be subdivided into smaller wells. When the assay format is in a microwell format, the liquid is retained in each well of a microtiter plate. In the alternative, or in addition, a gel matrix could be added to one or more wells.

B. Solid Substrate-Immobilized Formats

The nucleic acid analog or target polynucleotide may be immobilized on a solid substrate. The nucleic acid analog or the target polynucleotide may be immobilized on the solid substrate either directly or indirectly as exemplified below.

The P/TP hybrid may be immobilized on a surface. The immobilization may be accomplished by any suitable method known in the art, the suitability of which is determined functionally, i.e., that immobilization act occurs without substantial detriment to the activity of the same compound when free in solution. In an embodiment of this invention, either the nucleic acid analog or target polynucleotide is covalently linked to a second molecule that preferentially binds to a third molecule on the solid substrate.

One or more components are preferably immobilized on a solid substrate. For example, either the nucleic acid analog or the target polynucleotide may be immobilized. The P/TP hybrid may be immobilized either before or after formation of the hybrid. The dye may be added before or after immobilization and/or before or after hybridization. In other embodiments, the dye may be immobilized. Further, the light stimulus may be added either before or after immobilization on a solid substrate.

There are many types of solid substrates that the nucleic acid analog or target polynucleotide molecule may be attached to, including, but not limited to: cast membranes (e.g., nitrocellulose, nylon), ceramic, track-etched membranes (TEM), polyvinylidenedifluoride, latex, paramagnetic beads, plastic supports of all types, glass, powdered silica or alumina on a support matrix or treated or untreated filter paper (e.g., Whatman FTA cards). If a grid pattern is used, the immobilized nucleic acid analog or target polynucleotide forms a microarray. In another variation, the nucleic acid analog or target polynucleotide molecules are covalently modified to include a linking moiety, such as a biotin or amine linkage, which binds to membranes containing the protein streptavidin or amine reactive functionality, respectively. In a further variation, the nucleic acid analog or target polynucleotide molecules are immobilized via sequence-specific hybridization to one or more sequences. Any means of attaching a nucleic acid analog or target polynucleotide to a support is contemplated by the present invention. In one aspect, the nucleic acid analog or target polynucleotide may be attached directly to a membrane. The nucleic acid analog may be a PNA (e.g., Giger et al., NUCLEOTIDES AND NUCLEOSIDE 17:1717 (1998)). A solution of nucleic acid analogs or target polynucleotides (in water) is preferably applied to a charged or chemically-modified filter and allowed to air dry. The filter is then used for hybridization.

In another embodiment, a biotin-labeled nucleic acid analog or target polynucleotide is attached to a streptavidin-coated surface, such as a bead or well (see, e.g., Chandler et al., ANAL. BIOCHEM. 283:241-249 (2000)). Biotin-labeled nucleic acid analog or target polynucleotide can be mixed with streptavidin-labeled latex beads. The biotin binds strongly with streptavidin, allowing the nucleic acid analog or target polynucleotide to bind to the bead in a unidirectional fashion. The beads are then preferably applied to a non-charged membrane with a mesh size that is 25-30% greater than the diameter of the bead. Beads become trapped in the mesh, hence making a localized area of attached nucleic acid analogs or target polynucleotides. Direct synthesis of nucleic acid analog or target polynucleotides on a solid substrate, such as a polypropylene membrane, may be accomplished using standard 9-fluorenylmethoxycarbonyl (Fmoc) protein synthesis chemistry (see, e.g., S. Matysiak et al., BIOTECHNIQUES 31:896-904 (2001)).

In another embodiment, the nucleic acid analogs or target polynucleotides are fixed to a glass or other solid substrate by applying a solution containing nucleic acid analogs or target polynucleotides in water directly to the glass or other support and letting it air dry.

In yet another embodiment, a nucleic acid analog is designed to produce a net positive charge, and may bind a negatively charged membrane. For example, a positively-charged lysine or glycine at a 5' or 3' end of the nucleic acid analog molecule may be used to attach the nucleic acid analog molecule to a negatively-changed nylon membrane. The negatively charged membrane repels any nucleic acid that is not complementary and/or exactly complementary to the nucleic acid analog, thus minimizing non-specific binding.

In yet another embodiment, nucleic acid analogs or target polynucleotides are preferably attached to microspheres as described by Xu et al., NUC. ACIDS RES. 31:e43 (2003). For each conjugation reaction, approximately $4 \times 10^6$ carboxylated microspheres (Polysciences, Warrington, Pa.) can be pelleted and washed with 0.1 M imidazole buffer pH 7.0. After resuspension of microspheres in 20 µl of imidazole buffer pH 7.0 (10% solids), 1 µl of 100 mM oligos, and 100 µl of 200 mM EDAC (Acros, Pittsburgh, Pa.) in freshly made imidazole buffer pH 7.0 is added and the reaction mixture is incubated for about 2 hours at room temperature with continuous rotation. An additional 100 µl of 200 mM EDAC in freshly made imidazole buffer pH 7.0 is added and the room temperature incubation with rotation was continued for another 2 hours. Microspheres were then centrifuged, washed twice with water, and resuspended in 40 µl of phosphate-buffered saline (PBS), pH 7.4.

In other embodiments, nucleic acid analogs or target polynucleotides are attached to microspheres, as described by Running and Urdea, BIOTECHNIQUES 8:276 (1990).

Any target polynucleotide, or group of target polynucleotides, may be detected using the solid substrate-based system. In this case, a solid substrate contains multiple nucleic acid analogs or target polynucleotides immobilized on a solid substrate. A negative control nucleic acid analog or target polynucleotide that does not form nucleic acid analog/polynucleotide hybrid is preferably included on the solid substrate. A positive control nucleic acid analog that always forms a nucleic acid analog/polynucleotide hybrid is preferably included on the solid substrate.

An end of a monofilament can also serve as a solid substrate. In such an embodiment, a nucleic acid analog is preferably immobilized on the end of a monofilament, and a dye and target polynucleotide are preferably added to the tip. When light is applied to the end of the monofilament, the change in an optical property of the dye is monitored over time.

Fluorescent nanobeads such as quantum dots (Invitrogen Corporation, Carlsbad, Calif.) can serve as the solid substrate. Quantum dots cores are composed of semiconductor cadmium salts that fluoresce at different wavelengths based on salt and size. This core is enveloped in a shell that is composed of a non-emissive transparent, but structurally related, material that can be efficiently wed to the underlying core material. In this way, the core molecules are tricked into sensing what still appears to be a virtually infinite array of atoms in every direction; little or no reorganization is necessary and the fluorescent emission remains stable and bright over a long period of time.

In another embodiment, nucleic acid analogs are preferably conjugated to quantum dots that emit at different wavelengths. A single sequence can be conjugated to dots of a single wavelength or one or more sequences can be conjugated to dots of a single wavelength. These quantum dots of either a single or multiple wavelengths are preferably mixed with a polynucleotide mixture allowing hybrids to form. The dots with hybrids attached may be washed to remove non-complementary polynucleotide. A mixture with dye and reaction buffer is added to the dots. The dots with hybrid are then dispensed in fraction wells of a multiwell plate as described at U.S. Pat. No. 6,838,243. In each well there are many fraction wells. The fraction wells are of the correct size that each can accommodate a single dot. The amount of liquid dispersed is such that the fraction wells are not quite full. The mixture is then exposed to an activating light. After a period of time (or at multiple times) the colors/fluorescence of the fraction wells are determined. The fluorescence of the quantum dot identifies the target sequence and the disappearance of an optical property in the reaction indicates the presence of the target sequence in the polynucleotide mixture.

The reactions can be quantitative based on the number of quantum dots bioconjugated with a given sequence indicating the presence of that sequence. Other types of beads may be used, including but not limited to Luminex® beads (Mirai-Bio, Alameda, Calif.). In some embodiments, beads may be magnetic to assist in the washing. Centrifugation may be involved in the washing.

In certain embodiments, a solid support with a specific background color provides significantly improved detection of the target polynucleotide. Specific embodiments of solid supports can have any color background known in the art. In one particular embodiment, the solid support has a white background. The solid support can be a microtiter plate having a specific color of well, such as a microtiter plate having a white background. Alternatively, the compositions can include a sample surface modified to have the same interior as any plate described herein.

C. Gel-Based Formats

The methods disclosed herein can be used to determine the presence or amount of a target polynucleotide in a gel based assay. A gel, such as an agarose or acrylamide gel, that contains the dye is prepared. Alternatively, the dye is added to the gel after it is run or the dye is added to the sample before it is loaded onto the gel. A sample that may contain, does not contain, or is suspected of containing, or suspected of not containing, a target polynucleotide is added to the gel. The components of the sample can be separated from each other on the gel. A nucleic acid analog that is complementary to a target nucleic acid sequence of a target polynucleotide is added either before or after digestion of the sample polynucleotide but before an electric current is applied to the gel. Alternatively, the nucleic acid analog can be added after an electric field is applied to the gel. After the bands are allowed to migrate on the gel, a light stimulus is applied to the gel.

After the light stimulus is applied to the gel, the portion of the gel containing the P/TP hybrid has at least one different optical property relative to the rest of the gel. In one exemplary embodiment, when the gel is combined with 3,3'-diethylthiacarbocyanine iodide dye and exposed to a light stimulus, visually the resulting gel lacks any color (apart from the agarose-colored portions) where the P/TP hybrid is present. The remaining portion of the gel has a detectable color. In addition, by illumination with a 254 nm transilluminator, the gel will fluoresce except where the P/TP hybrid is absent. In the region of the P/TP hybrid, there is no fluorescence. The presence of a target nucleic acid sequence in a target polynucleotide is thereby identified on a gel.

The ability to determine the presence of a target polynucleotide sequence on a gel can be adapted to any number of conventional molecular biology techniques. For example, a conventional Southern blot can be adapted to the methods of determining the presence of a target polynucleotide on a gel. Target polynucleotides are digested by a conventional restriction digest and run on a conventional agarose gel that contains dye. A nucleic acid analog can be added to the target polynucleotides before, during, and/or after restriction digestion. In certain formats, the target nucleic acids can be denatured. Instead of transferring the polynucleotides to a membrane, the gel is exposed to light stimulus. The loss of fluorescence intensity of the dye corresponds to the location of a target polynucleotide containing the target nucleic acid sequence. In an alternative method, the nucleic acid analog is added to the gel. In various non-limiting embodiments, both the nucleic acid analog and the dye are added to the gel after the polynucleotides have been separated by the electric current. The electrically separated polynucleotides can be transferred to a membrane and the nucleic acid analog allowed to hybridize to the immobilized polynucleotides that have the complementary sequence. This membrane is then immersed in liquid containing dye and other reaction components, after some period of time the membrane is removed from the liquid and exposed to light stimulus. The presence of the complementary polynucleotide would be indicated by a clear spot on the membrane.

Unlike conventional Southern blot analysis, the presently described method does not require heat or salt-based denaturation of the nucleic acid, and does not require blotting to identify target polynucleotides having a specific nucleic acid sequence, that is the hybridization could occur before or after transfer of the polynucleotides or transfer is not even required.

The methods disclosed herein can also be adapted to a northwestern blot. A "Northwestern" analysis is the generic term for studying protein-RNA interactions in either a solution-phase format, a gel (electrophoresis) format, or a substrate (such as a membrane) blot format. A protein may bind to RNA in a sequence-specific manner (e.g., HIV tat protein binding to the TAR sequence) or in a sequence-independent manner (e.g., RNA-binding proteins). The methods can be used to identify specific sequences within RNA that are relevant to protein binding. For example, into a solution containing a RNA segment and a protein (thought to bind to a particular RNA sequence) is added a complementary nucleic analog and the dye. Upon exposure to light, the solution either changes color indicating that the nucleic acid analog hybridized to the RNA and the protein did not, or the solution does not change color indicating that the protein has bound to the RNA effectively blocking the nucleic acid analog from hybridizing.

The same methods can be performed in a gel electrophoresis format where the gel contains the dye. The gel is stained post electrophoresis. The sample containing the RNA, the protein, and the nucleic acid analog could be electrophoresed in a gel matrix followed by exposure of the gel to light. Identification of the band corresponding to nucleic acid analog hybridizing to the RNA is visualized by a loss of color (or "hole") in the gel. Absence of the "hole" would be indicative of protein-RNA interaction in a sequence-specific manner, thereby inhibiting binding of the NAA.

Similarly, for substrate blot experiments, the protein (or RNA) could be immobilized to a substrate, followed by incubations with RNA sequences (or protein), followed by incubations with the nucleic acid analog and dye, followed by exposure to light. The loss of color would indicate hybridization of the NAA at a specific RNA sequence not bound to the protein. The presence of color would indicate a protein—RNA interaction at the specific sequence inhibiting binding of the NAA.

Modification of a nucleic acid analog with a positively-charged molecule can be used to increase specificity of hybridization. For example, a nucleic acid analog can be modified to contain a positive charge or linked to a molecule or molecules having a positive charge. The positive current in a gel directs the positively charged nucleic acid analog and the target polynucleotide in opposite directions. The greater the number of hydrogen bonds between the nucleic acid analog bases and the target polynucleotide bases, the greater the likelihood that the P/TP hybrid will remain annealed. Depending on the current and potential applied across the gel, P/TP hybrids containing mismatched sequences can be pulled apart, resulting in denaturation of the P/TP hybrid. The absence of a hybrid will result in a baseline change in an optical property within/of the gel.

The methods of determining the presence or quantity of a target polynucleotide on a gel can be adapted to any gel-based method. For example, determining the presence of a target polynucleotide on a gel can be adapted to conventional Northern blot analysis, in which the target polynucleotide is RNA, not DNA. The methods of determining the presence or quantity of a target polynucleotide on a gel also can be adapted to northwestern analysis. Conventional methods are further disclosed, for example, in *Molecular Cloning: A Laboratory Manual*, third edition (Sambrook et al., 2000) Cold Spring Harbor Press and *Molecular Cloning: A Laboratory Manual*, second edition (Sambrook et al., 1989) Cold Spring Harbor Press, both of which are incorporated herein by reference in their entirety.

D. Detection of Polynucleotides Involved in Genetic Manipulation.

The different rate of change of an optical property of a mixture (or gel) in the presence of an P/TP hybrid can be used to screen for transformation of bacterial colonies in a colony dot-blot. In conventional dot-blot assays, putative transformed cells are grown into colonies on medium. The colonies are transferred to a membrane, their location is fixed, the cells are lysed, and the polynucleotides are attached to the membrane.

The dot blot can be adapted using the methods disclosed herein to determine the presence of target polynucleotide in transformed phage, other viral particles, genetic material, or detection of transfection or infection of eukaryotic cells. The detection of the target polynucleotide attached to the membrane could occur via several methods. In one non-limiting example, a membrane is washed and a nucleic acid analog that is complementary to the sequence of interest or designed to show disruption of the sequence of interest. After a wash step (s) the membrane is placed on a gel-based film that contains the dye. This sandwich is exposed to a light stimulus. Areas in which color is reduced or disappears (or fluorescent emission is reduced or disappears) indicate the presence of the P/TP hybrid and thus the polynucleotide sequence of interest.

In another variation, the nucleic acid analog and the dye may be both in the stationary phase of the gel and simultaneously sandwiched to the membrane with the attached polynucleotides. In yet another variation, the dye (with or without the nucleic acid analog) can be in a liquid gel that is poured on the membrane and areas in which color or fluorescent emission is reduced or gone after exposure to light stimulus indicate the presence (and location) of colonies with the sequence of interest. In a further variation, the colonies may not be transferred to a membrane, but are preferably rather lysed on the plate and any of the above detection schemes applied. In a yet further variation, the polynucleotides may never be attached to the membrane and allowed to interact with reaction components held in a stationary phase (such as a gel).

Alternatively the colonies may be picked into a reaction vessel and the reactions with the change in an optical property of a dye occur in the reaction vessel.

V. TARGET MOLECULE CAPTURE ASSAYS

A. Capture

In one aspect, the present invention relates to novel methods for isolating a target molecule from a sample suspected of containing the target molecule. As described in more detail below, the methods of the present invention may be employed to isolate any type of molecule for which there exists a binding molecule capable of binding specifically or non-specifically to the target molecule and which can be linked, directly or indirectly, to a nucleic acid molecule. Target molecules may include, for example, polynucleotide molecules, as well as non-polynucleotide molecules, such as protein molecules, polypeptide molecules, peptide molecules, oligosaccharide molecules, and other chemical substances, to name only a few.

In accordance with the present invention, it has been discovered that the combination of
 (i) a polynucleotide linked to target molecule,
 (ii) a nucleic acid analog that is complementary to the polynucleotide and is bound, directly or indirectly, to a solid substrate, and
 (iii) a light reactive dye,
 associate to form a light reactive complex bound to the solid substrate, which can then be separated as a unit (the solid substrate together with the complex), based on a property of the solid substrate or of the complex as whole, to thereby isolate the target polynucleotide.

The light reactive complexes of the present invention, and the methods for making and using such complexes, have been shown to be useful in many applications. Advantageously, the methods of the invention, involving capture of the target molecule and, optionally, release under light exposure, can be accomplished within relative brief periods of time, and under ambient light and temperature conditions, allowing the method to be performed without equipment typically required for nucleic acid hybridization and melting conditions used in polymerase chain reaction or other hybridization methods, while still achieving an acceptable level of specificity and sensitivity. The methods of the present invention may therefore be advantageously used, for example, in the field outside controlled laboratory conditions, for the detection and analysis of a multiplicity of compounds, including both chemical and biological compounds.

The mechanism of action involved in light reactive complex formation and release involved in any of the capture, release and detection steps of the present invention is not yet known. Examples illustrating the methods of capture/release using the immobilized light reactive complexes of the present invention are provided in Examples 29, 30 and 31, below. While these examples illustrate typical conditions under which light reactive complexes are formed, it is understood that such conditions may be varied and/or optimized in accordance with the particular objectives and results desired.

In one embodiment of the present invention, the methods of the present invention are used to isolate a target molecule that is a polynucleotide, such as a DNA or RNA molecule, by means of a direct interaction between a target polynucleotide and a bound nucleic acid analog polynucleotide that is complementary to the target polynucleotide or a portion thereof and is immobilized on a solid substrate. In accordance with such embodiments, the methods of the invention comprise the step of combining the following components:
 (i) a sample suspected of containing the target polynucleotide;
 (ii) a first nucleic acid analog immobilized to a solid substrate, wherein the first nucleic acid analog is complementary to a portion of the target polynucleotide; and
 (iii) a first light reactive dye;

to form, if the target polynucleotide is present in the sample, a light reactive complex comprising the target polynucleotide, the first nucleic acid analog, and the light reactive dye. In a subsequent step, the solid substrate and the light reactive complex immobilized thereon is separated from the sample, based on a property of the solid substrate, to thereby isolate the target polynucleotide from the sample.

In another embodiment, the methods of the present invention are used to isolate a target molecule that is a polynucleotide, such as a DNA or RNA molecule, by means of an indirect interaction between a target molecule and a capture polynucleotide immobilized on a solid substrate. In these embodiments, various intermediary constructs are used to link the target molecule, which may be a polynucleotide, a polypeptide, a sugar molecule, etc., with a bound polynucleotide immobilized to a solid support. The intermediary constructs are designed so as to provide at least one pair of complementary polynucleotides, at least one polynucleotide of which is a nucleic acid analog, such as, for example, a PNA polynucleotide, an LNA polynucleotide, or morpholino polynucleotide, that can associate with a light reactive dye to form a light reactive complex.

In one embodiment, illustrating an indirect interaction between a target molecule and a capture nucleic acid analog polynucleotide immobilized on a solid substrate, the present invention relates to a method of isolating a target molecule from a sample suspected of containing the target molecule, comprising the step of combining the following:
 (i) a sample suspected of containing a target molecule;
 (ii) a bound polynucleotide immobilized on a solid substrate;
 (ii) a chimeric molecule comprising (1) a bridging polynucleotide complementary to the bound polynucleotide, and (2) a target component capable of binding to a portion of the target molecule; and
 (iv) a light reactive dye.

In this particular embodiment, the target component binds to the target molecule, if present, and the target component is linked to a bridging polynucleotide (the target component and the bridging polynucleotide are collectively referred to as the "chimeric molecule"). The bridging polynucleotide is complementary to another polynucleotide that is directly or indirectly linked to the bound polynucleotide immobilized on the solid substrate. At least one of the (1) the bound polynucleotide immobilized on the solid substrate, and (2) the bridging polynucleotide of the chimeric molecule, is a nucleic acid analog polynucleotide that forms a light reactive complex with a complementary polynucleotide and the reactive dye which is immobilized on a solid substrate. Thus, the indirect interaction requires at least one complementary pair of polynucleotides that can associate with the light reactive dye to form a light reactive complex.

In some embodiments of the invention, the immobilized polynucleotide is a nucleic acid analog polynucleotide. For example, in some embodiments, the target molecule is a polynucleotide, the target component of the chimeric molecule is a nucleic acid analog polynucleotide complementary to the polynucleotide target molecule, the bridging polynucleotide of the chimeric molecule is a non-nucleic acid analog molecule, and the bound polynucleotide immobilized on the solid support is a nucleic acid analog polynucleotide that is complementary to the bridging polynucleotide.

In other embodiments, the immobilized polynucleotide is a non-nucleic acid analog polynucleotide and the bridging polynucleotide is a nucleic acid analog polynucleotide. For example, in some embodiments the target molecule is a polynucleotide, the target component of the chimeric molecule is a nucleic acid analog polynucleotide complementary to the polynucleotide target molecule, the bridging polynucleotide of the chimeric molecule is a nucleic acid analog molecule, and the bound polynucleotide immobilized on the solid support is a non-nucleic acid analog polynucleotide that is complementary to the bridging polynucleotide.

In yet another embodiment, illustrating another indirect interaction between a target molecule and a capture nucleic acid analog polynucleotide immobilized on a solid substrate, the present invention relates to a method of isolating a target molecule from a sample suspected of containing the target molecule, comprising the step of combining the following:

(i) a sample suspected of containing a target molecule,
(ii) a bound polynucleotide immobilized on a solid substrate,
(iii) an intermediary binding polynucleotide having a first binding region complementary to the bound polynucleotide and a second binding region,
(iv) a chimeric molecule comprising (1) a bridging polynucleotide complementary to the second binding region of the intermediary binding polynucleotide, and (2) a target component capable of specifically binding to the target molecule, and
(v) a light reactive dye.

In this embodiment, the target component binds to the target molecule, if present, and the target component is linked to a bridging polynucleotide. In contrast to the embodiment described in the preceding paragraph (where the bridging polynucleotide forms a complex directly with the bound polynucleotide immobilized on the solid substrate), this embodiment contemplates the use of an intermediary binding polynucleotide, having a first binding region complementary to the bound polynucleotide immobilized on the solid substrate, and a second binding region that is complementary to the bridging polynucleotide of the chimeric molecule to which the target molecule is linked. In this construct, there are at least two regions of complementarity between separate polynucleotides: the first region of complementarity is between the bound polynucleotide and the first binding region of the intermediary binding polynucleotide; the second region of complementarity is between the bridging polynucleotide and the second binding region of the intermediary binding polynucleotide. Either one or both of these regions may form a light reactive complex with a light reactive dye, provided that at least one of the polynucleotides of the complementary pair comprise a nucleic acid analog, such as, for example, a PNA polynucleotide, an LNA polynucleotide, or a morpholino polynucleotide, which nucleic acid analog polynucleotide can associate with its complementary polynucleotide and a light reactive dye to form a light reactive complex (immobilized on a solid substrate). Thus, at least one of (1) the bound polynucleotide immobilized on the solid substrate, (2) the first binding region of the intermediary binding polynucleotide, (3) the second binding region of the intermediary binding polynucleotide, and (4) the bridging polynucleotide of the chimeric molecule, is a nucleic acid analog polynucleotide that forms a light reactive complex with a complementary polynucleotide and the reactive dye which is immobilized on a solid substrate.

In some embodiments, the bound polynucleotide immobilized on the solid substrate is a non-nucleic acid analog polynucleotide, the bridging polynucleotide of the chimeric molecule is a non-nucleic acid analog polynucleotide, and the intermediary polynucleotide is a nucleic acid analog polynucleotide.

In other embodiments, the bound polynucleotide immobilized on the solid substrate is a nucleic acid analog polynucleotide, the bridging polynucleotide of the chimeric molecule is a nucleic acid analog polynucleotide, and the intermediary polynucleotide is a non-nucleic acid analog polynucleotide.

In yet other embodiments, the first portion of the intermediary polynucleotide is a non-nucleic acid analog polynucleotide, the bound polynucleotide immobilized on the solid substrate is a nucleic acid analog polynucleotide, the second portion of the intermediary polynucleotide is a nucleic acid analog polynucleotide, and the bridging polynucleotide of the chimeric molecule is a non-nucleic acid analog polynucleotide.

In yet other embodiments, the first portion of the intermediary polynucleotide is a nucleic acid analog polynucleotide, the bound polynucleotide immobilized on the solid substrate is a non-nucleic acid analog polynucleotide, the second portion of the intermediary polynucleotide is a non-nucleic acid analog polynucleotide, and the bridging polynucleotide of the chimeric molecule is a nucleic acid analog polynucleotide.

It is contemplated that the methods of the present invention may be used to capture and isolate any number of different types of target molecules. For example, in some embodiments of the invention, the target molecule is a polynucleotide and the target component of the chimeric molecule is a nucleic acid analog polynucleotide complementary to the polynucleotide target molecule.

In other embodiments, the immobilized polynucleotide is a nucleic acid analog polynucleotide and the bridging polynucleotide is a non-nucleic acid analog polynucleotide.

In still other embodiments, the target molecule is a polynucleotide, the target component of the chimeric molecule is a nucleic acid analog polynucleotide complementary to the polynucleotide target molecule, the bridging polynucleotide of the chimeric molecule is a non-nucleic acid analog molecule, and the bound polynucleotide immobilized on the solid support is a nucleic acid analog polynucleotide that is complementary to the bridging polynucleotide.

As will be appreciated by those skilled in the art, other combinations of polypeptide and non-polypeptide linkages may be utilized to accomplish the purposes of the invention, provided that at least one complementary polynucleotide pair comprises at least one nucleic acid analog that can form a complex with a complementary polynucleotide and a light reactive dye.

B. Separation

The steps described in the above embodiments illustrate various means by which a target molecule of interest can be captured and immobilized on a solid substrate. In another aspect, the methods of the present invention include the step of separating the solid substrate (to which the target molecule is directly or indirectly attached) from the mixture, to thereby isolate the target molecule. Solid substrates include any of the various substrates used for separation, purification and detection of biological substances, including solid beads, gels, and the like, as discussed above in more detail. Thus, in one embodiment of the invention, the target molecule immobilized to the solid substrate via at least one light reactive complex, is isolated from a mixture, based on a property of the solid substrate, to thereby isolate the target polynucleotide from the sample. It will be understood that isolation of the solid substrate/target polynucleotide complex from the sample may include removal of the solid substrate from the sample mixture, or removal of the sample mixture from the solid substrate by washing the solid substrate with appropriate washing solutions, or combinations of the foregoing.

In typical applications, the target molecule will originate from a heterogeneous mixture, such as a blood sample, a water sample, a tissue sample, etc., comprising various contaminants mixed with the target molecule of interest. The methods of the present invention are particularly useful in separating a target molecule from such a heterogeneous mixture. As described in more detail in the examples below, various solid substrates may be used to immobilize a target molecule. Such immobilization techniques are well known in the art, as are techniques for the separation of a solid substrate from components not bound to the substrate, and need not be described herein.

C. Light Conditions

As illustrated in the examples, one of the principal advantages of the methods of the invention is that complexes formed a with a specific target molecule can be isolated and released under ordinary ambient light conditions. Capture/release experiments have been shown to work in ordinary room conditions, with no sunlight and only the light from the fluorescent overhead light fixtures. Light conditions were observed using a LaserCheck light meter, which indicated that the light level was approximately 66.7 $\mu W/cm^2$ in the room with fluorescent lights on and windows, and 34.1 $\mu W/cm^2$ in the room with fluorescent lights on and no windows. Other than the location of the release step, the capture/release/detection reactions were the same. The initial slope at 2 minutes was 68.5 (std. dev. 2.8) for the reactions released in the lab (with lights and windows). The initial slope at 2 minutes was 70.8 (std. dev. 0.7) for the reactions released in the room (with lights and no windows).

In some instances, the present invention may also be practiced under controlled light conditions, using an instrument that carefully controls light level, wavelength and exposure time, so as to provide more control over assay results.

D. Temperature Conditions

In accordance with the present invention, the capture of target molecules by means of light reactive complex formation may be accomplished under ambient temperature conditions. In some embodiments, the light reactive complex is formed at room temperature. In other embodiments, the light reactive complex is formed at a temperature less than about 37° C. In yet other embodiments, the light reactive complex is formed at a temperature less than about 45° C. The above light conditions are substantially below those temperature conditions ordinarily required for the rapid formation of complexes between complementary polynucleotide molecules.

E. Release

In yet another aspect of the present invention, the target molecule, captured via formation of a light reactive complex between complementary polynucleotides immobilized to a solid substrate, is released from the light reactive complex.

In one embodiment, the present invention optionally includes the step of exposing the light reactive complex, formed as described above, to light, to thereby elute the target polynucleotide from the solid substrate into the eluant to provide a purified target polynucleotide.

Any one or more of the light reactive dyes described herein may be used in the capture assays of the present invention. The light reactive dyes capable of being used in the methods of the invention are described in more detail in the definition of "dye," above, and in section IV.A, below. For example, some preferred light reactive dyes include the following: 3,3'-diethylthiacarbocyanine, 3,3'-diallylthiacarbocyanine, 3,3'-diethyl-9-methylthiacarbocyanine, 3,3'-dibutylthiacarbocyanine, 3,3'-dipropylthiacarbocyanine, 3,3'-dipentylthiacarbocyanine, and 1,1'-diethyl-2,2'-carbocyanine, and salts thereof. One dye found to be particularly useful is 3,3'-Diethylthiacarbocyanine or salts thereof. Preferred salts include, for example, iodide and bromide salts.

The nucleic acid analogs used in the various embodiments of the capture and release assays have been described previously herein. In some embodiments of the invention, the nucleic acid analogs include, for example, PNA polynucleotides, LNA polynucleotides and morpholino polynucleotides. PNA polynucleotides have been found to be especially amenable to light reactive complex formation with the light reactive dyes of the invention. As discussed elsewhere, the nucleic acid analogs may be of various lengths. Particularly useful nucleic acid analogs range from 10-30 bases in length, from 12-25 bases in length, less than about 20 bases in length, or less than about 15 bases in length. In some embodiments, the nucleic acid analogs are about 17 bases in length. The length of particular nucleic acid analogs can vary considerably; however, due to the enhanced stability of the light reactive complexes of the invention (which comprise nucleic acid analog polypeptides having a greater degree of stability, together with the light reactive dye) the capture assays of the present invention enable use of nucleic acid analog polynucleotides of shorter length than ordinarily used for PCR based probes and primers, while still achieving acceptable levels of specificity and sensitivity.

The capture and release assays described above may be used to isolate a target molecule from a heterogeneous mixture, preparatory to detection in accordance with the detection methods described herein, which may utilize light reactive complexes formed between polynucleotides and nucleic acid analog polynucleotides. It is understood that the same nucleic acid analogs used in conjunction with the target molecule capture and release steps of the invention, may also be use in the subsequent detection steps. Alternatively, it may be desirable in some circumstances to utilize nucleic acid analog polynucleotides that are complementary to entirely different polynucleotides. For example, in the case of nucleic acid analog polynucleotides that are complementary to, and form a complex directly with, a target polynucleotide itself, the nucleic acid analog polynucleotides used in the capture or release steps may be designed to be complementary to a completely different region of the target polynucleotide. Although the mechanism of action responsible for light induced dissolution of the light reactive complexes is unknown, experiments have demonstrated that under some conditions the region of complementarity between a polypeptide and a nucleic acid analog, which forms a complex with the light reactive dye, is not subsequent to complex dissolution, amenable to hybridization with complementary nucleic acid primers, and cannot, for example, be used as a primer site for PCR amplification. Although data indicates that the complex is no longer associated with the solid substrate to which is was previously bound, this phenomena may be explained by any one of various theories: (1) the complex may be intact (i.e., the binding site of the primer may be inaccessible because it is occupied by the dye, the complementary analog nucleic acid polypeptide, or both, and therefore unavailable for hybridization), (2) the complex may be destroy (i.e., no complementary binding site exists), or (3) may be modified in such a manner that it is no longer amenable to hybridization with a complementary polynucleotide. In any event, in those circumstances where the region of complementarity of a target polynucleotide cannot be used in subsequent steps, it is possible to utilize nucleic acid analog polynucleotides that are complementary to different regions of the target polynucleotide.

In view of the fact that the mechanism of action for dissolution of the light reactive complexes from the solid substrate is not known, nor is it known whether the complex is partially or completely intact, or destroyed, it is to be understood that references to "eluting" the target polynucleotide from the solid substrate into the eluant to provide a purified target polynucleotide does not require or imply that the target polynucleotide itself remains intact or retains biological activity. As described in the above paragraph, the target molecule may become disassociated from the solid substrate to which is was immobilized, and exist in any of a number of forms, remaining complexed with one or more of the nucleic acid analog polynucleotide and the dye, or the binding region to which the complementary nucleic acid analog polynucleotide may be disrupted by the light reactive dye upon exposure to light, resulting in destruction and/or cleavage of the region of complementarity. Thus, the term "eluting" is intended to be construed liberally to mean that the solid substrate is disassociated, released or separated from the target molecule, without implying the state or condition of the target molecule or the light reactive complex (or of the solid support) with which is was associated prior to exposure to light.

VI. QUANTIFYING THE AMOUNT OF A TARGET POLYNUCLEOTIDE

The methods and compositions disclosed herein may be used to quantify the amount of target polynucleotide in a sample. In one embodiment, the amount of a target polynucleotide may be detected by establishing serial dilutions of the nucleic acid analog molecule, adding various amounts of the target polynucleotide samples, and comparing the samples to controls of known concentrations. In another embodiment, the amount of a target polynucleotide may be detected by establishing serial dilutions of the target polynucleotide, adding various amounts of the nucleic acid analogs or target polynucleotides, and comparing the samples to controls of known concentrations.

Alternatively, the amount of a target polynucleotide can be detected by measuring the kinetics of the assay based on time. Measurements of the dye in the combined mixture are taken at regular intervals after preparation of the mixture, or after application of light stimulus. The dye may be detected at distinct times after combination of the mixture, or after application of the light stimulus. The time may be any fixed time, for example the total time for the change in optical property, or the time required for the optical property to have changed by a certain percentage, such as, but not limited to, about 20%. The reactions can be frozen (further change stopped), for example with the addition of solvents such as 20% methanol, 15% isopropanol, 15% DMSO, or 10% butanol.

The quantity of polynucleotide in a sample may be determined after exposure to the light stimulus. The change in the optical property of the dye may be measured following pre-exposure to the light stimulus for the starting optical property. Measurements may be taken at distinct times (for example, but not limited to, taken at 30 second intervals, 1 second intervals, millisecond intervals, or microsecond intervals) after exposure to the light stimulus. The reactions can be frozen (further change stopped) as described above.

Changes in the sample due to exposure to the light stimulus can be observed in several ways. The change in the optical property may be observed as a change in color, absorbance, transmittance, fluorescence, reflectance, chemiluminescence, or a combination thereof. Alternatively, the change in optical property can be read using a reader. This change is measured using a spectrophotometer or a fluorometer, such as Tecan Genios or a Tecan Safire. Specific observation wavelengths may be selected, for example by a filter. A positive control expresses a change in absorbance faster than a negative test. It can be measured as a difference in the rate of change, or the difference in the change at a set time. If a light stimulus is used and fluorescent properties are observed, the light stimulus provided to the sample is at a higher energy (lower wavelength) than the observed emission. The excitation may be at, for example, 535 nm and the emission may be read at 590 nm. The fluorescence may be measured as a difference in the rate of change or the difference in the change at a set time or at a minimum time.

VII. TARGET BINDING COMPLEXES

The methods and associated compositions disclosed herein can also be used as a reporter to facilitate identification of molecular interactions, such as protein-protein interactions or protein-glycoprotein interactions.

A target binding complex includes a target binding component and a reporter complex. Target binding components, discussed in more detail below, are any molecule that is capable of binding a target. A reporter complex includes a first reporter nucleotide sequence, a second reporter nucleotide sequence, and a dye. At least one component of the reporter complex is covalently bonded to a target binding component to form a modified target binding component. The modified target binding component is introduced to a sample suspected of containing a target. Preferably, washing steps are performed to remove target binding component that is not bound to the target. The remaining components of the reporter complex are added to form a target binding complex. The order of addition of the target binding complex or the remaining components of the reporter complex to the sample is not critical, and can be in reverse order. Optionally, a light stimulus is provided; preferably, the light stimulus is provided. The rate of change in an optical property of the sample (now including the dye) is determined, as described above for P/TP hybrids. The presence or amount of the target is thereby determined.

It will be understood that any other components described in the methods in the present invention can be added to the target binding complex in any combination.

Further, it will be understood that methods of detecting targets can be performed using any format disclosed herein. For example, the target-binding complex can be adapted to a liquid-based format, solid-based format, or gel-based format. Non-limiting examples of formats include gel matrix platforms, electrophoretic platforms, membrane-bound platforms, chromatographic platforms, immobilized plates, and immobilized beads.

A. Reporter Complex

The reporter complex is similar to, and in some cases the same as, the combination of target polynucleotide, nucleic acid analog, and dye disclosed in the methods of detecting a target polynucleotide. As noted above, the reporter complex includes a first reporter nucleotide sequence, a second reporter nucleotide sequence, and a dye. The first reporter nucleotide sequence can be a DNA, RNA, or a nucleic acid analog. Likewise, the second reporter nucleotide sequence can be, independently of the first reporter nucleotide, a DNA, RNA, or a nucleic acid analog. The first and second reporter nucleotide sequences hybridize to form a double-stranded hybrid.

In certain embodiments, the first reporter nucleotide sequence is covalently bonded to the target-binding component. The second reporter nucleotide sequence and dye are subsequently added to form the mixture. The order in which the second reporter nucleotide sequence and dye are added is not critical.

Alternatively, the first reporter nucleotide sequence and second reporter nucleotide sequence can be covalently linked in a 5'-3' arrangement to form a self-hybridizing hairpin, or can be crosslinked. The hairpin or crosslinking stabilizes hybrid formation, and minimizes loss of single-stranded polynucleotide. In this embodiment, the dye is then added to form the target binding complex. In another alternative, the dye can be covalently bonded to the first reporter nucleotide sequence or the second reporter nucleotide sequence.

In certain embodiments, the first reporter nucleotide sequence and/or the second reporter nucleotide sequence can have a non-complementary overhang. It will be understood that the first and second reporter nucleotide sequences are complementary while still maintaining one or more overhangs.

The components of the reporter complex can be covalently linked to the target binding component by any means known in the art. The functional groups of amino acids of ligands suitable for covalent binding under mild conditions include but are not limited to (i) the alpha amino groups of the chain and the epsilon amino groups of lysine and arginine, (ii) the alpha carboxyl group of the chain end and the beta and gamma carboxyl groups of aspartic and glutamic acids, (iii) the phenol ring of tyrosine, (iv) the thiol group of cysteine, (v) the hydroxyl groups of serine and threonine, (vi) the imidazile group of histidine, and (vii) the indole group of tryptophan. Similarly, the nucleic acid analog can be synthesized to contain any of these chemical moieties.

Those skilled in the art will recognize any number of established chemical conjugating techniques for covalently attaching nucleic acid analogs to ligands. Some non-limiting examples include cyanogen bromide formation of reactive cyclic-imido carbamate for covalent coupling of amines, carbodiimide formation of O-acyl isourea for coupling of amines, maleimidobenzoyl NHS ester formation for coupling of amines and sulfhydryls, and maleimidocaproic acid hydrazide HCl for coupling of sulfhydryls and carbohydrates. Non-covalent attachments can be accomplished by creating oxidized disulfide bonds between cysteines from nucleic acid analogs and ligands. These can be easily reduced by dithiothreitol (DTT) or tris(2-carboxyethyl) phosphine (TCEP) thereby releasing the nucleic acid analog/polynucleotide hybrid from the ligand as needed.

The target binding component can be covalently attached to the at least one component of the reporter complex by a linking group. Linking groups are chemical moieties that link or connect reactive groups to ITPs. The linking group can be any linking group can include one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heteroaryl groups, and substituted heteroaryl groups. Linking groups may also comprise poly ethoxy aminoacids such as AEA ((2-amino) ethoxy acetic acid) or a preferred linking group AEEA ([2-(2-amino)ethoxy)]ethoxy acetic acid).

The sequence of the first and second reporter nucleotide sequences may be designed in a variety of ways. By way of example and not limitation, different reporter nucleotide sequence sequences may be optimized to produce an increased rate of change in optical property of a sample that includes the dye. Empirically determined "universal" first and second reporter nucleotide sequences will be used to maximally meet assay requirements.

A series of first and second reporter nucleotide sequences can be prepared by any method known in the art. For example, the reporter nucleotide sequences can be synthesized in vitro or in vivo (such as by recombinant methods). After the reporter nucleotide sequences are annealed, the rate of change of the sample that includes the dye can be tested under a number of different conditions. The greater the rate of change for first and second reporter nucleotide sequences have a specific sequence, the when the first and second reporter nucleotide sequences are covalently linked in a 5' to 3' arrangement.

The first and second reporter nucleotide sequence sequences can be of any length, provided that they hybridize together. The length of the first and second reporter nucleotide sequences also can be optimized, as discussed above.

The optimization methods can be adapted for any embodiment of first reporter nucleotide sequence, second reporter nucleotide sequence, and dye. For example, the first or second reporter nucleotide sequences can be covalently bonded to the target binding component, and the assay rate of change in the assay can be determined. The dye can be covalently bound to the target binding component.

It will be understood that screening methods can be optimized for the addition of any compound disclosed in the present invention.

B. Target binding components

The target binding component may be any molecule that is capable of selectively interacting with a desired target. Exemplary targets include, but are not limited to, cells, microorganisms (such as bacteria, fungi, and viruses), polypeptides, nucleic acids (such as polynucleotides, cDNA molecules, or genomic DNA fragments), hormones, cytokines, drug molecules, carbohydrates, pesticides, dyes, amino acids, or small organic or inorganic molecules. Target binding components having limited cross-reactivity are generally preferred. Exemplary target binding components include, for example, antibodies, antibody fragments, non-antibody receptor molecules, template imprinted materials, lectins, enzymes, and organic or inorganic binding elements.

Some of the specific embodiments of target binding components are explained in more detail below. This disclosure does not limit the scope of the target binding components, as used herein.

1. Antibodies and Antibody Fragments

In certain embodiments, the target binding component may be an antibody or an antibody fragment. For example, target binding components may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and fragments thereof, humanized antibodies and fragments thereof, and multivalent versions of the foregoing. Multivalent target binding components include without limitation: monospecific or bispecific antibodies, such as disulfide stabilized Fv fragments, scFv tandems ((ScFV)$_2$ fragments), diabodies, tribodies or tetrabodies, which typically are covalently linked or otherwise stabilized (e.g., leucine zipper or helix stabilized) scFv fragments; receptor molecules that naturally interact with a desired target molecule.

In one embodiment, the target binding component is preferably an antibody. Preparation of antibodies may be accomplished by any number of well-known methods. For generating monoclonal antibodies, presuming that the antigen of interest is known and available, the first step is immunization of animals, typically mice, with a desired antigen (e.g., a desired target molecule or fragment thereof). Once the mice have been immunized, and preferably boosted one or more times with the desired antigen(s), monoclonal antibody-producing hybridomas are preferably prepared and screened according to well-known methods (see, e.g., Kuby, Janis, IMMUNOLOGY, Third Edition, pp. 131-139, W.H. Freeman & Co. (1997), for a general overview of monoclonal antibody production, that portion of which is incorporated herein by reference).

In vitro methods that combine antibody recognition and phage display techniques allow one to amplify and select antibodies with very specific binding capabilities. See, e.g., Holt et al., Current Opinion in Biotechnology 11:445 (2000). These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In another embodiment, the target binding component may be an antibody fragment. Preparation of antibody fragments may be accomplished by any number of well-known methods. In one embodiment, phage display technology may be used to generate antibody fragment target binding components that are specific for a desired target molecule, including, for example, Fab fragments, Fv's with an engineered intermolecular disulfide bond to stabilize the VH-VL pair, scFvs, or diabody fragments. As an example, production of scFv antibody fragments using phage display is described below.

For phage display, an immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired VH and VL chains, to yield cDNA. The desired VH and VL chains are amplified by polymerase chain reaction (PCR) typically using VH and VL specific primer sets, and are ligated together, separated by a linker. VH and VL specific primer sets are commercially available, for instance from Stratagene, Inc. of La Jolla, Calif.

Assembled VH-linker-VL product (encoding an scFv fragment) is selected for and amplified by PCR. Restriction sites are introduced into the ends of the VH-linker-VL product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as fd and M1 3, typically M13.

In phage display vectors, the VH-linker-VL sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M1 3) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction and screening methods are described in detail in, among others, U.S. Pat. Nos. 5,702,892, 5,750,373, 5,821,047, and 6,127,132.

Typically, once phage are produced that display a desired antibody fragment, epitope specific phage are selected by their affinity for the desired immunogen and, optionally, their lack of affinity to compounds containing certain other structural features. A variety of methods may be used for physically separating immunogen-binding phage from non-binding phage. Typically the immunogen is fixed to a surface and the phage are contacted with the surface. Non-binding phage are washed away while binding phage remain bound. Bound phage are later eluted and are used to re-infect cells to amplify the selected species. A number of rounds of affinity selection typically are used, often increasingly higher stringency washes, to amplify immunogen binding phage of increasing affinity. Negative selection techniques also may be used to select for lack of binding to a desired target. In that case, un-bound (washed) phage are amplified.

Although it is preferred to use spleen cells and/or B-lymphocytes from animals pre-immunized with a desired immunogen as a source of cDNA from which the sequences of the VH and VL chains are amplified by RT-PCR, naive (un-immunized with the target immunogen) splenocytes and/or B-cells may be used as a source of cDNA to produce a polyclonal set of VH and VL chains that are selected in vitro by affinity, typically by the above-described phage display (phagemid) method. When naive B-cells are used, during affinity selection, the washing of the first selection step typically is of very low stringency so as to avoid loss of any single clone that may be present in very low copy number in the polyclonal phage library. By this naive method, B-cells may be obtained from any polyclonal source. B-cell or splenocyte cDNA libraries also are a source of cDNA from which the VH and VL chains may be amplified. For example, suitable murine and human B-cell, lymphocyte and splenocyte cDNA libraries are commercially available from Stratagene, Inc. and from Clontech Laboratories, Inc. of Palo Alto, Calif. Phagemid antibody libraries and related screening services are provided commercially by Cambridge Antibody Technology of the U.K. or MorphoSys USA, Inc.) of Charlotte, N.C.

The target binding components do not have to originate from biological sources, such as from naive or immunized immune cells of animals or humans. The target binding components may be screened from a combinatorial library of synthetic peptides. One such method is described in U.S. Pat. No. 5,948,635, which described the production of phagemid libraries having random amino acid insertions in the pIII gene of M1 3. These phage may be clonally amplified by affinity selection as described above.

Panning in a culture dish or flask is one way to physically separate binding phage from non-binding phage. Panning may be carried out in 96 well plates in which desired immunogen structures have been immobilized. Functionalized 96 well plates, typically used as ELISA plates, may be purchased from Pierce Biotechnology, Inc. of Rockford, Ill. Polypeptide immunogens may be synthesized directly on $NH_2$ or COOH functionalized plates in an N-terminal to C-terminal direction. Other affinity methods for isolating phage having a desired specificity include affixing the immunogen to beads. The beads may be placed in a column and phage may be bound to the column, washed and eluted according to standard procedures. Alternatively, the beads may be magnetic so as to permit magnetic separation of the binding particles from the non-binding particles. The immunogen also may be affixed to a porous membrane or matrix, permitting easy washing and elution of the binding phage.

In certain embodiments, it may be desirable to increase the specificity of the target binding component for a given target molecule using a negative selection step in the affinity selection process. For example, target binding component displaying phage may be contacted with a surface funtionalized with immunogens distinct from the target molecule. Phage are washed from the surface and non-binding phage are grown to clonally expand the population of non-binding phage thereby de-selecting phage that are not specific for the desired target molecule. In certain-embodiments, random synthetic peptides may be used in the negative selection step. In other embodiments, one or more immunogens having structural similarity to the target molecule may be used in the negative selection step. For example, for a target molecule comprising a polypeptide, structurally similar immunogens may be polypeptides having conservative amino acid substitutions, including but not limited to the conservative substitution groups such as: (i) a charged group, consisting of Glu, Asp, Lys, Arg, and H is, (ii) a positively-charged group, consisting of Lys, Arg, and H is, (iii) a negatively-charged group, consisting of Glu and Asp, (iv) an aromatic group, consisting of Phe, Tyr, and Trp, (v) a nitrogen ring group, consisting of His and Trp, (vi) a large aliphatic nonpolar group, consisting of Val, Leu, and Ile, (vii) a slightly polar group, consisting of Met and Cys, (viii) a small-residue group, consisting of Ser, Thr, Asp, Asn, Gly, Ala, Glu, Gln, and Pro, (ix) an aliphatic group consisting of Val, Leu, Ile, Met, and Cys, and (x) a small hydroxyl group consisting of Ser and Thr. Conservative substitutions also may be determined by one or more methods, such as those used by the BLAST (Basic Local Alignment Search Tool) algorithm, such as a BLOSUM Substitution Scoring Matrix, such as the BLOSUM 62 matrix, and the like. A functional way to define common properties between individual amino acids is to analyze the normalized frequencies of amino acid changes between corresponding proteins of homologous organisms (Schulz and Schirmer, PRINCIPLES OF PROTEIN STRUCTURE: Springer Advanced Texts in Chemistry, Springer-Verlag, New York, 1990).

Screening of target binding components will best be accomplished by high throughput parallel selection, as described in Holt et al. Alternatively, high throughput parallel selection may be conducted by commercial entities, such as by Cambridge Antibody Technologies or MorphoSys USA, Inc.

Alternatively, selection of a desired target binding component-displaying phage may be carried out using the following method.

Step 1: Affinity purify phage under low stringency conditions for their ability to bind to an immunogen fixed to a solid support (for instance, beads in a column).

Step 2: Elute the bound phage and grow the eluted phage. Steps 1 and 2 may be repeated with more stringent washes in Step 1.

Step 3: Absorb the phage under moderate stringency with a given protein mixture digested with a proteolytic agent of interest. Wash away the unbound phage with a moderately stringent wash and grow the washed phage. Step 3 may be repeated with less stringent washes.

Step 4: Affinity purify phage under high stringency for their ability to bind to the immunogen fixed to a solid support. Elute the bound phage and grow the eluted phage.

Step 5: Plate the phage to select single plaques. Independently grow phage selected from each plaque and confirm the specificity to the desired immunogen.

This is a general guideline for the clonal expansion of immunogen-specific target binding components. Additional steps of varying stringency may be added at any stage to optimize the selection process, or steps may be omitted or re-ordered. One or more steps may be added where the phage population is selected for its inability to bind to other immunogens by absorption of the phage population with those other immunogens and amplification of the unbound phage population. That step may be performed at any stage, but typically would be performed after step 4.

In certain embodiments, it may be desirable to mutate the binding region of the target binding component and select for target binding components with superior binding characteristics as compared to the un-mutated target binding component. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the target binding components may be modified to make them more resistant to cleavage by proteases. For example, the stability of the target binding components of the present invention that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the target binding components may be of the D configuration. The switch from L to D amino acids neutralizes the digestion capabilities of many of the ubiquitous peptidases found in the digestive tract. Alternatively, enhanced stability of the target binding components of the invention may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the target binding components may be achieved by intercalating one or more dextrorotatory amino acids (such as, dextrorotatory phenylalanine or dextrorotatory tryptophan) between the amino acids of the target binding component. In exemplary embodiments, such modifications increase the protease resistance of the target binding components without affecting their activity or specificity of interaction with a desired target molecule.

In certain embodiments, the antibodies or variants thereof, may be modified to make them less immunogenic when administered to a subject. For example, if the subject is human, the antibody may be "humanized"; where the complementarity determining region(s) of the hybridoma-derived antibody has been transplanted into a human monoclonal antibody, for example as described in Jones et al., NATURE 321:522 (1986), Tempest et al. BIOTECHNOLOGY 9:266 (1991), and U.S. Pat. No. 6,407,213. Also, transgenic mice, or other mammals, may be used to express humanized antibodies. Such humanization may be partial or complete.

In another embodiment, the target binding component is a Fab fragment. Fab antibody fragments may be obtained by proteolysis of an immunoglobulin molecule using the protease papain. Papain digestion yields two identical antigen-binding fragments, termed "Fab fragments", each with a single antigen-binding site, and a residual "Fc fragment". In an exemplary embodiment, papain is first activated by reducing the sulfhydryl group in the active site with cysteine, mercaptoethanol or dithiothreitol. Heavy metals in the stock enzyme may be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

In still another embodiment, the target binding component is an $F(ab')_2$ fragment. $F(ab')_2$ antibody fragments may be prepared from IgG molecules using limited proteolysis with the enzyme pepsin. Exemplary conditions for pepsin proteolysis are 100 times antibody excess w/w in acetate buffer at pH 4.5 and 37° C. Pepsin treatment of intact immunoglobulin molecules yields a $F(ab')_2$ fragment that has two antigen-combining sites and is still capable of crosslinking antigen. Fab' antibody fragments may be obtained by reducing $F(ab')_2$ fragments using mercaptoethylamine. The Fab' fragments may be separated from unsplit $F(ab')_2$ fragments and concentrated by application to a Sephadex G-25 column (M=46,000-58,000).

2. Non-Antibody Embodiments

In other embodiments, the target binding component may be a non-antibody receptor molecule, including, for example, receptors that naturally recognize a desired target molecule, receptors that have been modified to increase their specificity of interaction with a target molecule, receptor molecules that have been modified to interact with a desired target molecule not naturally recognized by the receptor, and fragments of such receptor molecules (see, e.g., Skerra, MOLECULAR RECOGNITION 13:167 (2000)).

3. Template Imprinting Materials

In other embodiments, the target binding components may be a template imprinted material. Template imprinted materials are structures that have an outer sugar layer and an underlying plasma-deposited layer. The outer sugar layer contains indentations or imprints that are complementary in shape to a desired target molecule or template so as to allow specific interaction between the template imprinted structure and the target molecule to which it is complementary. Template imprinting can be utilized on the surface of a variety of structures, including, for example, medical prostheses (such as artificial heart valves, artificial limb joints, contact lenses and stents), microchips (preferably silicon-based microchips), and components of diagnostic equipment designed to detect specific microorganisms, such as viruses or bacteria.

Template-imprinted materials are discussed in U.S. Pat. No. 6,131,580.

In another embodiment, a target binding component of the invention may be modified so that its rate of traversing the cellular membrane is increased. For example, the target binding component may be attached to a peptide that promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, CELL 55:1179 (1989)).

Alternatively, the internalizing peptide may be derived from the *Drosophila antennapedia* protein, or homologs thereof. The 60 amino acid long homoeodomain of the homeo-protein antennapedia has been demonstrated to translocate through biological membranes and can facilitate the translocation of heterologous polypeptides to which it is coupled. Thus, target binding components may be fused to a peptide consisting of about amino acids 42-58 of *Drosophila antennapedia* or shorter fragments for transcytosis (Derossi et al., J. BIOL. CHEM. 271:18188 (1996); Derossi et al., J. BIOL. CHEM. 269:10444 (1994); and Perez et al., J. CELL Sci. 102:717 (1992). The transcytosis polypeptide may also be a non-naturally-occurring membrane-translocating sequence (MTS), such as the peptide sequences disclosed in U.S. Pat. No. 6,248,558.

In exemplary embodiments, the dissociation constant of the target binding component for a target molecule is optimized to allow real time monitoring of the presence and/or concentration of the analyte in a given patient, sample, or environment.

4. Lectins

The target binding component can be a lectin. Lectins are a class of carbohydrate-binding proteins found in plants, viruses, microorganisms and animals. Frequently, lectins are multimeric having two or more of non-covalently associated subunits. A lectin may contain two or more of the same subunit, such as ConA, or different subunits, such as *Phaseolus vulgaris* agglutinin. At least one component of the reporter complex can be covalently bonded to the lectin.

Because of the specificity that each lectin has toward a particular carbohydrate structure, oligosaccharides with identical sugar compositions can be distinguished or separated. Certain lectins will bind only to structures with mannose or glucose residues, while others may recognize only galactose residues. Certain other lectins require that the particular sugar be in a terminal non-reducing position in the oligosaccharide, while others can bind to sugars within the oligosaccharide chain. Some lectins do not discriminate between a and b anomers, while others require not only the correct anomeric structure, but a specific sequence of sugars for binding. The affinity between a lectin and its receptor may vary a great deal due to small changes in the carbohydrate structure of the receptor. All of these properties that are peculiar to lectins enable one to discriminate between structures, to isolate one glycoconjugate, cell, or virus from a mixture, or to study one process among several. Because virtually all biological membranes and cell walls contain glycoconjugates, all living organisms can be studied with lectins.

In certain embodiments, a target binding component can include a chemical handle that facilitates its isolation, immobilization, identification, or detection, additionally, or in the alternative, the chemical handle can serve to increase the solubility of the target binding component. In various embodiments, chemical handles may be a polypeptide, a polynucleotide, a carbohydrate, a polymer, or a chemical moiety, or combinations or variants thereof. In certain embodiments, exemplary chemical handles include glutathione S-transferase (GST), protein A, protein G, calmodulin-binding peptide, thioredoxin, maltose binding protein, HA, myc, poly arginine, poly H is, poly His-Asp or FLAG tags. Additional exemplary chemical handles include polypeptides that alter protein localization in vivo, such as signal peptides, type III secretion system-targeting peptides, transcytosis domains, nuclear localization signals, and the like. In various embodiments, a target binding component of the invention may include one or more chemical handles, including multiple copies of the same chemical handle or two or more different chemical handles. It is also within the scope of the invention to include a linker (such as a polypeptide sequence or a chemical moiety) between a target binding component of the invention and the chemical handle in order to facilitate construction of the molecule or to optimize its structural constraints. In another embodiment, the target binding complex including a chemical handle may be constructed so as to contain protease cleavage sites between the chemical handle and the target binding component of the invention in order to remove the chemical handle. Examples of suitable endoproteases for removal of a chemical handle include Factor Xa and TEV proteases.

In other embodiments, the target binding component can be a drug, a putative drug, a drug target, or a putative drug target. Drugs are disclosed, for example, in the MERCK INDEX 13$^{th}$ Ed. (2001).

It will be understood that the target binding components discussed above are only exemplary. Any other target binding component that binds a target can be used.

VIII. COMPOSITIONS

The present invention also contemplates compositions including components used in the methods disclosed herein.

In certain embodiments, the compositions include at least two of the components that can be used in the methods disclosed herein. By way of example and not limitation, the composition can include a dye and a specific nucleic acid analog. More specially, the composition can include a dye, and at least one of a chiral PNA, an LNA, a morpholino nucleic acid, a TNA, or a metal-linked nucleic acid. Such compositions can further include a surfactant and/or a target. In certain circumstances, alcohol is added in combination with a surfactant.

In other embodiments, the composition can include a detergent and at least one of the other components used in the method. For example, a composition can include a detergent and a nucleic acid analog, a dye, and/or a target polynucleotide. The detergent can be any detergent known in the art. In certain formulations, the detergent can be a cationic, anionic, non-ionic, or zwitterionic detergent. In certain formulations, the detergent can be at least one of TMAC, LSS, SDS, Tween® 20, Tween® 40, Tween® 80, NP40 Tergitol®, Span® 20, Span® 80, and CHAPS. In certain other formulations, the detergent can be at least one of Tween® 20, Tween® 40, Tween® 80, Tergitol® NP40, LSS, TMAC, and CHAPS. The composition can also include a PNA, an LNA, a morpholino nucleic acid, a TNA, or a metal-linked nucleic acid. The composition can include methanol, ethanol, isopropanol, butanol or other organic solvents known in the art.

The composition can also include a dye combined with a target polynucleotide and nucleic acid analog. For example, the composition can include a target polynucleotide/nucleic acid analog hybrid, combined with a dye. The composition can further include one or more of any other component disclosed in the methods herein.

The composition can also include a reagent that stops further change in the optical property of the dye. By way of example and not limitation, the stopping reagent can be a solvent such as 20% methanol, 15% isopropanol, 15% DMSO, or 10% butanol. If a surfactant is present for example, Tween® 80 at a concentration of about 0.05%, then a higher concentration of solvents is needed, such as in the range of about 40-50% methanol.

The composition can also include reagents such as 5 mM phosphate adjusted to pH 5.5. The composition can also include buffers such as 10 mM Homopipes, pH 5.0 with 0.05% Tween 80, or 1×TE with 0.05% Tween 80.

In certain embodiments, a solid support with a specific background color provides significantly improved detection of the target polynucleotide. Compositions can include a solid surface with any color background, including a white background. The solid support, for example, can be a microtiter plate having a white background. Alternatively, the compositions can include a sample surface modified to have the same interior as any plate described herein.

The compositions can include any other compound, compounds, or device used in the methods disclosed herein, in any combination.

IX. KITS

In one aspect, the present invention provides a kit for detecting target polynucleotides. A kit may include one or more reagents useful in the methods or compositions disclosed herein. For example, kits can include dyes, nucleic acid analogs (immobilized or not), surfactants, sources of light stimulus, buffers, alcohols, standards used for controls, keys illustrating positives and negatives of control samples for interpreting reaction results, and instructions. The kits may further include suitable packaging of the respective compositions and/or other optional components as disclosed below. The specific components may be provided in suitable containers.

A. Dyes

The kits provided herein include one or more dyes. The dyes can include any dye disclosed herein. The dyes can be provided in pre-packages amounts, or can be provided in a single tube from which aliquots can be apportioned or diluted and then apportioned. The dyes may be further packaged in any suitable packaging for segregation from other components of the kit and to facilitate dispensing of the composition.

B. Nucleic Acid Analogs

The kits may also include one or more nucleic acid analogs. The nucleic acid analog may be any nucleic acid analog, as described herein. The nucleic acid analog may have any sequence that is complementary or fully complementary to a target nucleic acid sequence. The sequence may be any sequence known in the art. In one embodiment, the nucleic acid analog has a sequence disclosed herein.

In one embodiment, the kit contains one or more nucleic acid analog provided in any suitable container or containers (if the multiple nucleic acid analogs are packaged separately). The nucleic acid analog(s) may be pre-aliquoted into usable amounts, or provided in a single tube to be apportioned (with or without), or may be already immobilized on a solid surface. The container may be further packaged in any suitable packaging for segregation from other components of the kit and to facilitate dispensing aliquots. In another embodiment, two or more the nucleic acid analog sequences may be contained in the same package. Nucleic acid analogs having differing sequences can be a mixture in each tube, or they can be separately packaged two or more tubes, each with a single-sequence analog.

The kits may also include a vehicle to facilitate effective hybridization of the nucleic acid analog to the target polynucleotide, such as a non-specific carrier polynucleotide, or other compound, such as glycerol, or a vehicle that disrupts effective hybridization (possibly in the absence of surfactants), such as methanol, ethanol, butanol, DMSO, sodium hydroxide, and formamide.

C. Detergents

The kits preferably also include one or more detergents used in the methods and compositions disclosed herein. The detergent can be any detergent known in the art. In certain other formulations, the detergent can be a cationic, anionic, non-ionic, or zwitterionic surfactant. In certain formulations, the surfactant can be at least one of TMAC, LSS, SDS, Tween® 20, Tween® 40, Tween® 80, NP40 Tergitol®, Span® 20, Span® 80, and CHAPS. In still other formulations, the surfactant can be at least one of Tween® 20, Tween® 40, Tween® 80, Tergitol® NP40, LSS, TMAC, Triton X100, Brij35, and CHAPS. The concentration of surfactant can be concentrated such that mixtures that include the surfactant have a specific concentration when diluted with other components.

The addition of alcohol to a mixture containing the detergent further reduces the photobleaching of the dye in the absence of a P/TP hybrid, but does not proportionally reduce the photobleaching of the dye in the presence of a P/TP hybrid. The aspect of the present invention is surprising because, in the absence of detergent, the addition of alcohol causes a greater photobleaching reduction in reactions with P/TP hybrid than in reactions without P/TP hybrid.

Any alcohol is preferably added so long as the added alcohol does not preclude the hybridization of the NAA to its complement, or otherwise preclude the catalytic activity of the NAA/NA hybrid. In certain embodiments, from about 8-12% ethanol or about 12-14% methanol is preferably added in tandem with a detergent at about 0.05%-0.5%.

D. Source of Light Stimulus

The kits are preferably outfitted with a source of light stimulus. The light source is preferably any light source known in the art. The light source can be capable of adjusting intensity and/or wavelength. Non-limiting examples of light sources include the Sylvania Cool White T8-CW, General Electric T8-C50, Fritz Aurora 50/50, a Sylvania dulux S9W CF$_9$DS/blue, Osram F9TT/50K, halogen autolamp, and SiC, InGaN, GaP, GaAsP, GaN+SiC, GaN-based Light Emitting Diodes (such as Jameco #183222 a 470 nm LED, Jameco #334473 a 505 nm LED, Jameco #183214 a 515 nm LED, or a white multiwavelength (420-700 nm) LED #LLW5210200), or solid-state lasers.

E. Polynucleotide Manipulating Components

The kits may also include components used to manipulate or preserve polynucleotides, such as buffers, enzymes, columns, and other materials.

The buffers, enzymes, columns, and other materials can include those that are used to lyse cells or extract DNA or RNA from a cell. The buffers, enzymes, columns, and other materials can also include components used to manipulate polynucleotides, including DNA and RNA. Such components include, for example, those disclosed in MOLECULAR CLONING: A LABORATORY MANUAL, third edition (Sambrook et al, 2000) Cold Spring Harbor Press, or any other reference disclosed herein.

F. Instructions

Kits preferably include instructions for performing the methods described herein. Instructions may be included as a separate insert and/or as part of the packaging or container, e.g., as a label affixed to a container or as writing or other communication integrated as part of a container. The instructions may inform the user of methods for application and/or removal of the contents of the kit, precautions and methods concerning handling of materials, expected results, warnings concerning improper use, and the like.

G. Additional Optional Components of the Kits

Kits may further contain components useful in practicing the methods disclosed herein. Exemplary additional components include chemical-resistant disposal bags, tubes, diluent, gloves, scissors, marking pens and eye protection.

The compositions can also include any type of solid surface described herein. The solid surface can be a specific color. In certain circumstances, the solid surface is white. The solid surface may, for example, be a microtiter plate having a number of white wells.

H. Computer Hardware and Software

The kits can also include computer hardware and/or computer software that can be used to measure the optical property of the mixture or gel or surface where the dye is included or placed. The hardware can include any detector used to measure the optical property. The software can include any algorithm used to note when a change in the optical property occurs, or determine a rate of change in the optical property. The kits can also include automated devices, such as those disclosed herein.

X. SOURCES OF TARGET POLYNUCLEOTIDES

The methods, compositions, and kits described herein have a variety of uses. Non-limiting examples of these uses include detecting and quantifying organisms, including the subset thereof referred to as pathogens, toxins, and the like. Pathogens of interest that may be detected using the present invention include foodborne pathogens, environmental pathogens, waterborne pathogens, or pathogens implicated in bio- or agroterrorism. Other non-limiting uses include disease diagnosis, such as sexually transmitted disease diagnosis, detection of genes conferring antibiotic resistance, detection of genes conferring a predisposition for drug responses, detection of genes implicated in an effective drug response, detection of genetically-modified organisms, detection of nonindigenous flora or fauna, detection of specific cancer-related genes, and mRNA levels. Additional non-limiting applications, relating, for example, to plant strain and/or grain quality, include agricultural applications and veterinary applications, many of which are the same or similar as the test developed for humans.

Examples, for illustration and not for limitation, are listed and described in the U.S. Ser. No. 60/655,929 ("the '929 application"), which is incorporated herein in its entirety. In particular, the '929 application sets forth detailed information regarding useful target polynucleotides, or descriptions of such polynucleotides, relating to pathogens (pp. 50-57), host response polynucleotides (pp. 57-58), foodborne and environmental pathogens (pp. 58-61), waterborne pathogens (pp. 61-62), bio- and agroterrorism (pp. 62-63), disease diagnostics such as genetic diseases and cancers (pp. 64-69), sexually-transmitted diseases (pp. 69-71), antibiotic resistance (pp. 71-72), genetic screening for a predisposition for drug responses (pp. 72-73), genes implicated in effective drug response (pp. 73-80), genetically-modified organisms (p. 80), nonidigenous flora and fauna (pp. 80-81), and agricultural and/or veterinary applications (pp. 81-83).

One embodiment of the present invention relates to methods, materials, and kits directed at the detection the tuberculosis pathogens, including *Mycobacterium tuberculosis*. Nucleic acid analogs may be designed to have sequences or fragments of sequences similar or identical to PCR primers used to identify tuberculosis. Examples of these PCR primers are disclosed in the art (see, e.g., M. J. Torres et al., DIAGN.

MICROBIOL. INFECT. DIS. 45:207-12 (2003); B. Bhattacharya et al., TROP. MED. INT. HEALTH 8:150-7 (2003); M. Kafwabulula et al., INT. J. TUBERC. LUNG DIS. 6:732-7 (2002)).

In another embodiment, nucleic acid analogs are designed that bind to target polynucleotides common to an entire group of pathogens. For example, nucleic acid analogs may be designed to detect all bacteria (BP6) universal probe set, gram positive bacteria probe set (BP19), gram negative bacteria probe set (BP3), and Fungi probe set (FP8). Any sequence in a set may be used. Examples of the sequences of the nucleic acid analogs for BP6, BP19, BP3, and FP8 are shown below. S=G and C mixture, M=A and C mixture, Y=C and T mixture, and W=A and T mixture according to IUB codes for mixed base sites.

TABLE 2

| Pathogen Group | | Sequence | SEQ ID NO: |
|---|---|---|---|
| BP6 | oI2018 | 5' gaaSSMYcYaacacYtagcact | 12 |
|  | oI2019 | 5' tacaaMgagYYgcWagacSgYgaS | 13 |
| BP19 | oI2021 | 5' gcagYWaacgcattaagcact | 14 |
|  | oI2022 | 5' acgacacgagctgacgacaa | 15 |
| BP3 | oI2003 | 5' tctagctggtctgagaggatgac | 16 |
|  | oI2004 | 5' gagttagccggtgcttcttct | 17 |
| FP8 | oI2055 | 5' cctgcggcttaatttgactca | 18 |
|  | oI2057 | 5' tagcgacgggcggtgtgta | 19 |

The nucleic acid analogs can be used in clinical applications for the diagnosis of the microbial cause of sepsis or in other applications where the microbial content of products in important in evaluating their shelf-life and stability or other products where the sterility is being assessed.

Target polynucleotides may be specific to ribosomal RNA sequences, such as 16S RNA in E. coli. Ribosomal RNA contains specific sequences that are characteristic to their organism. By using nucleic acid analog sequences that are complementary or exactly complementary to a target polynucleotide characteristic of the ribosomal RNA sequence, pathogens may be identified based on their ribosomal RNA sequences. Ribosomal RNA sequences characteristic of different pathogens or strains of pathogens, may be found, for example, at D. J. Patel et al., J. MOL. BIOL. 272:645-664 (1997).

The foregoing examples, and those incorporated by reference from the '181 application, are presented here to illustrate the breadth of application for the present invention. Other examples of target polynucleotides usefully employed in the context of the present invention certainly exist, and more are identified daily as the natural result of scientific investigators attempting to understand the basis and develop cures for the many and various pathogens and diseases of humankind, plants, and animals. Additionally, target polynucleotides that measure the state of a locality's environment and other non-medical or non-veterinary or non-agricultural applications are also contemplated as usefully employed with the present invention.

EXAMPLES

The following non-limiting examples serve to more fully describe the manner of using the above-described methods and compositions. It is understood that these examples in no way serve to limit the scope of the subject matter described herein, but rather are presented for illustrative purposes.

Throughout the examples, the term 'smartDNA assay' is used in reference to an assay that employs the methods of the present invention.

All nucleic acid analog and DNA stock solutions in the following examples were made in 5 mM phosphate buffer, pH 5.5 unless otherwise noted. The 5 mM phosphate buffer, pH 5.5, was used as the reaction buffer in all examples, unless otherwise noted. The stock dye was made in methanol or DMSO.

Example 1

This example illustrates uses and effects of different detergents on the diagnostic method of the present invention.

The addition of different classes of detergents at different concentrations was shown to have different effects on the signal to noise ratio. Some detergents increased the ratio while others had less dramatic effects. In one embodiment, detergent added to the reaction buffer increased the rate of change of the optical property in the test. In addition, each detergent reduced photobleaching of the dye in negative controls that lacked target polynucleotide.

Different detergents were added to the nucleic acid analog/target polynucleotide (P/TP) mixture, which included one of two target polynucleotides, one of two nucleic acid analogs, and a dye in a 5 mM phosphate buffer pH 5.5, at room temperature. Several different types of detergents were used, including cationic detergents, (specifically, tetramethyl ammonium chloride ("TMAC")), anionic surfactants (specifically, N-lauroyl sarcosine sodium salt ("LSS") and sodium dodecyl sulfate ("SDS")), nonionic detergents (specifically, various polyethylene glycol sorbitan monooleate solutions, sold under the trade names Tween® 20, Tween® 40, and Tween® 80, a polyglycol ether detergent sold under the trade name Tergitol® NP-40; sorbitan monolaurate, sold under the trade name Span® 20; and sorbitane monooleate, sold under the trade name Span® 80), and zwitterionic detergents (specifically, 3-[(3-cholamidopropyl)dimethylammonio]-1-propanesulfonate, commonly known by its acronym "CHAPS"). The various detergents were purchased from Sigma-Aldrich, St. Louis, Mo. The term "detergent" is used herein synonymously with the term "surfactant".

Aliquots of buffer reaction (each 5 mM phosphate, pH 5.5) containing different surfactants were prepared, and P/TP mixtures with the surfactants individually added were tested for the ability to (i) increase the sensitivity of the reaction and, separately, (ii) reduce photobleaching activity of the dye in a negative control. Each experiment contained four wells: (1) test well (non-chiral PNA, target polynucleotide, 3,3'-diethylthiacarbocyanine iodide dye and reaction buffer, with surfactant); (2) negative control well (non-chiral PNA, non-targeted polynucleotide, 3,3'-diethylthiacarbocyanine iodide dye, and reaction buffer, with and without surfactant); (3) dye control well (3,3'-diethylthiacarbocyanine iodide dye and reaction buffer, with and without surfactant); and (4) buffer control well (50 µl of reaction buffer, with and without surfactant). 10 pmoles 16S ncPNA (5' ACTGCTGCCTCCCG-TAG 3' [SEQ ID NO:8] or 5' TGCCTCCCGTAG 3' [SEQ ID NO:9]), 10 pmoles of complementary oligo (5'CTACGG-GAGGCAGCAGT 3' [SEQ ID NO:10] or 5'CTACGG-GAGGC 3' [SEQ ID NO: 11]), and 4 nmoles of 3,3'-diethylthiacarbocyanine iodide ("DTCC"; Sigma-Aldrich, St. Louis, Mo.) were placed in a 50 µl total reaction volume. ncPNAs (Applied Biosystems, Foster City, Calif.) and oligos (Sigma Genosys, St. Louis, Mo.) were reconstituted in water that was both DNase- and RNase-free as 100 µM stocks and further diluted to 2 µM working stocks. The DTCC dye was dissolved in dimethyl sulfoxide ("DMSO"; Sigma-Aldrich, St. Louis, Mo.) as an 8 mM stock. This stock was further diluted to a 2 mM working stock in 5 mM phosphate buffer (pH 5.5).

An initial fluorescence measurement was taken at time zero using a Tecan Genios microplate reader with the wavelengths set at 535 nm (for excitation) and 590 nm (for emission). The mixtures were then exposed to a light stimulus using the Aurora 50/50 (Fritz Industries, Inc., Mesquite, Tex.) for 1 minute intervals with fluorescence readings taken after each exposure for 5 minutes. For each reaction, the fluorescent emission values from the test well were compared to the fluorescent emission value from the negative control well (containing only ncPNA, dye, and reaction buffer) and converted to the percent changed. The percent change is calculated by the equation $$100-[(RFU_{TW}) \div (RFU_{NC})] \times 100,$$

where $RFU_{TW}$ represents the fluorescent emission in relative fluorescent units of a reaction mixture in a test well that includes all required components of the test and $RFU_{NC}$ represents the fluorescent emission in relative fluorescent units of a reaction mixture in a negative control well that does not include a target polynucleotide. The percent change is calculated at each time point. The percent difference between the measured rate in samples containing the target polynucleotide and the measured rate in samples not containing target polynucleotide was used to indicated the relative ability to detect presence of the target polynucleotide sequence.

FIG. 1 graphically presents the data collected in the studies detailed here. The reactions were each conducted in the presence of a detergent having a concentration of 0.05% v/v. Detergents added to the reaction buffer included the nonionic detergents Tween® 20 (♦), Tween® 40 (◊), Tween® 80 (○), and Tergitol® NP-40 (●); the anionic detergent LSS (■); the cationic detergent, TMAC (□); and the zwitterionic detergent CHAPS (x); where the symbols identified parenthetically after each of the named detergents are those used in the graphs of FIGS. 1 and 2. Improved sensitivity resulted upon the addition of 0.05% of any of the detergents when compared to the absence of detergent added. Decreased change in fluorescent emission of the dye in the absence of a nucleic acid analog/target polynucleotide hybrid compared to the dye alone was observed with the addition of Tween® 20, Tween® 40, Tween® 80, Tergitol® NP-40, LSS, TMAC and CHAPS. The rate of change was measured as the percent change in fluorescence of the test well as compared to the negative control in a concentration dependent manner.

Figure 2:
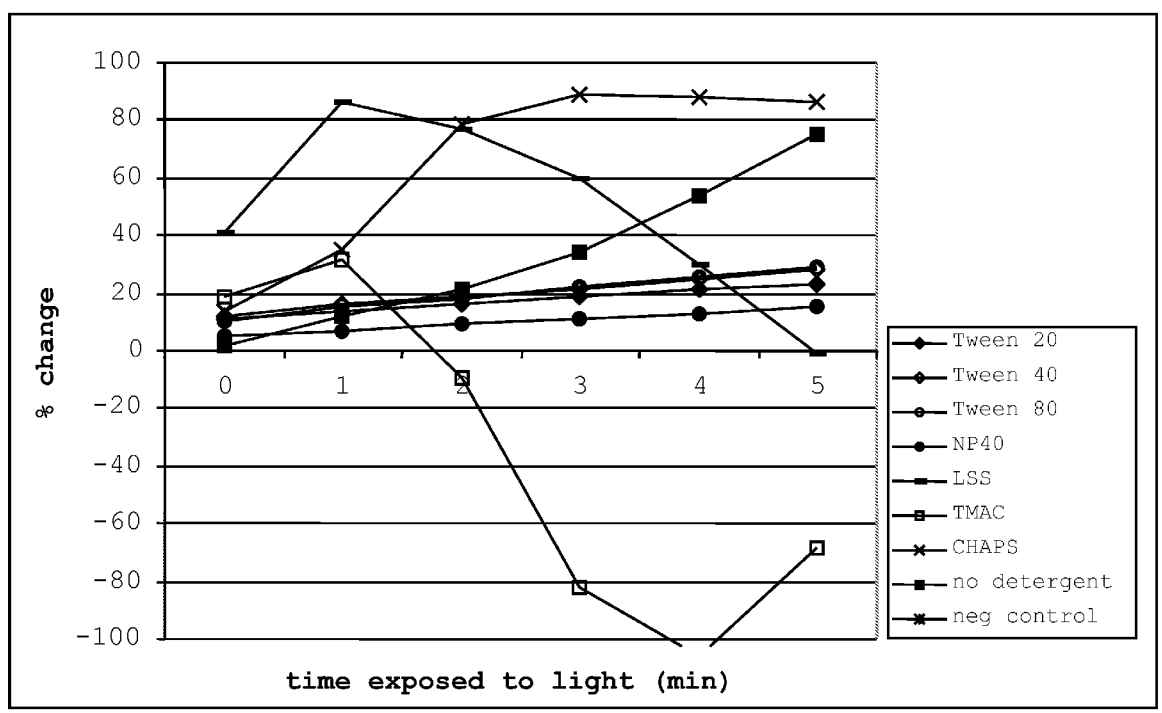
FIG. 2 depicts the percent change in fluorescence intensity as a function of time exposed to light in mixtures that include 3,3' diethylthiacarbocyanine iodide dye, ncPNA, target polynucleotide, and one of a series of surfactants at 5.0% concentration by volume.

Decreased change in fluorescent emission of the dye in the absence of a nucleic acid analog/target polynucleotide hybrid compared to the dye alone was not observed when the concentration of detergent was increased to 5.0%, however. FIG. 2 depicts the addition of detergents at a concentration of 5.0% to the reaction buffer. Detergents added to the reaction buffer included the nonionic detergents Tween® 20 (♦), Tween® 40 (◊), Tween® 80 (○), and Tergitol® NP-40 (●); the anionic detergent LSS (■); the cationic detergent TMAC (□); and the zwitterionic detergent CHAPS (x). Increasing the detergent to 5.0% in the reaction buffers resulted in a smaller percent change in the fluorescent rate for all reactions except those that included detergents LSS and CHAPS.

Example 2

This example illustrates the usefulness of adding surfactants to the reaction buffer, which was sufficient for preparing samples for testing.

The addition of certain surfactants to the reaction buffer was found to permeabilize and/or lyse bacterial cells. Suprisingly, the assay for determining whether a particular target polynucleotide was present did not require further purification of the so-permeabilized/lysed cells.

Reaction buffer with different surfactants was used as permeabilization/hybridization buffer for bacteria to test whether separate nucleic acid isolation steps were necessary to perform the diagnostic method of the present invention. The addition of 0.5% Tween® 20, Tween® 40, Tergitol® NP-40, N-lauryl sarcosine sodium salt (LSS), or CHAPS to the phosphate reaction buffer effectively permeabilized and/or lysed bacteria from cultures grown overnight in tryptic soy broth, as demonstrated in the following experiment.

300 µl of overnight *E. coli* bacterial culture was centrifuged using standard procedures, resulting in a pellet of bacteria at the bottom of the tube. The supernatant was removed by aspiration. The pellet was then re-suspended in 390 µl of reaction buffer (5 mM phosphate) or lysis buffer (5 mM phosphate, pH 5.5, 0.05% surfactant) and incubated at room temperature for 10 minutes before an aliquot was used in the diagnostic reaction. 5 µl of the cells as resuspended in the two buffers were respectively and separately combined with 10 pmoles of 16S ncPNA (5'-ACT GCT GCC TCC CGT AG-3' [SEQ ID NO:8] or 5'-TGC CTC CCG TAG-3' [SEQ ID NO:9]) and 4 nmoles of 3,3'-diethylthiacarbocyanine iodide (DTCC dye) in a 50 µl total reaction volume. In all cases tested, the reaction buffer without surfactant showed a reaction indicating the presence of a target polynucleotide, but it was slower and of a lesser extent of reaction than were those samples subjected to the lysis buffer. Accordingly, further testing focused on use of the lysis buffer.

Figure 3:
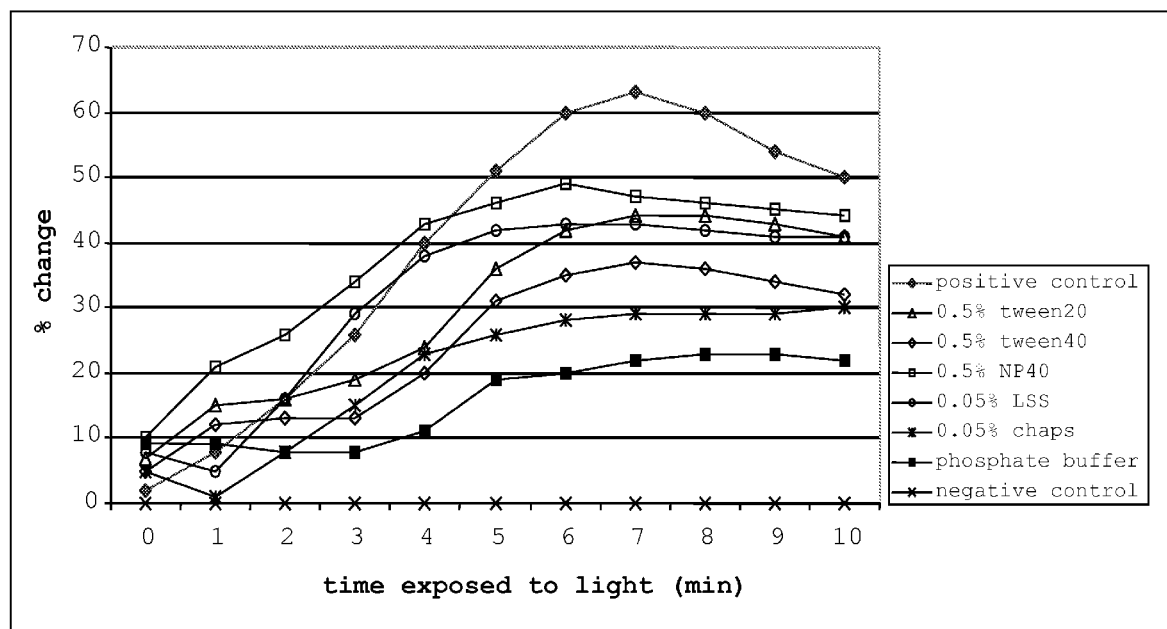
FIG. 3 depicts the percent change in fluorescence intensity as a function of time exposed to light in mixtures that include 3,3' diethylthiacarbocyanine iodide dye, bacterial cells containing target polynucleotide, and one of a series of surfactants at indicated concentration by volume.

The data generated in these studies were used to create the graph of FIG. 3. All reactions were conducted in reaction buffer with one of the surfactants at a concentration of 0.5%, which surfactants were: Tween® 20 (Δ), 0.5% Tween® 40 (◊), 0.5% Tergitol® NP-40 (□), 0.05% laurylサrcosine salt (○) or 0.05% CHAPS (*) in phosphate buffer. The positive control (♦) used purified bacterial DNA in standard phosphate buffer; and the negative control (x) included all elements of the standard reaction apart from a target polynucleotide. A phosphate buffer control (■) was included as well.

For each surfactant, the test well contained non-chiral PNA, target nucleic acid, 3,3'-diethylthiacarbocyanine iodide dye and lysis buffer (with surfactant). The test well was compared to the negative control that contained non-chiral PNA, 3,3'-diethylthiacarbocyanine iodide dye and lysis buffer (with surfactant). The phosphate buffer only test (E) contained non-chiral PNA, target polynucleotide, 3,3'-diethylthiacarbocyanine iodide dye and reaction buffer (without surfactant). The phosphate buffer only well was compared to the negative control phosphate buffer that contained non-chiral PNA, 3,3'-diethylthiacarbocyanine iodide dye and reaction buffer (without surfactant).

An initial fluorescence reading was taken at time zero in the Tecan Genios microplate reader with the wavelengths set at 535 nm excitation and 590 nm emission. The mixtures were then exposed to a light stimulus using the Aurora 50/50 for 1 minute intervals with fluorescence reading being taken after each exposure for 10 minutes. For each reaction, the fluorescent emission values from the test well were compared to the negative control well and converted to the percent changed. The percent difference between the measured rate in samples containing the target nucleic acid and the rate in which the amount of target nucleic acid was zero indicated the presence of the target nucleic acid sequence. The difference corresponds to a relative decrease in fluorescence intensity of the test sample.

The presence of a target polynucleotide was detected in the presence of cell lysate, without requiring additional purification.

FIG. 3 shows the percent change in fluorescence compared to the lysis/hybridization buffer containing only phosphate buffer. The presence of the target nucleic acid sequence was determined for surfactants at 0.05% and 0.5% concentration. When light stimulus was applied, the rate of change in the fluorescence compared to the control corresponded to the presence of the target polynucleotide. The percent change in fluorescence was a decrease in the fluorescence intensity of the dye.

Example 3

This example illustrates the effect of using different nucleic acid analogs in the diagnostic test of the present invention.

Different nucleic acid analogs were used to determine the presence or quantity of nucleic acid in a sample. Chiral PNA molecules, LNA molecules, and morpholino nucleic acid analogs were compared with non-chiral PNA molecules.

The non-chiral PNA and the chiral PNA had the sequence 5' TGC CTC CCG TAG 3' [SEQ ID NO:9], where the phosphodiester bonded sugar backbone of the native polynucleotide were replaced with a peptide bonded polypeptide backbone, as described further herein and well known within the art. Three LNA molecules designated LNA1, LNA2, and LNA3 were used, each having the same sequence of bases described here as SEQ ID NO:9, where one or more of the included nucleotides included a methylene bridge on their respective ribofuranose rings (forming a "locked" residue), as indicated: (1) LNA1 includes only locked residues; (2) LNA2 and (3) LNA3 include a subset of locked residues identified by the upper case letters at certain places on the sequence, as follows: 5' TgC cTc CcG tAg 3' for LNA2 and 5' tGc cTc cCg tAg 3' for LNA3. Morpholino nucleic acid analogs used here also had the base sequence of SEQ ID NO:9, formed from the analog nucleotides.

10 pmoles of nucleic acid analog, 10 pmoles of target polynucleotide having the sequence 5'CTA CGG GAG GCA 3' [SEQ ID NO:12], and 4 nmoles of 3,3'-diethylthiacarbocyanine iodide dye were placed in a 50 μl total reaction volume to form a mixture. A negative control containing nucleic acid analog, 3,3'-diethylthiacarbocyanine iodide dye, reaction buffer, and a known (zero) amount of target polynucleotide was also tested. All the nucleic acid analogs and target polynucleotides were reconstituted in DNase- and RNase-free water to 100 μM stock and further diluted to 2 μM working stocks. The dye was dissolved in DMSO to generate an 8 mM stock. The 8 mM dye stock was further diluted to generate a 2 mM working stock in 5 mM phosphate buffer (pH 5.5). The reaction buffer was a 5 mM phosphate buffer (pH 5.5).

An initial fluorescence reading was taken at time zero in the Tecan Genios microplate reader with the wavelengths set at 535 nm for excitation and 590 nm for emission. The mixtures were then exposed to a 2000 foot-candle light stimulus using the Aurora 50/50 for 1 minute intervals and measuring the fluorescence at one minute intervals for 5 minutes. For each reaction, the fluorescent emission values from the test well (nucleic acid analog, target polynucleotide, dye, and reaction buffer) was compared to the negative control well (nucleic acid analog, dye and reaction buffer). The change in fluorescence was converted to the percent changed and normalized to the negative control containing only dye. The percent difference between the measured rate in samples containing the target nucleic acid and the rate in which the amount of target nucleic acid was zero indicated the presence of the target nucleic acid sequence.

Figure 4:
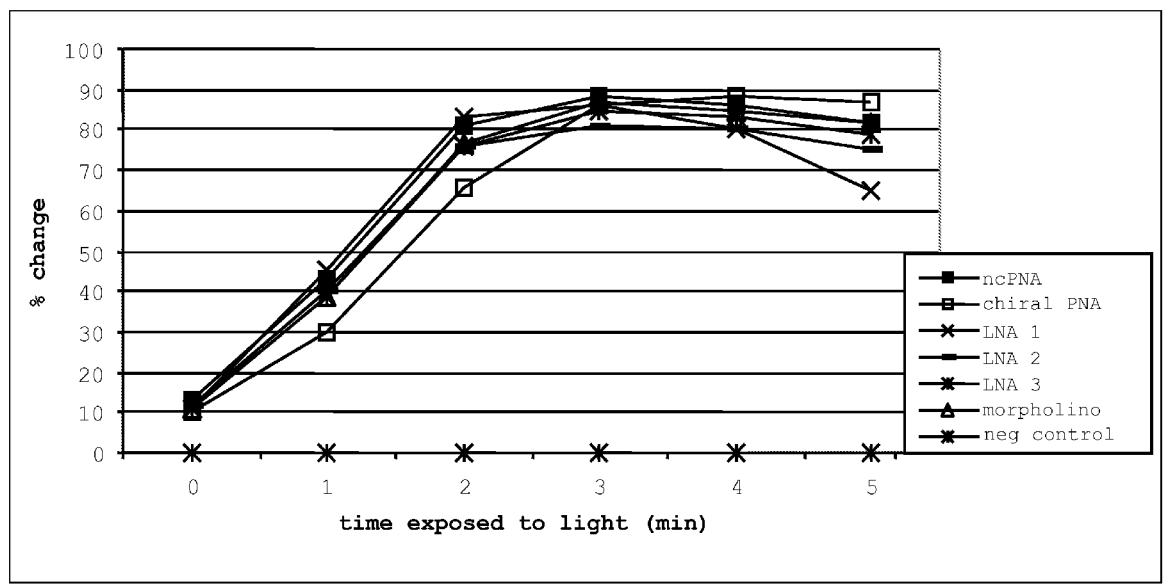
FIG. 4 depicts the percent change in fluorescence intensity as a function of time exposed to light in mixtures that include 3,3' diethylthiacarbocyanine iodide dye, target polynucleotide, and one of a series of nucleic acid analogs.
Figure 5:
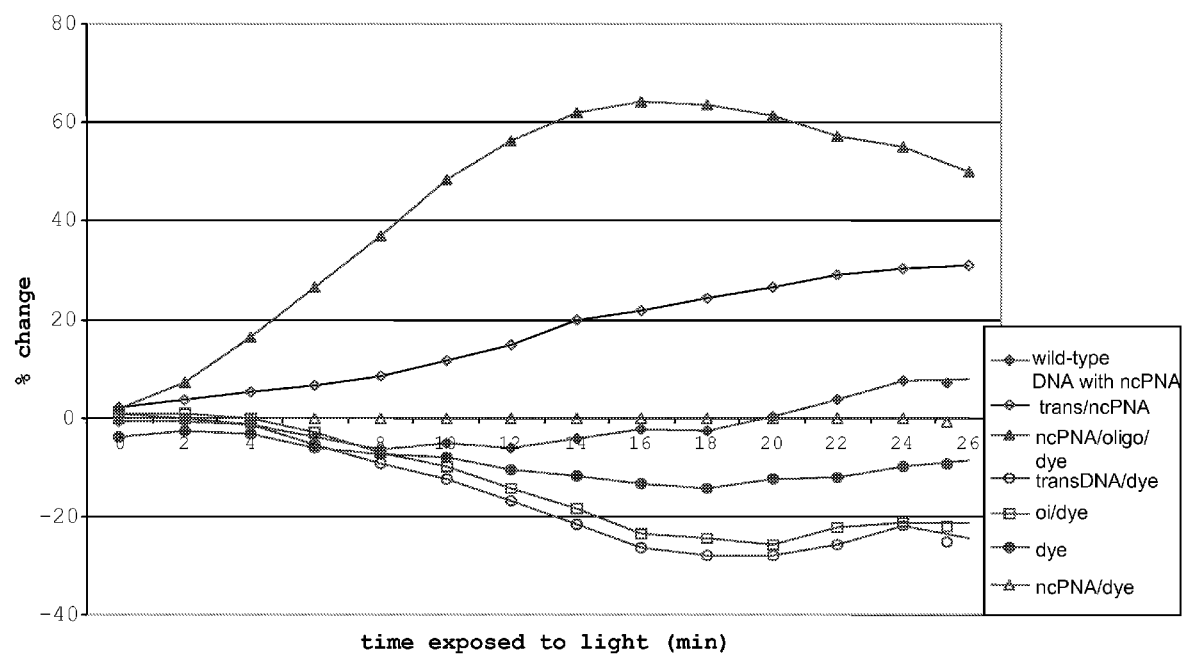

FIG. 4 displays a graph that is based on the data collected in the study of this example and manipulated as indicated above. As can be seen in the graph, the percent change in fluorescence intensity of each nucleic acid analog tested follows approximately the same profile of reaching in excess of 80% reduction in fluorescence emission by three minutes exposure to the light stimulus. Mixtures including non-chiral PNA (■), chiral PNA (□), LNA 1, 2, and 3 (respectively represented by x, ▬, *), and morpholino (Δ) nucleic acid analogs showed a difference in the rate of change in an optical property of the dye compared to when no nucleic acid analog was present in the mixture (i.e., the negative control (the * indicating 0% change)). Of the various nucleic acid analogs tested, the chiral PNA may require more activation exposure in view of the percent change differences between mixtures including the chiral PNA and all others: after one and two minutes of light stimulus exposure, the cPNA mixture evidenced 30% and 65% changes in fluorescence, respectively; in contrast, the other reaction mixtures containing any of the other nucleic acid analogs evidenced at least 38% and 75% changes, respectively. Nonetheless, the data presented here supports the usefulness of all nucleic acid analogs tested for inclusion in the diagnostic method of the present invention.

Example 4

This example illustrates different approaches for identifying dyes that are usefully employed in the context of the diagnostic method of the present invention.

In particular, this example presents data directed at determining if selected dyes exhibit a photo-induced change in fluorescence or absorbance based on results observed from light stimulus activation of the combinations of the respective dyes and: (1) a nucleic acid analog, namely a non-chiral PNA probe [SEQ ID NO:1], or (2) a target oligonucleotide ("oligo") that is exactly complementary to the PNA probe; or (3) the hybridized combination of the two. Each of these results were compared to a negative control mixture lacking ncPNA and oligo.

All dyes tested were from Sigma (St. Louis, Mo.) except the following: 3,3'-Diethylthiacyanine ethylsulfate (Organica), 3-Ethyl-9-methyl-3'-(3-sulfatobutyl)thiacarbocyanine betaine (Organica), 3-Carboxymethyl-3',9-diethyl-5,5'-dimethylthiacarbocyanine betaine (Organica), 3,3'-Diallylthiacarbocyanine Bromide (Pfaltz and Bauer), 3,3'-Diethyl-2,2'-Oxathiacarbocyanine Iodide (Pfaltz and Bauer), [5-[2-(3-Ethyl-3H-benzothiazol-2-ylidene)-ethylidene]-4-oxo-2-thioxo-thiazolidin-3-yl]-acetic acid (FEW), 1-Butyl-2-[3-(1-butyl-1H-benzo[cd]indol-2-ylidene)-propenyl]-benzo[cd]indolium tetrafluoroborate (FEW), 5,6-Dichloro-2-[3-(5,6-dichloro-1,3-diethyl-1,3-dihydro-benzimidazol-2-ylidene)-propenyl]-1,3-diethyl-3H-benzimidazolium iodide, and d) 1,3,3-Trimethyl-2-(2-[2-phenylsulfanyl-3-[2-(1,3,3-trimethyl-1,3-dihydro-indol-2-ylidene)-ethylidene]-cyclohex-1-enyl]-vinyl)-3H-indolium chloride (FEW).

Xenon Protocol: In one test protocol, a xenon light source was used to photoactivate reaction mixtures over a one minute period. Solutions containing concentrations of dye at 6 µM were prepared by diluting a stock solution of 5 mM dye (in methanol) in buffer (5 mM $PO_4$) plus surfactant (0.05% Tween® 80). The dyes used to prepare the 6 µM dye solutions are set forth in the summary of dyes studied that appears below in Table 3.

For the Xenon protocol, a 48 µL aliquot of each 6 µM dye solution was added to four wells of a 384-well microtiter plate (Costar, #3705). For each dye: a 1 µL aliquot of 5 µM oligo [SEQ ID NO:20] was added to the first and second well, a 1 µL aliquot of 5 µM ncPNA [SEQ ID NO: 1] was added to the first and third well, a 1 µL aliquot of $ddH_2O$ (Nanopure) was added to the second and third well, and a 2 µL aliquot of $ddH_2O$ was added to the fourth well.

Fluorescent spectra at $T_0$ were obtained for each well using a Tecan Safire2 microplate reader. Parameters for the spectral scanning were: excitation range of 300 to 652 nm with a resolution (step size) of 11 nm, emission range of 375 to 723 nm with a resolution of 6 nm. The plate was then exposed to a 450W Xenon arc lamp (Ushio, #UXL-451-O) for 1 minute of photoactivation and fluorescent spectra were then read as before. Under the conditions used, dyes that showed a difference in an optical property of test reaction mixtures (containing ncPNA/target oligo) compared to the same optical property of dye-only reaction mixtures are indicated by a "yes" in Table 3. Distinctions between types of differences are not distinguished in Table 3.

Aurora Protocol: In a second protocol, the reaction mixtures were exposed to the Aurora 50/50 light activation source and observed from 0 to 30 minutes. Solutions containing concentrations of dye at 25 µM were prepared by diluting stock solutions of 5 mM dye (in methanol) in molecular biology grade water (Hyclone, catalog #SH30538.03). The dyes used to prepare the 25 µM dye solutions are set forth in the summary of dyes studied that appears in Table 3.

For the Aurora Protocol, two different reaction mixtures were prepared for each dye. The first mixture consisted of 1 mL of 25 µM dye in water. The second mixture was identical to the first with the exception that 1 µL of a 50 µM ncPNA [SEQ ID NO: 1]/target oligo [SEQ ID NO:20] mixture was added to the dye mixture. Spectral scans of the reaction mixtures were done using a 1 mL quartz cuvette (against water in a second reference cuvette) in a Shimadzu 160UV Spectrophotometer. A spectrum from 200 nm to 800 nm for each reaction mixture was taken prior to exposure to a light stimulus (a 15 watt Aurora 50/50 fluorescent bulb, Fritz Industries). Parafilm was wrapped around the top of the cuvettes to prevent spillage of the solutions when the cuvettes were placed horizontally (length-wise) across the fluorescent light bulb. The solutions in the cuvettes were exposed to light for 5 minutes, followed by a spectral scan. This exposure-spectral scan cycle was repeated out to at least 10 minutes total light exposure. For each dye tested, the absorbance at lambda max (for time zero) of each spectrum was plotted as a function of time to determine the rate of absorbance decay for the ncPNA/target oligo mixture relative to the rate of absorbance decay for the dye only mixture. Under the conditions used, dyes that showed a difference in an optical property of test reaction mixtures (containing ncPNA/target oligo) compared to the same optical property of dye only reaction mixtures are indicated by a "yes" in Table 3. Distinctions between types of differences are not distinguished in Table 3.

LED Protocol. In embodiment C, solutions containing various concentrations of dye were prepared by diluting stock solutions of 5 mM dye (in methanol or DMSO) in buffer (10 mM TE) with surfactant (0.1% Tween® 80) to a final concentration which provided an absorbance at lambda-max of 0.5-1.0 absorbance units (in a 50 µL volume in a 384-well white/clear microplate [NUNC, #242763]. The dyes used to prepare the dye solutions are set forth in the summary of dyes studied that appears in Table 3.

In this embodiment, four different reaction mixtures were prepared for each dye. The test reaction mixture was prepared by adding 30 µL dye solution, 10 µL of 500 nM ncPNA (in water) [SEQ ID NO:1] and 10 µL of 500 nM target oligo (in water) [SEQ ID NO:20] to a first well. The target oligo control reaction mixture was prepared by adding 30 µL dye solution, 10 µL molecular biology grade water (Hyclone) and 10 µL 500 nM target oligo [SEQ ID NO:20] to a second well. The ncPNA (probe) control reaction mixture was prepared by adding 30 µL dye solution, 10 µL of 500 nM ncPNA [SEQ ID NO:1] and 10 µL molecular biology grade water to a third well. The dye only control reaction mixture was prepared by adding 30 µL dye solution and 20 µL molecular biology grade water to a fourth well. Using a Safire2 microplate reader, absorbance measurements were taken at the lambda max of each dye tested. The plate was then removed from the reader and exposed to light from various banks of LEDs at various peak wavelengths. After 10 minutes photoactivation, the plate was removed from the light source and absorbance measurements were taken as previously. The plate was then removed from the reader, exposed to light from the photoactivator for an additional 50 minutes, and final absorbance measurements were taken. The absorbance at lambda max (for time zero, for each dye tested) was plotted against time to determine the rate of absorbance decay for the test reaction mixture, for the target oligo control reaction mixture, for the ncPNA control reaction mixture, and for the dye only control reaction mixture. Under the conditions used, dyes which showed a difference in an optical property of test reaction mixtures (containing ncPNA/target oligo) compared to the same optical property of dye only reaction mixtures are indicated by a "yes" in Table 3. Distinctions between types of differences are not distinguished in Table 3.

TABLE 3

| # | Dye | Xenon Protocol | Aurora Protocol | LED Protocol |
|---|---|---|---|---|
| 1 | 3,3'-Dimethyloxacarbocyanine iodide | Yes | No | No |
| 2 | 3,3'-Diethylthiacyanine iodide | Yes | No | No |
| 3 | 3,3'-Diethylthiacyanine ethylsulfate | ND | No | No |
| 4 | 3,3'-Diethylthiacarbocyanine iodide | Yes | Yes | Yes |
| 5 | 3,3'-Diethyl-9-methylthiacarbocyanine iodide | Yes | Yes | Yes |
| 6 | 3-Ethyl-9-methyl-3'-(3-sulfatobutyl)thiacarbocyanine betaine | ND | No | No |
| 7 | 3-Carboxymethyl-3',9-diethyl-5,5'-dimethylthiacarbocyanine betaine | ND | No | No |
| 8 | 3,3'-Diethylthiadicarbocyanine iodide | Yes | No | Yes |
| 9 | 3,3'-Diethylthiatricarbocyanine iodide | Yes | No | No |
| 10 | 3,3'-Diethylthiatricarbocyanine perchlorate | Yes | No | No |
| 11 | 3,3'-Diethyloxacarbocyanine iodide | Yes | No | No |
| 12 | 3,3'-Diethyloxadicarbocyanine iodide | Yes | Yes | No |
| 13 | 3,3'-Dipropylthiacarbocyanine iodide | Yes | Yes | Yes |
| 14 | 3,3'-Dipropylthiadicarbocyanine iodide | No | No | No |
| 15 | 3,3'-Dipropyloxacarbocyanine iodide | No | No | No |
| 16 | 3,3'-Dibutylthiacarbocyanine iodide | Yes | Yes | Yes |
| 17 | 3,3'-Dipentylthiacarbocyanine iodide | Yes | Yes | Yes |
| 18 | 3,3'-Dihexyloxacarbocyanine iodide | No | No | No |
| 19 | 3,3'-Diallylthiacarbocyanine Bromide | Yes | Yes | Yes |
| 20 | 3,3'-Diethyl-2,2'-Oxathiacarbocyanine Iodide | Yes | No | No |
| 21 | 1,1'-Diethyl-2,2'-cyanine iodide | Yes | No | No |

TABLE 3-continued

| # | Dye | Xenon Protocol | Aurora Protocol | LED Protocol |
|---|-----|----------------|-----------------|--------------|
| 22 | 1-1'-Diethyl-2,2'-carbocyanine iodide | Yes | Yes | Yes |
| 23 | 1,1'-Diethyl-2,2'-carbocyanine bromide | ND | Yes | Yes |
| 24 | 1,1'-Diethyl-4,4'-carbocyanine iodide | No | No | No |
| 25 | 1,1'-Diethyl-3,3,3',3'-tetramethylindocarbocyanine iodide | No | No | No |
| 26 | 1,1'-Dipropyl-3,3,3',3'-tetramethylindocarbocyanine iodine | No | No | No |
| 27 | [5-[2-(3-Ethyl-3H-benzothiazol-2-ylidene)-ethylidene]-4-oxo-2-thioxo-thiazolidin-3-yl]-acetic acid | ND | No | No |
| 28 | 1-Butyl-2-[3-(1-butyl-1H-benzo[cd]indol-2-ylidene)-propenyl]-benzo[cd]indolium tetrafluoroborate | ND | No | No |
| 29 | 5,6-Dichloro-2-[3-(5,6-dichloro-1,3-diethyl-1,3-dihydro-benzimidazol-2-ylidene)-propenyl]-1,3-diethyl-3H-benzimidazolium iodide | ND | No | ND |
| 30 | 1,3,3-Trimethyl-2-(2-[2-phenylsulfanyl-3-[2-(1,3,3-trimethyl-1,3-dihydro-indol-2-ylidene)-ethylidene]-cyclohex-1-enyl]-vinyl)-3H-indolium chloride | ND | No | No |
| 31 | 4,5,4',5'-Dibenzo-3,3'-diethyl-9-methyl-thiacarbocyanine bromide | ND | No | No |

Of 31 dyes tested using the three different protocols set forth above, only six were shown to not change color; another eight have not demonstrated positive results, but were not tested with all three protocols as yet and therefore remain inconclusive. Over half of the total number of dyes tested displayed positive results. Accordingly, placing the eight that are as yet incompletely tested to the side, the results are currently indicating that 17 out of 23 fully tested dyes show positive results, i.e., a 74% rate of success.

Example 5

A method of target Nucleic Acid (NA) elution that was previously captured to PNA microparticles (Streptavidin based).

All steps were performed at room temperature. The solid state light source consisted of 192 2000-mcd 470 nm light emitting diodes (LED) (Jameco Electronics P/N 183222) arranged in a 5×7 inch rectangular array placed 2 inches above the microplate surface. With a 15V power supply, this configuration produced an irradiance of approximately 2 mWcm$^{-2}$ at the surface of a standard microplate. The effect of the voltage of the power supply used with the light source on the elution was determined and compared to elution on a benchtop (with ambient light) and in the dark. The light source was used with different voltage of power suppliers, including 12V, 15V and 18V.

In this method, 20 pmole capture capacity of PNA microparticles were used in reaction mixtures containing either 8 ng of MTB DNA and 16 ng of human DNA (as the nonspecific DNA), or containing 16 ng of human DNA only, via a smartDNA capture assay.

The capture and elution procedures are all done in a 1.5 ml eppendorf tubes.

In this assay the target NA was incubated with the PNA microparticles for 30 minutes with shaking, in 100 µl capture buffer: 10 mM Homopipes buffer, pH 5, 18 µM DiSC$_2$(3), 0.1% Tween-80 and 0.5 mM EDTA. After washing with wash buffer (10 mM Homopipes buffer, pH 5, 9 µM DiSC$_2$(3), 0.05% Tween-80 and 0.5 mM EDTA) for 3 times (200 µl each time), the elution buffer (100 µl 1 mM EDTA) was added to contents of the tubes in low light and subjected to one of five treatments:

1). Incubation in low light (dark room) for 30 minutes
2). Incubation on benchtop for 30 minutes
3). Exposed to LED 470 nm, 12V for 5 minutes
4). Exposed to LED 470 nm, 15V for 5 minutes
5). Exposed to LED 470 nm, 18V for 5 minutes After the elution, the liquid (~100 µl) (with no microparticles) was aliquoted into triplicate wells in a microplate (each reaction contain 25 µl of the eluate), and to each well, PNA and dye mixture (25 µl, with 320 nM of PNA, 18 µM of DiSC$_2$(3), in 20 mM Homopipes buffer, pH 5, 0.1% Tween 80) was added. The mixture was then incubated for 10 minutes in the dark room.

The initial dye color change rates were measured. Results are summarized in Table 4 below.

TABLE 4

Initial dye color change rate (mAbsorbance units/minute) of samples after 5 different elution parameters

| DNA | dark | benchtop | 12 V | 15 V | 18 V |
|-----|------|----------|------|------|------|
| MTB and human | 81 | 112 | 98 | 123 | 160 |
| human | 18.3 | 33.5 | 22.2 | 31.4 | 42.9 |

Comparing with the standard elution procedure (benchtop for 30 min), the elution in the 15V LED box for 5 min resulted in a similar sensitivity and specificity. Thus 15V LED elution can be used as alternative to benchtop elution, and can shorten the total time required to run the entire assay.

Example 6

This example illustrates one embodiment of a gel-based assay using the diagnostic test of the present invention.

Figure 7:
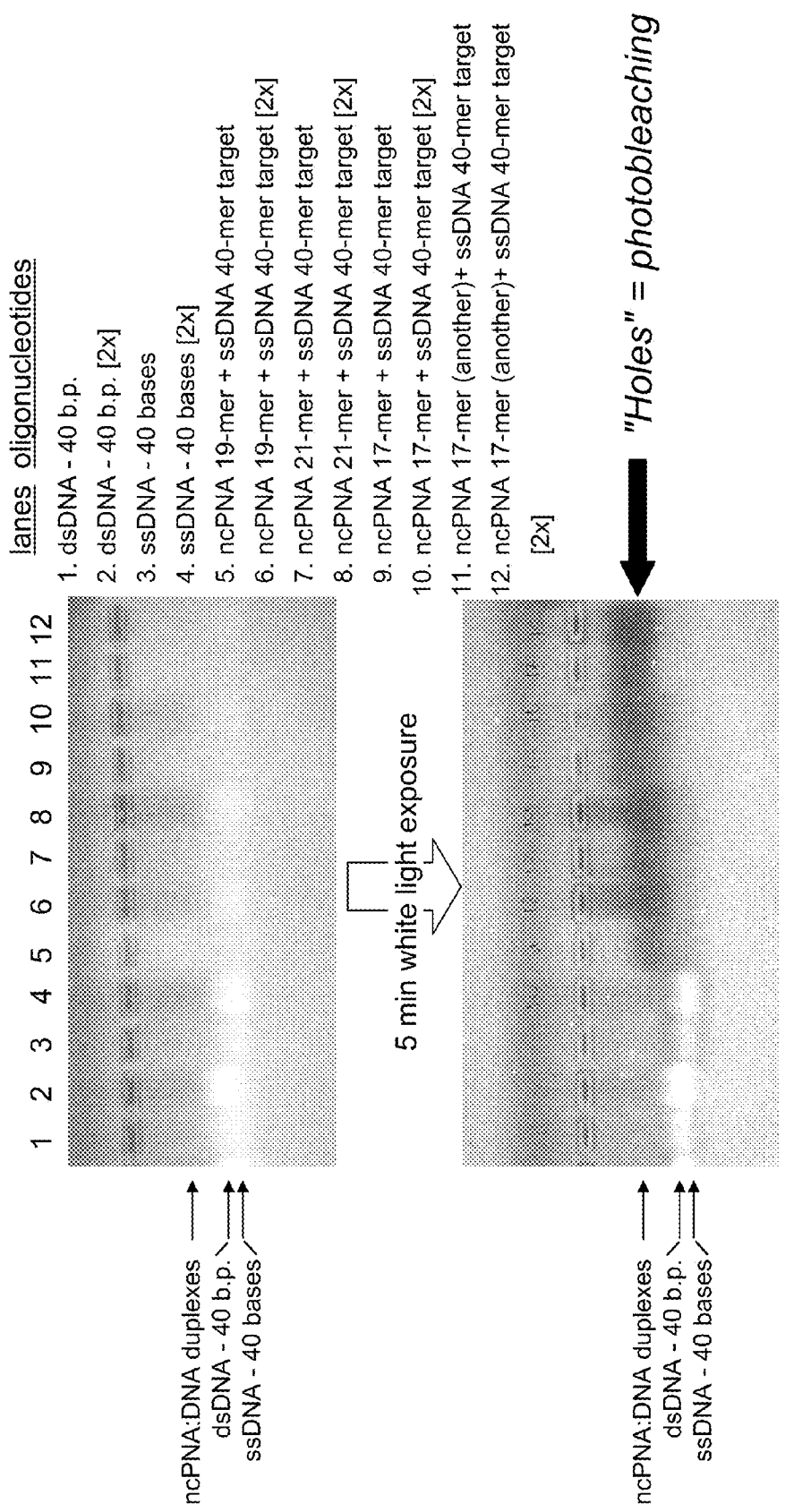
FIG. 7 depicts an agarose gel containing 3,3'-diethylthiacarbocyanine iodide dye in which a non-chiral PNA/target polynucleotide hybrid is resolved.

The methods presented herein can be used to identify the presence of a target polynucleotide in a gel-based assay. Complementary pairs of ncPNA and single-strand polynucleotides were mixed together for at least 30 minutes at room temperature and loaded onto a 3% agarose gel. The agarose gel contained 2.5 µM of DTCC. As shown in FIG. 7, the first four lanes contained double- and single-stranded DNA size standards of 40 base pairs (or 40 bases) each, as follows:

Lane 1 100 pmoles double-stranded DNA (5'-CCAGGAC-GACCGGGTCCTTTCTTGGATCAACCCGCTCAAT-3' [SEQ ID NO: 48], plus complementary strand 5'-AT-TGAGCGGGTTGATCCAAGAAAGGACCCG-GTCGTCCTGG-3' [SEQ ID NO: 49]);

Lane 2 200 pmoles double-stranded DNA (same as above);

Lane 3 100 pmoles single-stranded DNA (5'-TGCTAGC-CGAGTAGTGTTGGGTCGCGAAAGGCCTTGTGGT-3' [SEQ ID NO: 50]; and Lane 4 200 pmoles single-stranded DNA (same as above)

The remaining lanes contained different combinations of ncPNA and its respective complementary single-stranded target polynucleotide sequences, as follows: Lane 5, 100 pmoles ncPNA 19-mer having the following sequence GTTGATC-CAAGAAAGGACC-lysine [SEQ ID NO: 51] plus 100 pmoles of single-stranded DNA 40-mer target polynucleotide having the following sequence 5'-CCAGGACGAC-CGGGTCCTTTCTTGGATCAACCCGCTCAAT-3' [SEQ ID NO: 48]; Lane 6, same as lane 5 except 200 pmoles of ncPNA 19-mer plus 200 pmoles of single-stranded DNA 40-mer target polynucleotide; Lane 7, 100 pmoles ncPNA 21-mer having the following sequence GTTGATCCAA-GAAAGGACCCG-lysine [SEQ ID NO: 51] plus 100 pmoles single-stranded DNA 40-mer target polynucleotide having the following sequence 5'-CCAGGACGACCGGGTC-CTTTCTTGGATCAACCCGCTCAAT-3' [SEQ ID NO: 48]; Lane 8, same as lane 7 except 200 pmoles of ncPNA and 200 pmoles of single-stranded 40-mer DNA target; Lane 9, 100 pmoles ncPNA 17-mer having the following sequence TTTCGCGACCCAACACT-lysine [SEQ ID NO: 53] plus 100 pmoles of single-stranded DNA 40-mer target polynucleotide having the following sequence 5'-TGCTAGCCGAG-TAGTGTTGGGTCGCGAAAGGCCTTGTGGT-3' [SEQ ID NO: 50]; Lane 10, same as lane 9 except 200 pmoles ncPNA 17-mer and 200 pmoles single-stranded DNA 40-mer target polynucleotide; lane 11, 100 pmoles of another ncPNA 17-mer having the following sequence AGTGT-TGGGTCGCGAAA-lysine [SEQ ID NO: 55] plus 100 pmoles of single-stranded DNA 40-mer target polynucleotide having the following sequence 5'-ACCACAAGGC-CTTTCGCGACCCAACACTACTCGGCTAGCA-3' [SEQ ID NO: 56].

Electrophoresis was conducted in the 3% agarose/2.5 µM DTCC/1×TBE gel at 200V for 20 minutes. After illuminating the gel with white light from the Aurora 50/50 for 5 minutes, the gel was observed. A 254 nm UV transilluminator and B&W Polaroid camera were used to photograph the gel before and after photoactivation (upper and lower panels, respectively). The gel generally had a pink color with a faint pink band in lanes 1-4 that contain ssDNA and dsDNA. The ncPNA/target polynucleotide hybrid was expected to migrate more slowly than either the single-stranded or double-stranded DNA 40 bp standards in lanes 1-4. Indeed, at the expected location was a region that lacked color after photo-activation. These "holes" show up as a darker area on the second panel of FIG. 7 identified the presence of the P/TP hybrid.

The method of identifying the target polynucleotides in gel-based systems according to the methods disclosed herein can be adapted to any gel-based method of identifying target polynucleotides, including Southern, Northern, and North-western blotting techniques. Additionally, other agarose gels containing the dye 3,3'-diallylthiacarbocyanine iodide dye demonstrated similar results. Other dyes are anticipated to work similarly Example 7

This example demonstrates detection of single nucleotide polymorphisms (SNPs) using two nucleic acid analog sequences.

Figure 6D:
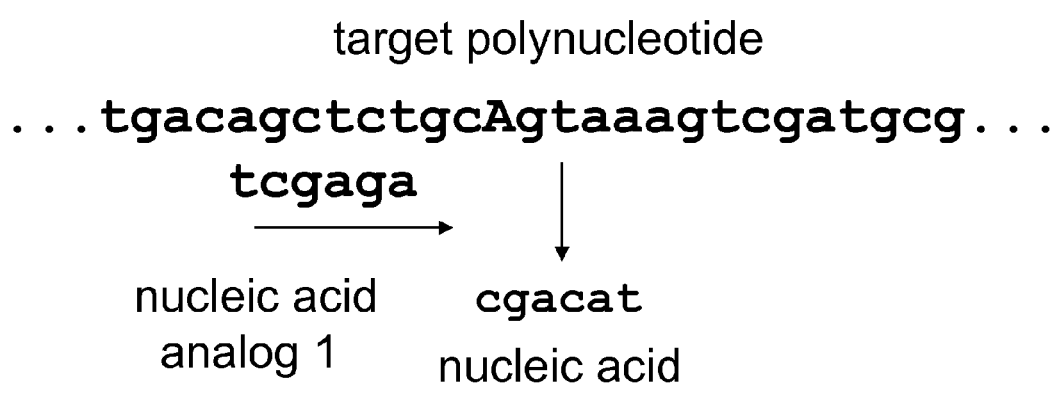

An example of the strategy for detecting point, insertion, and deletion mutations can be found in FIGS. 6C and 6D. PNAs which only partially hybridize to target DNA (due to mutations) may form helical duplexes too short to participate in light-activated photobleaching of $DiSC_2(3)$. The following experiment illustrates the affects of point mutations in the assay for the detection of SNPs.

The sequence of ncPNA1 was 5' Bio-OOOOO-GAT-AGTGGGATTGTGCGT 3' [SEQ ID NO:1]. The sequence of ncPNA2 was 5' TCACATCAATCCACT-lys 3' [SEQ ID NO:21]. The "O" represents the linker molecule 8-amino-3,6-dioxaoctanoic acid.

Table 5 lists the DNA oligonucleotide sequences with the mismatch bases in lower case. 100 µM single-stranded DNA stock solutions containing different single-stranded DNA 12-mers were prepared. Wild-type DNA oligonucleotide [considered to be the (−) strand] was fully complementary to six bases on ncPNA1 (3' end) and to six bases on ncPNA2 (5' end). Four other DNA oligonucleotides contained 1 or 2 or 4 point mutations (mu1, mu2, mu3, mu4) were mismatches with bases on either ncPNA1 or ncPNA2. Each of the 5 DNA oligonucleotides also had an exact complementary DNA oligonucleotide [considered to be the (+) strands].

To prepare the double-stranded complementary and mutated sequences, 1.2 µl of 100 µM of each (+) DNA strand was mixed with 1 µl of the 100 µM complementary (−) DNA strand and diluted to a final concentration of 2 µM. These solutions were heated to 95° C. for 5 minutes and allowed to cool to room temperature to promote annealing. The sequences of the complementary sequence and the mutated sequences (mu1-mu4) are set forth in Table 5.

TABLE 5

| Name | + seq 5' to 3' | − seq 5' to 3' |
|------|----------------|----------------|
| wild type | GTGCGTTCACAT [SEQ ID NO: 22] | ATGTGAACGCAC [SEQ ID NO: 23] |
| mu1 | cTGCGTTCACAT [SEQ ID NO: 24] | ATGTGAACGCAg [SEQ ID NO: 25] |
| mu2 | GTGCGTTCACAa [SEQ ID NO: 26] | tTGTGAACGCAC [SEQ ID NO: 27] |
| mu3 | caGCGTTCACAT [SEQ ID NO: 28] | ATGTGAACGCtg [SEQ ID NO: 29] |
| mu4 | caGCGTTCAGgt [SEQ ID NO: 30] | acCTGAACGCtg [SEQ ID NO: 31] |

A ncPNA master mix was made by combining 105 µl of 2 µM ncPNA1, 105 µl of 2 µM ncPNA2, 693 µl of 5 mM phosphate buffer (pH 5.5) containing 0.05% Tween® 80, 14% methanol, and 42 µl of 0.75 mM 3,3'-diethylthiacarbocyanine iodide dye. This mixture contains final concentrations of 220 nM ncPNA1, 220 nM ncPNA2, and 33 µM 3,3'-diethylthiacarbocyanine iodide dye. For reactions that contained both ncPNAs and the dsDNA, 15 µl of each double-stranded polynucleotide and 135 µl of the ncPNA master mix was added to each tube. From each tube a 50 µl aliquot of each mix was transferred to three wells of the white microtiter plate (Greiner).

A control "DNA and dye" only tube that contained complementary DNA oligonucleotides and dye was prepared by combining 20 µl of annealed wild-type DNA, 8 µl of a 0.75 mM solution of 3,3'-diethylthiacarbocyanine iodide dye, and 172 µl of 5 mM phosphate buffer (pH 5.5) containing 0.05% Tween® 80 and 14% methanol. Three 50 µl aliquots of this mixture was dispensed into three wells. Two control "PNA and dye" tubes containing ncPNA1 or ncPNA2 were made by combining 20 µl of either ncPNA1 or ncPNA2, 8 µl of the 0.75 mM solution of 3,3'-diethylthiacarbocyanine iodide dye, and 172 µl of the 5 mM phosphate buffer (pH 5.5) containing 0.05% Tween® 80 and 14% methanol. 50 µl of this mixture was aliquoted into three wells. The plate was placed in the Tecan Genios microplate reader and an initial fluorescence was read. Samples were exposed to the Aurora 50/50 fluorescent light and readings were taken after every one minute of light stimulus for five minutes.

As can be seen in the FIG. 8, fluorescence emission over a period of five minutes remained substantially stable at about 27000 to 32000 relative fluorescence units (RFUs) in sample mixtures lacking ncPNA1 or ncPNA2 or exactly complementary DNA relative to the nucleic acid analog sequence defined by both ncPNA1 and ncPNA2. After four minutes of light exposure, the fully complementary sequence can easily be differentiated (open diamonds) from the ncPNA only (1 or 2), DNA only and SNP DNA with both ncPNAs by the substantial reduction in fluorescence. Interestingly, the start of fluorescence emission reduction started in samples that included the SNP variances mu1 and mu2 at about four to five minutes of incubation. This observation is extended in the data illustrated in FIG. 9, when the fluorescent emission after light stimulation of the mixture containing a fully complementary sequence versus a mixture containing a mutated oligonucleotide with two or four mutations (i.e., one or two, 2 base-pair changes). Again, where one of the two nucleic acid analogs (ncPNA1 or ncPNA2) were absent, the fluorescence emission remained unwaveringly high at about 32000 relative fluorescence units. Lacking exactly complementary DNA with respect to the sequence of ncPNA1 and ncPNA2 provided the same result, essentially. Where both nucleic acid analog and exactly complementary DNA is included in the mixtures, fluorescent emissions dropped off dramatically at some point after the second minute of light exposure, and decidedly so between the third and fourth minute of exposure. The reactions using the same ncPNAs with variants having two or four mismatches, fluorescent emission could be seen to have started dropping off by the fourth minute of light exposure.

Example 8

This example compares the two detergents, Tween® 80 and Tergitol® NP-40, in a buffer containing 5 mM sodium phosphate (pH 5.5) in reactions with and without P/TP hybrids to demonstrate increased dye resistance to photoactivation.

In the following example, identical mixtures were made in buffer containing either 0.05% Tergol® NP-40 (Sigma Catalog NO: 127087) or 0.05% Tween® 80 (Sigma, Catalog NO: P1754). The use of the white plate correlated with readings of an accelerated reaction rate A 100 µM stock solution of ncPNA having the sequence 5' Bio-OOOOO-GATAGTGGGATTGTGCGT 3' [SEQ ID NO: 1] was diluted to 2 µM in 5 mM sodium phosphate buffer (pH 5.5) with 0.05% Tween® 80 ("tw80 buffer"). An identical dilution was created using 5 mM sodium phosphate buffer (pH 5.5) with 0.05% NP-40 (NP40 buffer). In separate tubes, a 100 µM stock of complementary DNA with the sequence 5' ACGCACAATCCCACTATC 3' [SEQ ID NO:20] was diluted to a concentration of 2 µM using either the tw80 buffer or the NP40 buffer as above.

The mixture set forth in Table 6 was made.

TABLE 6

| Component | amount | multiplier | Total |
|---|---|---|---|
| ncPNA | 5 µl | × 13 | 65 µl |
| Oligo | 5 µl | × 13 | 65 µl |
| Buffer (tw80) or (NP40) | 38 µl | × 26 | 988 µl |
| Dye (0.75 mM) | 2 µl | × 26 | 56 µl |

The dye was first added to the buffer and mixed. For the P/TP reactions, 520 µl of buffer/dye mixture, 65 µl of ncPNA, and 65 µl of oligo were added and mixed. For the "Dye Only" control, 520 µl was transferred to a fresh tube and an additional 130 µl of buffer (either with Tw80 or NP40) was added. Aliquots of 50 µl were dispensed into 12 wells (for each detergent buffer and the "Dye Only" control) of a white Greiner 96-well microtiter plate (Catalog NO: 655088).

The plate was then placed in a Tecan Genios microplate reader and an initial fluorescence was measured. The plate was exposed to the Aurora 50/50 photoactivator and readings were taken after every 1 minute of light exposure up to 7 minutes of total exposure.

Figure 10:
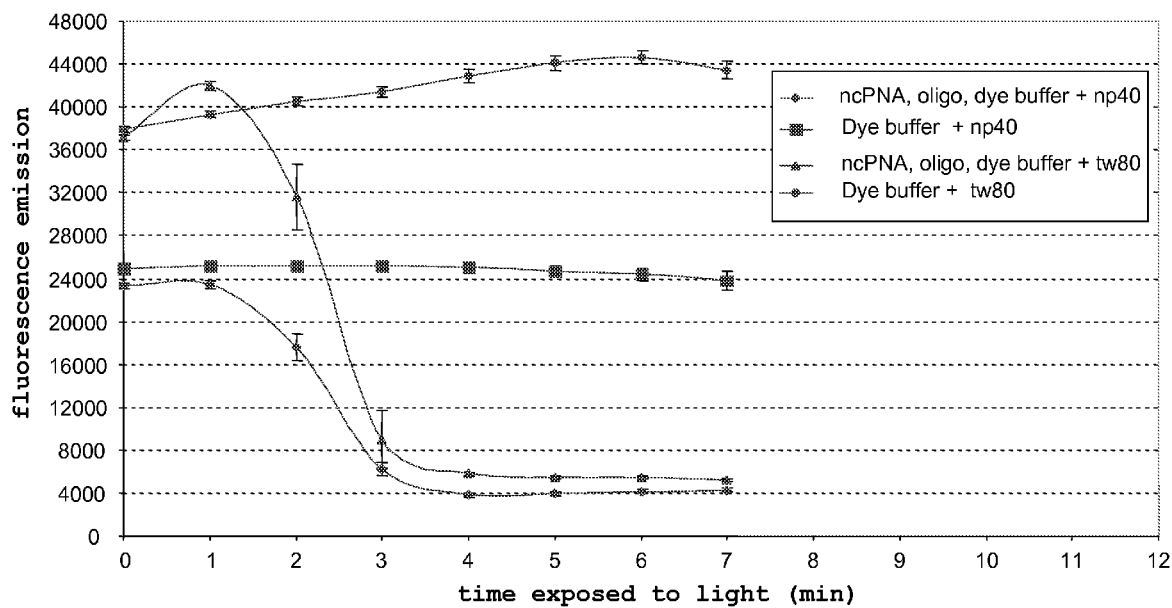
FIG. 10 depicts the change in fluorescence over time using different surfactants in a white plate under lower light intensity.

The fluorescence at various times (of total exposure to the Aurora 50/50 light) is presented graphically in FIG. 10. The lines on the graph represented data from the identified reactions: Solid circle, the control of dye only in tw80 buffer; solid triangles, the ncPNA/oligo reaction in tw80 buffer; the solid squares, the control of dye only in NP40 buffer; and solid diamonds, the ncPNA/oligo reaction in NP40 buffer. As clearly indicated on the graph, the two controls of dye only demonstrate that the fluorescent emissions remained constant over the observed seven minutes of light exposure. Additionally, dye in solution with Tween® 80 had and maintained fluorescent emission at approximately a 50% greater level than that of the dye in solution with NP-40. Both reactions demonstrated observable responses by the second minute after light exposure began, and dramatically so by the third minute after the start of light exposure.

Accordingly, this example demonstrates two aspects of the present invention: (1) use of surfactants NP-40 and Tween® 80, both non-ionic, correlated with increased dye fluorescence stability upon photoactivation, and (2) Tween® 80 correlates with about a 50% increased level of fluorescent emission as compared to reactions with NP-40.

Example 9

This example illustrates the effect that different plates have regarding the profiles of the reactions of the amino acid analog, target polynucleotide, and dye, in accordance with the present invention.

The microliter plates listed in Table 7 were obtained and tested to determine whether different color schemes of such materials have an effect on the reaction of a nucleic acid analog, a complementary target polynucleotide, and a dye, as provided by the present invention.

TABLE 7

| Plate Brands | Description | Color Scheme |
|---|---|---|
| 1. Greiner 655073 | 96-well | white with white bottom |
| 2. Greiner 655088 | 96-well, µclear | black with clear bottom |
| 3. Greiner 355892 | 96-well, glass bottom | black with clear bottom |
| 4. Greiner 655095 | 96-well, µclear | white with clear bottom |
| 5. Greiner 655096 | 96-well, µclear | black with clear bottom |
| 6. Greiner 781091 | 384-well | black with clear bottom |
| 7. Greiner 788096 | 384-well, small volume | black with clear bottom |
| 8. Greiner 788092 | 384-well, small volume | black with clear bottom |
| 9. Greiner 781892 | 384-well, glass bottom | black with clear bottom |
| 10. NUNC 436014 | 96-well, streptavidin | clear with clear bottom |
| 11. NUNC 265302 | 96-well | white with white bottom |
| 12. NUNC 237105 | 96-well | black with black bottom |
| 13. NUNC 265301 | 96-well, optical bottom | black with clear bottom |
| 14. NUNC 265301 | 96-well, optical bottom | white with clear bottom |
| 15. Costar 3601 | 96-well, high binding | black with clear bottom |
| 16. Corning 3651 | 96-well | black with clear bottom |
| 17. Costar 3631 | 96-well | black with clear bottom |
| 18. Costar 3615 | 96-well, special optics | black with clear bottom |
| 19. Costar 3632 | 96-well | white with clear bottom |
| 20. Costar 3693 | 96-well, ½ area | white with white bottom |
| 21. BD Biosciences 353241 | 96-well, streptavidin | black with black bottom |
| 22. BD Biosciences 354742 | 96 well | white with white bottom |
| 23. Matriplate | 384-well, glass bottom | black with clear bottom |

Each plate listed in Table 7 was tested. In a 50 µL test reaction, an 18-mer ncPNA with the sequence 5' GAT-AGTGGGATTGTGCGT 3' [SEQ ID NO: 1] (N-terminus to C-terminus) and a complementary DNA oligonucleotide target (final concentration 200 nM for both) were mixed with 3,3'-diethylthiacarbocyanine iodide dye (final concentration 300 μM) in a phosphate buffer with NP-40. A 50 μL control reaction mixture of phosphate buffer with NP-40 with 3,3'-diethylthiacarbocyanine iodide dye (final concentration) was run simultaneously. Light was applied to the plates, and the fluorescence intensity over time was measured.

In plates with clear bottoms, light was projected upwards through the well. The distance between the light source and the bottom of the well was approximately ¼ inch. In plates with black or white bottoms, light was projected downwards into the well at a distance of about 1 inch from the surface of the liquid. A fluorescent reading prior to light exposure was taken followed by subsequent readings every 60 seconds during exposure to light. Data were plotted as fluorescence vs. time with each data point representing at least 12 identical reactions, plus and minus the standard deviation.

Figure 11A:
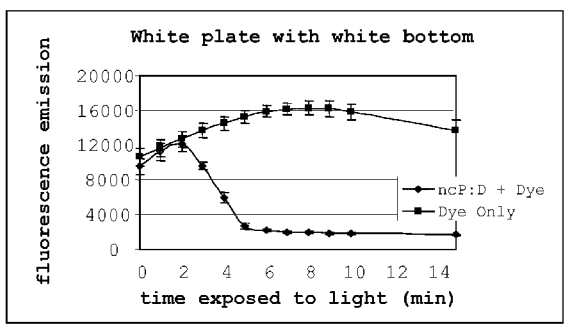
FIGS. 11A-D depict the change in fluorescence intensity as a function of time exposed to light of the "non-chiral PNA:DNA+Dye" reactions and the "Dye Only" reactions using different microtiter plates.
Figure 11C:
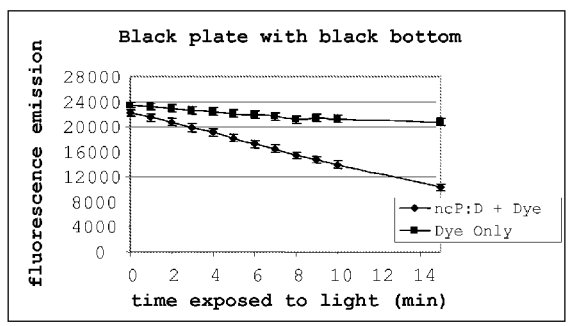
Figure 11B:
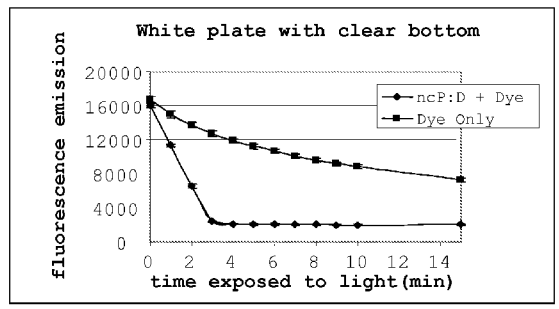
Figure 11D:
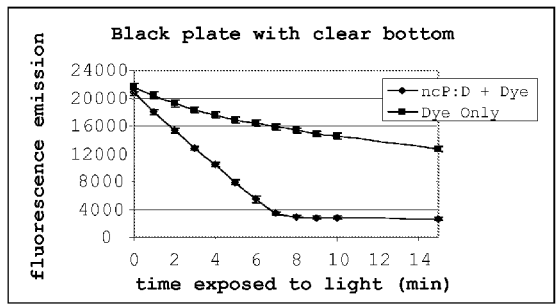

FIGS. 11A-D present the data graphically of replicate test reactions and controls reactions which were run in a white plate with white bottom (FIG. 11A); a white plate with clean bottom (FIG. 11B); a black bottom (FIG. 11C); and a black plate with clear bottom (FIG. 11D). This experiment demonstrates a considerable effect of the reflective (i.e., white) or absorptive (i.e., black) nature of the plate on the rate of fluorescence decay of 3,3'-diethylthiacarbocyanine iodide dye.

When the light source projected downward into the reaction (FIGS. 11A and 11B), there was an accelerated rate of fluorescence decay of the test reaction while the control reaction demonstrated minimal fluorescence decay. When a white plate with white bottom was used, the fluorescence of the "Dye Only" reaction increases from time zero to 15 minutes (FIG. 11B). In a black plate with a black bottom the rate of fluorescence decay of the test reaction was significantly slower than the same reaction in a white plate with the white bottom.

In plates containing clear bottoms (where the light was projected upwards through the wells), the white plates demonstrated a faster rate of fluorescence decay of the test reactions compared to the black plates (FIGS. 11C and 11D), reaching the minimum observed value in about three minutes versus about seven minutes. The control reactions also demonstrated a slightly faster rate of fluorescence decay in the white plates compared to the black plates.

In general, the results were not significantly different using different brands (i.e., NUNC, Greiner, or Costar) of microplates. It was observed, however, that the black plates correlated with nearly a 50% increase in fluorescence emission relative to the white plates (see the 0 time fluorescence level for each set of experiments, for example). It was also observed that the white plates correlated with a test reaction that was faster in reaching the minimum fluorescence level.

Example 10

This example describes an experiment and results thereof that tested the use of a modified reaction buffer that included surfactant and alcohol.

A modified phosphate buffer was identified that provides greatly enhanced stabilization of dye and reduced background signal. The modified buffer consisted of the 5 mM phosphate buffer described above, plus 0.05% Tween 80 and 14% methanol. Stabilization of the dye was also enhanced by using less light. The reactions described in this example were conducted in a white 96 well flat white bottom microtiter plate (Greiner).

Reactions were set up in triplicate and loaded on the microtiter plate. Reaction mixes were made from 7.5 mM 3,3'-diethylthiacarbocyanine iodide dye stock, 100 μM ncPNA stock, Bio 18 (5' Bio-oooooo-GATAGTGGGATTGTGCGT 3' [SEQ ID NO:1]), 100 μM complementary DNA set (5' GATAGTGGGATTGTGCGT 3' [SEQ ID NO:1]; 5' ACGCA-CAATCCCACTATC 3' [SEQ ID NO:20]), 1 μl of each homologous DNA pair was mixed equally in annealing buffer (Sambrook, et al) at a concentration of 2 μM and heated to 95° C. for five minutes, then allowed to cool to room temperature. The ncPNA were diluted to 2 μM working stock.

In a PCR strip tube, 20 μl of 2 μM ncPNA and 20 μl of complementary DNA was mixed, making a test reaction mixture. 20 μl of ncPNA and 20 of buffer was added to a well making a ncPNA/dye control reaction mixture. 20 μl of DNA and 20 μl of buffer were added to a well making a DNA/dye control reaction mixture, and 40 μl of buffer was added to the dye only control reaction mixture. A master dye buffer mix was made by adding 36 μl of 0.75 mM dye to 684 μl of 5 mM $PO_4$ buffer plus 0.05% Tween® 80 with 14% methanol. The solution was mixed and 160 μl was dispensed to each of the 4 wells of the PCR strip tube. The solutions were mixed and 50 μl of each reaction mix was dispensed into 3 wells (triplicate) of the white plate. The plate was placed in the Tecan Genios microplate reader and an initial fluorescence measurement was taken (before photoactivation). Samples were exposed to the Aurora 50/50 fluorescent light at half its light intensity and fluorescence measurements were taken after every 1 minute of light exposure for 10 minutes.

Figure 12:
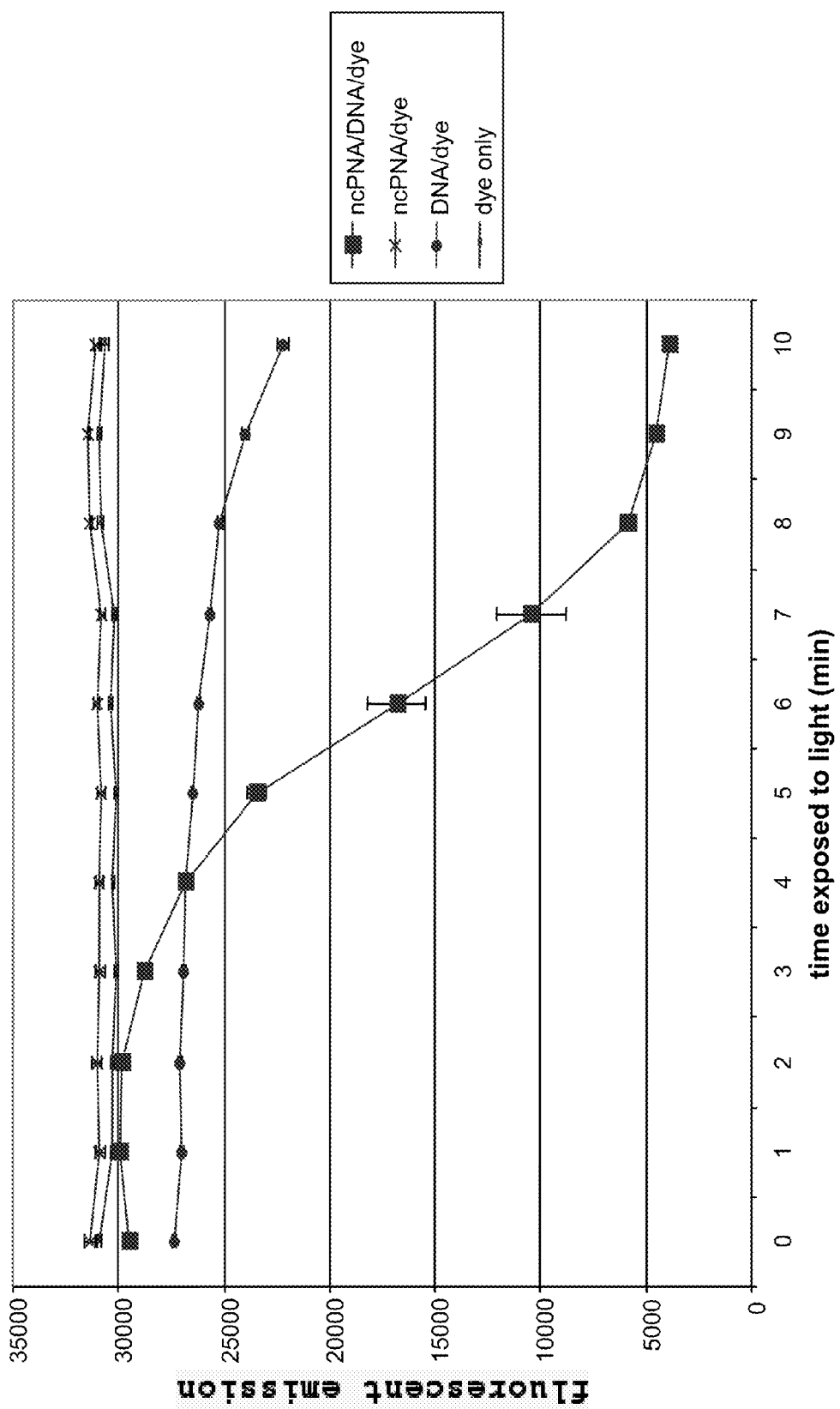
FIG. 12 depicts the reduction in background noise signal from actual signal using a modified phosphate buffer, altered light intensity with a white plate.

The results are graphically displayed in FIG. 12. The dye only control reaction mixture (■) and ncPNA/dye control reaction mixture (x) exhibited greatly enhanced stabilization of the zero time fluorescent emission (referred to here as the background signal) by showing virtually no reduction in fluorescence. The DNA/dye control reaction mixture showed a small reduction in fluorescence, however the reduction was negligible through at least seven minutes of light exposure. The test reaction mixture had a fast rate of decrease in fluorescent emission, starting within the third minute. The addition of the alcohol in tandem with surfactant correlates with the enhanced dye stabilization; as illustrated by negative controls in FIG. 11, for example.

Example 11

This example illustrates a fast method for preparing a cellular sample for testing whether a particular target polynucleotide is present. Reaction buffer (0.5 mM phosphate) containing 0.05% NP-40 was used to permeabilize and/or lyse fresh overnight cultures of E. coli and B. cereus grown in tryptic soy broth. Tests from the diluted samples were prepared by using 300 μl from each culture sample. Samples were spun down to a pellet and supernatant removed. Pellets were resuspended in 390 μl of reaction buffer and incubated at room temperature for 10 minutes before use in the test reaction. Each test sample contained 10 pmoles of 16S nucleic acid analog (ncPNA) probe (5'-ACT GCT GCC TCC CGT AG-3' [SEQ ID NO:8]) or 10 pmoles of HCV-specific biotinylated nucleic acid analog (ncPNA) probe (5' Bio-(O)$_{10}$-CGCAGACCACTA 3' [SEQ ID NO:35]), 5 μl of each lysate dilution test and 4 nmoles of 3,3'-diethylthiacarbocyanine iodide (DTCC dye). The so-constituted test samples were diluted to a 50 μl total reaction volume with 5 mM tw80 buffer. Tests were done either with 16S ncPNA as probe, which should detect the E. coli and B. cereus bacteria, and a non-specific HCV probe that should not recognize any bacterial DNA in this system. The positive control well contained 16S ncPNA probe, 10 ng of isolated E. coli DNA, dye and buffer. The probe only well contained either the HCV ncPNA probe or 16S ncPNA probe, and dye and buffer. The dye only well contained dye and buffer.

ncPNAs were reconstituted in DNase-, RNase-free water to 100 μM stock and further diluted to 2 μM working stocks. The DTCC dye was dissolved in DMSO to 8 mM stocks. This was further diluted to 2 mM working stock in 5 mM phosphate buffer (pH 5.5)+NP-40 0.05%. An initial fluorescence reading was taken at time zero in the Tecan Genios microplate reader with the wavelengths set at 535 nm for excitation and 590 nm for emission. The samples were then exposed to a light stimulus using the Aurora 50/50 for 1 minute intervals with fluorescence reading being taken after each exposure for 10 minutes.

The data were used to calculate the percent change in the test wells containing bacterial lysate and either the HCV ncPNA probe or the 16S ncPNA probe compared to the reaction well containing dye and the analogous HCV ncPNA probe or 16S ncPNA probe. By so comparing the percent change in fluorescence readings after differing numbers of minutes of light exposure, the rate of change of fluorescence emission was determined (which is directly related to the presence of target molecules).

Figure 13:
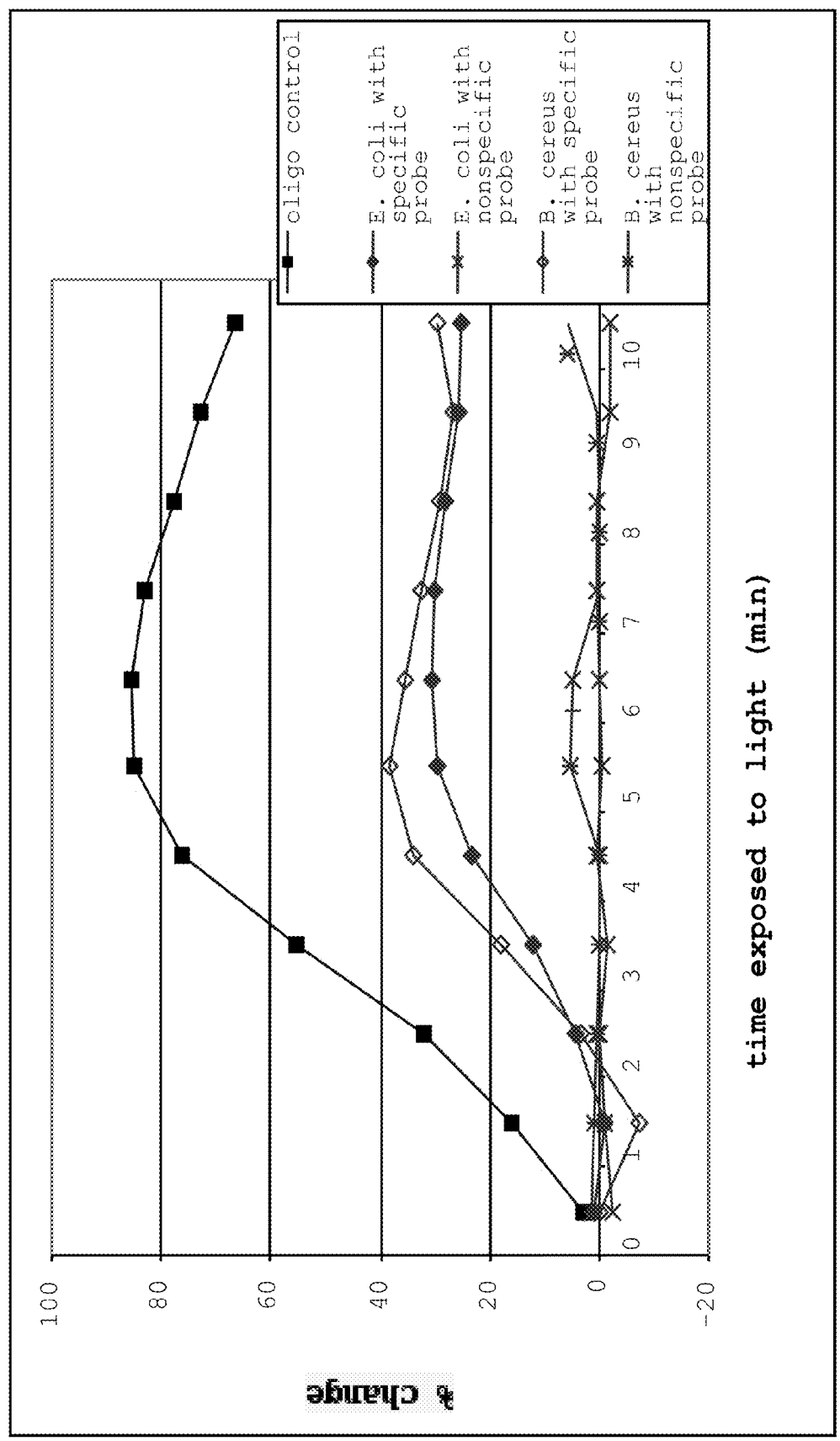
FIG. 13 depicts the use of a bacterial permeabilization/lysis buffer on a gram positive bacterial and a gram negative bacterial sample with bacterial specific and non-specific nucleic acid analog probes.

The results are graphically presented in FIG. 13. A strong signal can be seen from the positive control reaction containing bacterial DNA. Test samples containing the 16S ncPNA probe with either *E. coli* or *B. cereus* lysates produced robust signals as well, which demonstrates that the method of the present invention is well-suited for bacterial identification using suitable sequences of nucleic acid analogs. Test samples with bacterial lysate and the non-specific HCV ncPNA probe remained at background levels, indicating that one should not expect false-positive results from the herein described method despite the use of crude bacterial lysates for the samples that were tested. Accordingly, the permibilization/lysis buffer producing a crude lysate is sufficient for the detection method disclosed herein.

Example 12

This example further explores using a crude bacterial lysate as the source of a sample for testing whether a target polynucleotide is present.

Reaction buffer (0.5 mM $PO_4$) containing 0.05% NP 40 was used to permeabilize and/or lyse diluted aliquots of fresh overnight cultures of *E. coli* cells that were grown in tryptic soy broth. A sample from the culture was serial diluted and plated on LB agar plates for later colony counts to determine the cell concentration. Analogous serial dilutions of *E. coli* cells (10 fold dilutions) were made in tryptic soy broth. A "zero" sample contained broth only. Samples were prepared by taking 250 µl of each diluted sample, centrifuging to pellet the cells, and removing supernatant. Pellets were resuspended in 390 µl of buffer and incubated at room temperature for 10 minutes before an aliquot thereof was used in the test reaction. Each test sample contained 10 pmoles of 16S ncPNA probe (5' ACT GCT GCC TCC CGT AG 3' [SEQ ID NO:8]), 5 µl of each lysate dilution, and 4 nmoles of 3,3'-diethylthiacarbocyanine iodide (DTCC dye); placed in a 50 µl total reaction volume using 5 mM $PO_4$/NP-40. The positive control well contained 16S ncPNA probe, complementary oligo, dye and buffer. The probe only well contained probe, dye and buffer. The dye only well contained dye and buffer.

ncPNAs were reconstituted in DNase- and RNase-free water to 100 µM stock and further diluted to 2 µM working stocks. The DTCC dye was dissolved in DMSO to 8 mM stocks. This was further diluted to 2 mM working stock in 5 mM phosphate buffer (pH 5.5)+0.05% NP 40. An initial fluorescence reading was taken at time zero in the Tecan Genios microplate reader with the wavelengths set at 535 nm for excitation and 590 nm for emission. The samples were then exposed to a light stimulus using the Aurora 50/50 for 2 minute intervals with fluorescence reading being taken after each exposure for 20 minutes.

The data were used to calculate the percent change in the reaction test well containing the ncPNA probe and the diluted bacterial lysate compared to the reaction well containing only the ncPNA probe/dye.

Figure 14:
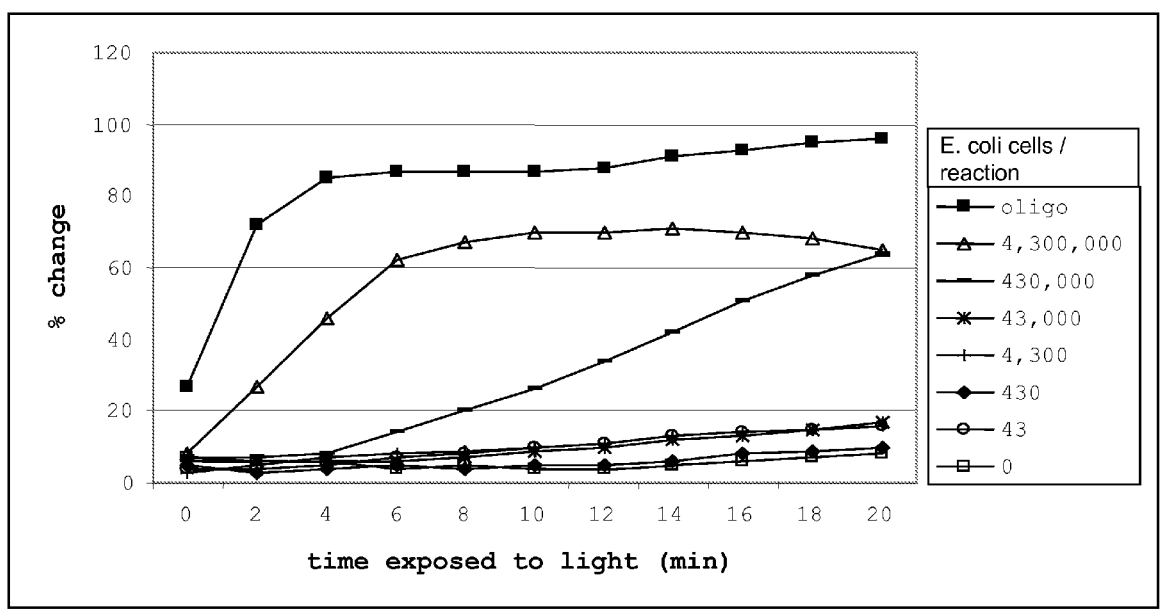
FIG. 14 depicts the use of an altered bacterial permeabilization/lysis buffer and quantitative detection of a bacterial target on a serially diluted culture of bacterial cells.

FIG. 14 graphically displays the results. The samples of bacteria that were tested contained the following numbers of bacterial cells: 4.3 million (Δ); 430,000 (▬); 43,000 (*); 4,300 (|); 430 (♦); 43 (○); and 0 (□). Additionally a positive control (■) was included, which had a very strong signal. Similarly, the signal from a reaction mixture having 4,300, 000 cells was also very clear, and the signal from a reaction mixture using 430,000 cells, while still clear, departed from the robustness of the signal from a positive control reaction mixture. Counts of 43,000 cells and below resulted in data that was virtually indistinguishable from background levels. These results demonstrate the ability of the method to quantitate in a system of crude cellular lysates.

Example 13

This example illustrates further the combined effect of Tween 80 and methanol in the reaction buffer, and compares the effect to that of methanol alone.

The effect of methanol in conjunction with Tween 80 at greatly increasing the signal-to-noise ratio in a reaction was described above. (See Example 10). The combined effects with Tween 80 are much greater than when the same concentration of methanol is used alone. Two reactions were made, one with Tween 80 and another without. The modified buffers were made having the following content: (1) 5 mM $PO_4$ buffer plus 0.05% Tween 80 with 14% methanol; and (2) 5 mM $PO_4$ buffer with just 14% methanol. Reactions were run using a white 96-well flat-bottom microtiter plate (Greiner) and the Aurora 50/50 fluorescent light at half its intensity.

Reactions were set up in triplicate and loaded in the wells of the 96-well microtiter plate. Reaction mixes were made from the following: 7.5 mM Dye stock, 100 µM ncPNA stock, (5' Bio-ooooo-GATAGTGGGATTGTGCGT 3' [SEQ ID NO:1]), 100 µM complementary oligo set (5' GATAGTGG-GATTGTGCGT 3' [SEQ ID NO: 1], 5' ACGCACAATC-CCACTATC 3' [SEQ ID NO:20]); 1 µl of each exactly complementary oligo pair was mixed equally in annealing buffer (Sambrook, et al) at a concentration of 2 µM and heated to 95° C. for 5 minutes, then cooled to room temperature. The ncPNA were diluted to 2 µM working stock.

Figure 15:
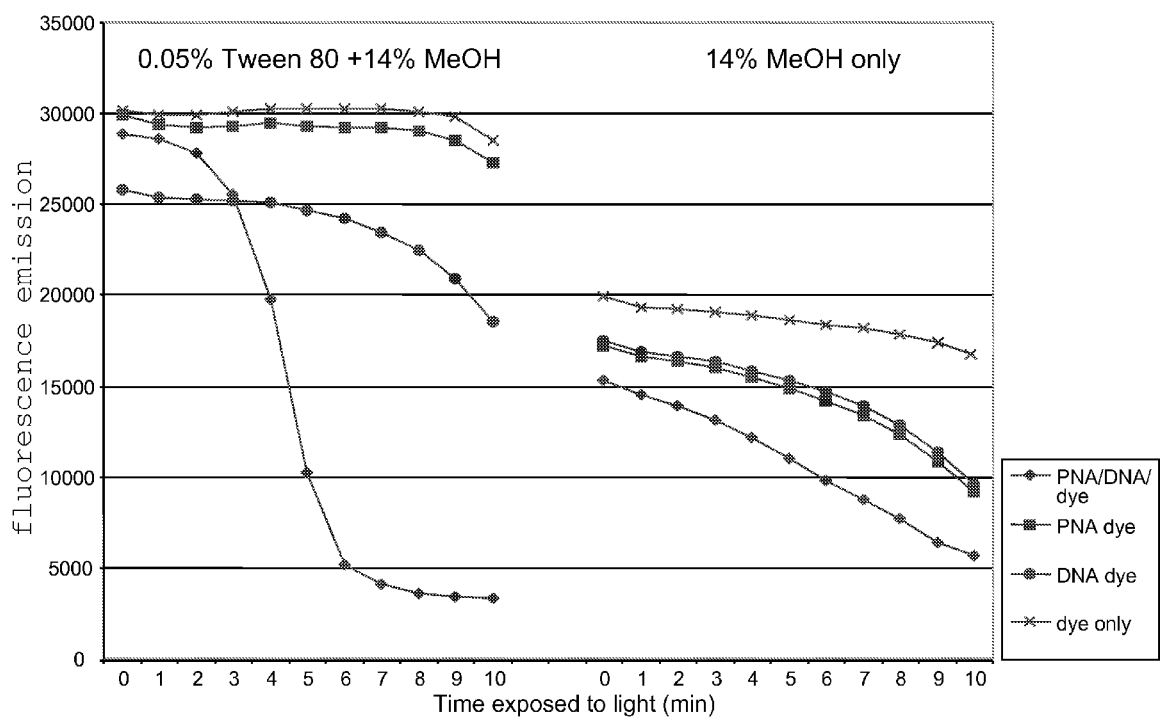
FIG. 15 depicts the reduction of background noise signal from a specific signal by use of both Tween® 80 and methanol in the buffer compared to methanol alone. Tests were done at reduced light intensities in a white plate.
Figure 16B:
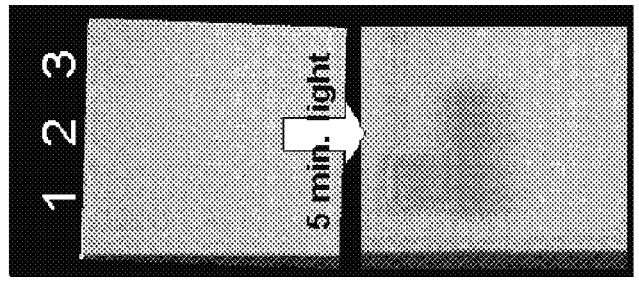
FIGS. 16A-B is, respectively, a schematic of a P/TP as a "detector" attached to an antibody and an agarose gel shift assay.
Figure 16A:
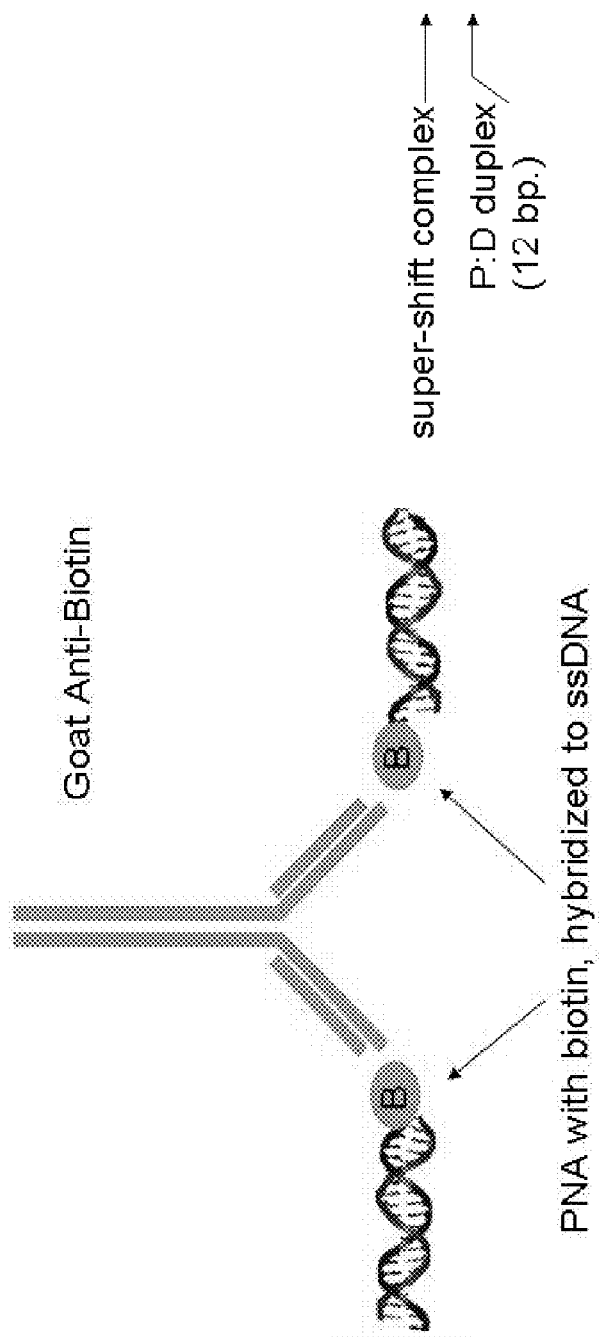

A master dye buffer mix was made by adding 36 µl of 0.75 mM dye to 684 µl of 5 mM $PO_4$ buffer plus 0.05% Tween® 80 with 14% methanol. The solution was mixed and 160 µl was dispensed to each of 4 wells of a strip tube (Perkin Elmer, Catalog #N801-0580). In the first tube, 20 µl of 2 µM ncPNA and 20 µl of DNA were mixed, making a test reaction mixture. Additionally, these different negative controls were tested in parallel: in a second tube 20 µl of ncPNA and 20 µl of buffer was added making a ncPNA/dye only reaction mixture, in a third tube 20 µl of oligo and 20 µl of buffer was added making the oligo/dye only reaction mixture, and to a forth tube 40 µl of buffer only was added making the dye only reaction mixture. An identical set of reaction mixtures was made as above, but 5 mM $PO_4$ buffer plus 14% methanol (without Tween® 80] was used. The solution was mixed and 50 µl of each reaction mix was dispensed into 4 wells of the white plate. The plate was placed in the Tecan Genios microplate reader and an initial fluorescence was read without light exposure. Samples were exposed to the Aurora 50/50 fluorescent light at half its light intensity, as above, and readings were taken after every minute of light exposure for 10 minutes. The data were recorded as presented graphically in FIG. 15.

Fluorescent emission at $T_0$ was greater for reaction mixtures containing the surfactant/alcohol combination in the reaction buffer as compared to reaction mixtures not containing the surfactant/alcohol combination in the reaction buffer. Moreover, all negative control reaction mixtures (PNA+dye, ■; DNA+dye, ●; and dye only, x) showed increased stability of the fluorescence signal over time, which translates to reduced background noise compared to target polynucleotide, when methanol is used in conjunction with Tween® 80 (left graph set). The dye only and ncPNA/dye reaction mixtures exhibited very little change in fluorescence signal over time. The DNA/dye reaction mixture exhibited minor change in fluorescence signal over time while the test reaction mixture exhibited a very rapid reduction in fluorescence signal over time.

When 14% methanol is used alone there is a much lower relative change in fluorescence signal of the test reaction mixture as compared to the change in fluorescence signal of all control reaction mixtures.

Example 14

This example illustrates two methods for analyzing a change in an optical property as a function of time as it relates to the present invention.

Experimental data were obtained using the following protocol. Samples containing or not containing genomic nucleic acid (NA) isolated from *Mycobacterium tuberculosis* (MTB CDC 1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.08 ng/μL in molecular biology grade water (Hyclone, catalog #SH30538.03).

At this point, a 50 μM PNA probe mix was prepared from freezer stocks. Sequences used were Sequence ID NO: 42, 43, 44, 45, 46 and 47. Freezer stocks (at ~200 μM in $H_2O$) were put in a hotblock at 65° C. for five minutes, and a 50 μM solution of each ncPNA was prepared by diluting the freezer stock ncPNA in molecular biology grade $H_2O$ (Hyclone, catalog #SH30538.03). Equal volumes of each 50 μM ncPNA solution were added to create a 50 μM total PNA concentration, i.e., 8.33 μM per ncPNA. This 50 μM PNA probe mix was put in the hotblock at 65° C. for five minutes, and was then further diluted in phosphate buffer (10 mM) with surfactant to a final concentration of 320 nM. The 320 nM PNA probe mix was placed in a water bath at 65° C. for five minutes, removed, and given 30 minutes to cool to room temperature.

Dye solution was prepared by diluting 7.5 mM 3,3'-diethylthiacarbocyanine ("$DiSC_2(3)$") (solubilized in DMSO) into phosphate buffer with surfactant to a working concentration of 36 μM.

Serial 1:2 dilutions of the 0.08 ng/μL MTB NA (in water) were prepared down to a low concentration of 0.0025 ng/μL; referred to herein as "DNA standards". Aliquots of 25 μL of each of the DNA standards were dispensed into a 384 well white/clear plate (NUNC, catalog #242763) to set up a concentration curve with six replicates in individual columns on the plate. The columns were set up as follows: Rows 1-6 and 9-14 were assay wells with 2 ng, 1 ng, 0.5 ng, 0.25 ng, 0.125 ng, and 0.0625 ng MTB DNA per well, Row 7 and 15 were control wells with 0 ng DNA and Row 8 and 16 were control wells with 2 ng MTB DNA and no PNA.

Because of the sensitivity of the optical measurements, care was taken to ensure that the surfaces of the solutions in the microtiter plate were uniform. The solutions were dispensed using a reverse-pipetting technique described by B. Brando et al. (CYTOMETRY 42:327 (2000)). Briefly, the technique involves pushing the plunger on a mechanical pipettor past the first stop for the initial reagent draw, and pushing the plunger only to the first stop for dispensing, ensuring that a small volume of liquid remains in the pipettor after dispensing. The assay microplate was briefly centrifuged at 500 RPM (34×g) in a Sorvall benchtop centrifuge (Model RT6000D) after the addition of each reagent type.

After the DNA standards were dispensed into the microplate, and the microplate was centrifuged, two dye mixtures were then prepared. The reaction set-up steps involving the dye were performed in a dimly lit room. The first control dye solution was prepared by mixing equal volumes of 36 μM $DiSC_2(3)$ with phosphate buffer (with surfactant). This 18 μM $DiSC_2(3)$ control solution was mixed by inversion in a 15 mL conical tube, and poured into a reagent reservoir. A 25 μL aliquot of the control dye solution was then dispensed to each well along Row 8 [H] of the microplate. The second, dye+PNA probe mix was prepared by mixing equal volumes of 36 μM $DiSC_2(3)$ with the 320 nM PNA probe mix. This 18 μM $DiSC_2(3)$+160 nM PNA probe mix was mixed by inversion in a 15 mL conical tube, and poured into a reagent reservoir. A 25 μL aliquot of the dye+PNA probe mix was then dispensed to each well along Rows 1-7 [A-G] of the microplate. The microplate was then briefly centrifuged at 500 RPM.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 44 minutes total exposure to light.

Figure 18:
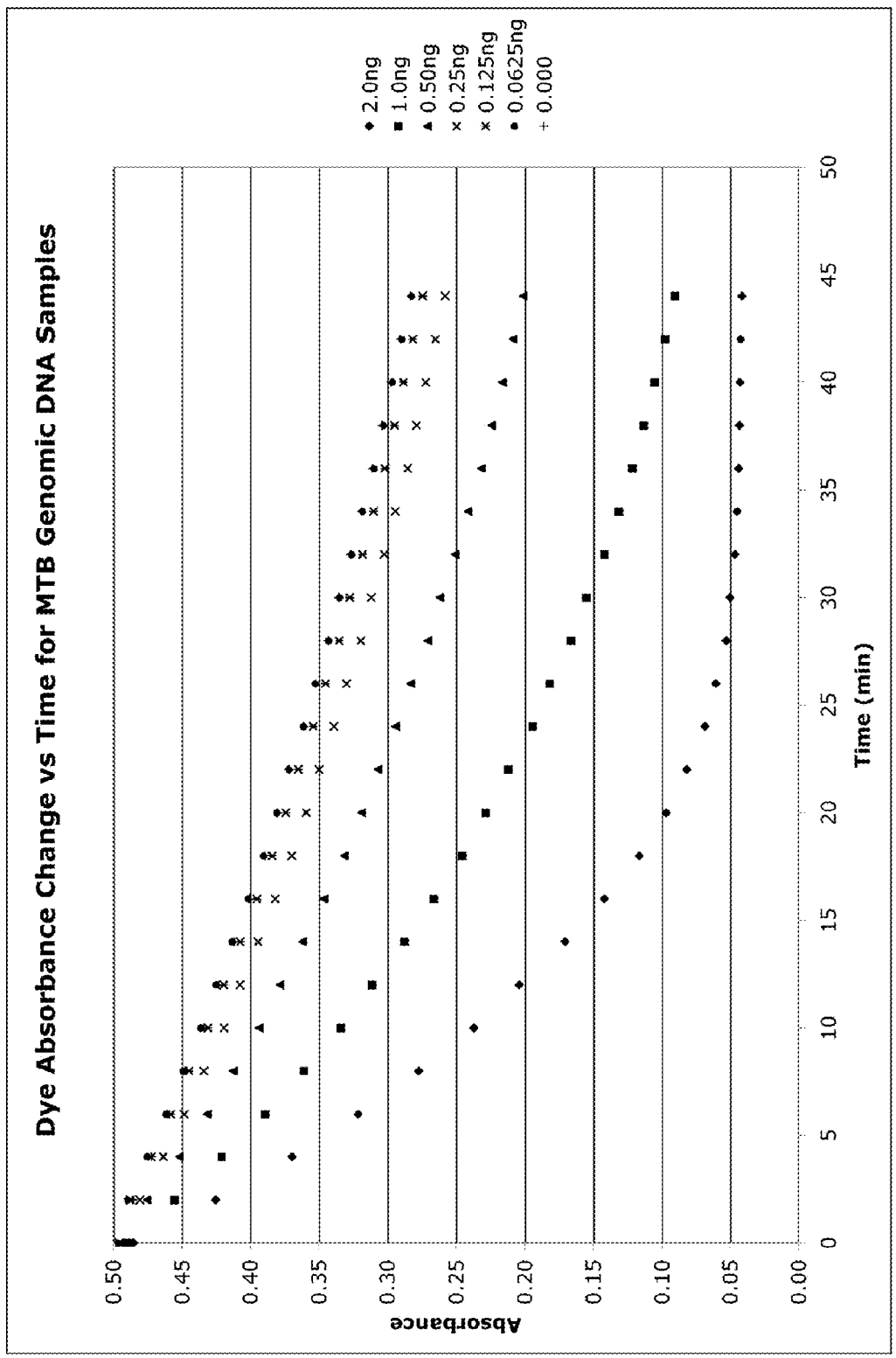
FIG. 18 depicts typical dye absorbance change vs. time data for the varying amounts of MTB genomic DNA.

Dye bleaching reactions catalyzed by a PNA-DNA complex in the presence of the above light stimulus exhibit decreasing absorbance as a function of time when monitored at the absorption maxima of the dye, typically 556 nm. Typical absorbance vs. time data for the varying amounts of MTB DNA as described in the preceding experimental protocol are displayed in FIG. 18. Each data point on the graph is the average of 48 individual determinations on the 384 well assay plate, standard deviations are not shown in the graph but were typically less than 5%.

Figure 19:
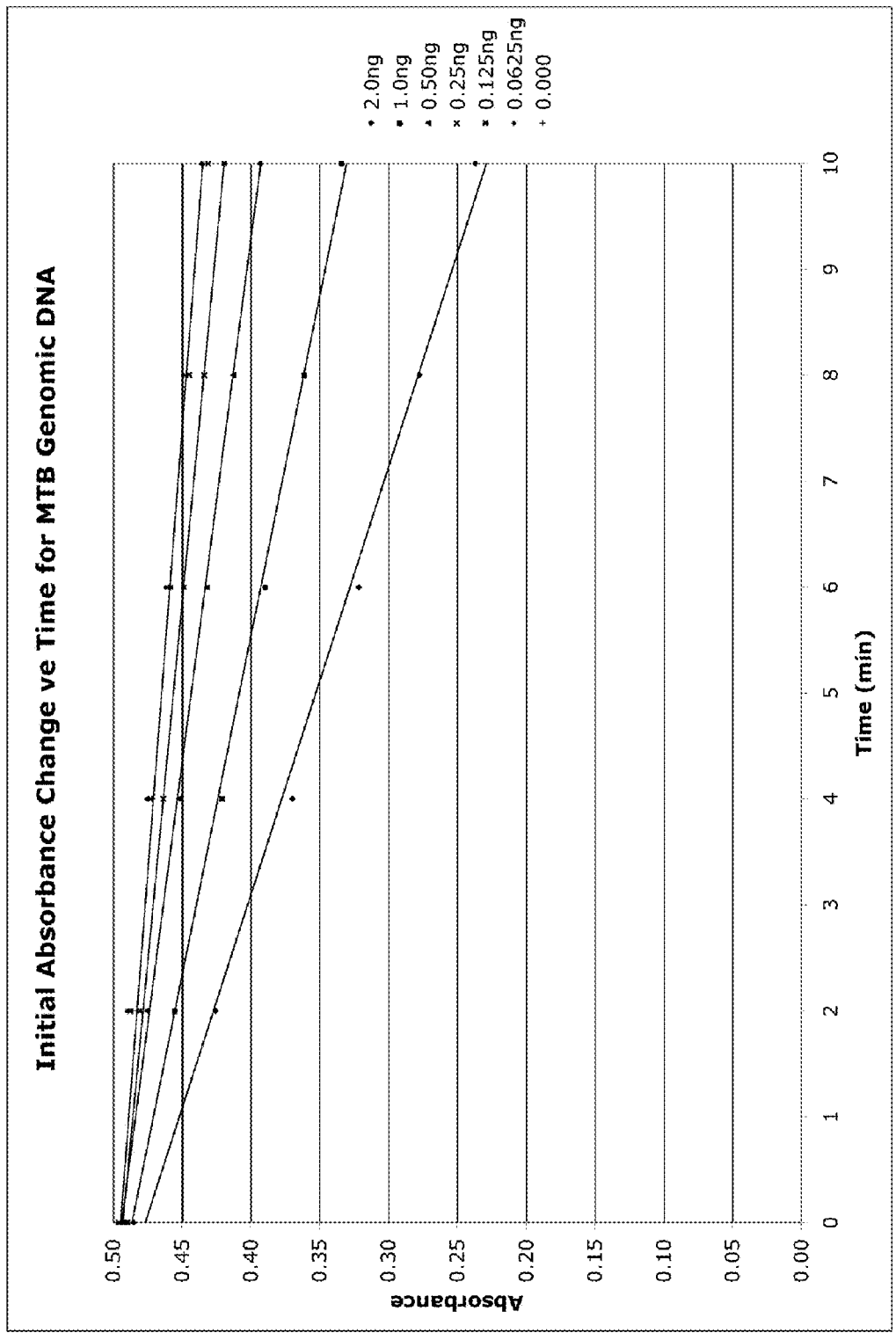
FIG. 19 depicts initial absorbance change vs. time data for different concentrations of MTB genomic DNA

Absorbance change vs. time data can be used to estimate concentration of target nucleic acids in two ways. In the first preferred method absorbance rate changes are extracted from the experimental data during the initial portion of the reactions when the rate of change varies linearly with time (FIG. 19). Absorbance changes in this linear region may be approximated by a linear equation in the first 2-10 min of observation, after this initial phase the reactions exhibit significant non-linearity. The initial data can be fit to a linear equation using the method of least squares and the slope of the initial data can then be estimated from the resulting linear equations. This method has the advantage of also allowing the correlation coefficient $R^2$ to be calculated for the data thereby providing a measure of how good the data fit to the linear equation. Alternately the initial slope of a reaction may be estimated by subtracting the absorbance at a fixed time point, say 10 minutes, in the linear portion of the reaction from the starting absorbance at 0 minutes and dividing the result by the time interval between the two points. Initial rates of change for different concentrations of MTB DNA were calculated for the data displayed in FIG. 19 by fitting the data to a linear equation using the "add trendline" analysis function in the program Microsoft Excel. The initial slopes were also calculated subtracting absorbance at time 0 from absorbance at 10 minutes and dividing the result by 10. The results of both methods of calculation are shown in Table 8 and are in good agreement with one another.

TABLE 8

Estimation of Initial Reaction Rate Slope

| | Amount MTB | | | | | | |
|---|---|---|---|---|---|---|---|
| | 2.0 ng | 1.0 ng | 0.50 ng | 0.25 ng | 0.125 ng | 0.0625 ng | 0 |
| Average Absorbance 0 min | 0.4853 | 0.4895 | 0.4935 | 0.4912 | 0.4958 | 0.4966 | 0.4914 |
| Average Absorbance 10 min | 0.2370 | 0.3340 | 0.3935 | 0.4192 | 0.4311 | 0.4360 | 0.4340 |
| Slope 0-10 min | 2.48E−02 | 1.56E−02 | 1.00E−02 | 7.20E−03 | 6.47E−03 | 6.06E−03 | 5.74E−03 |
| Slope from Graph | 2.48E−02 | 1.56E−02 | 1.01E−02 | 7.37E−02 | 6.66E−03 | 6.26E−03 | 5.96E−03 |
| Fit Line $R^2$ Value | 0.994 | 0.997 | 0.999 | 0.997 | 0.995 | 0.994 | 0.992 |

Figure 20:
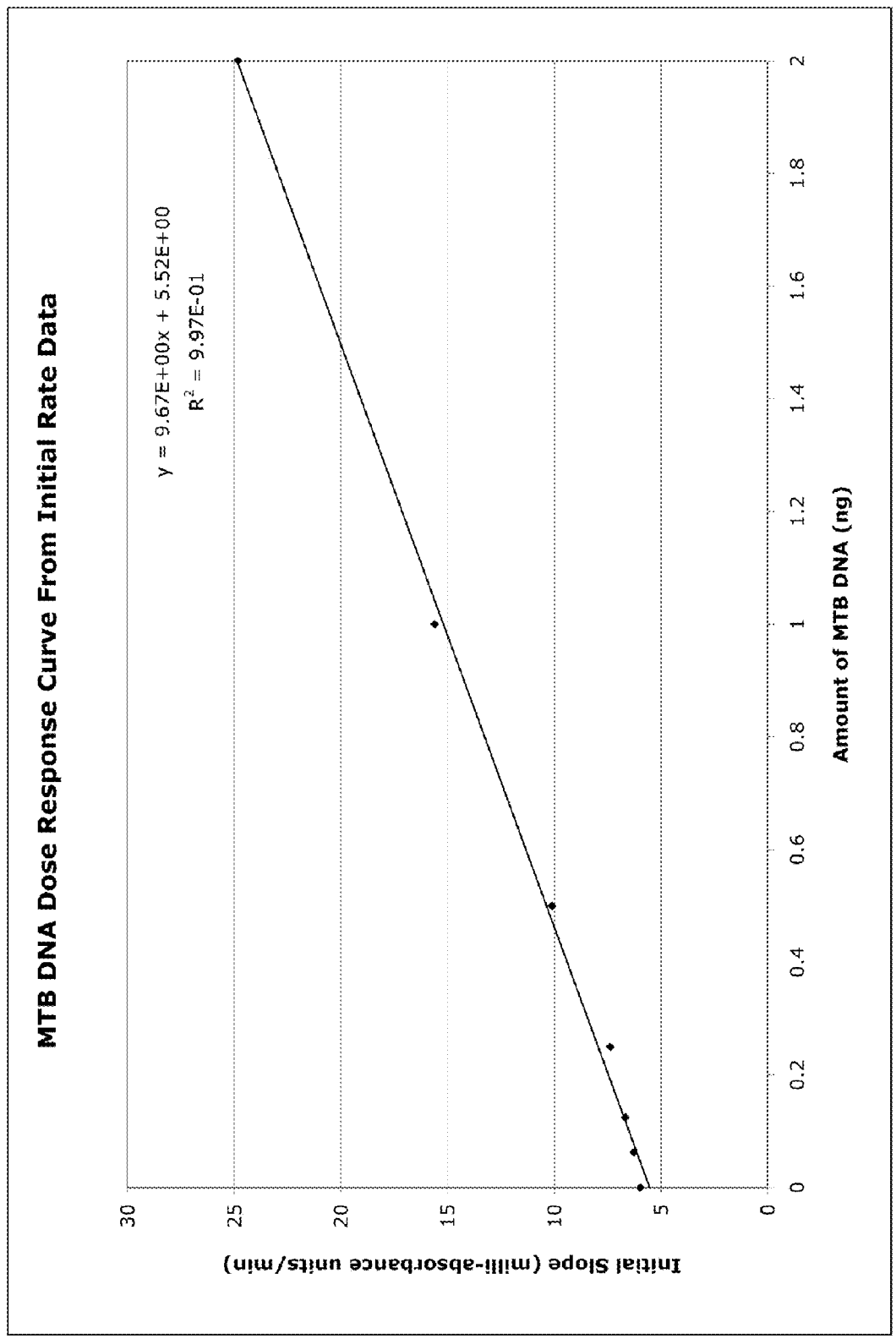
FIG. 20 shows an MTB DNA dose response curve from initial rate data demonstrating a linear relationship between analyte concentration and initial slope value.

In addition, $R^2$ values for the fitted lines indicate that the data fit well to a linear equation. Slope values are expressed as positive numbers. A dose response curve constructed from these data exhibits a linear relationship between analyte concentration and initial slope value as shown in FIG. 20. Linear fitting of the experimental data was accomplished using "add trendline" analysis function in the program Microsoft Excel. Once again examination of the $R^2$ value for this data show they fit well to a linear equation. Thus the assay method when combined with this process of data reduction allows quantitative measurements of target analytes in a straightforward manner.

Figure 21:
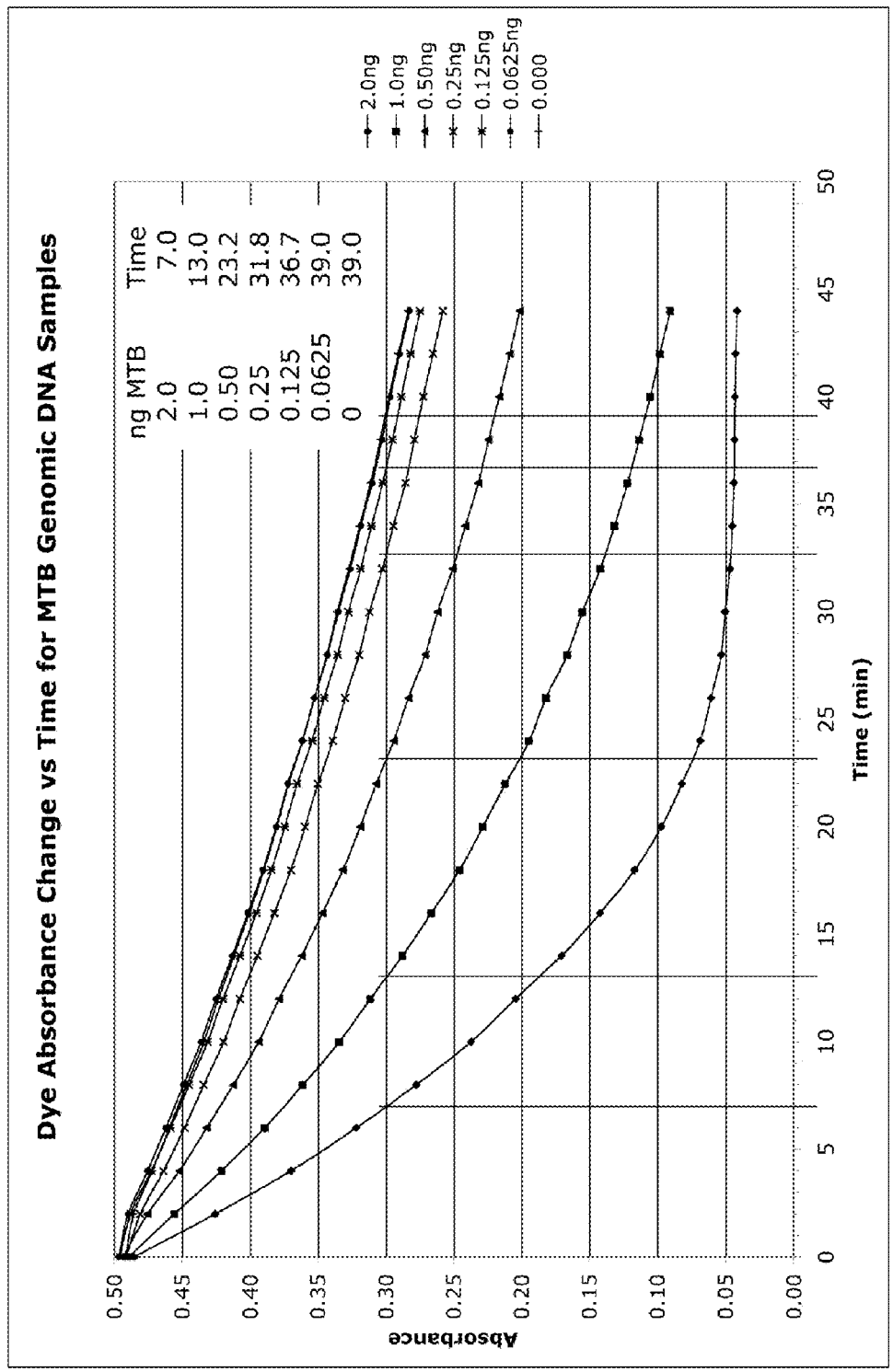
FIG. 21 depicts dye absorbance change vs. time data for different concentrations of MTB genomic DNA samples
Figure 22:
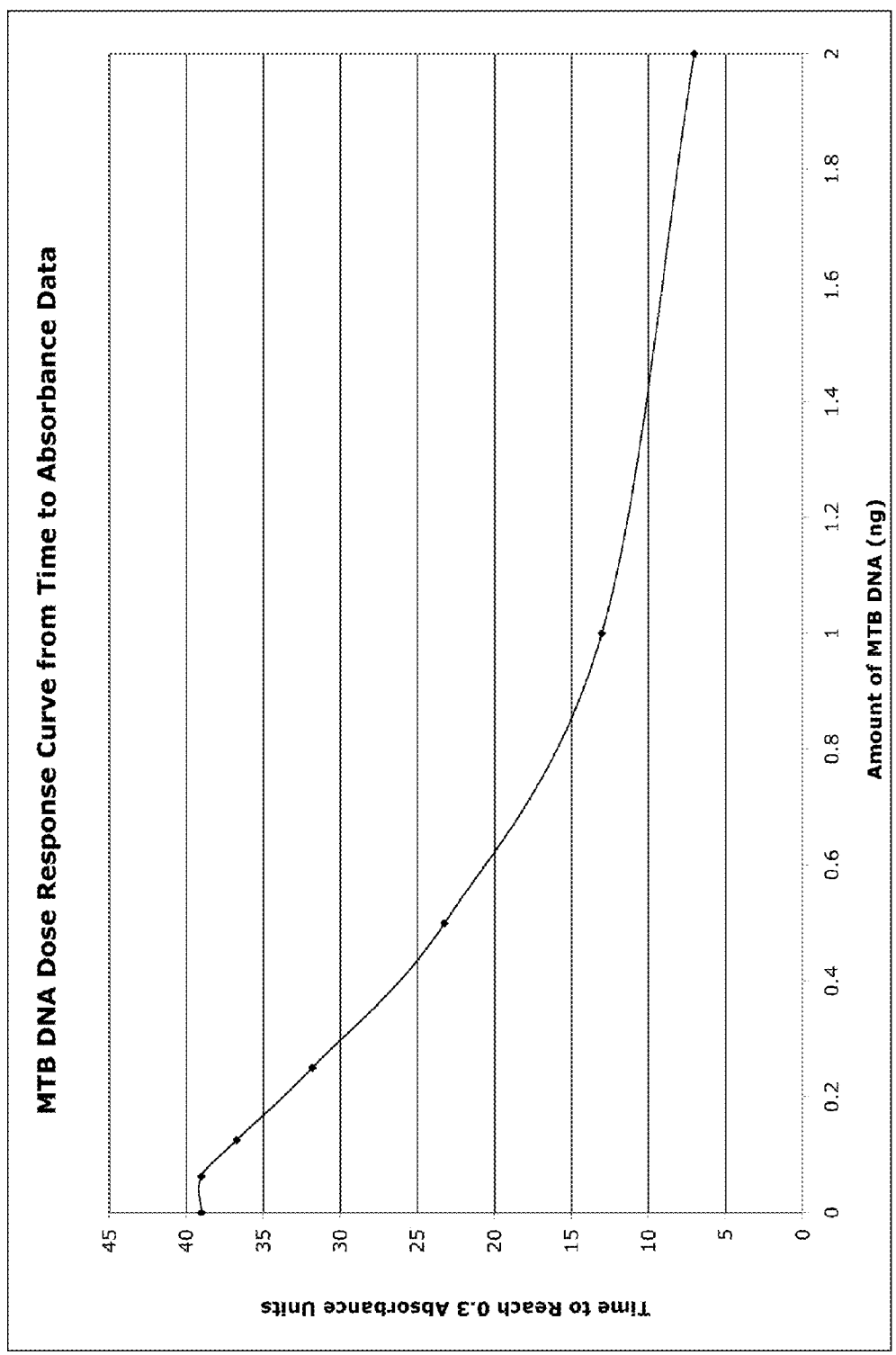
FIG. 22 depicts an MTB DNA dose response curve from time to absorbance date where the relation between time to absorbance and analyte concentration is not typically linear
Figure 23:
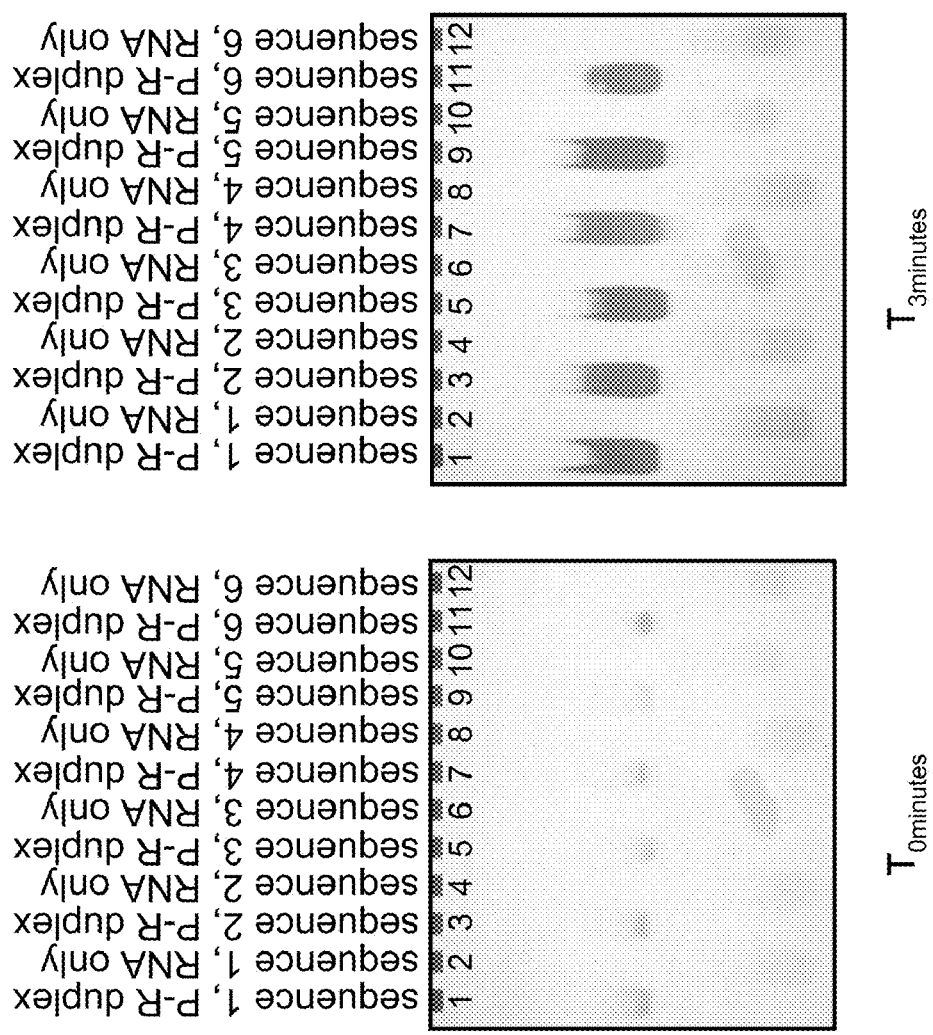
FIG. 23 depicts a polyacrylamide gel showing dark areas in the gel where photobleaching occurred (samples containing PNA-RNA duplexes).

A second method of data reduction can also be used to analyze dye bleaching reactions in order to derive dose response curves. In this method the time required to observe a given change in absorbance is estimated for each analyte concentration and that time is plotted vs. analyte concentration to produce a dose response curve. The present experiments start at an absorbance of approximately 0.5 absorbance units and the time interval for each reaction to reach 0.3 absorbance units was estimated graphically from the data as shown in FIG. 21. Reduction by 0.2 absorbance units has a physical sense: this change in absorbance corresponds to a reduction of transmission of approximately 1.6 fold (log(1.6)=0.2). The relation between time to absorbance and analyte concentration derived by this method is not typically linear, FIG. 22. The method does provide a good way of comparing many experimental conditions, especially if the data is not well behaved with the Initial Slope Method.

Example 15

This example sets forth tests conducted to assess the effects of different detergents on diagnostic reactions of the present invention.

In a 96-well white with clear bottom NUNC microtiter plate, 100 µL of a 5 mM phosphate buffer (pH 5.5) was mixed with one of a collection of detergents (also referred to as surfactants), which are listed in Table 9.

TABLE 9

| Trade or Common Name of Detergent Studied* | Synonyms; Molecular Formula | Type of Detergent |
|---|---|---|
| CHAPS (100 mg) | 3-[(3-cholamidopropyl)dimethylammonio]-1-propanesulfonate hydrate | zwitterionic |
| octyl-β-glucoside (100 mg) | octylglucopyranoside | nonionic |
| octyl-β-D-thioglucoside (100 mg) | octylthioglucopyranoside; OTG | nonionic |
| Surfact-Amps ™ X-100 (a 10% aqueous solution of Triton ® X-100) | octylphenol (ethoxylate)$_n$ where n is 9 or 10 on average | nonionic |
| Surfact-Amps ™ X-114 (a 10% aqueous solution of Triton ® X-114) | octylphenol (ethoxylate)$_n$ where n is 7 or 8 on average | nonionic |
| Surfact-Amps ™ NP-40 (a 10% aqueous solution of Nonidet P-40) | [octylphenoxy]polyethoxyethanol | nonionic |
| Surfact-Amps ™ 20 (a 10% aqueous solution of Tween ® 20) | polyoxyethylene sorbitan monolaurate; polysorbate 20; $C_{58}H_{114}O_{26}$ | nonionic |
| Surfact-Amps ™ 80 (a 10% aqueous solution of Tween ® 80) | polyoxyethylenesorbitan monooleate; polysorbate 80 | nonionic |
| Surfact-Amps ™ 35 (a 10% | polyoxyethylene monolauryl ether; n | nonionic |

TABLE 9-continued

| Trade or Common Name of Detergent Studied* | Synonyms; Molecular Formula | Type of Detergent |
|---|---|---|
| aqueous solution of Brij ® 35) Surfact-Amps ™ 58 (a 10% aqueous solution of Brij ® 58) | ca. 23 polyethylene oxide hexadecyl ether | nonionic |

*The full collection of detergents studied was purchased from Pierce Biotechnology, Inc., Rockford, IL; catalog #28340.

Each of the "Surfact-Amps" detergents was further diluted with 5 mM phosphate buffer (pH 5.5) to a final concentration of 0.05%. The 100 mg quantities of CHAPS, octyl-β-D-glucoside, and octyl-β-D-thioglucoside were respectively dissolved in 5 mM phosphate buffer (pH 5.5) to a final concentration of 0.05 mg/mL (w/v). Also included with the phosphate/detergent solution was the dye dipropylthiacarbocyanine iodide ($DiSC_3(3)$), which was included at a final concentration of 18 µM. A comparison was made between those phosphate/detergent solutions with 100 nM (final concentration) of a pre-annealed PNA:DNA hybrid to those same phosphate/detergent solutions without the PNA:DNA hybrid. The PNA:DNA hybrid used was formed by the combination of PNA sequence biotin-(O)-GATAGTGGGATTGTGCGT [SEQ ID NO: 1] and its complementary DNA oligonucleotide sequence 5' ACGCACAATCCCACTATC 3' [SEQ ID NO:20]. Also included in the study were phosphate solutions with no detergent, which were with or without the PNA:DNA hybrid. The Aurora 50/50 light was used for photoactivation, with fluorescence readings (excitation 540 nm, emission 585 nm) taken at $T_0$ and 2 minute intervals out to 20 minutes using a dual-monochromator, multi-detection microplate reader known as Spectramax M5 (sold by Molecular Devices Corporation, Sunnyvale, Calif.). The Spectramax M5 microplate reader generated data points in relative fluorescence units (RFUs), which were recorded and presented in the tables below.

Table 10 presents the fluorescence data from light-exposed reaction mixtures that included 18 µM $DiSC_3(3)$ with 0.1 µM PNA:DNA in 5 mM phosphate buffer with different detergents at 0.05% concentration.

Each detergent gave a different initial $T_0$ emission reading, but all behaved similarly in the rates of change in fluorescence upon photoactivation when the PNA:DNA hybrid was present. Based on the data set forth above, from $T_0$ $T_8$, i.e., the first eight minutes of light exposure, the rates of change in fluorescence in the reaction mixture were each between nearly 800 and about 1000 RFU per minute. In contrast, without a detergent included in the reaction mixture, the rate of change over the same eight minutes was about 285 RFU per minute, i.e., about one-third the rate of the detergent-containing reaction mixtures. Because of the approximately three-fold increased rate of change exhibited by the detergent-containing protocol, one can perceive a difference in optical property with the naked eye in a 50 µl to 100 µl reaction mixture within a minute or two, and certainly within five minutes, of the start of photoactivation at ambient temperature.

Table 11 illustrates the percent change between the "ncPNA:DNA" reaction (data in Table 10) and the "dye only" reaction (data in Table 12), relative to the "dye only" reaction at each time point. Comparative analysis between the results of reaction mixtures after a given time of light exposure and having the identified detergents or water in the presence of the P/TP or not. The percentage difference is shown in accordance with the following formula:

$$[[(RFU_{Table\ C})-(RFU_{Table\ A})]\div RFU_{Table\ C}]\times 100.$$

A remarkable similarity of effect is seen for all tested detergents. The presence of and type of detergent in the reaction affects the time at which maximal percent change between reactions containing dye only and reactions containing dye with ncPNA:DNA occurs. All reactions with detergent (at 0.05%) gave a greater percent change than reactions without detergent relative to dye only reactions.

TABLE 10

| Time | Relative Fluorescence Units (RFUs) at Stated Minutes of Light Exposure | | | | | | | | | | |
|---|---|---|---|---|---|---|---|---|---|---|---|
| exposed to light (min) | CHAPS | octyl-B-glucoside | 1-s-B-thioglucopyranoside | Tween20 | Tween80 | NP40 | TritonX100 | TritonX114 | Brij 35 | Brij 58 | $H_2O$ |
| 0 | 3171 | 2949 | 3106 | 8623 | 9147 | 12095 | 10841 | 7876 | 8564 | 9364 | 3036 |
| 2 | 2153 | 2106 | 2237 | 7283 | 7737 | 10242 | 9407 | 6706 | 7394 | 8154 | 2112 |
| 4 | 1275 | 1384 | 1593 | 5583 | 5923 | 8324 | 7785 | 5147 | 6023 | 6621 | 1585 |
| 6 | 396 | 746 | 829 | 3438 | 3846 | 6221 | 6065 | 3323 | 4382 | 4879 | 1109 |
| 8 | 116 | 246 | 337 | 1376 | 1643 | 4178 | 4357 | 1548 | 2300 | 3077 | 732 |
| 10 | 102 | 106 | 124 | 544 | 690 | 2190 | 2830 | 1097 | 1206 | 1368 | 452 |
| 12 | 93 | 87 | 103 | 385 | 460 | 1447 | 1487 | 928 | 649 | 751 | 308 |
| 14 | 85 | 77 | 91 | 328 | 389 | 1120 | 1011 | 852 | 483 | 548 | 197 |
| 16 | 82 | 66 | 82 | 301 | 352 | 972 | 818 | 789 | 418 | 477 | 135 |
| 18 | 78 | 62 | 76 | 279 | 322 | 885 | 731 | 731 | 381 | 427 | 94 |
| 20 | 75 | 59 | 73 | 263 | 306 | 832 | 670 | 699 | 357 | 403 | 79 |

TABLE 11

Percent Change Relative to "Dye Only"

| Time exposed to light (min) | CHAPS | octyl-B-glucoside | 1-s-B-thioglucopyranoside | Tween20 | Tween80 | NP40 | TritonX100 | TritonX114 | Brij 35 | Brij 58 | H₂O |
|---|---|---|---|---|---|---|---|---|---|---|---|
| 0 | 3.8 | 5.2 | 1.9 | 0.6 | 1.0 | 0.7 | 0.4 | 1.8 | 0.7 | 2.5 | 5.8 |
| 2 | 27.3 | 23.3 | 22.4 | 9.7 | 9.0 | 7.4 | 6.3 | 5.6 | 8.6 | 8.7 | 4.8 |
| 4 | 52.1 | 29.8 | 24.1 | 26.6 | 26.1 | 20.4 | 18.0 | 19.6 | 20.9 | 20.9 | 10.3 |
| 6 | 81.0 | 53.9 | 52.0 | 50.8 | 49.5 | 37.6 | 33.1 | 43.7 | 39.2 | 38.1 | 18.7 |
| 8 | 93.9 | 81.6 | 77.7 | 79.5 | 77.7 | 56.6 | 50.3 | 71.8 | 66.4 | 59.2 | 27.1 |
| 10 | 93.8 | 89.5 | 89.6 | 91.6 | 90.4 | 76.7 | 66.6 | 78.5 | 82.1 | 81.6 | 36.1 |
| 12 | 93.9 | 89.7 | 89.8 | 93.9 | 93.4 | 84.3 | 82.1 | 80.6 | 90.1 | 89.7 | 37.6 |
| 14 | 93.7 | 88.7 | 88.9 | 94.7 | 94.3 | 87.6 | 87.5 | 80.8 | 92.4 | 92.2 | 42.8 |
| 16 | 93.2 | 87.1 | 87.2 | 94.9 | 94.7 | 89.1 | 89.7 | 80.8 | 93.2 | 93.1 | 39.5 |
| 18 | 92.8 | 84.7 | 85.5 | 95.2 | 95.0 | 89.8 | 90.4 | 80.7 | 93.7 | 93.7 | 35.6 |
| 20 | 92.1 | 81.4 | 83.0 | 95.3 | 95.2 | 90.3 | 91.2 | 80.7 | 93.9 | 93.9 | 19.9 |

Identical experiments containing the same detergents but excluding the PNA:DNA hybrid demonstrated the stabilizing effect that certain detergents have on the dye, and thus on the optical property of the reaction mixture. The data was generated using 540 nm exposure of the reaction mixture for excitation of the dye and reading of emitted fluorescence at 585 nm. The data generated from reaction mixtures containing the identified detergents or water without inclusion of a P/TP are set forth in Table 12 below.

TABLE 12

| Time exposed to light (min) | CHAPS | octyl-B-glucoside | 1-s-B-thioglucopyranoside | Tween20 | Tween80 | NP40 | TritonX100 | TritonX114 | Brij 35 | Brij 58 | H₂O |
|---|---|---|---|---|---|---|---|---|---|---|---|
| 0 | 3297 | 3110 | 3164 | 8674 | 9244 | 12010 | 10880 | 7737 | 8622 | 9600 | 3222 |
| 2 | 2959 | 2744 | 2883 | 8061 | 8500 | 11056 | 10041 | 7102 | 8086 | 8931 | 2219 |
| 4 | 2662 | 1971 | 2098 | 7606 | 8012 | 10462 | 9495 | 6404 | 7617 | 8372 | 1767 |
| 6 | 2086 | 1618 | 1727 | 6995 | 7617 | 9966 | 9067 | 5904 | 7203 | 7878 | 1365 |
| 8 | 1895 | 1333 | 1515 | 6714 | 7371 | 9627 | 8774 | 5493 | 6851 | 7535 | 1004 |
| 10 | 1650 | 1008 | 1185 | 6488 | 7163 | 9385 | 8483 | 5096 | 6731 | 7430 | 708 |
| 12 | 1518 | 846 | 1002 | 6285 | 6992 | 9200 | 8322 | 4789 | 6531 | 7283 | 493 |
| 14 | 1350 | 678 | 817 | 6133 | 6853 | 9065 | 8090 | 4432 | 6311 | 7058 | 344 |
| 16 | 1203 | 513 | 646 | 5950 | 6592 | 8890 | 7918 | 4120 | 6190 | 6921 | 223 |
| 18 | 1071 | 409 | 523 | 5776 | 6483 | 8687 | 7650 | 3796 | 6021 | 6750 | 146 |
| 20 | 960 | 317 | 431 | 5641 | 6386 | 8546 | 7582 | 3616 | 5853 | 6626 | 98 |

While a decrease in fluorescence was seen in all of the reactions using the various detergents, or no detergent, the fastest rate of change of the fluorescence was no greater than about a third of the rate of change noted above for reactions where the PNA:DNA hybrid was present. Reactions with the two glucoside derivatized detergents, the only zwitterionic detergent (i.e., CHAPS), or water behaved similarly: These reaction mixtures had $T_0$ readings that were substantially less than those of the other reactions that included Triton® X, Tween®, and NP-40 non-ionictype detergents. Furthermore, the low level of fluorescence that was present in the glucosides or CHAPS degraded further to near zero over the 20 minute exposure to light. Other dyes were tested, including $DiSC_4(3)$ and $DiSC_5(3)$, and exhibited similar results Example 16

This example illustrates an embodiment of the present invention where an increasing fluorescent signal correlates to a decreasing absorbance of the reaction mixture, thereby providing a simple method for assessing a given reaction.

The top of a 96-well microtiter plate (Nunc #265302) was sealed and the optical bottom was coated with fluorescent yellow paint (Rust-Oleum®, catalog #1942). It is believed that any other optically-identified coating or, in the alternative, an optically-identified inclusion in the material of the reaction vessel or in the reaction mixture itself would work equally well. One simple alternative approach to painting of the reaction vessel, for example, includes, for example, affixing tape or plastic to a surface of the reaction vessel.

ncPNA probe and oligonucleotide complement ("oiDNA") solutions were prepared by diluting 100 μM stock solutions 1:50 in ddH₂O (Nanopure), resulting in a 2 μM solution of biotinylated ncPNA [SEQ ID NO: 1] and a 2 μM solution of the oiDNA that is complementary to the ncPNA [SEQ ID NO:20].

Two master mixes were then prepared: One negative control reaction mixture without target nucleic acid or ncPNA and one test reaction mixture containing the ncPNA and target nucleic acid. The negative control reaction mixture was prepared by adding 24 μL $DiSC_2(3)$ (at 0.75 mM in 10% methanol) and 84 μL of 10% methanol to 492 μL reaction buffer (10 mM $PO_4$+0.05% Tween® 80). The test reaction mixture was prepared by adding 24 μL $DiSC_2(3)$, 60 μL ncPNA, 60 μL oiDNA and 84 μL 10% methanol to 372 μL of buffer. Each mixture was then dispensed to 12 wells of the painted plate, 50 μL per well.

The fluorescence (excitation at 485 nm, emission at 535 nm, corresponding to the fluorescence of the yellow paint on the plate) of each well at zero time ($T_0$; no light exposure prior thereto) was then read using a Tecan GENios microplate reader. Average fluorescent signal was determined for each control or experimental reaction, standard deviations were calculated, and the data were recorded.

Reactions were then activated with the Aurora 50/50 illuminator for 1 minute. Fluorescence was measured with the same parameters as the $T_0$ measurement. This cycle of photoactivation followed by an immediate fluorescence measurement was continued out to 10 minutes of exposure to light. The data are provided in the following Table 13, where fluorescence data is presented from test reaction mixtures and negative control reaction mixtures. The fluorescence measured relates to fluorescent material painted on the outside of the reaction vessels.

TABLE 13

|  | DNA | PNA | DYE | \multicolumn{11}{c|}{RFU* after stated time of light exposure (min)} |
|---|---|---|---|---|---|---|---|---|---|---|---|---|---|---|
|  | DNA | PNA | DYE | 0 | 1 | 2 | 3 | 4 | 5 | 6 | 7 | 8 | 9 | 10 |
| Test Reaction | + | + | + | 7821 | 11526 | 14876 | 19213 | 25229 | 33175 | 35938 | 36793 | 37252 | 37617 | 37545 |
| Negative Control | − | − | + | 7748 | 8397 | 8928 | 9513 | 10070 | 10615 | 11220 | 11743 | 12271 | 12844 | 13306 |

*The acronym RFU refers to units of relative fluorescence.

The increasing fluorescence seen in the experimental reaction correlates to a decreasing opacity of the reaction mixture itself, which is perceivable with the naked eye. The decreasing opacity of the test reaction mixture was evident in the reaction vessels as a progressive clearing of color from the reaction mixture, which was noticed as of about one minute of light exposure. In contrast, in the negative control, the substantially constant relative fluorescence units seen in the experiment correlate to the substantially constant opacity of the reaction mixture. Indeed, the negative control reaction mixture appeared to substantially maintain the same intensity of color through the entire time course of the experiment.

The fluorescence noted in the experimental reaction emanates from the painted bottom of the microtiter wells, which wells were identical to those in which the negative controls were run. Accordingly, the characteristic that is actively changing in the reaction is the absorbance, which, as it decreases in the test reaction mixture over time, reveals more of the fluorescent paint coated onto the well. A further conclusion arising from this example is that one does not have to measure an optical property that derives from the chemical state of a dye; instead, one can more simply measure, or, truly, merely notice an uncovering of a second optical property of the reaction mixture and/or reaction vessel that contains the reaction mixture. The optical property of the dye included in the reaction mixture obscures a well-chosen second optical property of the reaction mixture and/or reaction vessel. To the extent that the chemical state of the dye alters in the reaction mixture such that a decreasing concentration of the original dye remains over time of the assay, the optical property contributed by the dye to the reaction mixture diminishes, thereby revealing the presence of the second optical property, which can be used to trigger realization of the presence or quantity of a target polynucleotide.

Example 17

This example sets forth an investigation of molecular weight changes in a dye over the course of a diagnostic reaction according to the present invention.

A mass spectroscopic analysis of a dye exposed to light in the presence or absence of a ncPNA:DNA hybrid was accomplished, as follows:

Using a 96-well clear, streptavidin-coated microtiter plate (Nalge Nunc International, Rochester, N.Y.; NUNC Immobilizer™ Streptavidin plates), a biotinylated ncPNA (i.e., biotin-(oo)-TGCCTCCCGTAG [SEQ ID NO:9]) was used to capture isolated E. coli DNA. The PNA used in this experiment is specific for a ubiquitous bacterial 16S sequence. To prepare the microplate used in the experiment, the following steps were undertaken: (1) each well was washed three times with 300 μL phosphate-buffered saline solution with 0.05% Tween® 20 ("PBST"); (2) 50 μL aliquots of a solution containing 2.5 μL of 2 μM biotinylated ncPNA (5 pmoles), 5 μL of 10 ng/μL E. coli genomic DNA (50 ng), and 42.5 μL of 5 mM phosphate buffer (pH 5.5) were introduced into wells of the microplate; (3) the microplate was sealed and placed on a rotamixer for 60 minutes (at room temperature) to allow biotin-streptavidin interactions to occur; and (4) the wells were aspirated and washed five times with 200 μL PBST to remove unbound DNA and ncPNA.

A $DiSC_2(3)$ solution was made by diluting an 8 mM (in DMSO) stock solution to 2 mM with 5 mM phosphate buffer (pH 5.5). The dye solution was further diluted to 80 μM with a 5 mM phosphate/0.05% Tween® 20 solution; aliquots of the diluted dye solution were introduced into each well. The plate was then placed on top of an Aurora 50/50 light for 30 minutes before the solutions were pooled into a 15 mL conical container with an aluminum foil shroud, thereby keeping ambient light from the contained solution. In order to have enough reaction product for liquid chromatography-mass spectrometry ("LC/MS") experiments, 12 identical wells were prepared for each reaction and pooled. Also included were control wells with ncPNA only and with DNA only. Only those wells that were exposed to light and a ncPNA:DNA hybrid displayed the expected reduction in fluorescence associated with the diagnostic method of the present invention.

The pooled products were then further analyzed by LC/MS using standard methods and instrumentation via the services of a commercial analytical chemistry laboratory. No ncPNA:DNA-specific dye product could be found, which was determined by comparison to LC analysis of products of the "Dye Only" control wells. However, an LC sample fraction collected at 9.8 minutes included a new product of apparent molecular weight 427.1 mass units ("mu"). The original parent dye compound, $DiSC_2(3)$, can be represented by $C_{21}H_{21}N_2S_2$, which is 365.5 mass units not including the iodide counterion. One new product of 427.1 mu corresponds to an oxygen molecule (+15.56 mu) added to the parent dye compound, which subsequently forms an adduct with formic acid (+46.01 mu) during the liquid chromatography run. The new product has the empirical formula of $C_{21}H_{21}N_2OS_2$.

Addition of the oxygen apparently disrupted conjugation within the dye molecule rendering it colorless. The exact mechanism(s) of this reaction remains to be elucidated.

Example 18

This example is illustrative of a smartDNA reaction in a gel matrix, bound to a protein (or large macromolecule). Agarose super-shift assays were performed. A biotinylated ncPNA (biotin-OO-TGCCTCCCGTAG [SEQ ID NO:9]) was hybridized to a complementary DNA oligonucleotide (5'-CTACGGGAGGCA-3' [SEQ ID NO:57]) at a final concentration of 25 μM. Goat anti-biotin antibody (Immunology Consultants Laboratory, ICL) at 1 mg/mL was used undiluted. In a microfuge tube, 1 μL of ncPNA:DNA duplex was mixed with 1 μL antibody and allowed to sit at room temperature for thirty minutes to permit biotin-streptavidin interactions. For comparison, a second and third tube contained 1 μL ncPNA:DNA duplex only or antibody only, respectively. Each of these solutions was mixed with 5 μL of a 50% glycerol solution and loaded into the wells of a 1% agarose (1×TBE) gel containing 2.5 μM $DiSC_2(3)$ (added while the agarose was molten). Electrophoresis proceeded at 50V for 60 minutes in 1×TBE running buffer. An initial time zero photograph was taken of the gel illuminated with a UV transilluminator. The gel was then exposed to a light stimulus Aurora 50/50 for 5 minutes before a second photograph was taken.

Lanes 1 and 2 show "holes" (loss of fluorescence) for a fast migrating species corresponding to a ncPNA:DNA duplex (unbound to antibody) breaking down the dye after 5 minutes of exposure to light. Lane 1 shows a (super-shift) slower migrating "hole" suggesting that the ncPNA:DNA duplex is bound to the antibody through a biotin-streptavidin interaction and that this interaction does not interfere with the photobleaching. Lane 3 (antibody only) shows no photobleaching thereby confirming that the super-shift "hole" in Lane 1 is not due to the antibody.

Future experiments include chemically coupling the ncPNA:DNA duplex to an antibody which is specific for a given antigen.

Example 19

This example illustrates an embodiment of the present invention with varying lengths of ncPNA.

Six different 17-mer and 12-mer ncPNA probes targeting similar nucleic acid sequences within isolated *Mycobacteria tuberculosis* (MTB) genomic DNA were tested.

Working solutions of 2 μM '12-mer nccocktail' were generated from equal volumes of 2 μM solutions of each individual 12-mer ncPNA. Working solutions of 2 μM '17-mer nccocktail' were generated from equal volumes of 2 μM solutions of each individual 17-mer ncPNA. The PNAs used are set forth in Table 14 below.

TABLE 14

| Code Name | PNA Sequence | SEQ ID NO: |
|---|---|---|
| TB01 | biotin-(OO)-GTCGTCAGACCCAAAAC | 36 |
| TB02 | biotin-(OO)-CGAGAGGGGACGGAAAC | 37 |
| TB03 | biotin-(OO)-TGAACCGCCCCGGCATG | 38 |
| TB04 | biotin-(OO)-ACCAAGTAGACGGGCGA | 39 |
| TB05 | biotin-(OO)-CATCCAACCGTCGGTCG | 40 |
| TB06 | biotin-(OO)-ACAAGACATGCATCCCG | 41 |
| TB07 | lysine-CAGACCCAAAAC | 42 |
| TB08 | lysine-CGAGAGGGGACG | 43 |
| TB09 | lysine-TGAACCGCCCCG | 44 |
| TB10 | lysine-ACCAAGTAGACG | 45 |
| TB11 | lysine-CATCCAACCGTC | 46 |
| TB12 | lysine-ACAAGACATGCA | 47 |

Introduced into a 384-well white with white bottom microtiter plate (purchased from Costar) were: 2 μL of a 1 ng/μL solution of MTB genomic DNA (obtained from MRL, Department of Microbiology, Ft. Collins, Colo.), 2 μL of the 2 μM 'cocktail' of 12-mer ncPNAs or 2 μL of the 2 μM 'cocktail' of 17-mer PNAs, and 16 μL $H_2O$ (Molecular Biology Grade). This solution was vigorously mixed for 5 seconds and allowed to incubate for 10 minutes at room temperature. Thirty microliters of a solution containing 5 mM phosphate (pH 5.5), 0.083% Tween® 80, and 15 μM diethylthiacarbocyanine iodide ($DiSC_2(3)$) was then added to each well (final concentration of 3 mM phosphate, 0.05% Tween® 80, 9 μM $DiSC_2(3)$) and mixed.

An initial $T_0$ reading (excitation 535 nm, emission 590 nm) was obtained using a Tecan Genios fluorescence microtiter plate reader. Next, the reactive mixtures in the microtiter wells were exposed to light using an Aurora 50/50 light. Fluorescence readings were taken every two minutes out to 30 minutes total light exposure time. To assess non-specific binding of ncPNAs, an identical experiment containing human genomic DNA (isolated from a B cell line (GM 14686; Coriell Cell Repositories, Camden, N.J.)) instead of MTB DNA was run in parallel. Control wells containing ncPNA only (no DNA) and DNA only (no ncPNA) were also included. The average fluorescence of four identical reactions was plotted along with standard error bars as a function of light exposure time.

Figure 17A:
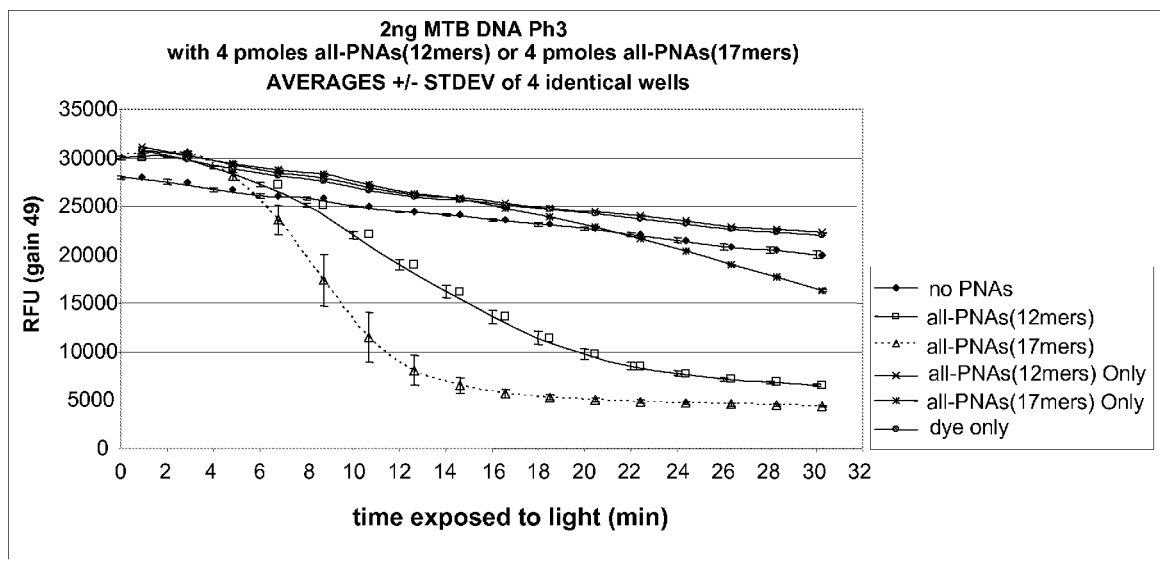
FIG. 17 is a comparison of a "cocktail" of 12mer PNAs and a "cocktail" of 17mer PNAs in reactions with MTB (A) or human (B) genomic DNA in the presence of the dye, exposed to light over time.
Figure 17B:
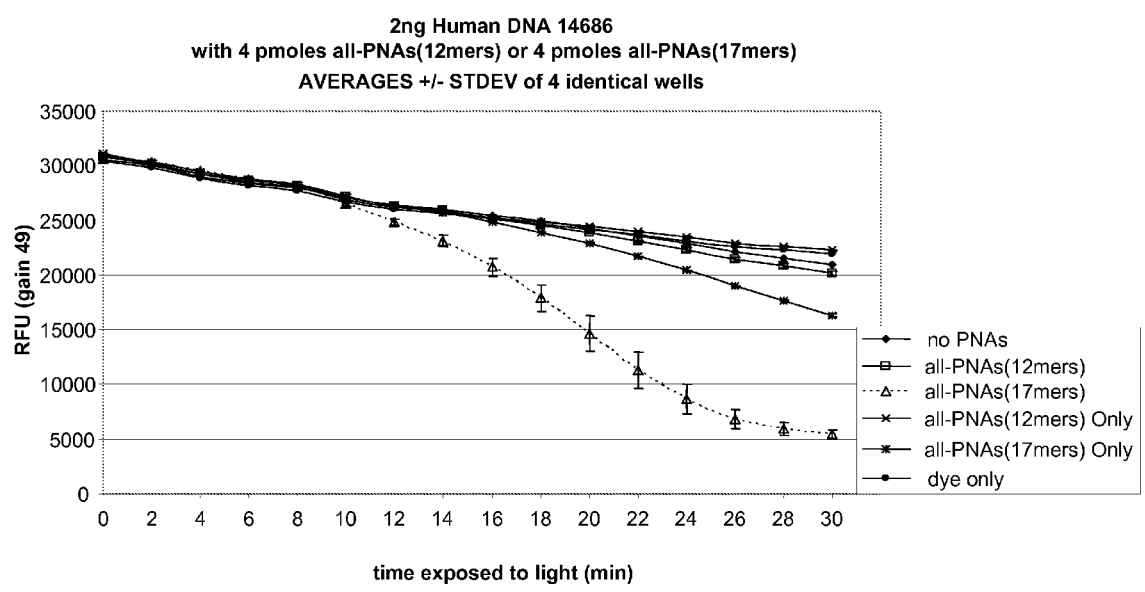

The data indicate that ncPNAs having 12 or 17 nucleotides are usefully employed with the present invention. Whereas the rate of change in fluorescence was indeed faster with the larger ncPNA targeting MTB DNA (see FIG. 17A), a greater level of non-specific activity was shown in data generated using the larger PNA (see FIG. 17B).

The data are consistent with the view that a 'cocktail' of 12-mer ncPNAs can drive a diagnostic reaction after incubation with isolated MTB genomic DNA at room temperature. Although a 'cocktail' of 12-mer ncPNA correlates to a slower rate than a 'cocktail' of 17-mer PNAs, fewer non-specific reactions were detected when the 12-mer PNAs were combined with the unrelated DNA as compared to when the 17-mer PNAs were combined with the unrelated DNA.

Example 20

This example illustrates the use of individual ncPNAs, as opposed to a "cocktail" of multiple different ncPNAs in concert, to detect MTB DNA.

In particular, ncPNA TB11 [SEQ ID NO:45] and ncPNA TB12 [SEQ ID NO:47] were used in the protocol set forth in Example 14 to detect isolated genomic MTB DNA at 2, 1, 0.5, 0.25, 0.0625, and 0 ng/50 µL reactions (with the exception that the "DNA Standards" were diluted in 10 mM Tris-Cl (pH 7.2), 1 mM EDTA, 0.05% Tween-80 buffer).

Briefly, 25 µL of the "DNA Standards" (0.08 ng/µL, 0.04 ng/µL, 0.02 ng/µL, 0.01 ng/µL, 0.005 ng/µL, 0.0025 ng/µL, and 0 ng/µL) were dispensed into a 384-well white with clear bottom microtiter plate (NUNC catalog #242763). From an 8.3 µM stock (prepared in $H_2O$), ncPNA TB10 (or ncPNA TB 12) was diluted to a working concentration of 53.3 nM in Tris-Cl (pH 7.2), 1 mM EDTA, 0.05% Tween® 80 buffer. This solution was mixed with equal volumes of a solution containing 36 µM $DiSC_2(3)$ in Tris-Cl (pH 7.2), 1 mM EDTA, 0.05% Tween® 80 buffer. Twenty-five microliters of this mixture were added to the "DNA standard" in the microtiter, followed by centrifugation of the plate, shaking, and incubation at room temperature as per the protocol in Example 14.

Absorbance measurements at 556 nm were recorded at $T_0$ and every two minutes thereafter, up to 44 minutes of photoactivation. Photoactivation was done using a solid-state activator providing illumination at 470 nm with a power density of 2 $mW/cm^2$. Data was compiled and assessed for the time at which absorbance had reached 50% of initial starting absorbance (defined as the $T_{50}\%$) as depicted in the Table 15 below.

TABLE 15

Time to reach 50% absorbance, ($T_{50\%}$) in minutes

| amount of DNA per well | ncPNA TB10 | ncPNA TB12 |
|---|---|---|
| 2 ng | 11.3 | 10 |
| 1 ng | 14.6 | 12.5 |
| 0.5 ng | 16.7 | 16.5 |
| 0.25 ng | 23.2 | 23.7 |
| 0.125 ng | 28.3 | 21.7 |
| 0.0625 ng | 32.1 | 28.2 |
| ncPNA Only (No DNA) | 34.2 | 33.1 |
| 2 ng DNA Only (No ncPNA) | 38.6 | 33.9 |

The reactions containing ncPNA TB12 had lower $T_{50}\%$ times as compared to ncPNA TB 10, suggesting faster detection of MTB DNA. This difference in performance between the two ncPNAs could be attributed to either sequence-specificity difference (of the particular ncPNA:DNA duplexes formed), or a targeting ability (strand-invasion into a genomic region), or a target copy number difference of each ncPNA. While ncPNA TB 10 has the potential to bind upwards of 20 sequences within the MTB genome (IS6110 transposon sequence of variable copy number), ncPNA TB 12 only has a single genomic target (rDNA), but is also specific for MTB rRNA that may be present (residual) in the genomic DNA preparations.

Example 21

The following example illustrates the present invention in one embodiment where DNA is used as a "detector" for assays involving photoactivation of light-sensitive dyes.

In photoactivation reactions, interaction of the dye with a charged polymer is important for increasing light-sensitivity of the dye. This experiment demonstrates that the amount of DNA present in a reaction (in the absence of a nucleic acid analog) can accelerate photoactivation of the dye. This suggests that photoactivation of the dye can be used to detect quantities of unknown DNA in a solution, if compared to a standard curve of known quantities of DNA. It also suggests that DNA alone (without hybridizing a nucleic acid analog) can be used as a detector if coupled to a ligand that participates in receptor-ligand interactions in solid-support formats.

Lyophilized calf thymus DNA (Sigma Catalog #D4764) was dissolved in 10 mM Tris, 1 mM EDTA (pH 7.5) to concentrations of 19.5 ng/µL. From this solution, a series of two-fold dilutions were created down to a concentration of 0.075 ng/µL.

Into wells of a 384-well white microtiter plate (Greiner) were dispensed 2 µL of each DNA dilution along with 20 µL of molecular grade $H_2O$. An additional 30 µL of a 5 mM phosphate buffer (pH 5.5) with NP-40 (0.05%) with DiSC2 (3) (final 9 µM) was introduced into the well. An initial fluorescence measurement (excitation at 535 nm, emission at 590 nm) was taken with a Tecan Genios microtiter plate reader. The wells were photoactivated with the Aurora 50/50 and fluorescent readings were recorded every two minutes. Table 16 lists the relative fluorescence units for each DNA concentration every two minutes.

TABLE 16

| time exposed to light (min) | RFUs of photoactivation assays of increasing amounts of DNA | | | | | | | | |
|---|---|---|---|---|---|---|---|---|---|
| | 39 ng | 19.5 ng | 9.8 ng | 4.9 ng | 2.4 ng | 1.2 ng | 0.6 ng | 0.3 ng | 0.15 ng |
| 0 | 9236 | 10912 | 11763 | 12066 | 12331 | 12441 | 12580 | 12506 | 12681 |
| 2 | 4076 | 9424 | 11391 | 11786 | 12005 | 12138 | 12294 | 12252 | 12325 |
| 4 | 3538 | 6119 | 10141 | 11152 | 11419 | 11669 | 11803 | 11795 | 11817 |
| 6 | 3792 | 4344 | 8541 | 10633 | 11093 | 11431 | 11602 | 11602 | 11649 |

As can be seen from the data in Table 15, the higher DNA concentrations (39 ng/well and 19.5 ng/well) gave an initial ($T_0$) of lower RFUs relative to the lower DNA concentrations. In addition, the higher DNA concentrations also caused a greater rate of decrease in RFUs during the first 6 minutes of photoactivation. This "DNA standard curve" provides a comparison against solutions containing unknown amounts of DNA.

Alternatively, when the DNA is linked to a protein or ligand, the DNA acts as a "detector" for protein-receptor or ligand-receptor interactions on solid support formats where no extraneous DNA is expected to be present. DNA remaining on the solid support (following washes) (through indirect binding) cause photobleaching of the dye upon exposure to a photoactivator.

Example 22

This example illustrates one embodiment of the present invention for comparison of different cyanine dyes and using LED at different wavelengths in smartDNA reaction.

2 types of probe-nucleic acid (NA) target systems were used in the study. The first one was referred as oligo system, which includes a 18mer DNA and its complementary PNA probe. The 18mer DNA has the sequence: 5'-ACGCA-CAATCCCACTATC-3' (SEQ ID NO: 20), and was ordered from IDTDNA. The DNA was resuspended in molecular biology grade water (Hyclone, catalog #SH30538.03) for freezer storage, and initially quantified by converting the absorbance of the NA solution at 260 nm (measured with a Hewlett-Packard Model NO: HP8452A diode-array spectrophotometer) using standard methods. Stock solution of the 18mer in $H_2O$ at 250 nM was prepared and stored in 4° C. and ready to use.

PNA bio18, with the sequence of: GATAGTGGGATTGT-GCGT from N to C termini and with biotin tag at the N-terminus (SEQ ID NO: 1) was used as the probe for the oligo system. A 50 μM PNA probe mix was prepared from freezer stocks, and from this stock a 250 nM PNA stock in $H_2O$ was further prepared and stored at 4° C. and ready for use.

Another screening system was referred as the genomic system in the present example. Samples containing or not containing genomic nucleic acid (NA) isolated from *Mycobacterium tuberculosis* (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.08 ng/μL in TE buffer (Tris-C1 10 mM, pH 7.2, 1 mM EDTA, with 0.05% Tween-80).

For the genomic system, a PNA mixture of 12mer PNAs were used as the probe. A 50 μM PNA probe mix was prepared from freezer stocks. Sequences used were SEQ ID NOS: 42, 43, 44, 45, 46 and 47. Freezer stocks (at 200 μM in $H_2O$) were put in a hotblock at 65° C. for five minutes, and a 50 μM solution of each ncPNA was prepared by diluting the freezer stock ncPNA in molecular biology grade $H_2O$ (Hyclone, catalog #SH30538.03). Equal volumes of each 50 μM ncPNA solution were added to create a 50 μM total PNA concentration, i.e., 8.33 μM per ncPNA. This 50 μM PNA probe mix was put in the hotblock at 65° C. for five minutes, and was then further diluted in TE buffer (Tris-C1 10 mM, pH 7.2, 1 mM EDTA) with surfactant (0.05% Tween-80) to a final concentration of 320 nM. The 320 nM PNA probe mix was placed in a water bath at 65° C. for five minutes, removed, and given 30 minutes to cool to room temperature.

Various dye stock solutions were prepared, including the standard dye in smartDNA assay, 3,3'-diethylthiacarbocyanine("DiSC$_2$(3)"). For the standard dye, the stock was prepared by diluting 7.5 mM DiSC$_2$(3) (solubilized in DMSO) into phosphate buffer with surfactant (0.05% Tween-80) to a working concentration of 36 μM. Other dyes tested include derivatives of the standard dye. Among them a few examples were 3,3'-di(propyl, allyl, butyl or pentyl) thiacarbocyanine (the substituents variations), 3,3'-diethyloxycarbocyanine, and 3,3'-diethylthia(di, tri)carbocyanine.

For the oligo system, 4 reaction mixtures in triplicate were set up for each dye, for each wavelength of LED exposure. The first well contains only the dye in buffer, and was referred as "dye only." The second well contains dye and the PNA probe (bio18) and was referred as "PNA only." The third well contains dye and the NA target (either the oligo or the genome), and was referred as "DNA only." The forth well contains dye, the NA target and the corresponding PNA probe and was referred as "PNA/DNA." The final concentration in the reaction mixture for dye was 9 μM, PNA 100 nM, DNA 100 nM, or PNA/DNA 50 nM, if applicable.

For genomic system, Serial 1:2 dilutions of the 0.08 ng/μL MTB NA (in 10 mM TE buffer, with 0.05% Tween-80) were prepared down to a low concentration of 0.0025 ng/μL; referred to herein as "DNA standards." Aliquots of 25 μL of each of the DNA standards were dispensed into a 384 well white/clear plate (NUNC, catalog #242763) to set up a concentration curve with triplicate in individual columns on the plate. The columns were set up as follows: columns 1-6, 9-14 and 17-22 were assay wells with 2 ng, 1 ng, 0.5 ng, 0.25 ng, 0.125 ng, and 0.0625 ng MTB DNA per well, column 7, 15 and 23 was a control well with 0 ng DNA and column 8, 16 and 24 was a control well with 2 ng MTB DNA.

After the buffer or the DNA standards were dispensed into the microplate, and the microplate was centrifuged, two dye mixtures were then prepared. The reaction set-up steps were performed in a dimly lit room. The first control dye solution was prepared by mixing equal volumes of 36 μM DiSC$_2$(3) with TE buffer (with 0.05% Tween-80.) This 18 μM DiSC$_2$(3) control solution was mixed directly in a reagent reservoir. A 25 μL aliquot of the control dye solution was then dispensed to "dye only" and "DNA only" wells on the microplate. The second, dye+PNA probe mix was prepared by mixing equal volumes of 36 μM DiSC$_2$(3) with the 320 nM 12mer PNA probe mix (for the genomic system). This 18 μM DiSC$_2$(3)+ 160 nM PNA probe was mixed directly in a reagent reservoir. A 25 μL aliquot of the dye+PNA probe mix was then dispensed to "PNA only" and "PNA/DNA" wells on the microplate giving final concentrations of 9 μM and 80 nM for the dye and PNA, respectively. The microplate was then briefly centrifuged at 500 RPM.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. For the oligo system, after the initial optical measurement, the plate was removed from the microplate reader, and subjected to photoactivation for 10 minutes. The light for photoactivation was provided by a solid-state activator providing illumination with different peak wavelength of: 390 nm (425 µW/cm$^2$) (Lumex SSL-LX5093SUVC), 410 nm (446 µW/cm$^2$) (Lumex SSL-LX5093UVC), 470 nm (1400 µW/cm$^2$) (Jameco #183222), 490 nm (1340 µW/cm$^2$) (Marubeni America Corporation, L490-33U), 505 nm (1300 µW/cm$^2$) (Jameco #334473), 515 nm (1000 µW/cm$^2$) (Jameco #183214), 574 nm (124 µW/cm$^2$) (Toshiba TLGE158P), 620 nm (423 µW/cm$^2$) (Liteon Electronics Inc, 2F3VAKTN), 640 nm (2060 µW/cm$^2$) (Liteon Electronics Inc, 2F3VRKTN), and 660 nm (948 µW/cm$^2$) (QT Optoelectronics MV8114), as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second. Then the plate was removed from the microplate reader and subjected to photoactivation for additional 50 minutes. The microplate was reinserted into the reader and each well was measured as indicated above.

For the genomic system, after the initial optical measurement the plate was removed from the microplate reader and subjected to photoactivation for a two minute interval. The microplate was reinserted into the reader and each well was measured as indicated above, however with a shortened orbital shake and settle time of one second each. This two minute photoactivation followed by absorbance detection cycle was performed over a period of 60 minutes total exposure to light.

Dyes that were photobleached after 60 minutes preferentially in PNA/DNA samples were selected as potential candidates for smartDNA reaction. Table 17 summarizes the optical properties of the dyes when exposed to different wavelength of LEDs (at different intensities) in the 4 reaction mixtures. For those dyes that were photobleached after 60 minutes preferentially in PNA/DNA samples, the wavelength of the specific working LED is given.

TABLE 17

Dye number, chemical name, $\lambda_{max}$ for absorbance and observed optical properties when exposed to LED in the 4 reaction mixture using oligo system.. In the description of response to LED exposure, "no difference" means there was no difference in absorbance change of at least one controls, "dye only", "PNA only", or "DNA only" comparing with "PNA/DNA" samples.

| Dye Number | Chemical Name | Maximum Absorbance(nm) | Response to LED Exposure |
|---|---|---|---|
| 1 | 3,3'-Diethylthiacarbocyanine iodide | 554 | 470, 490, 505, and 515 nm, works fast, 5-10 min. |
| 2 | 3,3'-Diethyl-9-methylthiacarbocyanine iodide | 540 | non-specific decrease, 390-515 nm all photobleaching. |
| 3 | 3,3'-Diethylthiacyanine iodide | 422 | no difference, robust to various LEDs. |
| 4 | 3,3'-Diethylthiadicarbocyanine iodide | 648 | no difference, but photobleached by 505-660 |
| 5 | 3,3'-Diethylthiatricarbocyanine iodide | 754 | no difference, but photobleached by 505-660 |
| 6 | 3,3'-Diethylthiatricarbocyanine perchlorate | 752 | no difference, but photobleached by 505-660 |
| 7 | 3,3'-Diallylthiacarbocyanine Bromide | 556 | 470, 505, and 515 nm |
| 8 | 3,3'-Diethyloxacarbocyanine iodide | 480 | no difference, robust to various LEDs. |
| 9 | 3,3'-Diethyl-2,2'-Oxathiacarbocyanine Iodide | 386 | no difference, robust to various LEDs. |
| 10 | 3,3'-Dimethyloxacarbocyanine iodide | 480 | no difference, robust to various LEDs. |
| 11 | 3,3'-Diethyloxadicarbocyanine iodide | 578 | no difference, photobleached by 505, 515. |
| 12 | 3,3'-Dipropylthiacarbocyanine iodide | 556 | 470, 505, and 515 nm |
| 13 | 3,3'-Dipropylthiadicarbocyanine iodide | 650 | no difference, but photobleached by 620, 640 and 660 nm |
| 14 | 3,3'-Dipropyloxacarbocyanine iodide | 482 | no difference, robust to various LEDs. |
| 15 | 3,3'-Dibutylthiacarbocyanine iodide | 556 | 470 and 490 nm. |
| 16 | 3,3'-Dipentylthiacarbocyanine iodide | 556 | 470 and 490 nm. |
| 17 | 3,3'-Dihexyloxacarbocyanine iodide | 554 | no difference, robust to various LEDs. |
| 18 | 1,1'-Diethyl-2,2'-cyanine iodide | 522 | no difference, robust to various LEDs. |
| 19 | 1-1'-Diethyl-2,2'-carbocyanine iodide | 600 | 505 and 515 nm |
| 20 | 1,1'-Diethyl-2,2'-carbocyanine bromide | 600 | 505 and 515 nm |

TABLE 17-continued

Dye number, chemical name, $\lambda_{max}$ for absorbance and observed optical properties when exposed to LED in the 4 reaction mixture using oligo system.. In the description of response to LED exposure, "no difference" means there was no difference in absorbance change of at least one controls, "dye only", "PNA only", or "DNA only" comparing with "PNA/DNA" samples.

| Dye Number | Chemical Name | Maximum Absorbance(nm) | Response to LED Exposure |
|---|---|---|---|
| 21 | 1,1'-Diethyl-4,4'-carbocyanine iodide | 698 | no difference, but photobleached by 640 and 660 nm |
| 22 | 1,1'-Diethyl-3,3,3',3'-tetramethylindocarbocyanine iodide | 544 | no difference, robust to various LEDs. |
| 23 | 1,1'-Dipropyl-3,3,3',3'-tetramethylindocarbocyanine iodide | 544 | no difference, robust to various LEDs. |
| 24 | 1-[[3-Ethyl-2(3H)-benzothiazolylidene]ethylidene]-2(1H)-naphthalenone | 548 | no difference, robust to various LEDs. |
| 25 | 3,3'-Diethylthiacyanine ethylsulfate | 422 | no difference |
| 26 | 3-Ethyl-9-methyl-3'-(3-sulfatobutyl) thiacarbocyanine betaine | 540 | no difference, but photobleached by 470 nmLED. |
| 27 | 3-Carboxymethyl-3',9-diethyl-5,5'-dimethylthiacarbocyanine betaine | 548 | no difference, but photobleached by 470 nmLED. |
| 28 | 3,3'-Diethyloxatricarbocyanine iodide | 680 | no difference, decay |
| 29 | thiazole orange | 502 | no difference, but photobleached by 470 nmLED. |
| 30 | 1,1'-Diethyl-2,4'-cyanine iodide | 556 | no difference |
| 31 | [5-[2-(3-Ethyl-3H-benzothiazol-2-ylidene)-ethylidene]-4-oxo-2-thioxo-thiazolidin-3-yl]-acetic acid | 540 | no difference |
| 32 | 1-Butyl-2-[3-(1-butyl-1H-benzo[cd]indol-2-ylidene)-propenyl]-benzo[cd]indolium tetrafluoroborate | 680-750 | no difference |
| 33 | 1,3,3-Trimethyl-2-(2-[2-phenylsulfanyl-3-[2-(1,3,3-trimethyl-1,3-dihydro-indol-2-ylidene)-ethylidene]-cyclohex-1-enyl]-vinyl)-3H-indolium chloride | 782 | no difference, decay |
| 34 | 4,5,4',5'-Dibenzo-3,3'-diethyl-9-methyl-thiacarbocyanine bromide | 644 | no difference, decay |

For the standard dye $DiSC_2(3)$, the absorbance change in the reaction mixtures when exposed to the different LEDs, and in oligo system for "DNA only" and "PNA/DNA" reaction mixtures were measured and summarized in Tables 18, 19, and 20. "PNA only" and "dye only" mixtures always had a similar or lower changes in absorbance compared with "DNA only" controls and thus were not listed here.

TABLE 18

Absorbance change of reaction mixture for "DNA only" (DNA + wavelength) and "PNA/DNA" (PD + wavelength) after exposure of LED wavelengths: 390 nm, 410 nm or 490 nm.

|    | DNA390 | PD390 | DNA410 | PD410 | DNA490 | PD490 |
|---|---|---|---|---|---|---|
| 0 | 0.51 | 0.51 | 0.51 | 0.51 | 0.52 | 0.52 |
| 10 | 0.48 | 0.43 | 0.49 | 0.48 | 0.31 | 0.10 |
| 60 | 0.39 | 0.21 | 0.38 | 0.28 | 0.17 | 0.05 |

TABLE 19

Absorbance change of reaction mixture for "DNA only" (DNA + wavelength) and "PNA/DNA" (PD + wavelength) after exposure of LED wavelengths: 470 nm, 505 nm or 515 nm.

|    | DNA470 | PD470 | DNA505 | PD505 | DNA515 | PD515 |
|---|---|---|---|---|---|---|
| 0 | 0.52 | 0.52 | 0.52 | 0.52 | 0.52 | 0.52 |
| 10 | 0.32 | 0.13 | 0.31 | 0.12 | 0.33 | 0.19 |
| 60 | 0.15 | 0.04 | 0.11 | 0.04 | 0.13 | 0.04 |

TABLE 20

Absorbance change reaction mixture for "DNA only" (DNA + wavelength) and "PNA/DNA" (PD + wavelength) after exposure of LED wavelength: 620 nm, 640 nm or 660 nm.

|    | DNA620 | PD620 | DNA640 | PD640 | DNA660 | PD660 |
|---|---|---|---|---|---|---|
| 0 | 0.43 | 0.43 | 0.43 | 0.43 | 0.52 | 0.44 |
| 10 | 0.40 | 0.38 | 0.39 | 0.34 | 0.50 | 0.42 |
| 60 | 0.32 | 0.24 | 0.27 | 0.07 | 0.44 | 0.33 |

From the above data, it was demonstrated that 470 nm and 505 nm LED were the 2 wavelengths that resulted the higher rate in photobleaching for "PNA/DNA" samples. Another wavelength worth notice was the 640 nm LED, which also resulted selectively photobleaching of "PNA/DNA" samples.

Standard curve experiments were performed on $DiSC_2(3)$ with 470 nm or 640 nm LEDs as the light source. The results of the slope of dye color change at different NA amount per 50 µl reaction mixture for 470 nm and 640 nm LED were summarized in Table 21.

TABLE 21

Slope of dye color change (mAbsorbance/min for the first 4 min.) with 0, 0.0625 ng, 0.125 ng, 0.25 ng, 0.5 ng, 1 ng and 2 ng MTB genomic NA in homogeneous smartDNA reactions, exposed to 470 nm or 640 nm LED.

|  | 470 nm | 640 nm |
| --- | --- | --- |
| 0 | 11.8 | 1.6 |
| 0.0625 ng | 13.9 | 1.9 |
| 0.125 ng | 13.2 | 2.5 |
| 0.25 ng | 18.1 | 2.8 |
| 0.5 ng | 29.0 | 3.7 |
| 1 ng | 47.9 | 6.1 |
| 2 ng | 64.1 | 7.7 |

From Table 21, it was demonstrated that 470 nm was the more efficient LED exposure source for smartDNA assay, as the reaction rate for dye color change was much higher.

Example 23

This example illustrates one embodiment of the present invention for comparison of LEDs with different intensity in smartDNA assay.

Samples containing or not containing genomic nucleic acid (NA) isolated from *Mycobacterium tuberculosis* (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.08 ng/µL in phosphate buffer (10 mM) with surfactant (0.05% Tween-80). All reagents were prepared using molecular biology grade water (Hyclone, catalog #SH30538.03).

At this point, a 50 µM PNA probe mix was prepared from freezer stocks. Sequences used were SEQ ID NOS: 42, 43, 44, 45, 46 and 47. Freezer stocks (at ~200 µM in $H_2O$) were put in a hotblock at 65° C. for five minutes, and a 50 µM solution of each ncPNA was prepared by diluting the freezer stock ncPNA in molecular biology grade $H_2O$ (Hyclone, catalog #SH30538.03). Equal volumes of each 50 µM ncPNA solution were added to create a 50 µM total PNA concentration, i.e., 8.33 µM per ncPNA. This 50 µM PNA probe mix was put in the hotblock at 65° C. for five minutes, and was then further diluted in phosphate buffer (10 mM) with surfactant to a final concentration of 320 nM. The 320 nM PNA probe mix was placed in a water bath at 65° C. for five minutes, removed, and given 30 minutes to cool to room temperature.

Four dye stock solution were prepared by diluting 7.5 mM 3,3'-diethylthiacarbocyanine ("$DiSC_2(3)$") (solubilized in DMSO) into phosphate buffer with surfactant to working concentrations of 18, 36, 60 and 80 µM, and were referred as 4× dye stocks.

Serial 1:2 dilutions of the 0.08 ng/µL MTB NA (in 10 mM TE buffer, with 0.05% Tween-80) were prepared down to a low concentration of 0.0025 ng/µL; referred to herein as "DNA standards". Aliquots of 25 µL of each of the DNA standards were dispensed into a 384 well white/clear plate (NUNC, catalog #242763) to set up a concentration curve with triplicate in individual columns on the plate. The columns were set up as follows: columns 1-6, 9-14 and 17-22 were assay wells with 2 ng, 1 ng, 0.5 ng, 0.25 ng, 0.125 ng, and 0.0625 ng MTB DNA per well, column 7, 15 and 23 was a control well with 0 ng DNA and column 8, 16 and 24 was a control well with 2 ng MTB DNA. 4 rows of such were prepared.

For each of the 4 dye stock solutions, two dye mixtures were then prepared. The reaction set-up steps involving the dye were performed in a dimly lit room. The first control dye solution was prepared by mixing equal volumes of each of the 4× $DiSC_2(3)$ with phosphate buffer (with 0.05% Tween-80.) The resulted 2× $DiSC_2(3)$ control solution were mixed directly in a reagent reservoir. A 25 µL aliquot of the control dye solution was then dispensed to each well along column 8 and other triplicate wells of the microplate, respectively. The second, dye+PNA probe mix was prepared by mixing equal volumes of each of the 4× $DiSC_2(3)$ with the 320 nM PNA probe mix. This 2× $DiSC_2(3)$+160 nM PNA probe mix was mixed directly in a reagent reservoir. A 25 µL aliquot of the dye+PNA probe mix was then dispensed to each well along column 1-7 and all the other triplicates of the microplate, in respective rows.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm, with different power densities provided by power supply voltages of 12V, 13.8V, 15V and 18V yielding 4 different power densities on the microplate. The power supply voltages yielded power densities of 1.8, 1.1, 0.7, and 0.32, 0.7, 1.1, and 1.8 mW/cm$^2$, respectively, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 20 minutes total exposure to light.

Results of standard smartDNA assay, in homogenous solutions, with 4 different dye concentrations, and at 4 different power outputs were summarized in Tables 22, 23, 24, and 25 below.

TABLE 22

Slope of dye color change (mAbsorbance/min) for 4.5 µM dye at various LED power supply.

| DNA amount(ng) | 18 V | 15 V | 13.8 V | 12 V |
|---|---|---|---|---|
| 0 | 8.3 | 7 | 7.7 | 1.9 |
| 0.0625 | 8 | 5.6 | 5.1 | 1.9 |
| 0.125 | 8.7 | 6.7 | 7.1 | 1.9 |
| 0.25 | 11.4 | 9 | 8.8 | 3.3 |
| 0.5 | 16.4 | 13.7 | 12.8 | 5.3 |
| 1 | 24.9 | 21.5 | 17.3 | 8.6 |
| 2 | 35.3 | 30.4 | 24.3 | 12.5 |

TABLE 23

Slope of dye color change (mAbsorbance/min) for 9 µM dye at various LED power supply.

| DNA amount(ng) | 18 V | 15 V | 13.8 V | 12 V |
|---|---|---|---|---|
| 0 | 18 | 13.9 | 13.7 | 2.3 |
| 0.0625 | 17.7 | 13.4 | 12.4 | 4.1 |
| 0.125 | 19.3 | 15 | 14 | 4.1 |
| 0.25 | 23 | 18.3 | 18.4 | 5.6 |
| 0.5 | 31.4 | 25.5 | 24.6 | 9.6 |
| 1 | 45.3 | 38.5 | 34.3 | 14.9 |
| 2 | 60.1 | 51.4 | 45.4 | 21 |

TABLE 24

Slope of dye color change (mAbsorbance/min) for 15 µm dye at various LED power supply.

| DNA amount(ng) | 18 V | 15 V | 13.8 V | 12 V |
|---|---|---|---|---|
| 0 | 33.9 | 23.9 | 22.4 | 5.5 |
| 0.0625 | 31.9 | 23.4 | 20.4 | 7.1 |
| 0.125 | 34.3 | 25 | 22.2 | 7.1 |
| 0.25 | 37.6 | 27.3 | 24.8 | 8.5 |
| 0.5 | 46 | 34.8 | 31.2 | 12.1 |
| 1 | 61.1 | 48.4 | 41.9 | 16.1 |
| 2 | 75.4 | 61.4 | 52.3 | 21.9 |

TABLE 25

Slope of dye color change (mAbsorbance/min) for 20 µM dye at various LED power supply.

| DNA amount(ng) | 18 V | 15 V | 13.8 V | 12 V |
|---|---|---|---|---|
| 0 | 45.1 | 34 | 30.5 | 7.2 |
| 0.0625 | 43.3 | 34 | 28.7 | 8.8 |
| 0.125 | 46.2 | 34 | 32.2 | 9.7 |
| 0.25 | 49 | 34.9 | 36 | 10.8 |
| 0.5 | 55.8 | 41.1 | 39.7 | 13.5 |
| 1 | 68.8 | 53.6 | 49.6 | 17.6 |
| 2 | 87.2 | 65.7 | 55.5 | 23.2 |

The results demonstrated higher bleaching rate at higher LED power for the same NA amount and same dye concentration, but also increased the background bleaching rate. Same trend was observed for higher dye concentration, where the background bleaching rate was also increased. At the experimental conditions, a dye concentration between 9 µM to 15 µM was the optimal concentration range, where the background bleaching was not increased significantly, and a power supply from 15V to 18V was the optimal LED power supply range.

Example 24

This example illustrates one embodiment of the present invention for effects of different detergents in smartDNA assay.

Samples containing or not containing genomic nucleic acid (NA) isolated from *Mycobacterium tuberculosis* (MTB CDC1551) (Colorado State University) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.04 ng/µL in 1 mM EDTA. All reagents were prepared using molecular biology grade water (Hyclone, catalog #SH30538.03).

A 50 µM solution of each ncPNA was prepared by diluting the freezer stock ncPNA in molecular biology grade $H_2O$. The sequence of the PNA was TGA ACC GCC CCG GCA TG from N to C terminus, with 1 biotin at the N terminus (TB03; SEQ ID NO: 38). This 50 µM PNA probe stock was further diluted in homopipes buffer (pH 5.0, 20 mM) without surfactant to a final concentration of 320 nM. The 320 nM PNA probes were stored in 4° C. and used at room temperature.

Detergents used in this study were purchased from Pierce, catalogue # 28328, which contains 10% stock solutions or solid power of the following detergents: Tween-80, Tween-20, Triton 110, Triton 114, Brij 35, Brij 58, NP40, Chaps, octyl glucoside, octylthio glucoside, and cetyltrimethylammonium bromide (CTAB). The detergents were used directly from the 10% stock, or 10% stock was prepared by dissolving the solid power in molecular grade $H_2O$.

Dye stock was prepared by diluting 7.5 mM 3,3'-diethylthiacarbocyanine ("$DiSC_2(3)$") (solubilized in DMSO) into homopipes buffer without surfactant to a working concentration of 36 µM.

For each of the detergents, a series of dilutions in the 0.04 ng/µL MTB NA (in 1 mM EDTA) were prepared, so that the final concentration of the detergents in the reaction mixture would be 0, 0.02%, 0.04%, 0.08%, 0.12%, 0.16% and 0.2%. Aliquots of 25 t of the solutions were dispensed into a 384 well white/clear plate (NUNC, catalog #242763) to set up a concentration curve for each of the detergent with triplicate in individual columns on the plate. Thus, the final mixture would contain the expected amount of a certain detergent, and 1 ng of MTB NA. (1 ng of MTB NA corresponds to approximately 200,000 genomes). Duplicate rows were set up for each detergent as described above.

After the DNA dilutions with the increasing amount of detergents were dispensed into the microplate, 2 dye mixtures were then prepared. The reaction set-up steps involving the dye were performed in a dimly lit room. The first control dye solution was prepared by mixing equal volumes of 36 µM $DiSC_2(3)$ with the 10 mM homopipes buffer (pH 5.0, no surfactant). This 18 µM $DiSC_2(3)$ control solution was prepared directly in a reagent reservoir. Dye+PNA probe mix was prepared by mixing equal volumes of 36 µM DiSC$_2$(3) with 320 nM PNA probe in 10 mM homopipes buffer. A 25 µL aliquot of the control solution (dye only) was dispensed to all wells of the first row of the duplicate rows, and dye+PNA probe mix was then dispensed to each well of the second row. This gave final concentrations of 9 µM and 80 nM dye and ncPNA, respectively.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 20 minutes total exposure to light.

Table 26 shows the change in absorbance based on the first 4 minutes upon exposure to light (milliAbsorbance/minute) for each detergent at each concentration (average of triplicate reactions). Each detergent has 2 rows of data. The first row data corresponds to the DNA+PNA+dye solution, and the second row corresponds to the dye+PNA solution.

80 is the standard detergent for smartDNA assay because at a concentration between 0.04% to 0.08% there was an increased difference between the control row (no PNA) and the sample row (with PNA). The same trend was also true for Brij 58 (at about 0.08%) and Tween-20 (at about 0.08%) because at these conditions they contributed to decreased background photobleaching rate of the dye, while minimizing interference with the specific smartDNA photobleaching reaction.

Example 25

This example illustrates one embodiment of the present invention for determining the optimal buffer conditions and optimal PNA sequences in the smartDNA detection. In this example the homogeneous assay is used.

Samples containing or not containing genomic nucleic acid (NA) isolated from *Mycobacterium tuberculosis* (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed. *S. pneumoniae* (ATCC# BAA-3340) and Human DNA (from Sigma, lot #123K$_{3796}$) were used as nonspecific NA.

The concentration of isolated MTB NA (in water for freezer storage) and nonspecific DNA was initially quantified by converting the absorbance of the NA solution at 260 nm (measured with a Hewlett-Packard Model NO: HP8452A diode-array spectrophotometer) using standard methods. For the reaction mixtures, the nonspecific and specific NA were diluted down to a concentration of 0.04 ng/µL in 1 mM EDTA. All reagents were prepared using molecular biology grade water (Hyclone, catalog #SH30538.03).

Series of buffers with various pH were prepared. Phosphate-citrate buffer was prepared by mixing stock solutions

TABLE 26

Slope of dye color change (in mAbs/min) for increasing amounts of detergent in a homogenous smartDNA assay using TB03, Homopipes pH 5.0 buffer with or without DNA.

| Detergent | 0.00% | 0.02% | 0.04% | 0.08% | 0.12% | 0.16% | 0.20% |
|---|---|---|---|---|---|---|---|
| Tween-80 | 34.7 | 22.8 | 20.2 | 15.2 | 11.8 | 9.1 | 7.5 |
| Tween-80 | 37.6 | 27.3 | 23.3 | 19.9 | 14.7 | 12.0 | 10.1 |
| Tween-20 | 40.9 | 40.9 | 27.3 | 23.5 | 18.0 | 14.6 | 12.1 |
| Tween-20 | 41.8 | 41.8 | 29.6 | 26.0 | 22.3 | 18.4 | 13.7 |
| Triton-100 | 41.0 | 27.8 | 21.9 | 13.4 | 9.7 | 7.9 | 6.8 |
| Triton-100 | 39.2 | 29.0 | 24.3 | 14.8 | 9.5 | 8.0 | 6.7 |
| Triton-114 | 42.9 | 34.1 | 30.8 | 25.7 | 19.9 | 16.1 | 11.8 |
| Triton-114 | 42.4 | 34.7 | 33.1 | 27.3 | 21.8 | 19.0 | 14.0 |
| Brij-35 | 41.2 | 26.6 | 22.7 | 15.5 | 10.6 | 8.0 | 6.8 |
| Brij-35 | 41.4 | 31.2 | 26.9 | 19.5 | 14.1 | 11.0 | 8.0 |
| Brij-58 | 43.8 | 24.2 | 20.3 | 10.8 | 8.6 | 6.3 | 5.4 |
| Brij-58 | 44.0 | 27.2 | 24.2 | 16.4 | 12.5 | 9.3 | 6.6 |
| NP40 | 43.5 | 25.3 | 20.5 | 12.7 | 9.9 | 8.0 | 6.5 |
| NP40 | 45.2 | 26.9 | 22.2 | 14.5 | 10.4 | 7.4 | 6.2 |
| CHAPS | 42.6 | 37.5 | 33.5 | 32.0 | 30.2 | 29.3 | 28.8 |
| CHAPS | 45.5 | 38.3 | 36.1 | 35.5 | 34.5 | 33.5 | 31.6 |
| Octyl glucoside | 33.6 | 41.2 | 39.3 | 36.4 | 34.7 | 31.7 | 31.2 |
| Octyl glucoside | 37.4 | 47.5 | 46.3 | 43.8 | 40.9 | 39.2 | 39.0 |
| Octylthio glucoside | 34.1 | 0.0 | 39.5 | 41.3 | 40.9 | 37.9 | 38.0 |
| Octylthio glucoside | 38.5 | 40.0 | 44.1 | 44.3 | 46.8 | 44.7 | 45.6 |
| SDS | 37.5 | 16.8 | 18.6 | 24.7 | 29.9 | 26.5 | 19.1 |
| SDS | 42.0 | 39.9 | 20.4 | 24.4 | 27.8 | 21.4 | 19.7 |
| CTAB | 38.4 | 24.8 | 23.9 | 22.9 | 21.3 | 19.8 | 17.4 |
| CTAB | 39.9 | 27.6 | 25.3 | 24.4 | 20.9 | 19.1 | 18.2 |

Optimal detergents for smartDNA reaction demonstrate the greatest differential in change in absorbance between reactions with and without DNA, without significantly decreasing the overall rate of the smartDNA reaction. Tweenof 0.2M $Na_2HPO_4$ (from Teknova, catalogue # S0215) and 0.1M citric acid (from Teknova, catalogue # C2440) to a final pH of 4.0, 4.2, 4.4, 4.6 and 4.8. Homopipes buffers were prepared by titrating 20 mM homopipes using 4% NaOH to a final pH of 4.0, 4.2, 4.4, 4.6, 4.8 and 5.0. Tris-EDTA buffer 1M stock of pH 7.2, 7.4, 8.0, 8.5 and 9.0 were purchased from Teknova (catalogue # T5072, T5074, T5080, T5085, T5090, respectively) and diluted to working concentration with molecular biology grade $H_2O$ for usage.

At this point, a 50 µM PNA probe stock was prepared from freezer stocks. Sequences used were TB01: GTC GTC AGA CCC AAA AC (SEQ ID NO: 36), TB03: TGA ACC GCC CCG GCA TG (SEQ ID NO: 38), TB04: ACC AAG TAG ACG GGC GA (SEQ ID NO: 39), and these 3 have a biotin tag at the N-terminus; TB24: GTC GTC AGA CCC AAA AC, with 1 lysine at the N and another lysine at the C terminus (SEQ ID NO: 57). All sequences are from N to C terminus. The 50 µM PNA probes were further diluted in buffers with different pH as described above with surfactant (0.1% Tween-80) to a final concentration of 320 nM, 640 nM and 1280 nM. The 320 nM, 640 nM and 1280 nM probes were stored in 4° C. and used at room temperature.

Dye solution was prepared by diluting 7.5 mM 3,3'-diethylthiacarbocyanine ("$DiSC_2(3)$") (solubilized in DMSO) into phosphate buffer with surfactant to a working concentration of 36 µM.

Aliquots of 25 µL of 0.04 ng/µL MTB NA, 25 µL of the 0.04 ng/µL nonspecific Human DNA, and 25 µL of 1 mM EDTA (as control) were dispensed into a 384 well white/clear plate (NUNC, catalog #242763) to set up a set of triplicate in individual columns on the plate. The columns were set up as follows: 1 ng MTB DNA, 1 ng Human DNA, 1 ng *S. pneumoniae* and EDTA blank.

After the DNA standards were dispensed into the microplate, for each PNA sequence, in each kind of buffer, five dye mixtures were then prepared. The reaction set-up steps involving the dye were performed in a dimly lit room. The first control dye solution was prepared by mixing equal volumes of 36 µM $DiSC_2(3)$ with a specific buffer (with surfactant (0.1% Tween-80)) as described. This 18 µM $DiSC_2(3)$ control solution was mixed directly in a reagent reservoir. A 25 µL aliquot of the control dye solution was then dispensed to each well along the specific NA, nonspecific NA and control wells on the microplate. The other, dye+PNA probe mix was prepared by mixing equal volumes of 36 µM $DiSC_2(3)$ with the 320, 640 and 1280 nM PNA probe mix. This 18 µM $DiSC_2(3)$+160, 320 and 640 nM PNA probe mix prepared directly in a reagent reservoir. A 25 µL aliquot of each of the dye+PNA probe mix was then dispensed to the specific NA, nonspecific NA and control wells on the microplate.

The microplate was inserted into the Tecan Safire[2] monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 $mW/cm^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 20 minutes total exposure to light.

The results of the reaction rate in the first 4 minutes in the units of milliAbsorbance per minute for each of the specific (MTB) and nonspecific NA (human) with TB01 (SEQ ID NO: 36), and at increasing PNA concentrations were summarized in Table 27. The buffers were phosphate-citrate buffer series.

TABLE 27

Slope of dye color change (mAbsorbance/min) with 1 ng MTB NA and 1 ng human NA in homogeneous smartDNA reactions with different TB01 (SEQ ID NO: 36) PNA concentrations and buffer pH.

|  | PNA Concentration | pH4.0 | pH4.4 | pH4.8 |
|---|---|---|---|---|
| MTB | 13.3 nM | 19.9 | 28.0 | 12.0 |
|  | 40 nM | 18.8 | 41.7 | 15.6 |
|  | 80 nM | 12.9 | 49.4 | 28.0 |
|  | 160 nM | 14.8 | 64.8 | 18.4 |
| Human | 13.3 nM | 15.3 | 23.9 | 14.2 |
|  | 40 nM | 16.1 | 26.4 | 17.0 |
|  | 80 nM | 16.9 | 31.2 | 26.6 |
|  | 160 nM | 19.3 | 43.1 | 20.1 |

The results of the reaction rate in the first 4 minutes in the units of milliAbsorbance per minute for each of the specific (MTB) and nonspecific NA (human) with TB03 (SEQ ID NO: 38), and at increasing PNA concentrations were summarized in Table 28. The buffers used were homopipes buffer series.

TABLE 28

Slope of dye color change (mAbsorbance/min) with 1 ng MTB NA and 1 ng human NA in homogeneous smartDNA reactions with different TB03 (SEQ ID NO: 38) PNA concentrations and buffer pH.

|  |  | pH4.0 | pH4.2 | pH4.4 | pH4.6 | pH4.8 | pH5.0 |
|---|---|---|---|---|---|---|---|
| MTB | 0 | 14.7 | 12.1 | 11.1 | 15.6 | 13.1 | 14.9 |
|  | 80 nM | 22.8 | 23 | 22.7 | 38.9 | 38.1 | 40.6 |
|  | 160 nM | 21.0 | 24.8 | 26.9 | 43.3 | 46.4 | 53.2 |
|  | 320 nM | 15.4 | 27.3 | 29.1 | 41.6 | 51.5 | 56.9 |
| Human | 0 | 18.4 | 15.1 | 14.5 | 18.0 | 16.3 | 18.0 |
|  | 80 nM | 21.2 | 18.4 | 18.7 | 28.7 | 24.2 | 22.6 |
|  | 160 nM | 18.5 | 19.5 | 21.3 | 29.2 | 23.8 | 25.2 |
|  | 320 nM | 16.4 | 20.6 | 24.8 | 26.9 | 26.3 | 26.8 |

The results of the reaction rate in the first 4 minutes in the units of milliAbsorbance per minute for each of the specific (MTB 1 ng/reaction) and nonspecific NA (human 1 ng/reaction) with TB04 (SEQ ID NO: 39), and at increasing PNA concentrations were summarized in Table 29, with the specific MTB NA and the Human nonspecific NA. The buffers used were homopipes buffer series.

TABLE 29

Slope of dye color change (mAbsorbance/min) with 1 ng MTB NA and 1 ng human NA in homogeneous smartDNA reactions with different TB04 (SEQ ID NO: 39) PNA concentrations and buffer pH.

|  |  | pH4.0 | pH4.2 | pH4.4 | pH4.6 | pH4.8 | pH5.0 |
|---|---|---|---|---|---|---|---|
| MTB | 0 | 13.7 | 12.4 | 13.7 | 15.6 | 11.9 | 13.2 |
|  | 80 nM | 29.9 | 33.8 | 33.1 | 39.4 | 35.8 | 36.4 |
|  | 160 nM | 32.7 | 38.7 | 41.5 | 50.8 | 47.4 | 49.5 |
|  | 320 nM | 34.4 | 41.3 | 51.8 | 57.5 | 57.1 | 61.2 |
| Human | 0 | 16.4 | 14.8 | 16.3 | 16.5 | 13.8 | 14.9 |
|  | 80 nM | 15.8 | 16.5 | 15.2 | 21.3 | 17.9 | 18.1 |

TABLE 29-continued

Slope of dye color change (mAbsorbance/min) with 1 ng MTB
NA and 1 ng human NA in homogeneous smartDNA reactions with
different TB04 (SEQ ID NO: 39) PNA concentrations and buffer pH.

|        | pH4.0 | pH4.2 | pH4.4 | pH4.6 | pH4.8 | pH5.0 |
|--------|-------|-------|-------|-------|-------|-------|
| 160 nM | 16.2  | 17.2  | 19.1  | 22.5  | 18.2  | 20.2  |
| 320 nM | 17.8  | 18.3  | 23.9  | 22.2  | 21.8  | 25.8  |

The results showed that for the above 3 PNA probes with biotin tags have an optimal pH. Increasing the concentration of PNA probes also increase the reaction rates. Both non-specific NA did not show interference in smartDNA assay.

The results of the reaction rate in the first 4 minutes in the units of milliAbsorbance per minute for each of the specific and nonspecific NA with TB24 (SEQ ID NO: 57), and at increasing PNA concentrations were summarized in Table 30, with the specific MTB NA 1 ng/reaction and the nonspecific S. pneumoniae NA 1 ng/reaction. The buffers used were Tris-EDTA buffer series.

TABLE 30

Slope of dye color change (mAbsorbance/min) with 1 ng MTB
NA and 1 ng S. pneumoniae in homogeneous smartDNA reactions with
different TB24 (SEQ ID NO: 57) PNA concentrations and buffer pH.

|               |        | pH7.2 | pH7.4 | pH8   | pH8.5 | pH9   |
|---------------|--------|-------|-------|-------|-------|-------|
| MTB           | 0      |       | 19.1  | 15.8  | 18.1  | 14.7  | 15.3 |
|               | 80 nM  | 65.8  | 74.0  | 72.2  | 78.0  | 84.9  |
|               | 160 nM | 82.1  | 83.4  | 114.9 | 87.4  | 83.8  |
| S. pneumoniae | 0      | 14.0  | 14.0  | 16.7  | 14.5  | 12.9  |
|               | 80 nM  | 17.1  | 22.0  | 16.2  | 17.2  | 20.3  |
|               | 160 nM | 22.6  | 21.4  | 32.9  | 18.2  | 21.2  |

The results showed that for TB24 (SEQ ID NO: 57), the PNA with 1 lysine at the N and 1 lysine at the C terminus, pH impacts the reaction sensitivity and specificity and the optima is above pH 7. Increasing the concentration of PNA probes also increase the reaction rates. Non-specific S. pneumoniae NA did not show interference in smartDNA assay.

Example 26

This example illustrates one embodiment of the present invention for sensitivity comparison of PNA probes that have the same sequence but include different number and position of lysine residues.

Samples containing or not containing genomic nucleic acid (NA) isolated from Mycobacterium tuberculosis (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.04 ng/µL in 1 mM EDTA (diluted from 500 mM EDTA, Teknova catalogue # E0306). All reagents were prepared using molecular biology grade water (Hyclone, catalog #SH30538.03).

At this point, a 50 µM PNA probe was prepared from freezer stocks. The sequence of the PNA was GTC GTC AGA CCC AAA AC from N to C terminus, with 1 lysine at the N terminus (TB 14; SEQ ID NO: 58); 2 lysines: 1 at the N terminus and the other at the C terminus (TB24; SEQ ID NO: 57); or 4 lysines: 2 at the N terminus and the other 2 at the C terminus (TB44; SEQ ID NO: 59). A 50 µM solution of each PNA was prepared by diluting the freezer stock PNA in molecular biology grade $H_2O$, using 1.5 mL protein Lo-bind tubes (Eppendorf, catalogue # 0030108116). This 50 µM PNA probe was further diluted in homopipes buffer (pH 5.0, 20 mM, prepared from Homopipes solid powder, Research Organics # 6047H) or TE buffer (pH 7.2, 20 mM Tris-Cl (diluted from 1M stock, Teknova catalogue # T5072), 2 mM EDTA) without surfactant to a final concentration of 640 nM. The 640 nM PNA probes were stored in 4° C. and used at room temperature.

Dye solution was prepared by diluting 7.5 mM 3,3'-diethylthiacarbocyanine ("$DiSC_2(3)$")(from SigmaAldrich, catalogue # 173738) (solubilized in DMSO, Sigma # D8418) into homopipes buffer or TE buffer with surfactant (0.2% Tween-80, from 10% stock, Pierce Biotech, # 28328) to a working concentration of 36 µM.

Serial dilutions using the 0.04 ng/µL MTB NA (in 1 mM EDTA) were prepared, and aliquots of 25 µL of each of the DNA dilutions were dispensed into a 384-well white with optical bottom microplate (NUNC, catalog #242763) to set up a concentration curve with triplicate in individual columns on the plate. The final amount of MTB NA in each well corresponds to approximately 80000, 40000, 20000, 10000, 5000 and 0 genomes per reaction (1 ng of MTB NA corresponds to approximately 200000 genomes).

After the DNA dilutions were dispensed into the microplate, dye mixtures were then prepared. The reaction set-up steps involving the dye were performed in a dimly lit room. Dye+PNA probe mix was prepared by mixing equal volumes of 36 µM $DiSC_2(3)$ in homopipes buffer or TE buffer with each of the 640 nM PNA probe in corresponding buffer. All 18 µM $DiSC_2(3)$+320 nM PNA probe mixtures were prepared directly in a reagent reservoir (Diversified Biotech, RESE 2000). A 25 µL aliquot of the dye+PNA probe mix was then dispensed to each well containing the DNA dilutions.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 20 minutes total exposure to light.

The results of the reaction rate in the first 4 minutes in the units of milliAbsorbance per minute for each of the NA dilutions with each of the various PNA probes were summarized in Table 31 and Table 32.

TABLE 31

Slope of dye color change for increasing amount of MTB genomes in a homogenous smartDNA assay using TB14 (SEQ ID NO: 58), Homopipes pH5.0 buffer or TB24 (SEQ ID NO: 57), TE pH7.2 buffer as probe. STDEV data for the TB24 (SEQ ID NO: 57) as probe were also listed.

| App. genomes per reaction | TB14 (SEQ ID NO: 58) | TB24 (SEQ ID NO: 57) | STDEV/TB24 (SEQ ID NO: 57) |
|---|---|---|---|
| 0 | 16.7 | 18.4 | 0.21 |
| 5000 | 17.9 | 20.6 | 0.63 |
| 10000 | 18.9 | 21.9 | 0.23 |
| 15000 | 20.4 | 24.1 | 1.85 |
| 20000 | 20.4 | 26.0 | 0.76 |
| 30000 | 22.2 | 31.3 | 2.32 |
| 40000 | 26.0 | 35.8 | 3.13 |
| 80000 | 37.0 | 51.3 | 1.66 |

TABLE 32

Slope of dye color change for increasing amount of MTB genomes in a homogenous smartDNA assay using TB14 (SEQ ID NO: 58) (in homopipes pH 5.0), TB24 (SEQ ID NO: 57) (in TE pH 7.2 buffer) or TB44 (SEQ ID NO: 59) (in TE pH 7.2 buffer) as probe.

| App. genomes per reaction | TB14 (SEQ ID NO: 58), HP5.0 | TB24 (SEQ ID NO: 57), TE7.2 | TB44 (SEQ ID NO: 59), TE7.2 |
|---|---|---|---|
| 0 | 15.3 | 16.7 | 21.6 |
| 25000 | 25.4 | 35.8 | 43.2 |
| 50000 | 30.8 | 45.0 | 47.8 |
| 100000 | 43.2 | 62.0 | 68.2 |
| 200000 | 51.9 | 93.1 | 100.8 |

The results show that by attaching 1 lysine to the N terminus and 1 lysine to the C terminus of the PNA probe the sensitivity of the detection (in TE buffer) was increased (the slope of the reaction rate (mAbs/min) vs. genomes per reaction was 42 compared with 25 changes of units per 100000 genomes). However, attaching 4 lysines, 2 each at the N and C terminus of the PNA probe did not change the sensitivity of the assay compared with the PNA with 1 lysine at each end in the same TE buffer.

Example 27

This example examines the relationship between PNA-DNA complex concentrations and the rate of turnover of the dye during the photo bleaching reaction. This analysis suggests that the PNA-DNA complex acts in a catalytic manner. Preparation and activation of reaction mixtures containing *M. tuberculosis* DNA (MTB DNA), PNA, and dye have been previously described. Absorbance vs. time data for these analyses were taken from FIG. 18. Turnover rates for the dye were calculated using the following procedure and illustrated in Table 33. For each concentration of MTB DNA and the PNA only control the initial rate of the reaction was calculated by subtracting the absorbance of the reaction solution obtained at 4 minutes from the initial value and dividing by 4. Initial absorbances of reaction solutions were normalized to a common minimum value using the following relationship, $$NA(t) = A(t) - (A(t_0) - A(\min t_0))$$

Where $NA(t)$ is the normalized value of the absorbance at any time t. $A(t)$ is the uncorrected absorbance at time t. $A(t_0)$ is the initial absorbance of each sample, and $A(\min t_0)$ is the initial absorbance value of the sample having the lowest absorbance. All other starting absorbances were normalized to this value. This procedure eliminates slight differences in the starting absorbances of the reaction solutions and allows a more straightforward comparison of turn over rates derived from these values. Initial rates of absorbance change were then converted to the number of molecules of dye turned over per minute by dividing the absorbance change by the molar absorptivity ($1.36\text{ E}+05\text{ cm}^{-1}\text{ M}^{-1}$) of the dye and then multiplying the result by the reaction volume (5.0E−05 l) and Avogadro's number (6.023 E+23). Since the dye photo bleaches in the presence of PNA alone this background rate of bleaching was then subtracted from the rates for each of the MTB DNA concentrations. The approximate number of MTB genomes was calculated from each sample amount using a genome size for MTB of 4411532 bp. The PNA probes used in this experiment can theoretically bind to 89 sites in the MTB genome, the number of potential catalytic sites was derived by dividing total genomes present by 89. This represents the lowest turnover number for the catalytic sites present. If not all sites are fully occupied with PNAs or functional the actual turnover number will be higher. Turnover numbers calculated in this manner are remarkably uniform in value and appear to have a constant value over the 30 fold variation in analyte concentration averaging 2.0 E+03 dye molecules/second with 16% relative standard deviation. This is consistent with the notion that the PNA-DNA complex can function as a catalyst. The turnover numbers obtained are also consistent with those obtained for common enzymes which are shown in Table 34.

TABLE 33

Dye Turnover Per Catalytic Site as a Function of Analyte Concentration

| MTB Amount (ng) | 2 | 1.0000 | 0.5000 | 0.2500 | 0.1250 | 0.0625 | PNA |
|---|---|---|---|---|---|---|---|
| Initial Absorbance (normalized) | 0.4859 | 0.4859 | 0.4859 | 0.4859 | 0.4859 | 0.4859 | 0.4859 |
| Absorbance at 4 minutes | 0.3771 | 0.4195 | 0.4460 | 0.4589 | 0.4631 | 0.4646 | 0.4671 |
| Delta Absorbance (0-4 min) | 0.1088 | 0.0664 | 0.0399 | 0.0270 | 0.0228 | 0.0213 | 0.0188 |
| Divide by dye molar absorptivity = 1.36E+05 (molarity) | 8.0E−07 | 4.9E−07 | 2.9E−07 | 2.0E−07 | 1.7E−07 | 1.6E−07 | 1.4E−07 |
| Divide by 4 (molar/min) | 2.0E−07 | 1.2E−07 | 7.3E−08 | 5.0E−08 | 4.2E−08 | 3.9E−08 | 3.5E−08 |
| Multiply by reaction volume 50 ul (moles/min) | 1.0E−11 | 6.1E−12 | 3.7E−12 | 2.5E−12 | 2.1E−12 | 2.0E−12 | 1.7E−12 |
| Multiply by 6 × 10²³ (molecules/min) | 6.0E+12 | 3.7E+12 | 2.2E+12 | 1.5E+12 | 1.3E+12 | 1.2E+12 | 1.0E+12 |
| Subtract out PNA background (molecules/min) | 5.0E+12 | 2.6E+12 | 1.2E+12 | 4.6E+11 | 2.2E+11 | 1.4E+11 | 0.0E+00 |
| TB Genomes (CDC1551 4403837bp) | 4.1E+05 | 2.1E+05 | 1.0E+05 | 5.2E+04 | 2.6E+04 | 1.3E+04 | — |
| PNA sites (for 6 PNA cocktail) | 8.9E+01 | 8.9E+01 | 8.9E+01 | 8.9E+01 | 8.9E+01 | 8.9E+01 | — |
| Catalytic Sites | 3.7E+07 | 1.8E+07 | 9.2E+06 | 4.6E+06 | 2.3E+06 | 1.2E+06 | — |
| Dye Turnover/Site (molecules/min) | 1.4E+05 | 1.4E+05 | 1.3E+05 | 9.9E+04 | 9.6E+04 | 1.2E+05 | — |
| Dye Turnover/Site (molecules/sec) | 2.3E+03 | 2.4E+03 | 2.1E+03 | 1.6E+03 | 1.6E+03 | 2.0E+03 | — |

TABLE 34

Turnover Rate of Common Enzymes

| Enzyme | Turnover Number (molecules/second) |
| --- | --- |
| Carbonic Anhydrase | 6.0E+05 |
| Acetylcholinesterase | 2.5E+04 |
| Amylase | 1.8E+04 |
| Penicillinase | 2.0E+03 |
| DNA Polymerase | 1.5E+01 |

Example 28

This example illustrates one embodiment of the present invention for effects of different preservatives in smartDNA assay.

Samples containing or not containing genomic nucleic acid (NA) isolated from *Mycobacterium tuberculosis* (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. For the reaction mixtures, the NA was diluted down to a concentration of 0.08 ng/μL in phosphate buffer (10 mM) with surfactant (0.05% Tween-80). All reagents were prepared using molecular biology grade water (Hyclone, catalog #SH30538.03).

At this point, a 50 μM PNA probe mix was prepared from freezer stocks. Sequences used were SEQ ID NOS: 42, 43, 44, 45, 46 and 47. Freezer stocks (at 200 μM in $H_2O$) were put in a hotblock at 65° C. for five minutes, and a 50 μM solution of each ncPNA was prepared by diluting the freezer stock ncPNA in molecular biology grade $H_2O$ (Hyclone, catalog #SH30538.03). Equal volumes of each 50 μM ncPNA solution were added to create a 50 μM total PNA concentration, i.e., 8.33 μM per ncPNA. This 50 μM PNA probe mix was put in the hotblock at 65° C. for five minutes, and was then further diluted in phosphate buffer (10 mM) with surfactant (0.05% Tween-80) to a final concentration of 320 nM. The 320 nM PNA probe mix was placed in a water bath at 65° C. for five minutes, removed, and given 30 minutes to cool to room temperature.

Dye solution was prepared by diluting 7.5 mM 3,3'-diethylthiacarbocyanine ("$DiSC_2(3)$") (solubilized in DMSO) into phosphate buffer with surfactant (0.05% Tween-80) to a working concentration of 36 μM.

Serial 1:2 dilutions of the 0.08 ng/μL MTB NA (in 10 mM TE buffer, with 0.05% Tween-80) were prepared down to a low concentration of 0.0025 ng/μL; referred to herein as "DNA standards". Aliquots of 25 μL of each of the DNA standards were dispensed into a 384 well white/clear plate (NUNC, catalog #242763) to set up a concentration curve with triplicate in individual columns on the plate. The columns were set up as follows: columns 1-6, 9-14 and 17-22 were assay wells with 2 ng, 1 ng, 0.5 ng, 0.25 ng, 0.125 ng, and 0.0625 ng MTB DNA per well, columns 7, 15 and 23 were control wells with 0 ng DNA and columns 8, 16 and 24 were control wells with 2 ng MTB DNA. 3 rows of such were prepared.

For the first row, two dye mixtures were then prepared. The reaction set-up steps involving the dye were performed in a dimly lit room. The first control dye solution was prepared by mixing equal volumes of 36 μM $DiSC_2(3)$ with phosphate buffer (with 0.05% Tween-80.) This 18 μM $DiSC_2(3)$ control solution was mixed directly in a reagent reservoir. A 25 μL aliquot of the control dye solution was then dispensed to each well along column 8 and all other triplicate of the microplate. The second, dye+PNA probe mix was prepared by mixing equal volumes of 36 μM $DiSC_2(3)$ with the 320 nM PNA probe mix. This 18 μM $DiSC_2(3)$+160 nM PNA probe mix was mixed directly in a reagent reservoir. A 25 μL aliquot of the dye+PNA probe mix was then dispensed to each well along columns 1-7 and all the other triplicates of the microplate.

For the second and third row, similar dye mixtures were then prepared. For both the 18 μM $DiSC_2(3)$ control solution and the dye+PNA probe mix, either sodium azide($NaN_3$) was added to a final of 0.2% from 2% stock (100 μl 2% $NaN_3$ stock per 1 ml of mixture), or Proclin 300 was added to a final of 0.1% from 3.49% stock solution (from SUPELCO, catalogue # 48119-U, and 28.6 μl 3.49% Proclin 300 stock per 1 ml of mixture). 25 μL aliquot of the final dye solution was then dispensed to each well along each column as described above.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 26 minutes total exposure to light.

The results for adding preservatives into the standard smartDNA assay was summarized in Table 35.

TABLE 35

Slope of dye color change (mAbsorbance/min) for increasing amount of MTB NA, without the presence of any preservatives, or in the presence of 0.1% $NaN_3$, or in the presence of 0.05% Proclin300.

| DNA amount(ng) | control | NaN3 | Proclin300 |
| --- | --- | --- | --- |
| 0 | 11.7 | 10.7 | 12.3 |
| 0.0625 | 12.6 | 11.4 | 12.7 |
| 0.125 | 14.2 | 11.9 | 14.5 |
| 0.25 | 17.9 | 13.1 | 17.4 |
| 0.5 | 23.5 | 14 | 23.7 |
| 1 | 36.3 | 15.8 | 34.7 |
| 2 | 48 | 19.1 | 46.2 |

Table 35 showed that the presence of 0.1% $NaN_3$ interfered with homogenous smartDNA assay, as the rate of dye color change is similar as background bleaching rate, and much lower than the control assay. However, the presence of 0.05% Proclin300 retains the same slope of dye color change in all DNA amounts. Thus 0.05% Proclin300 can be used as a preservative in the storage of smartDNA buffers.

Example 29

The microparticle-captured PNA:oligo assay was performed using PNA Bio18 (N-biotin-OOOOO-GATAGTGG-GATTGTGCGT-C(PNA); SEQ ID NO: 1) and its complementary oligo (5'-ACGCACAATCCCACTATC-3'; SEQ ID NO: 20).

In a 1.5 mL microcentrifuge tube, 10 picomoles binding capacity streptavidin polystyrene particles (Spherotech, catalog #SVP-40-5) were washed with 1 mL capture buffer (10 mM Tris pH 7.2, 1 mM EDTA, 150 mM NaCl, 0.05% Tween® 80); followed by centrifugation at 14,000 rpm for 2 minutes to pellet the microparticles. Washing was repeated 2 times.

Fifty μM PNA of SEQ ID NO: 1 and DNA of SEQ ID NO: 20 or bio-DNA (5'-biotin-TTTTT-GATAGTGGGATTGT-GCGT-3'; SEQ ID NO: 60) solutions were made by diluting concentrated stock solutions with molecular biology grade water (Hyclone, catalog #SH30538.03). As a control, a biotinylated DNA oligo with the same sequence as the PNA (SEQ ID NO: 60) was also included. Five μL of PNA solution (or biotinylated DNA oligo), 5 μL complementary DNA solution and 40 μL of hybridization buffer (10 mM Tris pH 7.2, 1 mM EDTA, 20 mM NaCl) were mixed and heated 95° C. in a heat block. The block was removed from the heater and allowed to cool to room temperature on the benchtop. Four μL PNA:DNA hybridization mixture (20 pmoles) or 4 μL biotinylated-DNA:DNA hybridization mixture was added to 96 μL of capture solution containing 10 pmole binding capacity of beads. This was set this up so that there were 10 reactions worth of PNA:DNA duplex and beads in the same tube. The tubes were gently agitated for 1.5 hours at room temperature to capture the biotinylated-PNA:DNA hybrid and the biotinylated-DNA:DNA to the streptavidin microparticles. The microparticles were then washed once with capture buffer as described above; followed by two washes with 1×HP4.8 buffer (10 mM Homopipes (Research Organics catalog #6047H) pH 4.8, 0.05% Tween® 80 (Pierce Biotechnology, catalog #28328). The microparticles were then resuspended in final volume of 500 μL 1×HP4.8 buffer, 0.5 mM EDTA and 9 μM DiSC$_2$(3).

The following reaction set-up steps involving the dye were performed in a dimly lit room. Aliquots of 50 μL of each of the samples were dispensed in triplicate sets into a 384-white-well optical bottom microtiter plate (NUNC, catalog #242763). The microplate was inserted into the Tecan Safire² monochromator-based microplate reader. The microplate was subjected to a 1 second medium-intensity orbital shake, followed by a 1 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm², as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 20 minutes total exposure to light.

The initial rates of dye photobleaching (initial dye color change rates) were calculated by subtracting the absorbance of the solution at time$_{4min}$ from the initial absorbance of the solution at Time$_{0min}$ and dividing by 4 minutes. Table 36 lists the initial dye color change rates depicted as change in milliabsorbance (mAbs) units per minute.

TABLE 36

| Sample | Initial Change in Dye Absorbance | Standard Deviation of Initial Dye Color Change Absorbance |
|---|---|---|
| PNA:DNA hybrid | 60.28 | 9.11 |
| PNA alone | 24.82 | 2.23 |
| DNA alone | 24.61 | 2.77 |
| Bio-DNA:DNA hybrid | 40.22 | 2.28 |
| Bio-DNA alone | 39.38 | 3.13 |
| DNA alone | 25.27 | 1.44 |
| microparticles only | 34.65 | 1.38 |

Example 30

This example illustrates one embodiment of the present invention for determining the LOD of isolated MTB genomic nucleic acid (NA) in the capture and release assay.

Samples containing or not containing target NA isolated from *Mycobacterium tuberculosis* (MTB CDC1551) were prepared and tested using a protocol of the present invention. These samples were then used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. A stock of 8 ng/μl NA solution was prepared from original stock using molecular biology grade water (Hyclone, catalog #SH30538.03).

At this point, a 50 μM PNA probe mix was prepared from freezer stocks. Sequence used was GTC GTC AGA CCC AAA AC from N to C terminus, with a biotin at the N-terminus (SEQ ID NO: 36) (for the capture portion of the assay), or 1 lysine at the N terminus and 1 lysine at the C terminus (SEQ ID NO:57) (for detection in the homogeneous released portion of the assay). A 50 μM solution of each ncPNA was prepared by diluting the freezer stock ncPNA in molecular biology grade H$_2$O (Hyclone, catalog #SH30538.03). This 50 μM PNA probe was further diluted in TE buffer (pH 7.2, 20 mM Tris-Cl, 2 mM EDTA) without surfactant to a final concentration of 640 nM. The 640 nM PNA probe stock was stored in 4° C. and used at room temperature.

Dye solution was prepared by diluting 7.5 mM 3,3'-diethylthiacarbocyanine ("DiSC$_2$(3)") (solubilized in DMSO) into 20 mM TE buffer with surfactant to a stock concentration of 36 μM.

PNA microparticles were prepared by conjugating biotin tagged PNA to streptavidin polystyrene particles (Spherotech, catalog #SVP-40-5), in microparticle coating buffer (150 mM NaCl, 1× Tris-EDTA, pH7.2, 0.05% Tween-80). Aliquot of 200 pmoles capture capacity of particles was washed 3× in coating buffer, resuspended in 500 ul coating buffer, and 8 ul of 50 uM of biotin tagged PNA was added. The mixture was shaking at room temperature for 3 hrs. After coating with PNA, the microparticles was washed 3×, first with coating buffer as described above, then twice with 2× homopipes (pH5.0) buffer, and stored in 1 mM EDTA at the final concentration of 20 pmole/50 ul for use.

20 pmoles (4×) of the PNA microparticles were used in each sample, and were divided to triplicate reaction mixtures on the micro titer plate. Thus, 5 pmoles binding capacity of the microparticles was used in each reaction mixture. Equal volume of dye stock was mixtured with the microparticles in EDTA. From a NA stock of 0.1 ng/μl (approximately 20000 genomes per μl), MTB NA were added to the microparticles and dye mixture, with final MTB amount 0, 20000, 40000, 80000, 160000 and 320000 genomes per tube. These amounts were four times the number of genomes in the final reaction tubes, thus the eluate was used in four reactions with 0, and approximately 5000, 10000, 20000, 40000 and 80000 genomes per reaction mixture in each well on the micro-titer plate The mixture was then incubated and shaken at room temperature in the dark for 30 minutes. After incubation, the microparticles were washed 3× with washing buffer (0.5 mM EDTA, 1× homopipes buffer, 0.05% Tween 80, 9 μM dye).

100 of 1 mM EDTA was added to the washed microparticles, pipetted to resuspend the pelleted microparticles, and the mixture incubated on the benchtop for 30 minutes to elute the captured NA on the microparticles.

The 100 ul mixture was then spun for 2 minutes to pellet the microparticles. The supernatant was aliquoted directly to microtiter plate, with 25 ul for each reaction mixture in triplicate. After the eluates were dispensed into the microplate, dye mixtures were then prepared. The following reaction set-up steps involving the dye were performed in a dimly lit room. Dye+PNA probe mix was prepared by mixing equal volumes of 36 μM DiSC$_2$(3) with the 320 nM PNA probe mix. This 18 μM DiSC$_2$(3)+160 nM PNA probe mix was mixed by inversion in a 15 mL conical tube, and poured into a reagent reservoir. A 25 μL aliquot of the dye+PNA probe mix was then dispensed to each well containing the elution.

The microplate was inserted into the Tecan Safire$^2$ monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 44 minutes total exposure to light.

The results of the reaction rate in the first 4 minutes in the units of mille Absorbance per minute for each of the NA capture samples with the PNA probes were summarized in Table 37.

TABLE 37

Slope of dye color change for different amount of target genomes in homogenous smartDNA assay.

| App. genomes per reaction | reaction rate(mAbs/min) | STDEV |
|---|---|---|
| 0 | 17.0 | 0.22 |
| 5000 | 18.4 | 0.24 |
| 10000 | 17.3 | 0.26 |
| 20000 | 22.6 | 0.66 |
| 40000 | 26.6 | 0.27 |
| 80000 | 35.3 | 0.71 |

These results suggested that isolated MTB can be captured to the PNA microparticles and released for smartDNA detection. Using 5 times STDEV above background to estimate the LOD, LOD of isolated MTB NA in the captured assay is 5000 genomes in the 50 ul reaction mixture.

Example 31

This example illustrates one embodiment of the present invention for detecting specific isolated DNA in the presence of non-specific DNA from various microorganisms. In this example the capture and release format is employed.

Samples containing or not containing genomic nucleic acid (NA) isolated from *Mycobacterium tuberculosis* (MTB CDC1551) were prepared and tested using a protocol of the present invention. Accordingly, the samples were used in generating reaction mixtures that further included a dye and a nucleic acid analog that specifically hybridizes to MTB DNA. Optical properties of the reaction mixture before and after exposure to a light source were observed.

The concentration of isolated MTB NA (in water for freezer storage) was initially quantified by converting the absorbance of the NA solution at 260 nm (measured with a Hewlett-Packard Model NO: HP8452A diode-array spectrophotometer) using standard methods. A stock of 32 ng/μl NA solution was prepared from original stock. The concentration of non-specific NA from various microorganisms were also determined using the same methods. Nonspecific NA from microorganisms used in this study were purchased from ATCC, and included: *S. aureus* (ATCC# 108320), *S. pneumoniae* (ATCC# BAA-3340), *H. influenzae* (ATCC# 51907D), *E. coli* (ATCC# 7009280), *N. meningitidis* (ATCC# 108320), *M. gordonae* (ATCC# 108320), *P. aeruginosa* (ATCC# 108320), *K. pneumonae* (ATCC# 108320). Nonspecific NA also included isolated Human DNA (from Sigma, lot#123K3796).

At this point, a 50 μM PNA probe mix was prepared from freezer stocks. Sequence used was GTC GTC AGA CCC AAA AC from N to C terminus, with a lysine (SEQ ID NO: 58) or a biotin (SEQ ID NO: 36) at the N terminus. A 50 μM solution of each ncPNA was prepared by diluting the freezer stock ncPNA in molecular biology grade H$_2$O (Hyclone, catalog #SH30538.03). This 50 μM PNA probe was further diluted in homopipes buffer (pH 5.0, 20 mM, referred as 2× buffer) without surfactant to a final concentration of 320 nM. The 320 nM PNA probe mix was stored in 4° C. and used at room temperature.

Dye solution was prepared by diluting 7.5 mM 3,3'-diethylthiacarbocyanine ("DiSC$_2$(3)") (solubilized in DMSO) into 20 mM homopipes buffer with surfactant to a working concentration of 36 μM.

PNA microparticles were prepared by conjugating biotin tagged PNA to streptavidin polystyrene particles (Spherotech, catalog#SVP-40-5), in microparticle coating buffer (150 mM NaCl, 1× Tris-EDTA, pH7.2, 0.05% Tween-80). Aliquot of 200 pmoles capture capacity of particles was washed 3× in coating buffer, resuspend in 500 ul coating buffer, and 8 ul of 50 uM of biotin tagged PNA was added. The mixture was shaking at room temperature for 3 hours. After coating with PNA, the microparticles was washed 3×, first with coating buffer, then twice with 2× homopipes buffer, and stored in 1 mM EDTA at the final concentration of 20 pmole/50 ul for use.

20 pmoles (4×) of the PNA microparticles were used in each sample, and will be divided to triplicate reaction mixtures on the micro titer plate. Thus 5 pmoles binding capacity of microparticles will be used in each reaction mixture. Equal volume of dye stock was mixed with the microparticles in EDTA, 32 ng of specific and/or nonspecific NA was added to the microparticle and dye mixture, the mixture was then incubated and shaken at room temperature in the dark for 30 minutes. After incubation, the microparticles was washed 3× with washing buffer (0.5 mM EDTA, 1× homopipes buffer, 0.05% Tween 80, 9 uM dye).

100 µl of 1 mM EDTA was added to the washed microparticles, pipetted to resuspend the pelleted microparticles, and the mixture was left on the benchtop for 30 minutes to elute the captured NA off the microparticles.

The 100 ul mixture was then spun for 2 minutes to pellet the microparticles, and the NA containing supernatant was aliquoted directly to microtiter plate, with 25 µl for each reaction mixture in triplicate. After the eluates were dispensed into the microplate, dye mixtures were prepared. The following reaction set-up steps involving the dye were performed in a dimly lit room. Dye+PNA probe mix was prepared by mixing equal volumes of 36 µM DiSC$_2$(3) with the 320 nM PNA probe mix. This 18 µM DiSC$_2$(3)+160 nM PNA probe mix was mixed by inversion in a 15 mL conical tube, and poured into a reagent reservoir. A 25 µL aliquot of the dye+PNA probe mix was then dispensed to each well containing the elution.

The microplate was inserted into the Tecan Safire² monochromator-based microplate reader. The microplate was subjected to a 10 second medium-intensity orbital shake, followed by a 600 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm², as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 10 to 20 minutes total exposure to light.

The results of the reaction rate in the first 4 minutes in the units of mille Absorbance per minute for captured specific NA in the background of nonspecific NA were summarized in Table 38.

TABLE 38

Slope of dye color change of the capture smartDNA assay, when the NA available for capture is nonspecific NA as listed below, or the nonspecific NA plus the specific MTB NA.

| Sample | Without specific MTB NA | With Specific MTB NA |
|---|---|---|
| Control (MTB) | 20.0 | 129.0 |
| Human DNA | 17.7 | 125.2 |
| S. aureus | 24.8 | 126.7 |
| S. pneumoniae | 21.8 | 128.7 |
| H. influenzae | 19.0 | 121.7 |
| E. coli | 20.8 | 125.1 |
| N. meningitotis | 22.7 | 123.4 |
| M. gordonae | 33.6 | 123.7 |
| P. aeruginosa | 19.8 | 123 |
| K. pneumonae | 21.8 | 118.8 |

The results showed that isolated MTB DNA can be selectively captured to the PNA microparticles in the background of equal amount of non-specific NA described above, and released for smartDNA detection. The interference NA summarized in Table 38 did not increase the background of the capture assay (except *M. gordonae*). The capture of target MTB NA had the same apparent efficiency whether interfering NA was present or not.

Example 32

The presence of DNA captured using the smartDNA assay was confirmed using polymerase chain reaction (PCR).

32 ng of genomic DNA from each *Mycobacterium bovis* (Genbank accession number NC_002945) and *Mycobacterium tuberculosis* was captured using 20 picomoles binding capacity TB01 (SEQ ID NO: 36)-microparticles using the standard smartDNA capture assay. DNA was eluted using 10 µL of molecular biology grade water (Hyclone, catalog #SH30538.03). The DNA solution was placed on ice and mixed with 4 µL 25 mM MgCl$_2$ (Promega catalog #A3511), 10 µL 5× GoTaq Flexi Green buffer (Promega catalog #M8911), 0.25 µL GoTaq Flexi DNA polymerase (Promega, catalog #M8295), 2 µL 10 mM dNTP mix (Promega, catalog #C1141), 2 µL 10 µM forward primer [5'-TGAACCGC-CCCGGCATGTCC-3' (SEQ ID NO: 61) for *M. bovis* and 5'-CCGGTTAGGTGCTGGTGGTC-3' (SEQ ID NO: 62) for *M. tuberculosis*] and 2 µL 10 µM reverse primer [SEQ ID NO: 61] for *M. bovis*, and 5'-CGCCCCATCGACCTACTACG-3' (SEQ ID NO: 63) for *M. tuberculosis*] and 20.75 µL of molecular biology grade water in a total reaction volume of 50 µL. The cycling conditions were as follows: (1) 94° C. for 4 minutes; (2) 94° C. for 60 seconds; (3) 55° C. for 60 seconds; (4) 72° C. for 3 minutes; (5) repeat steps (2) to (4) 35 more times; (6) 72° C. for 10 minutes; (7) 4° C. hold.

The 50 µL PCR reactions were run on 1.5% agarose 1×TBE gels. Bands were excised from the gels and purified using the QIAquick Gel Extaction Kit (Qiagen, catalog #28706) according to the manufacturer's instructions except that the DNA was eluted from the column using 35 µL of EB buffer.

The purified DNA was subcloned using the TOPO-TA cloning kit (Invitrogen, catalog #K4500-01) and the cloned inserts sequenced (by the Davis Sequencing Center, University of California at Davis, Calif.) using the M13 forward and M13 reverse primers. The resulting sequences were BLAST searched using the NCBI online search (http://www.ncbi.nlm.nih.gov/BLAST/) and aligned using the online sequence alignment tool ClustalW (http://www.ebi.ac.uk/clustalw/) to determine base pair identity between the cloned insert and the genome.

The *M. bovis* clone was 1345 bp in length and perfectly matched bases 259,504 to 260,858 of the *M. bovis* genome (Genbank accession number NC_002945.3), with the exception of 3 bases within the forward primer sequence [SEQ ID NO: 61]. Bases 14 to 16 are CAT in the primer (TGAACCGCCCCGGCATGTCC; SEQ ID NO: 61) and TGA in the genomic sequence (TGAACCGCCCCGGTGAGTCC; SEQ ID NO: 64). The *M. tuberculosis* 313 bp clone matched bases 3,120,580 to 3,120,893 of *Mycobacterium tuberculosis* H37Rv genome (Genbank accession number AL123456). Both of these sequences are within the Direct Repeat region of the genomes.

Example 33

This example illustrates the smartDNA reaction by PNA: RNA oligo hybrids in a non-denaturing PAGE gel.

RNA oligonucleotides (Sigma-Proligo) [SEQ ID NOS: 65-70, see Table 39] complementary to PNAs TB01-TB06 [SEQ ID NOS: 36-41, see Table 39], respectively, were diluted to 50 μM stocks with DEPC-treated molecular biology grade, RNase-free water (Hyclone, catalog #SH30538.03).

TABLE 39

| SEQ ID NO. | Sequence | Name |
|---|---|---|
| 65 | GUUUUGGGUCUGACGAC | rTB01comp |
| 66 | GUUUCCGUCCCCUCUCG | rTB02comp |
| 67 | CAUGCCGGGGCGGUUCA | rTB03comp |
| 68 | UCGCCCGUCUACUUGGU | rTB04comp |
| 69 | CGACCGACGGUUGGAUG | rTB05comp |
| 70 | CGGGAUGCAUGUCUUGU | rTB06comp |
| 36 | n-biotin-(OO)-GTCGTCAGACCCAAAAC-c | TB01 |
| 37 | n-biotin-(OO)-CGAGAGGGGACGGAAAC-c | TB02 |
| 38 | n-biotin-(OO)-TGAACCGCCCCGGCATG-c | TB03 |
| 39 | n-biotin-(OO)-ACCAAGTAGACGGGCGA-c | TB04 |
| 40 | n-biotin-(OO)-CATCCAACCGTCGGTCG-c | TB05 |
| 41 | n-biotin-(OO)-ACAAGACATGCATCCCG-c | TB06 |

5 μL of 50 μM stock (250 picomoles) of each RNA oligo was mixed with 5 μL of 50 μM stock (250 picomoles) of its complementary PNA in 1.5 mL microcentrifuge tubes (Eppendorf, catalog #022364111). The tubes were incubated at room temperature for 10 minutes. Five μL of 25% glycerol (JT Baker, catalog #4043-00) was added to each sample.

The samples were loaded onto a 10% non-denaturing PAGE (19:1 crosslinking; JT Baker, catalog #4968-00), 1×TBE gel. The gel was run at 300 volts, for 45 minutes in 1×TBE gel running buffer. The gel was stained with 15 μM $DiSC_2(3)$ in 1×TBE for 30 minutes with gentle agitation. The reactions were activated using the Fritz Aurora 50/50 fluorescent lamp (Fritz Industries, Inc., Mesquite, Tex.) for varying lengths of time from $T_{0min}$ to $T_{3min}$. Photographs of the gel were taken using a B&W Polaroid camera while the gel was illuminated with a 254 nm UV transilluminator. Prior to photoactivation, the gel was pink in color, with faint pink bands in lanes 1, 3, 5, 7, 9, 11 corresponding to the position of the PNA:RNA hybrids. Lanes 2, 4, 6, 8, 10, 12 also had faint bands corresponding to the position of the RNA oligos. As expected, the RNA:PNA hybrid migrated more slowly in the gel than the RNA oligos. During photoactivation, in lanes 1, 3, 5, 7, 9, 11 at the expected location of the PNA:RNA hybrids, regions lacking color appeared. These "holes" show up as darker areas on the second panel of FIG. 23, after 3 minutes of light activation time.

Example 34

The specificity of the homogeneous smartDNA assay was tested using 2 ng of non-specific genomic DNAs and PNA TB 19: n-lys-TGAACCGCCCCGGCATG-c (SEQ ID NO: 71).

Samples containing genomic DNA isolated from several non-specific organisms (see Table 40) were diluted to 2 ng per 25 μL in 1 mM EDTA. Aliquots of 25 μL of each of the DNA samples were dispensed in two triplicate sets into a 384-white-well optical bottom microtiter plate (NUNC, catalog #242763). One set was the DNA only sample set that contained DNA and dye plus buffer sample. One set was the DNA+PNA sample that contained DNA, PNA, dye plus buffer.

Buffer solution was prepared by dissolving 20 millimoles of homopipes buffer (Research Organics catalog #6047H) in one liter of molecular biology grade water (Hyclone, catalog #SH30538.03) and the pH was adjusted to 5.0 with sodium hydroxide. Tween® 80 (Pierce Biotechnology, catalog #28328) was added to the final concentration of 0.1% to generate 2×HP5.0 buffer. The resulting buffer solution was sterile filtered (MF75 Vacuum Filter Units, PES Membrane, Nalgene, catalog #566-0020).

Dye solution was prepared by diluting 7.5 mM 3,3'-diethylthiacarbocyanine ("$DiSC_2(3)$") (solubilized in DMSO) into 2×HP5.0 buffer to a working concentration of 36 μM. PNA probe mixture was prepared by diluting 50 μM PNA stock to 640 nM with 2×HP5.0 buffer.

After the DNA samples were dispensed into the microplate, two dye mixtures were then prepared. The reaction set-up steps involving the dye were performed in a dimly lit room. The first control dye solution was prepared by mixing equal volumes of 36 μM $DiSC_2(3)$ in 2×HP5.0 buffer with 2×HP5.0 buffer. This 18 μM $DiSC_2(3)$ control solution was mixed by inversion in a 15 mL conical tube, and poured into a reagent reservoir. A 25 μL aliquot of the control dye solution was then dispensed to the DNA only samples in the 384-well plate. The second, dye+PNA probe mix was prepared by mixing equal volumes of 36 μM $DiSC_2(3)$ with the 640 nM PNA probe mix. This 18 μM $DiSC_2(3)$+320 nM PNA probe mix was mixed by inversion in a 15 mL conical tube, and poured into a reagent reservoir. A 25 μL aliquot of the dye+PNA probe mix was then dispensed to each DNA sample in the DNA+PNA sample set and gently shaken to mix the solutions.

The microplate was inserted into the Tecan Safire$^2$ monochromator-based microplate reader. The microplate was subjected to a 1 second medium-intensity orbital shake, followed by a 1 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 $mW/cm^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 20 minutes total exposure to light.

The initial rates of dye photobleaching (initial dye color change rates) were calculated by subtracting the absorbance of the solution at $time_{4min}$ from the initial absorbance of the solution at $Time_{0min}$ and dividing by 4 minutes. Table 40 lists the initial dye color change rates depicted as change in milliabsorbance (mAbs) units per minute.

The PNA target sequence is absent from the human genome, several bacteria that are present in or cause disease in humans as well as the plant *Arabidopsis*. From examining the initial dye color change rates of the smartDNA reactions for these organisms, the specificity of this MTB-targeted DNA is apparent. We occasionally observed what appears to be a specific dye color change reaction, as is observed for *Arabidopsis*, when a perfect match to the PNA probe is absent. We believe that this maybe due to either the method of DNA isolation and purification or alternately the publicly available BLAST software was unable to determine the presence of the PNA binding site in *Arabidopsis* because the length of the PNA is only 17 base pairs.

TABLE 40

| | | initial dye color change rate (mAbs/min) | | standard deviation of initial dye color change rate | |
|---|---|---|---|---|---|
| DNA source | catalog # | DNA + PNA | DNA only | DNA + PNA | DNA only |
| *Arabidopsis thaliana* | | 42.05 | 14.11 | 3.82 | 0.05 |
| *E. coli* | | 17.13 | 14.50 | 1.27 | 1.30 |
| human | Sigma D7011 (lot 02153787) | 11.55 | 12.26 | 1.50 | 0.83 |
| human | Sigma D3035 (lot 123K3796) | 12.05 | 12.78 | 1.26 | 2.42 |
| *P. aeruginosa* | ATCC 17933D | 13.56 | 12.33 | 2.21 | 0.93 |
| *P. aeruginosa* | ATCC 47085D | 12.92 | 11.44 | 1.19 | 0.24 |
| *S. aureus* | ATCC 10832D | 16.66 | 12.75 | 0.18 | 1.59 |
| *H. influenza* | ATCC 51907D | 15.40 | 12.05 | 1.43 | 0.05 |
| *N. meningititis* | ATCC BAA-335D | 11.92 | 9.55 | 1.32 | 0.79 |
| *M. microti* | | 40.86 | 22.76 | 2.91 | 1.52 |
| *S. pneumoniae* | ATCC BAA-334D | 11.50 | 9.62 | 0.47 | 0.04 |
| *K. pneumonia* | ATCC 700721D | 21.02 | 19.34 | 0.15 | 10.26 |
| MTB 2 ng | | 58.25 | 12.10 | 4.05 | 0.17 |
| MTB 1 ng | | 37.98 | 11.92 | 0.26 | 0.50 |
| MTB 0.5 ng | | 19.93 | 10.96 | 0.31 | 0.33 |
| MTB 0.25 ng | | 14.42 | 10.43 | 0.23 | 1.00 |
| MTB 0.125 ng | | 12.35 | 10.82 | 1.13 | 1.69 |
| MTB 0.0625 ng | | 11.65 | 10.24 | 1.84 | 0.10 |
| PNA only | | 9.81 | 9.47 | 0.78 | 1.09 |

Example 35

This example illustrates one embodiment of the present invention for determining the presence of DNA in a crude cell lysate in a homogenous assay.

*Mycobacterium tuberculosis* (MTB H37Ra, ATCC catalog #25117) cells were grown in Middlebrook 7H9Broth with Tween® 80 (Remel Inc., catalog #R09556) were grown for 6 weeks at 37° C. with gentle agitation. Five mL of culture was diluted with 15 mL 1×PBS (Teknova, catalog #$PO_{200}$) plus 1 mM EDTA to an equivalent of McFarland standard of 1 (~$1\times10^8$ colony forming units/mL). For each sample, 1 mL of cells was placed in a 1.5 mL microcentrifuge tube (Eppendorf, catalog #022364111) and centrifuged for 1 minute at 14,000 rpm to pellet the cells. The supernatant was removed and the cells resuspended in 100 μL 1×PBS, 1 mM EDTA buffer. From a slurry of 0.1 mm glass beads (Scientific Industries, catalog #SI-BG01) and 1×PBS, 1 mM EDTA buffer, approximately 50 mg of beads were added to each tube. The tubes were shaken at full speed for 2 minutes using the Vortex Genie® 2 (Scientific Industries, catalog #SI-0236, model #G650) equipped with the TurboMix attachment for 1.5 mL microcentrifuge tubes (Scientific Industires, catalog #SI-0563). Following cell disruption, the tubes were placed on ice.

The concentration of DNA released from the cells was estimated by gel electrophoresis. Twenty μL of each cell lysate was run on 0.8% agarose, 1×TBE gel stained with ethidium bromide. As a standard for DNA concentration, 2-fold dilutions of salmon sperm DNA were run side-by-side on the gel. The concentration of DNA in the cell lysates was estimated by comparing the intensity of the bands of the samples with those of the standards.

Two-fold serial dilutions of the cell lysates were made using 1 mM EDTA to DNA concentrations of approximately 0.08 ng/μL; 0.04 ng/μL; 0.02 ng/μL; 0.01 ng/μL. 25 μL of each DNA dilution was placed in triplicate into a 384-white-well optical bottom microtiter plate (NUNC, catalog #242763) along with a no DNA control of 25 μL of 1 mM EDTA. In addition as a control, 2-fold dilutions of isolated MTB DNA was pipette in triplicate into the same 384-well microtiter plate.

Buffer solution was prepared by dissolving 20 millimoles of homopipes buffer (Research Organics catalog #6047H) in one liter of molecular biology grade water (Hyclone, catalog #SH30538.03) and the pH adjusted to 5.0 with sodium hydroxide. Tween® 80 (Pierce Biotechnology, catalog #28328) was added to the final concentration of 0.1% to generate 2×HP5.0 buffer. The resulting buffer solution was sterile filtered (MF75 Vacuum Filter Units, PES Membrane, Nalgene, catalog #566-0020).

Dye solution was prepared by diluting 7.5 mM 3,3'-diethylthiacarbocyanine ("$DiSC_2(3)$") (solubilized in DMSO) into 2×HP5.0 buffer to a working concentration of 36 μM. PNA probe mixture was prepared by diluting 50 μM PNA [TB 15, n-lys-ACCAAGTAGACGGGCGA-c (SEQ ID NO: 72)] stock to 640 nM with 2×HP5.0 buffer.

After the DNA samples were dispensed into the microplate, two dye mixtures were then prepared. The reaction set-up steps involving the dye were performed in a dimly lit room. The first control dye solution was prepared by mixing equal volumes of 36 μM $DiSC_2(3)$ in 2×HP5.0 buffer with 2×HP5.0 buffer. This 18 μM $DiSC_2(3)$ control solution was mixed by inversion in a 15 mL conical tube, and poured into a reagent reservoir. A 25 μL aliquot of the control dye solution was then dispensed to the DNA only samples in the 384-well plate. The second, dye+PNA probe mix was prepared by mixing equal volumes of 36 μM $DiSC_2(3)$ with the 640 nM PNA probe mix. This 18 μM $DiSC_2(3)$+320 nM PNA probe mix was mixed by inversion in a 15 mL conical tube, and poured into a reagent reservoir. A 25 μL aliquot of the dye+PNA probe mix was then dispensed to each DNA sample in the DNA+PNA sample set and gently shaken to mix the solutions.

The microplate was inserted into the Tecan $Safire^2$ monochromator-based microplate reader. The microplate was subjected to a 1 second medium-intensity orbital shake, followed by a 1 second settle time, followed by an absorbance measurement at 556 nm. The absorbance measurement was performed with a bandwidth of 20 nm, with 12 reads per well. After the initial optical measurement, the plate was removed from the microplate reader, and subjected to photoactivation for a two minute interval. The light for photoactivation was provided by a solid-state activator providing illumination with a peak wavelength of 470 nm and a power density of approximately 1.8 mW/cm$^2$, as measured with a laser-based power meter having the tradename LaserCheck™ (Coherent, Inc., Santa Clara, Calif.; catalog #0217-271-00). The microplate was reinserted into the reader and each well was measured as indicated above, however with a shortened orbital shake and settle time of one second each. This two minute photoactivation followed by absorbance detection cycle was performed over a period of 20 minutes total exposure to light.

The initial rates of dye photobleaching (initial dye color change rates) were calculated by subtracting the absorbance of the solution at time$_{4min}$ from the initial absorbance of the solution at Time$_{0min}$ and dividing by 4 minutes. Table 41 lists the initial dye color change rates depicted as change in milliabsorbance (mAbs) units per minute.

The initial dye color change rates for both the DNA in the cell lysates and the isolated DNA showed a dose response.

TABLE 41

|  | 2 ng | 1 ng | 0.5 ng | 0.25 ng | 0 ng |
|---|---|---|---|---|---|
|  | initial dye color change rate averages | | | | |
| cell lysate alone | 25.62 | 19.30 | 16.13 | 15.18 | 12.14 |
| cell lysate + 160 nM PNA | 63.92 | 42.94 | 29.15 | 22.43 | 13.89 |
| isolated DNA alone | 15.37 | 14.29 | 13.86 | 13.44 | 12.14 |
| isolated DNA + 160 nM PNA | 77.25 | 61.68 | 45.66 | 34.37 | 13.89 |
|  | standard deviations of initial dye color change rate | | | | |
| cell lysate alone | 0.64 | 0.54 | 1.13 | 0.81 | 0.44 |
| cell lysate + 160 nM PNA | 1.05 | 0.72 | 0.50 | 0.54 | 0.30 |
| isolated DNA alone | 0.63 | 0.70 | 0.96 | 0.66 | 0.44 |
| isolated DNA + 160 nM PNA | 6.65 | 2.71 | 2.69 | 1.04 | 0.30 |

Additional Embodiments

In one aspect, the invention relates to a method comprising the step of combining
(i) a sample that may or may not contain a target polynucleotide;
(ii) a nucleic acid analog immobilized to a solid substrate, wherein the nucleic acid analog is complementary to a portion of the target polynucleotide; and
(iii) a light reactive dye capable of forming a light reactive complex with the target polynucleotide and a complementary nucleic acid analog,
wherein the target polynucleotide, if present, forms a light reactive complex with the nucleic acid analog and the light reactive dye.

The method may further comprise the step of isolating the solid substrate, based on a property of the solid substrate. The method may further comprise the step of washing the solid substrate with a wash solution comprising the light reactive dye. The light reactive complex may be formed at a room temperature. The light reactive complex may alternatively be formed at a temperature of less than about 37° C. The light reactive complex may also be formed at a temperature of less than about 45° C. The light reactive dye may be selected from the group consisting of: 3,3'-diethylthiacarbocyanine, 3,3'-diallylthiacarbocyanine, 3,3'-diethyl-9-methylthiacarbocyanine, 3,3'-dibutylthiacarbocyanine, 3,3'-dipropylthiacarbocyanine, 3,3'-dipentylthiacarbocyanine, and 1,1'-diethyl-2,2'-carbocyanine, and salts thereof. The light reactive dye may be 3,3'-Diethylthiacarbocyanine or salts thereof. The nucleic acid analog may be less than 20 bases in length. The nucleic acid analog may be about 17 bases in length. The nucleic acid analog may be selected from the group consisting of: PNA polynucleotides, LNA polynucleotides and morpholino polynucleotides. The nucleic acid analog may be a PNA polynucleotide. The method may further comprise exposing the solid substrate to light under conditions sufficient to elute the target polynucleotide from the solid substrate. In the method, the step of exposing the light reactive complex to light may be performed under ambient light conditions. In the method, the step of exposing the light reactive complex to light may be performed at ambient room temperature. In the method, the step of exposing the light reactive complex to light may be performed at a temperature of less than about 37° C. In the method, the step of exposing the light reactive complex to light may be performed at a temperature of less than about 45° C. In the method, the step of exposing the light reactive complex to light may be performed for a period of less than 1 hour. In the method, the step of exposing the light reactive complex to light may be performed for a period of less than 30 minutes. In the method, the step of exposing the light reactive complex to light may be performed for a period of less than 5 minutes. In the method, the light may include a controlled light. In the method, the light may be from a light emitting diode (LED). In the method, the majority of the light may have a specific wavelength of between about 460 nm to about 480 nm.

In another embodiment, the invention relates to a method comprising the step of combining
(i) a sample that may or may not contain a target molecule;
(ii) an immobilized polynucleotide bound to a solid substrate;
(iii) a bridging complex comprising (1) a polynucleotide portion complementary to the immobilized polynucleotide, wherein at least one of the immobilized polynucleotide and the polynucleotide portion of the bridging complex is a nucleic acid analog polynucleotide, and (2) a target-specific portion capable of binding to the target molecule, wherein the bridging complex comprises one or more molecules complexed together; and
(iv) a light reactive dye capable of forming a light reactive complex with the immobilized polynucleotide and the complementary polynucleotide portion of the bridging complex.

The method may further comprise the step of separating the solid substrate from the sample, based on a property of the solid substrate. The method may further comprise the step of washing the solid substrate with a wash solution comprising the light reactive dye. The light reactive complex may be formed under ambient light conditions. The light reactive complex may be formed at room temperature. The light reactive complex may be formed at a temperature of less than about 37° C. The light reactive complex may be formed at a temperature of less than about 45° C. The light reactive dye may be selected from the group consisting of: 3,3'-diethylthiacarbocyanine, 3,3'-diallylthiacarbocyanine, 3,3'-diethyl-9-methylthiacarbocyanine, 3,3'-dibutylthiacarbocyanine, 3,3'-dipropylthiacarbocyanine, 3,3'-dipentylthiacarbocyanine, and 1,1'-diethyl-2,2'-carbocyanine, and salts thereof. The light reactive dye may be 3,3'-Diethylthiacarbocyanine or salts thereof. The nucleic acid analog may be less than 20 bases in length. The nucleic acid analog may be about 17 bases in length. The nucleic acid analog may be selected from the group consisting of: PNA polynucleotides, LNA polynucleotides and morpholino polynucleotides. The nucleic acid analog may be a PNA polynucleotide. The method may further comprise the step of detecting the relative change in an optical property of the light reactive complex. The method may further comprise exposing the solid substrate to light under conditions sufficient to elute the target molecule from the solid substrate. In the method, the step of exposing the light reactive complex to light may be performed under ambient light conditions. In the method, the step of exposing the light reactive complex to light may be performed at ambient room temperature. In the method, the step of exposing the light reactive complex to light may be performed at a temperature of less than about 37° C. In the method, the step of exposing the light reactive complex to light may be performed at a temperature of less than about 45° C. In the method, the step of exposing the light reactive complex to light may be performed for a period of less than 2 hours. In the method, the step of exposing the light reactive complex to light may be performed for a period less than 1 hour. In the method, the step of exposing the light reactive complex to light may be performed for a period less than 30 minutes. In the method, the step of exposing the light reactive complex to light may be performed for a period less than 5 minutes. In the method, the target molecule may be a polypeptide and the target-specific portion of the bridging complex is a polypeptide binding molecule capable of specifically binding the polypeptide target molecule. In the method, the target molecule may be a polypeptide and the target-specific portion of the bridging complex may be an antibody or binding fragment thereof capable of specifically binding the polypeptide target molecule. In the method, the target molecule may be an oligosaccharide moiety and the target-specific portion of the bridging complex may be selected from the group consisting of an antibody or binding fragment thereof or a lectin molecule, capable of specifically binding the polypeptide target molecule. In the method, the target molecule may be a hapten molecule and the target-specific portion of the bridging complex may be an antibody or binding fragment thereof capable of specifically binding the hapten target molecule. In the method, the target molecule may be a polynucleotide and the target-specific portion of the bridging complex may be a nucleic acid analog polynucleotide complementary to the polynucleotide target molecule.

In one other aspect, the invention relates to a method for making a nucleic acid diagnostic kit comprising the step of combining, in a packaged combination, (i) an immobilized nucleic acid analog bound to a solid substrate, wherein the nucleic acid analog is complementary to a portion of a target polynucleotide; and (ii) a light reactive dye in a container, wherein the light reactive dye is capable of forming a light reactive complex with the target polynucleotide and a complementary nucleic acid analog.

In yet further embodiment, the invention relates to a method for making a nucleic acid diagnostic kit comprising the step of combining, in a packaged combination, (i) an immobilized polynucleotide bound to a solid substrate; and (ii) a container comprising at least one of:

a bridging complex comprising (1) a polynucleotide portion complementary to the immobilized polynucleotide, wherein at least one of the immobilized polynucleotide and the polynucleotide portion of the bridging complex is a nucleic acid analog polynucleotide, and (2) a target-specific portion capable of binding to the target molecule, wherein the bridging complex comprises one or more molecules complexed together; and a light reactive dye capable of forming a light reactive complex with the immobilized polynucleotide and the complementary polynucleotide portion of the bridging complex;

All publications, patents, and patent applications cited herein are hereby incorporated by reference in their entireties, respectively, for all purposes and to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the disclosure.

We claim:

1. A method comprising
  (a) combining
    (i) a sample that may or may not contain a target polynucleotide;
    (ii) a nucleic acid analog immobilized to a solid substrate, wherein the nucleic acid analog is complementary to at least a portion of the target polynucleotide;
    (iii) a light reactive dye capable of forming a light reactive complex with the target polynucleotide and a complementary nucleic acid analog,
    wherein the target polynucleotide, if present, forms a light reactive complex with the nucleic acid analog and the light reactive dye; and
  (b) exposing the nucleic acid analog immobilized to the solid substrate to light under conditions sufficient to elute the target polynucleotide from the solid substrate.

2. The method of claim 1, wherein in the step of exposing the light reactive complex to light, the light used comprises ambient light.

3. The method of claim 1, wherein the step of exposing the light reactive complex to light is performed at ambient room temperature.

4. The method of claim 1, wherein the step of exposing the light reactive complex to light is performed at a temperature of less than about 37° C.

5. The method of claim 1, wherein the step of exposing the light reactive complex to light is performed at a temperature of less than about 45° C.

6. The method of claim 1, wherein the step of exposing the light reactive complex to light is performed for a period of less than 1 hour.

7. The method of claim 1, wherein the step of exposing the light reactive complex to light is performed for a period of less than 30 minutes.

8. The method of claim 1, wherein the step of exposing the light reactive complex to light is performed for a period of less than 5 minutes.

9. The method of claim 1, wherein the light comprises a controlled light.

10. The method of claim 1, wherein the light is from a light emitting diode.

11. The method of claim 1, wherein the majority of the light has a specific wavelength of between about 460 nm to about 480 nm.

12. A method comprising the steps of
  (a) combining
    (i) a sample that may or may not contain a target molecule;
    (ii) an immobilized polynucleotide bound to a solid substrate;
    (iii) a bridging complex comprising (1) a polynucleotide portion complementary to the immobilized polynucleotide, wherein at least one of the immobilized polynucleotide and the polynucleotide portion of the bridging complex is a nucleic acid analog polynucleotide, and (2) a target-specific portion capable of binding to the target molecule, wherein the bridging complex comprises one or more molecules complexed together; and
    (iv) a light reactive dye capable of forming a light reactive complex with the immobilized polynucleotide and the complementary polynucleotide portion of the bridging complex,
    wherein the target molecule, if present in the sample, binds to the target-specific portion of the bridging complex; and
  (b) exposing the immobilized polynucleotide bound to the solid substrate to light under conditions sufficient to elute the target polynucleotide from the solid substrate.

13. The method of claim 1, further comprising the step of isolating the solid substrate, based on a property of the solid substrate.

14. The method of claim 1, further comprising the step of washing the solid substrate with a wash solution comprising the light reactive dye.

15. The method of claim 1, wherein the light reactive complex is formed at a room temperature.

16. The method of claim 1, wherein the light reactive complex is formed at a temperature of less than about 37° C.

17. The method of claim 1, wherein the light reactive complex is formed at a temperature of less than about 45° C.

18. The method of claim 1, wherein the light reactive dye is selected from the group consisting of: 3,3'-diethylthiacarbocyanine, 3,3'-diallylthiacarbocyanine, 3,3'-diethyl-9-methylthiacarbocyanine, 3,3'-dibutylthiacarbocyanine, 3,3'-dipropylthiacarbocyanine, 3,3'-dipentylthiacarbocyanine, and 1,1'-diethyl-2,2'-carbocyanine, and salts thereof.

19. The method of claim 1, wherein the light reactive dye is 3,3'-diethylthiacarbocyanine or salts thereof.

20. The method of claim 1, wherein the nucleic acid analog is less than 20 bases in length.

21. The method of claim 1, wherein the nucleic acid analog is about 17 bases in length.

22. The method of claim 1, wherein the nucleic acid analog is about 15 bases in length.

23. The method of claim 1, wherein the nucleic acid analog is selected from the group consisting of: PNA polynucleotides, LNA polynucleotides and morpholino polynucleotides.

24. The method of claim 1, wherein the nucleic acid analog is a PNA polynucleotide.

* * * * *

SEQUENCE LISTING

```
<160> NUMBER OF SEQ ID NOS: 72

<210> SEQ ID NO 1
<211> LENGTH: 18
<212> TYPE: DNA
<213> ORGANISM: Artificial
<220> FEATURE:
<223> OTHER INFORMATION: probe for 35S CMV promotor

<400> SEQUENCE: 1
gatagtggga ttgtgcgt                                                 18

<210> SEQ ID NO 2
<211> LENGTH: 12
<212> TYPE: DNA
<213> ORGANISM: Artificial
<220> FEATURE:
```

<223> OTHER INFORMATION: probe for Maize zein control

<400> SEQUENCE: 2
acagttgctg ca                                                             12

<210> SEQ ID NO 3
<211> LENGTH: 12
<212> TYPE: DNA
<213> ORGANISM: Artificial
<220> FEATURE:
<223> OTHER INFORMATION: probe for Maize invertase

<400> SEQUENCE: 3
tgtatcacaa gg                                                             12

<210> SEQ ID NO 4
<211> LENGTH: 12
<212> TYPE: DNA
<213> ORGANISM: Artificial
<220> FEATURE:
<223> OTHER INFORMATION: probe for Maize adh

<400> SEQUENCE: 4
ctccgagacc ct                                                             12

<210> SEQ ID NO 5
<211> LENGTH: 12
<212> TYPE: DNA
<213> ORGANISM: Artificial
<220> FEATURE:
<223> OTHER INFORMATION: probe for soy lectin

<400> SEQUENCE: 5
ctattgtgac ct                                                             12

<210> SEQ ID NO 6
<211> LENGTH: 12
<212> TYPE: DNA
<213> ORGANISM: Artificial
<220> FEATURE:
<223> OTHER INFORMATION: probe for Shiga-like toxin 1

<400> SEQUENCE: 6
tcgttgacta ct                                                             12

<210> SEQ ID NO 7
<211> LENGTH: 12
<212> TYPE: DNA
<213> ORGANISM: Artificial
<220> FEATURE:
<223> OTHER INFORMATION: probe for Shiga-like toxin 2

<400> SEQUENCE: 7
aactgctcct gt                                                             12

<210> SEQ ID NO 8
<211> LENGTH: 17
<212> TYPE: DNA
<213> ORGANISM: Artificial
<220> FEATURE:
<223> OTHER INFORMATION: 16S nucleic acid analog (ncPNA) probe

<400> SEQUENCE: 8
actgctgcct cccgtag                                                        17

<210> SEQ ID NO 9
<211> LENGTH: 12
<212> TYPE: DNA
<213> ORGANISM: Artificial
<220> FEATURE:
<223> OTHER INFORMATION: 16S nucleic acid analog probe; ncPNA, cPNA, LNA, or Morpholino

<400> SEQUENCE: 9
tgcctcccgt ag                                                            12

<210> SEQ ID NO 10
<211> LENGTH: 17
<212> TYPE: DNA
<213> ORGANISM: Artificial
<220> FEATURE:
<223> OTHER INFORMATION: 16S nucleic acid analog (ncPNA) probe

<400> SEQUENCE: 10
ctacgggagg cagcagt                                                       17

<210> SEQ ID NO 11
<211> LENGTH: 11
<212> TYPE: DNA
<213> ORGANISM: Artificial
<220> FEATURE:
<223> OTHER INFORMATION: 16S nucleic acid analog (ncPNA) probe

<400> SEQUENCE: 11
ctacgggagg c                                                             11

<210> SEQ ID NO 12
<211> LENGTH: 22
<212> TYPE: DNA
<213> ORGANISM: Artificial
<220> FEATURE:
<223> OTHER INFORMATION: nucleic acid analog for detection of all bacteria (BP6) universal probe set; oI2018

<400> SEQUENCE: 12
gaassmycya acacytagca ct                                                 22

<210> SEQ ID NO 13
<211> LENGTH: 24
<212> TYPE: DNA
<213> ORGANISM: Artificial
<220> FEATURE:
<223> OTHER INFORMATION: nucleic acid analog for detection of all bacteria probe set (BP6); oI2019

<400> SEQUENCE: 13
tacaamgagy ygcwagacsg ygas                                               24

<210> SEQ ID NO 14
<211> LENGTH: 21
<212> TYPE: DNA
<213> ORGANISM: Artificial
<220> FEATURE:
<223> OTHER INFORMATION: nucleic acid analog for detection of gram positive bacteria probe set (BP19); oI2021

<400> SEQUENCE: 14
gcagywaacg cattaagcac t                                                  21

<210> SEQ ID NO 15
<211> LENGTH: 20
<212> TYPE: DNA

```
<213> ORGANISM: Artificial
<220> FEATURE:
<223> OTHER INFORMATION: nucleic acid analog for detection of gram
      positive bacteria probe set (BP19); oI2022

<400> SEQUENCE: 15
acgacacgag ctgacgacaa                                               20

<210> SEQ ID NO 16
<211> LENGTH: 23
<212> TYPE: DNA
<213> ORGANISM: Artificial
<220> FEATURE:
<223> OTHER INFORMATION: nucleic acid analog for detection of gram
      negative bacteria probe set (BP3); oI2003

<400> SEQUENCE: 16
tctagctggt ctgagaggat gac                                           23

<210> SEQ ID NO 17
<211> LENGTH: 21
<212> TYPE: DNA
<213> ORGANISM: Artificial
<220> FEATURE:
<223> OTHER INFORMATION: nucleic acid analog for detection of gram
      negative bacteria probe set (BP3); oI2004

<400> SEQUENCE: 17
gagttagccg gtgcttcttc t                                             21

<210> SEQ ID NO 18
<211> LENGTH: 21
<212> TYPE: DNA
<213> ORGANISM: Artificial
<220> FEATURE:
<223> OTHER INFORMATION: nucleic acid analog for detection of Fungi
      probe set (FP8); oI2055

<400> SEQUENCE: 18
cctgcggctt aatttgactc a                                             21

<210> SEQ ID NO 19
<211> LENGTH: 19
<212> TYPE: DNA
<213> ORGANISM: Artificial
<220> FEATURE:
<223> OTHER INFORMATION: nucleic acid analog for detection of Fungi
      probe set (FP8); oI2057

<400> SEQUENCE: 19
tagcgacggg cggtgtgta                                                19

<210> SEQ ID NO 20
<211> LENGTH: 18
<212> TYPE: DNA
<213> ORGANISM: Artificial
<220> FEATURE:
<223> OTHER INFORMATION: target polynucleotide; ncPNA

<400> SEQUENCE: 20
acgcacaatc ccactatc                                                 18

<210> SEQ ID NO 21
<211> LENGTH: 15
<212> TYPE: DNA
<213> ORGANISM: Artificial
<220> FEATURE:
```

```
<223> OTHER INFORMATION: ncPNA
<220> FEATURE:
<221> NAME/KEY: misc_feature
<222> LOCATION: (15)..()
<223> OTHER INFORMATION: lys

<400> SEQUENCE: 21
tcacatcaat ccact                                                     15

<210> SEQ ID NO 22
<211> LENGTH: 12
<212> TYPE: DNA
<213> ORGANISM: Artificial
<220> FEATURE:
<223> OTHER INFORMATION: wild type (+) oligonucleotide

<400> SEQUENCE: 22
gtgcgttcac at                                                        12

<210> SEQ ID NO 23
<211> LENGTH: 12
<212> TYPE: DNA
<213> ORGANISM: Artificial
<220> FEATURE:
<223> OTHER INFORMATION: wild type (-) oligonucleotide

<400> SEQUENCE: 23
atgtgaacgc ac                                                        12

<210> SEQ ID NO 24
<211> LENGTH: 12
<212> TYPE: DNA
<213> ORGANISM: Artificial
<220> FEATURE:
<223> OTHER INFORMATION: single base mutation (+) oligonucleotide

<400> SEQUENCE: 24
ctgcgttcac at                                                        12

<210> SEQ ID NO 25
<211> LENGTH: 12
<212> TYPE: DNA
<213> ORGANISM: Artificial
<220> FEATURE:
<223> OTHER INFORMATION: single base mutation (-) oligonucleotide

<400> SEQUENCE: 25
atgtgaacgc ag                                                        12

<210> SEQ ID NO 26
<211> LENGTH: 12
<212> TYPE: DNA
<213> ORGANISM: Artificial
<220> FEATURE:
<223> OTHER INFORMATION: single base mutation (+) oligonucleotide

<400> SEQUENCE: 26
gtgcgttcac aa                                                        12

<210> SEQ ID NO 27
<211> LENGTH: 12
<212> TYPE: DNA
<213> ORGANISM: Artificial
<220> FEATURE:
<223> OTHER INFORMATION: single base mutation (-) oligonucleotide

<400> SEQUENCE: 27
```

```
ttgtgaacgc ac                                                          12

<210> SEQ ID NO 28
<211> LENGTH: 12
<212> TYPE: DNA
<213> ORGANISM: Artificial
<220> FEATURE:
<223> OTHER INFORMATION: single 2-base pair mutation (+) oligonucleotide

<400> SEQUENCE: 28
cagcgttcac at                                                          12

<210> SEQ ID NO 29
<211> LENGTH: 12
<212> TYPE: DNA
<213> ORGANISM: Artificial
<220> FEATURE:
<223> OTHER INFORMATION: single 2-base pair mutation (-) oligonucleotide

<400> SEQUENCE: 29
atgtgaacgc tg                                                          12

<210> SEQ ID NO 30
<211> LENGTH: 12
<212> TYPE: DNA
<213> ORGANISM: Artificial
<220> FEATURE:
<223> OTHER INFORMATION: two, 2-base pair mutation (+) oligonucleotide

<400> SEQUENCE: 30
cagcgttcag gt                                                          12

<210> SEQ ID NO 31
<211> LENGTH: 12
<212> TYPE: DNA
<213> ORGANISM: Artificial
<220> FEATURE:
<223> OTHER INFORMATION: two, 2-base pair mutation (-) oligonucleotide

<400> SEQUENCE: 31
acctgaacgc tg                                                          12

<210> SEQ ID NO 32
<211> LENGTH: 6
<212> TYPE: DNA
<213> ORGANISM: Artificial
<220> FEATURE:
<223> OTHER INFORMATION: ncPNA

<400> SEQUENCE: 32 cacgca                                                                  6

<210> SEQ ID NO 33
<211> LENGTH: 33
<212> TYPE: DNA
<213> ORGANISM: Artificial
<220> FEATURE:
<223> OTHER INFORMATION: a secondary probe
<220> FEATURE:
<221> NAME/KEY: misc_feature
<223> OTHER INFORMATION: biotin molecule(s) attached to 5' end via
      hydrophobic flexible linker molecules of 8-amino-3,6-dioxaoctanoic
      acid
<220> FEATURE:
<221> NAME/KEY: misc_feature
<222> LOCATION: (33)..()
<223> OTHER INFORMATION: lys
```

-continued

```
<400> SEQUENCE: 33
gatagtggga ttgtgcgttc acatcaatcc act                                    33

<210> SEQ ID NO 34
<211> LENGTH: 6
<212> TYPE: DNA
<213> ORGANISM: Artificial
<220> FEATURE:
<223> OTHER INFORMATION: ncPNA

<400> SEQUENCE: 34 agtgta                                                                   6

<210> SEQ ID NO 35
<211> LENGTH: 12
<212> TYPE: DNA
<213> ORGANISM: Artificial
<220> FEATURE:
<223> OTHER INFORMATION: HCV-specific biotinylated nucleic acid analog
      (ncPNA) probe
<220> FEATURE:
<221> NAME/KEY: misc_feature
<223> OTHER INFORMATION: biotin molecule(s) attached to 5' end via
      hydrophobic flexible linker molecules of 8-amino-3,6-dioxaoctanoic
      acid (Bio-(o)10-)

<400> SEQUENCE: 35
cgcagaccac ta                                                           12

<210> SEQ ID NO 36
<211> LENGTH: 17
<212> TYPE: DNA
<213> ORGANISM: Artificial
<220> FEATURE:
<223> OTHER INFORMATION: probe for TB01
<220> FEATURE:
<221> NAME/KEY: misc_feature
<223> OTHER INFORMATION: biotin molecule(s) attached to 5' end via
      hydrophobic flexible linker molecules of 8-amino-3,6-dioxaoctanoic
      acid (Bio-oo-)

<400> SEQUENCE: 36
gtcgtcagac ccaaaac                                                      17

<210> SEQ ID NO 37
<211> LENGTH: 17
<212> TYPE: DNA
<213> ORGANISM: Artificial
<220> FEATURE:
<223> OTHER INFORMATION: probe for TB02
<220> FEATURE:
<221> NAME/KEY: misc_feature
<223> OTHER INFORMATION: biotin molecule(s) attached to 5' end via
      hydrophobic flexible linker molecules of 8-amino-3,6-dioxaoctanoic
      acid (Bio-oo-)

<400> SEQUENCE: 37
cgagagggga cggaaac                                                      17

<210> SEQ ID NO 38
<211> LENGTH: 17
<212> TYPE: DNA
<213> ORGANISM: Artificial
<220> FEATURE:
<223> OTHER INFORMATION: probe for TB03
<220> FEATURE:
<221> NAME/KEY: misc_feature
<223> OTHER INFORMATION: biotin molecule(s) attached to 5' end via
```

-continued hydrophobic flexible linker molecules of 8-amino-3,6-dioxaoctanoic
        acid (Bio-oo-)

<400> SEQUENCE: 38
tgaaccgccc cggcatg                                                  17

<210> SEQ ID NO 39
<211> LENGTH: 17
<212> TYPE: DNA
<213> ORGANISM: Artificial
<220> FEATURE:
<223> OTHER INFORMATION: probe for TB04
<220> FEATURE:
<221> NAME/KEY: misc_feature
<223> OTHER INFORMATION: biotin molecule(s) attached to 5' end via
        hydrophobic flexible linker molecules of 8-amino-3,6-dioxaoctanoic
        acid (Bio-oo-)

<400> SEQUENCE: 39
accaagtaga cgggcga                                                  17

<210> SEQ ID NO 40
<211> LENGTH: 17
<212> TYPE: DNA
<213> ORGANISM: Artificial
<220> FEATURE:
<223> OTHER INFORMATION: probe for TB05
<220> FEATURE:
<221> NAME/KEY: misc_feature
<223> OTHER INFORMATION: biotin molecule(s) attached to 5' end via
        hydrophobic flexible linker molecules of 8-amino-3,6-dioxaoctanoic
        acid (Bio-oo-)

<400> SEQUENCE: 40
catccaaccg tcggtcg                                                  17

<210> SEQ ID NO 41
<211> LENGTH: 17
<212> TYPE: DNA
<213> ORGANISM: Artificial
<220> FEATURE:
<223> OTHER INFORMATION: probe for TB06
<220> FEATURE:
<221> NAME/KEY: misc_feature
<223> OTHER INFORMATION: biotin molecule(s) attached to 5' end via
        hydrophobic flexible linker molecules of 8-amino-3,6-dioxaoctanoic
        acid (Bio-oo-)

<400> SEQUENCE: 41
acaagacatg catcccg                                                  17

<210> SEQ ID NO 42
<211> LENGTH: 12
<212> TYPE: DNA
<213> ORGANISM: Artificial
<220> FEATURE:
<223> OTHER INFORMATION: probe for TB07
<220> FEATURE:
<221> NAME/KEY: misc_feature
<223> OTHER INFORMATION: lys at 5' end

<400> SEQUENCE: 42
cagacccaaa ac                                                       12

<210> SEQ ID NO 43
<211> LENGTH: 12
<212> TYPE: DNA
<213> ORGANISM: Artificial
<220> FEATURE:

```
<223> OTHER INFORMATION: probe for TB08
<220> FEATURE:
<221> NAME/KEY: misc_feature
<223> OTHER INFORMATION: lys at 5' end

<400> SEQUENCE: 43
cgagagggga cg                                                              12

<210> SEQ ID NO 44
<211> LENGTH: 12
<212> TYPE: DNA
<213> ORGANISM: Artificial
<220> FEATURE:
<223> OTHER INFORMATION: probe for TB09
<220> FEATURE:
<221> NAME/KEY: misc_feature
<223> OTHER INFORMATION: lys at 5' end

<400> SEQUENCE: 44
tgaaccgccc cg                                                              12

<210> SEQ ID NO 45
<211> LENGTH: 12
<212> TYPE: DNA
<213> ORGANISM: Artificial
<220> FEATURE:
<223> OTHER INFORMATION: probe for TB10
<220> FEATURE:
<221> NAME/KEY: misc_feature
<223> OTHER INFORMATION: lys at 5' end

<400> SEQUENCE: 45
accaagtaga cg                                                              12

<210> SEQ ID NO 46
<211> LENGTH: 12
<212> TYPE: DNA
<213> ORGANISM: Artificial
<220> FEATURE:
<223> OTHER INFORMATION: probe for TB11
<220> FEATURE:
<221> NAME/KEY: misc_feature
<223> OTHER INFORMATION: lys at 5' end

<400> SEQUENCE: 46
catccaaccg tc                                                              12

<210> SEQ ID NO 47
<211> LENGTH: 12
<212> TYPE: DNA
<213> ORGANISM: Artificial
<220> FEATURE:
<223> OTHER INFORMATION: probe for TB12
<220> FEATURE:
<221> NAME/KEY: misc_feature
<223> OTHER INFORMATION: lys at 5' end

<400> SEQUENCE: 47
acaagacatg ca                                                              12

<210> SEQ ID NO 48
<211> LENGTH: 40
<212> TYPE: DNA
<213> ORGANISM: Artificial
<220> FEATURE:
<223> OTHER INFORMATION: ncPNA; target polynucleotide

<400> SEQUENCE: 48
```
ccaggacgac cgggtcctttt cttggatcaa cccgctcaat    40

<210> SEQ ID NO 49
<211> LENGTH: 40
<212> TYPE: DNA
<213> ORGANISM: Artificial
<220> FEATURE:
<223> OTHER INFORMATION: complementary strand

<400> SEQUENCE: 49
attgagcggg ttgatccaag aaaggacccg gtcgtcctgg    40

<210> SEQ ID NO 50
<211> LENGTH: 40
<212> TYPE: DNA
<213> ORGANISM: Artificial
<220> FEATURE:
<223> OTHER INFORMATION: oligonucleotide

<400> SEQUENCE: 50
tgctagccga gtagtgttgg gtcgcgaaag gccttgtggt    40

<210> SEQ ID NO 51
<211> LENGTH: 19
<212> TYPE: DNA
<213> ORGANISM: Artificial
<220> FEATURE:
<223> OTHER INFORMATION: ncPNA
<220> FEATURE:
<221> NAME/KEY: misc_feature
<222> LOCATION: (19)..()
<223> OTHER INFORMATION: lys at 3' end

<400> SEQUENCE: 51
gttgatccaa gaaaggacc    19

<210> SEQ ID NO 52
<211> LENGTH: 21
<212> TYPE: DNA
<213> ORGANISM: Artificial
<220> FEATURE:
<223> OTHER INFORMATION: ncPNA
<220> FEATURE:
<221> NAME/KEY: misc_feature
<222> LOCATION: (21)..()
<223> OTHER INFORMATION: lys at 3' end

<400> SEQUENCE: 52
gttgatccaa gaaaggaccc g    21

<210> SEQ ID NO 53
<211> LENGTH: 17
<212> TYPE: DNA
<213> ORGANISM: Artificial
<220> FEATURE:
<223> OTHER INFORMATION: ncPNA
<220> FEATURE:
<221> NAME/KEY: misc_feature
<222> LOCATION: (17)..()
<223> OTHER INFORMATION: lys at 3' end

<400> SEQUENCE: 53
tttcgcgacc caacact    17

<210> SEQ ID NO 54
<211> LENGTH: 40
<212> TYPE: DNA
<213> ORGANISM: Artificial

```
<220> FEATURE:
<223> OTHER INFORMATION: target polynucleotide

<400> SEQUENCE: 54
tgctagccga gtagtgttgg gtcgcgaaag gccttgtggt                              40

<210> SEQ ID NO 55
<211> LENGTH: 17
<212> TYPE: DNA
<213> ORGANISM: Artificial
<220> FEATURE:
<223> OTHER INFORMATION: ncPNA
<220> FEATURE:
<221> NAME/KEY: misc_feature
<222> LOCATION: (17)..()
<223> OTHER INFORMATION: lys at 3' end

<400> SEQUENCE: 55
agtgttgggt cgcgaaa                                                      17

<210> SEQ ID NO 56
<211> LENGTH: 40
<212> TYPE: DNA
<213> ORGANISM: Artificial
<220> FEATURE:
<223> OTHER INFORMATION: target polynucleotide

<400> SEQUENCE: 56
accacaaggc ctttcgcgac ccaacactac tcggctagca                              40

<210> SEQ ID NO 57
<211> LENGTH: 17
<212> TYPE: DNA
<213> ORGANISM: Artificial
<220> FEATURE:
<223> OTHER INFORMATION: PNA probe, TB24
<220> FEATURE:
<221> NAME/KEY: misc_feature
<222> LOCATION: (1)..(1)
<223> OTHER INFORMATION: lysine at N-terminus
<220> FEATURE:
<221> NAME/KEY: misc_feature
<222> LOCATION: (17)..(17)
<223> OTHER INFORMATION: lysine at C-terminus

<400> SEQUENCE: 57
gtcgtcagac ccaaaac                                                      17

<210> SEQ ID NO 58
<211> LENGTH: 17
<212> TYPE: DNA
<213> ORGANISM: Artificial
<220> FEATURE:
<223> OTHER INFORMATION: PNA probe, TB14
<220> FEATURE:
<221> NAME/KEY: misc_feature
<222> LOCATION: (1)..(1)
<223> OTHER INFORMATION: Lysine at N-terminus

<400> SEQUENCE: 58
gtcgtcagac ccaaaac                                                      17

<210> SEQ ID NO 59
<211> LENGTH: 17
<212> TYPE: DNA
<213> ORGANISM: Artificial
<220> FEATURE:
<223> OTHER INFORMATION: PNA probe, TB44
<220> FEATURE:
```

```
<221> NAME/KEY: misc_feature
<222> LOCATION: (1)..(1)
<223> OTHER INFORMATION: Two lysines at the N-terminus
<220> FEATURE:
<221> NAME/KEY: misc_feature
<222> LOCATION: (17)..(17)
<223> OTHER INFORMATION: Two lysines at the C-terminus

<400> SEQUENCE: 59
gtcgtcagac ccaaaac                                                   17

<210> SEQ ID NO 60
<211> LENGTH: 23
<212> TYPE: DNA
<213> ORGANISM: Artificial
<220> FEATURE:
<223> OTHER INFORMATION: PNA probe, bio-DNA
<220> FEATURE:
<221> NAME/KEY: misc_feature
<222> LOCATION: (1)..(1)
<223> OTHER INFORMATION: biotin molecule attached to the 5' end

<400> SEQUENCE: 60
tttttgatag tgggattgtg cgt                                            23

<210> SEQ ID NO 61
<211> LENGTH: 20
<212> TYPE: DNA
<213> ORGANISM: Artificial
<220> FEATURE:
<223> OTHER INFORMATION: forward and reverse primer for M. bovis

<400> SEQUENCE: 61
tgaaccgccc cggcatgtcc                                                20

<210> SEQ ID NO 62
<211> LENGTH: 20
<212> TYPE: DNA
<213> ORGANISM: Artificial
<220> FEATURE:
<223> OTHER INFORMATION: forward primer for M. tuberculosis

<400> SEQUENCE: 62
ccggttaggt gctggtggtc                                                20

<210> SEQ ID NO 63
<211> LENGTH: 20
<212> TYPE: DNA
<213> ORGANISM: Artificial
<220> FEATURE:
<223> OTHER INFORMATION: reverse primer for M. tuberculosis

<400> SEQUENCE: 63
cgccccatcg acctactacg                                                20

<210> SEQ ID NO 64
<211> LENGTH: 20
<212> TYPE: DNA
<213> ORGANISM: Mycobacterium bovis

<400> SEQUENCE: 64
tgaaccgccc cggtgagtcc                                                20

<210> SEQ ID NO 65
<211> LENGTH: 17
<212> TYPE: RNA
<213> ORGANISM: Artificial
```

-continued

```
<220> FEATURE:
<223> OTHER INFORMATION: RNA oligonucleotide; rTB01comp

<400> SEQUENCE: 65
guuugggguc ugacgac                                                    17

<210> SEQ ID NO 66
<211> LENGTH: 17
<212> TYPE: RNA
<213> ORGANISM: Artificial
<220> FEATURE:
<223> OTHER INFORMATION: RNA oligonucleotide; rTB02comp

<400> SEQUENCE: 66
guuuccgucc ccucucg                                                    17

<210> SEQ ID NO 67
<211> LENGTH: 17
<212> TYPE: RNA
<213> ORGANISM: Artificial
<220> FEATURE:
<223> OTHER INFORMATION: RNA oligonucleotide; rTB03comp

<400> SEQUENCE: 67
caugccgggg cgguuca                                                    17

<210> SEQ ID NO 68
<211> LENGTH: 17
<212> TYPE: RNA
<213> ORGANISM: Artificial
<220> FEATURE:
<223> OTHER INFORMATION: RNA oligonucleotide; rTB04comp

<400> SEQUENCE: 68
ucgcccgucu acuuggu                                                    17

<210> SEQ ID NO 69
<211> LENGTH: 17
<212> TYPE: RNA
<213> ORGANISM: Artificial
<220> FEATURE:
<223> OTHER INFORMATION: RNA oligonucleotide; rTB05comp

<400> SEQUENCE: 69
cgaccgacgg uuggaug                                                    17

<210> SEQ ID NO 70
<211> LENGTH: 17
<212> TYPE: RNA
<213> ORGANISM: Artificial
<220> FEATURE:
<223> OTHER INFORMATION: RNA oligonucleotide; rTB06comp

<400> SEQUENCE: 70
cgggaugcau gucuugu                                                    17

<210> SEQ ID NO 71
<211> LENGTH: 17
<212> TYPE: DNA
<213> ORGANISM: Artificial
<220> FEATURE:
<223> OTHER INFORMATION: PNA probe, TB19
<220> FEATURE:
<221> NAME/KEY: misc_feature
<222> LOCATION: (1)..(1)
<223> OTHER INFORMATION: One lysine at the N-terminus
```

-continued

```
<400> SEQUENCE: 71
tgaaccgccc cggcatg                                                    17

<210> SEQ ID NO 72
<211> LENGTH: 17
<212> TYPE: DNA
<213> ORGANISM: Artificial
<220> FEATURE:
<223> OTHER INFORMATION: PNA probe; TB15
<220> FEATURE:
<221> NAME/KEY: misc_feature
<222> LOCATION: (1)..(1)
<223> OTHER INFORMATION: One lysine at the N-terminus

<400> SEQUENCE: 72
accaagtaga cgggcga                                                    17
```